US009890214B2

(12) United States Patent
Anderson et al.

(10) Patent No.: US 9,890,214 B2
(45) Date of Patent: Feb. 13, 2018

(54) ANTIBODIES TO TNF α AND USE THEREOF

(71) Applicant: ALDERBIO HOLDINGS LLC, Las Vegas, NV (US)

(72) Inventors: Katie Anderson, Kirkland, WA (US); Benjamin H. Dutzar, Seattle, WA (US); Anne Elisabeth Carvalho Jensen, Snohomish, WA (US); Leon F. Garcia-Martinez, Woodinville, WA (US); Ethan W. Ojala, Snohomish, WA (US); John A. Latham, Seattle, WA (US)

(73) Assignee: ALDERBIO HOLDINGS LLC, Las Vegas, NV (US)

( * ) Notice: Subject to any disclaimer, the term of this patent is extended or adjusted under 35 U.S.C. 154(b) by 324 days.

(21) Appl. No.: 14/724,200

(22) Filed: May 28, 2015

(65) Prior Publication Data
US 2015/0337035 A1    Nov. 26, 2015

Related U.S. Application Data

(62) Division of application No. 12/153,611, filed on May 21, 2008, now Pat. No. 9,056,905.

(60) Provisional application No. 60/924,551, filed on May 21, 2007.

(51) Int. Cl.
| *A61K 39/395* | (2006.01) |
| *C07K 16/24* | (2006.01) |
| *A61K 49/00* | (2006.01) |
| *A61K 45/06* | (2006.01) |
| *A61K 51/10* | (2006.01) |
| *A61K 47/68* | (2017.01) |

(52) U.S. Cl.
CPC ........ *C07K 16/241* (2013.01); *A61K 39/3955* (2013.01); *A61K 45/06* (2013.01); *A61K 47/6815* (2017.08); *A61K 47/6845* (2017.08); *A61K 49/001* (2013.01); *A61K 49/0002* (2013.01); *A61K 51/1021* (2013.01); *C07K 2317/34* (2013.01); *C07K 2317/41* (2013.01); *C07K 2317/622* (2013.01)

(58) Field of Classification Search
None
See application file for complete search history.

(56) References Cited

U.S. PATENT DOCUMENTS

| 5,859,205 | A | 1/1999 | Adair et al. |
| 6,451,983 | B2 | 9/2002 | Rathjen et al. |
| 7,179,893 | B2 | 2/2007 | Le et al. |
| 2004/0185040 | A1 | 9/2004 | Garcia-Martinez et al. |
| 2005/0033031 | A1 | 2/2005 | Couto |
| 2005/0049402 | A1 | 3/2005 | Babcook et al. |
| 2005/0118652 | A1 | 6/2005 | Lee et al. |
| 2006/0024298 | A1 | 2/2006 | Lazar et al. |
| 2006/0099204 | A1 | 5/2006 | Couto et al. |
| 2006/0188502 | A1 | 8/2006 | Giles-Komar et al. |
| 2006/0257407 | A1 | 11/2006 | Chen et al. |
| 2007/0048300 | A1 | 3/2007 | Taylor et al. |
| 2007/0065426 | A1 | 3/2007 | Rathjen et al. |
| 2007/0092516 | A1 | 4/2007 | Waldmann et al. |
| 2008/0003643 | A1 | 1/2008 | Cregg et al. |
| 2008/0171014 | A1 | 7/2008 | Wu et al. |

FOREIGN PATENT DOCUMENTS

| EP | 0 488 470 | 6/1992 |
| WO | WO 91/02078 | 2/1991 |
| WO | WO 2003/045318 | 6/2003 |
| WO | WO 2004/039826 | 5/2004 |
| WO | WO 2004/106377 | 12/2004 |
| WO | WO 2006/119115 | 11/2006 |
| WO | WO 2007/104529 | 9/2007 |

OTHER PUBLICATIONS

International Search Report, PCT Application No. PCT/US08/64414, dated Nov. 6, 2008, 5 pages.
International Search Report, PCT Application No. PCT/US08/64432, dated Nov. 19, 2008, 5 pages.
European Search Report, EP Application No. 07861311.4, dated Jul. 20, 2009.
European Search Report, EP Application No. 08756095.9, dated Jul. 19, 2012.
Simonsson, et al., Single, Antigen-Specific B Cells Used to Generate Fab Fragments Using CD40-Mediated Amplification or Direct PCR Cloning, Biotechniques, Informa Life Sciences Publishing, vol. 18, No. 5, May 1, 1995, pp. 862, 864-869.
De Wildt, et al., Isolation and Characterization of Single Anti-U1A-specific B Cells from Autoimmune Patients, Annals of The New York Academy of Sciences, vol. 815, Apr. 5, 1997, pp. 440-442.
Weitkamp, et al., Generation of recombinant human monoclonal antibodies to rotavirus from simple antigen-specific B cells selected with fluorescent virus-like particles, Journal of Immunological Methods, Elsevier Science Publishers, vol. 275, No. 1-2, Apr. 1, 2003, pp. 223-237.

(Continued)

*Primary Examiner* — Zachary Skelding
(74) *Attorney, Agent, or Firm* — Robin L. Teskin; LeClairRyan, A Professional Corporation

(57) ABSTRACT

The present invention is directed to antibodies and fragments thereof having binding specificity for TNF-α. Another embodiment of this invention relates to the antibodies described herein, and binding fragments thereof, comprising the sequences of the $V_H$, $V_L$ and CDR polypeptides described herein, and the polynucleotides encoding them. The invention also contemplates conjugates of anti-TNF-α antibodies and binding fragments thereof conjugated to one or more functional or detectable moieties. The invention also contemplates methods of making said anti-TNF-α antibodies and binding fragments thereof. Embodiments of the invention also pertain to the use of anti-TNF-α antibodies, and binding fragments thereof, for the diagnosis, assessment and treatment of diseases and disorders associated with TNF-α.

8 Claims, 10 Drawing Sheets

(56) References Cited

OTHER PUBLICATIONS

Kodituwakku et al., "Isolation of antigen-specific B cells," Immunology and Cell Biology (2003) 81, 163-170.
Steenbakkers et al., "Efficient Generation of Monoclonal Antibodies from Preselected Antigen-Specific B Cells", Molecular Biology Reports 19: 125-134, (1994).
Heinrichs et al., "Universal cloning and direct sequencing of rearranged antibody V genes using C region primers, biotin-captured cDNA and one-side PCR," J Immunol Methods. Jan. 27, 1995;178(2):241-51.
Schroeder et al., "Preferential utilization of conserved immunoglobulin heavy chain variable gene segments during human fetal life," Proc Natl Acad Sci U.S.A. Aug. 1990; 87(16):6146-50.
Carter et al., "B cell epitope mapping using synthetic peptides," Current Protocols in Immunology (2004), John Wiley & Sons, Inc., pp. 9.4.1-9.4.23.
Damschroder et al., "Analysis of human and primate CD2 molecules by protein sequence and epitope mapping with anti-human CD2 antibodies," Mol Immunol. Aug. 2004;41(10):985-1000.
Eduardo Padlan, "Anatomy of the antibody molecule," Mol Immunol. Feb. 1994;31(3):169-217.
Portolano et al., "Lack of promiscuity in autoantigen-specific H and L chain combinations as revealed by human H and L chain 'roulette,'" J Immunol. Feb. 1, 1993;150(3):880-7.
Vajdos et al., "Comprehensive functional maps of the antigen-binding site of an anti-ErbB2 antibody obtained with shotgun scanning mutagenesis," J Mol Biol. Jul. 5, 2002;320(2):415-28.
O'Brien et al., "Humanization of monoclonal antibodies by CDR grafting," Methods Mol Biol. 2003;207:81-100.
Meager et al., "Preparation and characterization of monoclonal antibodies directed against antigenic determinants of recombinant human tumour necrosis factor (rTNF)," Hybridoma. Jun. 1987;6(3):305-11.
International Search Report, PCT Application No. PCT/US08/64421, dated Sep. 29, 2008, 3 pages.
Popkov, M. et al.: "Rabbit Immune Repertoires as Sources for Therapeutic Monoclonal Antibodies: The Impact of Kappa Allotype-correlated Variation in Cysteine Content on Antibody Libraries Selected by Phage Display" Journal of Molecular Biology, Academic Press, UK, vol. 325, No. 2, Jan. 10, 2003, pp. 325-335.
Salgado Roberto et al.: "Circulating Interleukin-6 Predicts Survival in Patients with Metatastic Breast Cancer." International Journal of Cancer, Feb. 20, 3003, 12492272, vol. 103, No. 5, pp. 642-646.
Hamzaoui K et al.: "Interleukin-6 in Peripheral Blood and Inflammatory Sites in Behcet's Disease." Mediators of Inflammation, 1992, 18475474, vol. 1, No. 4, pp. 281-285.
Dohmen, et al., Production of recombinant Ig molecules from antigen-selected single B cells and restricted usage of Ig-gene segments by anti-D antibodies, Journal of Immunological Methods, Elsevier Science Publishers, vol. 298, No. 1-2, Mar. 1, 2005, pp. 9-20.

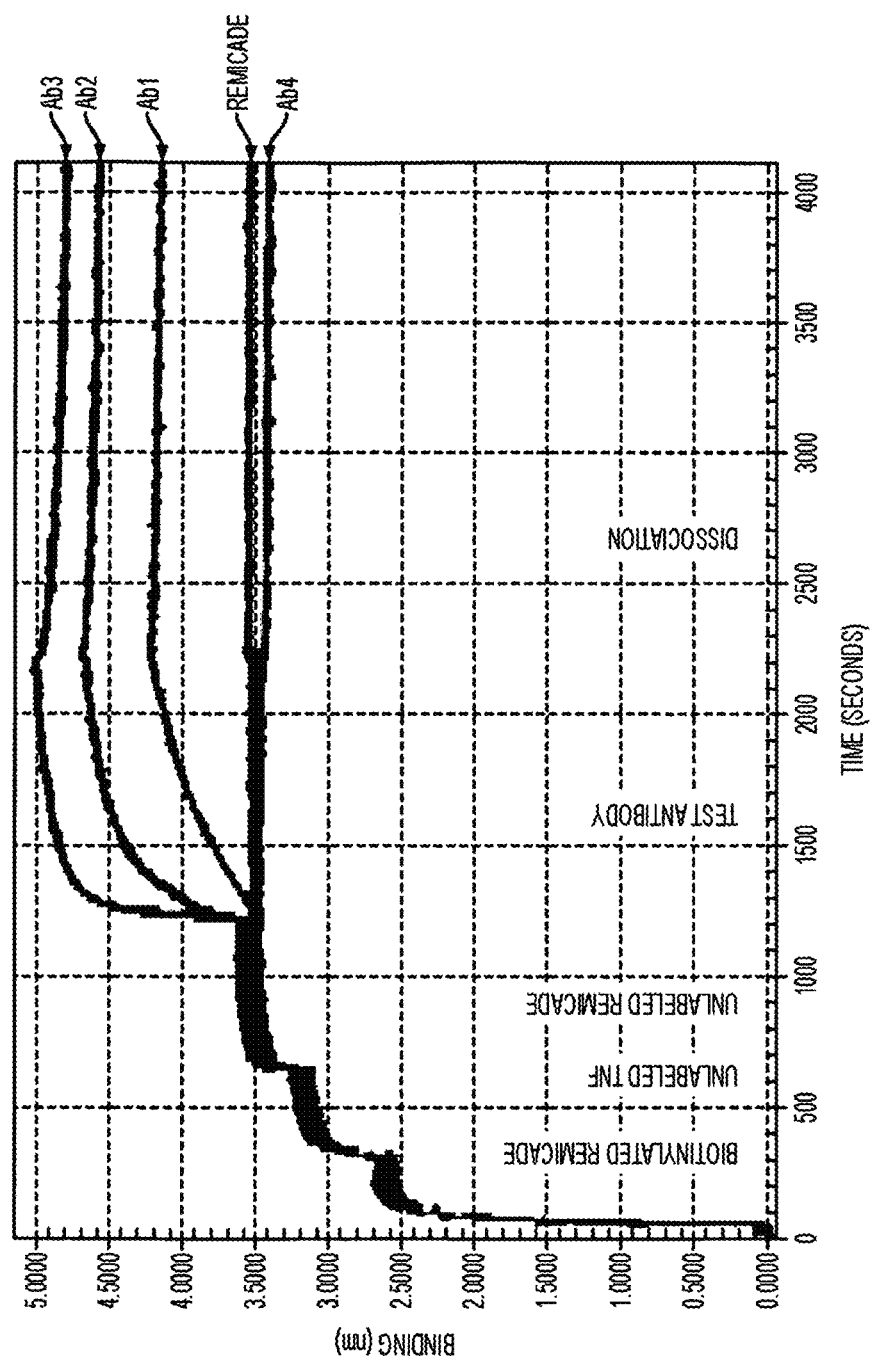

FIG. 2

```
        FR1                              CDR1         FR2              CDR2      FR3
        1                       23 24    34 35        49 50       56 57                                 88
RbtVL   AYDMTQTPASVEVAVGGTVTINC QASETIYSWLS WYQQKPGQPPKLLIY QASDLAS GVPSRFSGGAGTEYTLTISGVQCDDAATYYC
L12A    DIQMTQSPSTLSASVGDRVTITC RASQSISSWLA WYQQKPGKAPKLLIY KASSLES GVPSRFSGSGSGTEFTLTISSLQPDDFATYYC
V1      DIQMTQSPSTLSASVGDRVTITC RASQSISSWLA WYQQKPGKAPKLLIY DASSLES GVPSRFSGSGSGTEFTLTISSLQPDDFATYYC
Vx02    DIQMTQSPSSLSASVGDRVTITC RASQSISSYLN WYQQKPGKAPKLLIY AASSLQS GVPSRFSGSGSGTDFTLTISSLQPEDFATYYC

VLh     DIQMTQSPSTLSASVGDRVTITC QASETIYSWLS WYQQKPGKAPKLLIY QASDLAS GVPSRFSGSGSGTEFTLTISSLQPDDFATYYC

CDR3              FR4
        89          100 101    111
RbtVL   QQGYSGSNVDNV FGGGTEVVVKR
                    FGGGTKVEIKR

VLh     QQGYSGSNVDNV FGGGTKVEIKR

FR1                                        CDR1      FR2              CDR2            FR3
        1                            30 31 35     36        49 50             66 67                                       98
RbtVH   QEQLKESGGRLVTPGTLTLTCTASGFSLN DHAMG WVRQAPGKGLEYIG FINS-GGSARYASWAEG RFTISRTST--TVDLKMTSLTTEDTATYFCVR
3-64-04 QVQLVESGGGLVQPGGSLRLSCCASGFTFS SYAMH WVRQAPGKGLEYVS AISSNGGSTYYADSVKG RFTISRDNSKNTLYLQMNSLRAEDTAVYYCAR
3-66-04 EVQLVESGGGLVQPGGSLRLSCAASGFTVS SNYMS WVRQAPGKGLEWVS VIYS-GGSTYYADSVKG RFTISRDNSKNTLYLQMNSLRAEDTAVYYCAR
3-53-02 EVQLVETGGGLIQPGGSLRLSCAASGFTVS SNYMS WVRQAPGKGLEWVS VIYS-GGSTYYADSVKG RFTISRDNSKNTLYLQMNSLRAEDTAVYYCAR

VHh     QVQLVESGGGLVQPGGSLRLSCAASGFSLN DHAMG WVRQAPGKGLEYVG FINS-GGSARYASAEG RFTISRDNSKNTLYLQMNSLRAEDTAVYYCAR

CDR3              FR4
        99          110 111   121
RbtVH   GGAVWSIHSFDP WGPGTLVTVSS
                    WGQGTLVTVSS

VHh     GGAVWSIHSFDP WGQGTLVTVSS
```

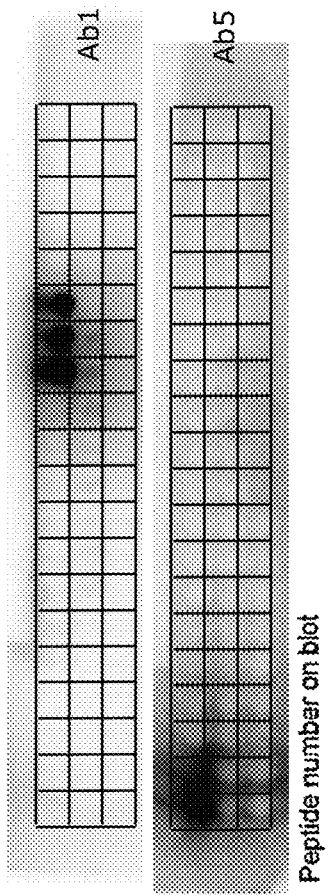

ANTIBODIES TO TNF α AND USE THEREOF

CROSS-REFERENCE TO RELATED APPLICATIONS

This application is a division of U.S. patent application Ser. No. 12/153,611, filed on May 21, 2008, which claims priority to U.S. provisional patent application No. 60/924,551 filed May 21, 2007, the disclosures of which are herein incorporated by reference in their entireties.

SEQUENCE LISTING

The sequence listing in the file named "43257o1603.txt" having a size of 151,149 bytes that was created May 28, 2015 is hereby incorporated by reference in its entirety.

BACKGROUND OF THE INVENTION

Field of the Invention

This invention pertains to antibodies and fragments thereof having binding specificity to Tumor Necrosis Factor-alpha (hereinafter "TNF-α"). The invention also pertains to methods of screening for diseases and disorders associated with TNF-α, and methods of preventing or treating diseases and disorders associated with TNF-α by administering said antibodies or fragments thereof.

Description of Related Art

TNF-α is a pleiotropic cytokine produced by a variety of cells, including activated macrophages, monocytes, T and B lymphocytes, natural killer cells, astrocytes, endothelial cells, smooth muscle cells, some tumor cells, and epithelial cells. Monocytes, for instance, express at least five different molecular forms of TNF-α with molecular masses of 21.5-28 kDa which mainly differ by post-translational alterations such as glycosylation and phosphorylation. See U.S. Patent Application Publication No. 2007/0015699.

TNF-α is a member of the TNF-ligand superfamily which includes TNF-α, TNF-β (lymphotoxin-a), LT-b, OX40L, FASL, CD30L, CD27L, CD40L, and 4-1BBL. The ligands of the TNF ligand superfamily are acidic, share approximately 20% sequence homology in the extracellular domains, and exist as membrane-bound forms with the biologically active form being a trimeric/multimeric complex. For example, TNF-α and TNF-β share 32% amino acid sequence homology. See U.S. Pat. No. 5,891,679.

Two distinct forms of TNF-α exist, a 26 kDa membrane (233 amino acid) form and the soluble 17 kDa (157 amino acid) cytokine which is derived from proteolytic cleavage of the 26 kDa membrane form. The soluble (mature) TNF-α polypeptide is 157 amino acids long and is secreted after cleavage of a 76-residue peptide from the amino terminus of the pro-protein. TNF-α is active as a homotrimer, each monomer of 157 residues is folded into a "jelly roll" structure of antiparallel beta strands, contains a single, intramolecular disulfide bridge, and is a trimer in solution. Reed, et al. (October 1997) "Crystal structure of TNF-α mutant R31D with greater affinity for receptor R1 compared with R2." Protein Eng. 10(10):1101-7; Eck and Sprang (October 1989) "The structure of tumor necrosis factor-alpha at 2.6 Å resolution. Implications for receptor binding" J. Biol. Chem., Vol. 264, Issue 29, 17595-17605; See U.S. Pat. No. 7,056,695.

TNF-α is a major mediator of inflammatory, immunological, and pathophysiological reactions. In vitro, TNF-α has diverse biological effects including the killing of transformed cells, stimulation of granulocytes and fibroblasts, damage to endothelial cells, psoriatic arthritis, and anti-parasitic effects. In vivo, TNF-α plays a key role as an endogenous mediator of inflammatory, immune and host defense functions and it is involved in a number of pathological conditions. TNF-α is capable of acting independently and in conjunction with other factors affecting a whole plethora of different body functions. These effects can either be beneficial or life-threatening to the host. Some of these effects are direct, others may be mediated via the induction of other secreted factors. See U.S. Pat. No. 5,891,679.

TNF-α exerts its biological effects through interaction with two distinct membrane TNF-α receptors, a 55 kDa species, designated p55 TNF-R and a 75 kDa species designated p75 TNF-R. The two TNF receptors exhibit 28% similarity at the amino acid level. This is confined to the extracellular domain and consists of four repeating cysteine-rich motifs, each of approximately 40 amino acids. Each motif contains four to six cysteines in conserved positions. See U.S. Pat. No. 7,056,695.

As set forth in greater detail below, TNF-α is believed to play a role in the development of a multitude of diseases and disorders, including but not limited to rheumatoid arthritis, psoriasis, asthma, Types I and II Diabetes, stroke, pulmonary fibrosis, depression and Alzheimer's disease. Due to the perceived involvement of TNF-α in a wide range of diseases and disorders, there remains a need in the art for compositions and methods useful for preventing or treating diseases associated with TNF-α, as well as methods of screening to identify patients having diseases or disorders associated with TNF-α. Particularly preferred anti-TNF-α compositions are those having minimal or minimizing adverse reactions when administered to the patient. Compositions or methods that reduce or inhibit diseases or disorders associated with TNF-α are beneficial to the patient in need thereof.

BRIEF SUMMARY OF THE INVENTION

The present invention is directed to specific antibodies and fragments thereof having binding specificity for TNF-α, in particular antibodies having specific epitopic specificity and/or functional properties. One embodiment of the invention encompasses specific humanized antibodies and fragments thereof capable of binding to TNF-α and/or the TNF-α/TNFR complex. Another embodiment of this invention relates to the antibodies described herein, comprising the sequences of the $V_H$, $V_L$, and CDR polypeptides described herein, and the polynucleotides encoding them. In more specific embodiments of the invention these antibodies will possess binding affinities (Kds) less than 50 picomolar and/or $K_{off}$ values less than or equal to $10^{-4}$ $S^{-1}$.

In another embodiment of the invention these antibodies and humanized versions will be derived from rabbit immune cells (B lymphocytes) and may be selected based on their homology (sequence identity) to human germ line sequences. These antibodies may require minimal or no sequence modifications, thereby facilitating retention of functional properties after humanization. A further embodiment of the invention is directed to fragments from anti-TNF-α antibodies encompassing $V_H$, $V_L$ and CDR polypeptides, e.g., derived from rabbit immune cells and the polynucleotides encoding the same, as well as the use of these antibody fragments and the polynucleotides encoding them in the creation of novel antibodies and polypeptide compositions capable of recognizing TNF-α and/or TNF-α/TNFR complexes.

The invention also contemplates conjugates of anti-TNF-α antibodies and binding fragments thereof conjugated to one or more functional or detectable moieties. The invention also contemplates methods of making said humanized anti-TNF-α or anti-TNF-α/TNFR complex antibodies and binding fragments thereof. In one embodiment, binding fragments include, but are not limited to, Fab, Fab', F(ab)$_2$, Fv, scFv fragments, SMIPs (small molecule immunopharmaceuticals), camelbodies, nanobodies, and IgNAR.

Embodiments of the invention pertain to the use of anti-TNF-α antibodies for the diagnosis, assessment and treatment of diseases and disorders associated with TNF-α or aberrant expression thereof. The invention also contemplates the use of fragments of anti-TNF-α antibodies for the diagnosis, assessment and treatment of diseases and disorders associated with TNF-α or aberrant expression thereof.

Other embodiments of the invention relate to the production of anti-TNF-α antibodies in recombinant host cells, preferably diploid yeast such as diploid *Pichia* and other yeast strains.

BRIEF DESCRIPTION OF THE SEVERAL VIEWS OF THE DRAWINGS

FIG. 1 shows that a variety of unique epitopes were recognized by the collection of anti-TNF-α antibodies (Antibodies Ab1, Ab2, Ab3 and Ab4) prepared by the antibody selection protocol. Epitope variability was confirmed by antibody-TNF-α binding competition studies (ForteBio Octet). Remicade was used as an anchor molecule to capture TNF to the surface and block that epitope from further recognition. Antibodies binding in this experiment do not share the same epitope for binding purposes.

FIG. 2 shows alignments of variable light and variable heavy sequences between rabbit antibody variable light and variable heavy sequences and homologous human sequences and the final humanized sequences. Framework regions are identified FR1-FR4. Complementarity determining regions (CDRs) are identified as CDR1-CDR3. Amino acid residues are numbered as shown. The initial rabbit sequences are called RbtVL and RbtVH for the variable light and variable heavy sequences respectively. Three of the most similar human germline antibody sequences, spanning from Framework 1 through to the end of Framework 3, are aligned below the rabbit sequences. The human sequence that is considered the most similar to the rabbit sequence is shown first. In this example those most similar sequences are L12A for the light chain and 3-64-04 for the heavy chain. Human CDR3 sequences are not shown. The closest human Framework 4 sequence is aligned below the rabbit Framework 4 sequence. The vertical dashes indicate a residue where the rabbit residue is identical with one or more of the human residues at the same position. The bold residues indicate that the human residue at that position is identical to the rabbit residue at the same position. The final humanized sequences are called VLh and VHh for the variable light and variable heavy sequences respectively. The underlined residues indicate that the residue is the same as the rabbit residue at that position but different than the human residues at that position in the three aligned human sequences.

FIG. 7 depicts the epitope mapping of anti-TNF-α antibodies Ab1 and Ab5. FIG. 7 shows blots corresponding to antibody binding of the linear peptide library. FIG. 7 also provides the sequences of the peptides in the linear peptide library.

DETAILED DESCRIPTION OF PREFERRED EMBODIMENTS

Definitions

Figure 3:
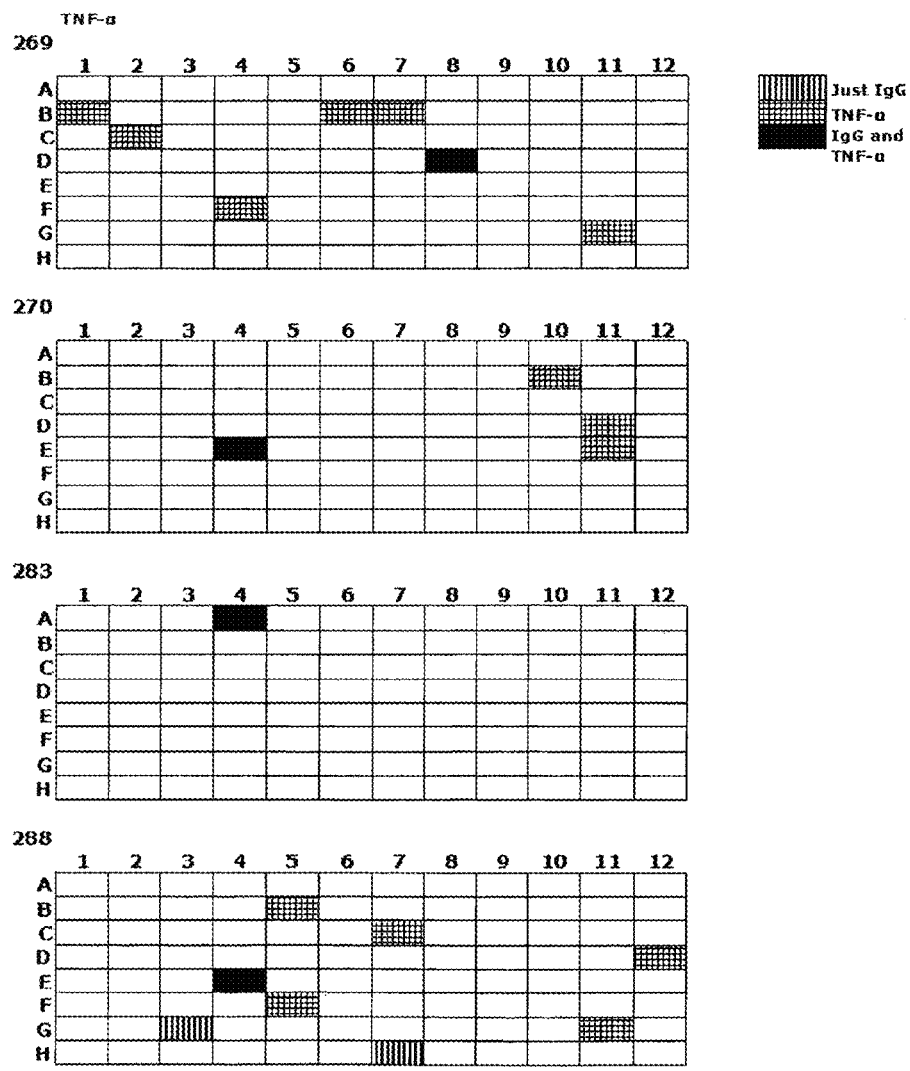
FIG. 3 demonstrates the high correlation between the IgG produced and antigen specificity for an exemplary huTNF-α protocol. 18 of 20 wells showed specific IgG correlation with antigen recognition.
Figure 4:
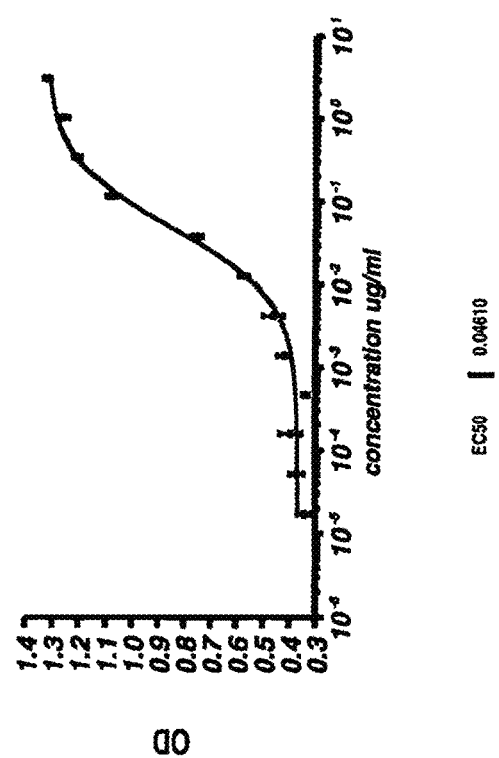
FIG. 4 depicts the binding affinity of the anti-TNF-α antibody Ab1.
Figure 5:
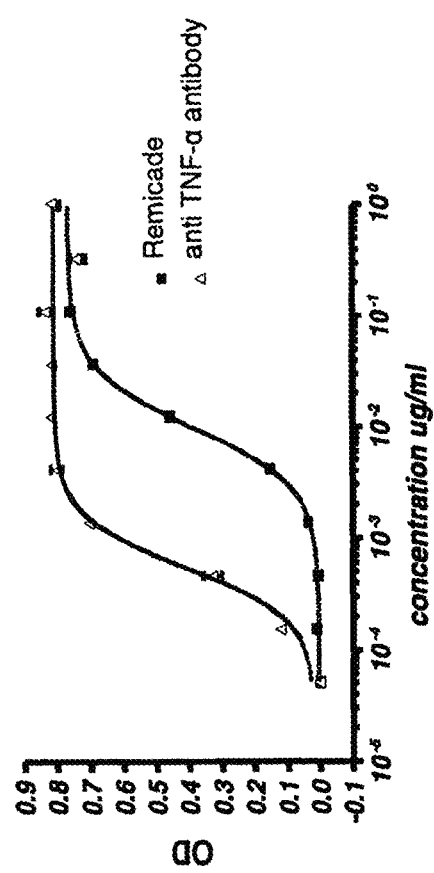
FIG. 5 compares the neutralizing binding affinity of Ab1 to Remicade®.

It is to be understood that this invention is not limited to the particular methodology, protocols, cell lines, animal species or genera, and reagents described, as such may vary. It is also to be understood that the terminology used herein is for the purpose of describing particular embodiments only, and, is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Tumor Necrosis Factor-Alpha (TNF-α):

As used herein, TNF-α encompasses not only the following 233 amino acid sequence available as GenBank Protein Accession No. CAA26669 (*Homo sapiens* TNF-α):

(SEQ ID NO: 1)
MSTESMIRDVELAEEALPKKTGGPQGSRRCLFLSLFSFLIVAGATTLFCL

LHFGVIGPQREEFPRDLSLISPLAQAVRSSSRTPSDKPVAHVVANPQAEG

QLQWLNRRANALLANGVELRDNQLVVPSEGLYLIYSQVLFKGQGCPSTHV

LLTHTISRIAVSYQTKVNLLSAIKSPCQRETPEGAEAKPWYEPIYLGGVF

QLEKGDRLSAEINRPDYLDFAESGQVYFGIIAL, but also any pre-pro, pro-, mature, soluble, and/or membrane-bound forms of this TNF-α amino acid sequence, as well as mutants (mutiens), splice variants, orthologues, homologues and variants of this sequence.

Mating Competent Yeast Species:

In the present invention this is intended to broadly encompass any diploid or tetraploid yeast which can be grown in culture. Such species of yeast may exist in a haploid, diploid, or tetraploid form. The cells of a given ploidy may, under appropriate conditions, proliferate for indefinite number of generations in that form. Diploid cells can also sporulate to form haploid cells. Sequential mating can result in tetraploid strains through further mating or fusion of diploid strains. In the present invention the diploid or polyploidal yeast cells are preferably produced by mating or spheroplast fusion.

In one embodiment of the invention, the mating competent yeast is a member of the Saccharomycetaceae family, which includes the genera *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis;* and *Zygosaccharomyces*. Other types of yeast potentially useful in the invention include *Yarrowia, Rhodosporidium, Candida, Hansenula, Filobasium, Filobasidellla, Sporidiobolus, Bullera, Leucosporidium* and *Filobasidella*.

In a preferred embodiment of the invention, the mating competent yeast is a member of the genus *Pichia*. In a further preferred embodiment of the invention, the mating competent yeast, of the genus *Pichia* is one of the following species: *Pichia pastoris, Pichia methanolica,* and *Hansenula polymorpha (Pichia angusta)*. In a particularly preferred embodiment of the invention, the mating competent yeast of the genus *Pichia* is the species *Pichia pastoris*.

Haploid Yeast Cell: A cell having a single copy of each gene of its normal genomic (chromosomal) complement.

Polyploid Yeast Cell: A cell having more than one copy of its normal genomic (chromosomal) complement.

Diploid Yeast Cell: A cell having two copies (alleles) of essentially every gene of its normal genomic complement, typically formed by the process of fusion (mating) of two haploid cells.

Tetraploid Yeast Cell: A cell having four copies (alleles) of essentially every gene of its normal genomic complement, typically formed by the process of fusion (mating) of two haploid cells. Tetraploids may carry two, three, four or more different expression cassettes. Such tetraploids might be obtained in *S. cerevisiae* by selective mating homozygotic heterothallic a/a and alpha/alpha diploids and in *Pichia* by sequential mating of haploids to obtain auxotrophic diploids. For example, a [met his] haploid can be mated with [ade his] haploid to obtain diploid [his]; and a [met arg] haploid can be mated with [ade arg] haploid to obtain diploid [arg]; then the diploid [his]×diploid [arg] to obtain a tetraploid prototroph. It will be understood by those of skill in the art that reference to the benefits and uses of diploid cells may also apply to tetraploid cells.

Yeast Mating: The process by which two haploid yeast cells naturally fuse to form one diploid yeast cell.

Meiosis: The process by which a diploid yeast cell undergoes reductive division to form four haploid spore products. Each spore may then germinate and form a haploid vegetatively growing cell line.

Selectable Marker: A selectable marker is a gene or gene fragment that confers a growth phenotype (physical growth characteristic) on a cell receiving that gene as, for example through a transformation event. The selectable marker allows that cell to survive and grow in a selective growth medium under conditions in which cells that do not receive that selectable marker gene cannot grow. Selectable marker genes generally fall into several types, including positive selectable marker genes such as a gene that confers on a cell resistance to an antibiotic or other drug, temperature when two ts mutants are crossed or a ts mutant is transformed; negative selectable marker genes such as a biosynthetic gene that confers on a cell the ability to grow in a medium without a specific nutrient needed by all cells that do not have that biosynthetic gene, or a mutagenized biosynthetic gene that confers on a cell inability to grow by cells that do not have the wild type gene; and the like. Suitable markers include but are not limited to: ZEO; G418; LYS3; MET1; MET3a; ADE1; ADE3; URA3; and the like.

Expression Vector: These DNA vectors contain elements that facilitate manipulation for the expression of a foreign protein within the target host cell. Conveniently, manipulation of sequences and production of DNA for transformation is first performed in a bacterial host, e.g. *E. coli*, and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, D., Dawson, D., & Stearns, T. (2000). Methods in yeast genetics: a Cold Spring Harbor Laboratory course manual. Plainview, N.Y.: Cold Spring Harbor Laboratory Press.

Expression vectors for use in the methods of the invention will further include yeast specific sequences, including a selectable auxotrophic or drug marker for identifying transformed yeast strains. A drug marker may further be used to amplify copy number of the vector in a yeast host cell.

The polypeptide coding sequence of interest is operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included, e.g. a signal sequence, and the like. A yeast origin of replication is optional, as expression vectors are often integrated into the yeast genome. In one embodiment of the invention, the polypeptide of interest is operably linked, or fused, to sequences providing for optimized secretion of the polypeptide from yeast diploid cells.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (Gateway® Technology; Invitrogen, Carlsbad Calif.). If such sites do not exist, the synthetic oligonucleotide adapters or linkers are used in accordance with conventional practice.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (that increase levels of transcription in, response to absence of a repressor). Inducible promoters may initiate increased levels of transcription from DNA under their control in response to some change in culture conditions, e.g., the presence or absence of a nutrient or a change in temperature.

The yeast promoter fragment may also serve as the site for homologous recombination and integration of the expression vector into the same site in the yeast genome; alternatively a selectable marker is used as the site for homologous recombination. *Pichia* transformation is described in Cregg et al. (1985) *Mol. Cell. Biol.* 5:3376-3385.

Examples of suitable promoters from *Pichia* include the AOX1 and promoter (Cregg et al. (1989) *Mol. Cell. Biol.* 9:1316-1323); 1CL1 promoter (Menendez et al. (2003) *Yeast* 20(13):1097-108); glyceraldehyde-3-phosphate dehydrogenase promoter (GAP) (Waterham et al. (1997) *Gene* 186(1): 37-44); and FLD1 promoter (Shen et al. (1998) *Gene* 216(1):93-102). The GAP promoter is a strong constitutive promoter and the AOX and FLD1 promoters are inducible.

Other yeast promoters include ADH1, alcohol dehydrogenase II, GAL4, PHO3, PHO5, Pyk, and chimeric promoters derived therefrom. Additionally, non-yeast promoters may be used in the invention such as mammalian, insect, plant, reptile, amphibian, viral, and avian promoters. Most typically the promoter will comprise a mammalian promoter (potentially endogenous to the expressed genes) or will comprise a yeast or viral promoter that provides for efficient transcription in yeast systems.

The polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the host cell. The *S. cerevisiae* alpha factor pre-pro signal has proven effective in the secretion of a variety of recombinant proteins from *P. pastoris*. Other yeast signal sequences include the alpha mating factor signal sequence, the invertase signal, sequence, and signal sequences derived from other secreted yeast polypeptides. Additionally, these signal peptide sequences may be engineered to provide for enhanced secretion in diploid yeast expression systems. Other secretion signals of interest also include mammalian signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 preprotoxin sequence, PHA-E, FACE, human MCP-1, human serum albumin signal sequences, human Ig heavy chain, human Ig light chain, and the like. For example, see Hashimoto et. al. Protein Eng 11(2) 75 (1998); and Kobayashi et. al. Therapeutic Apheresis 2(4) 257 (1998).

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin) where appropriate. Plasmids from the transformants are prepared, analyzed by restriction endonuclease digestion and/or sequenced.

As an alternative to restriction and ligation of fragments, recombination methods based on att sites and recombination enzymes may be used to insert DNA sequences into a vector. Such methods are described, for example, by Landy (1989) Ann. Rev. Biochem. 58:913-949; and are known to those of skill in the art. Such methods utilize intermolecular DNA recombination that is mediated by a mixture of lambda and *E. coli*-encoded recombination proteins. Recombination occurs between specific attachment (att) sites on the interacting DNA molecules. For a description of att sites see Weisberg and Landy (1983) Site-Specific Recombination in Phage Lambda, in *Lambda II*, Weisberg, ed. (Cold Spring Harbor, N.Y.: Cold Spring Harbor Press), pp. 211-250. The DNA segments flanking the recombination sites are switched; such that after recombination, the att sites are hybrid sequences comprised of sequences donated by each parental vector. The recombination can occur between DNAs of any topology.

Att sites may be introduced into a sequence of interest by ligating the sequence of interest into an appropriate vector; generating a PCR product containing att B sites through the use of specific primers; generating a cDNA library cloned into an appropriate vector containing att sites; and the like.

Folding, as used herein, refers to the three-dimensional structure of polypeptides and proteins, where interactions between amino acid residues act to stabilize the structure. While non-covalent interactions are important in determining structure, usually the proteins of interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The expression host may be further modified by the introduction of sequences encoding one or more enzymes that enhance folding and disulfide bond formation, i.e.

foldases, chaperonins, etc. Such sequences may be constitutively or inducibly expressed in the yeast host cell, using vectors, markers, etc. as known in the art. Preferably the sequences, including transcriptional regulatory elements sufficient for the desired pattern of expression, are stably integrated in the yeast genome through a targeted methodology.

For example, the eukaryotic PDI is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of BIP (immunoglobulin heavy chain binding protein); cyclophilin; and the like. In one embodiment of the invention, each of the haploid parental strains expresses a distinct folding enzyme, e.g. one strain may express BIP, and the other strain may express PDI or combinations thereof.

The terms "desired protein" or "target protein" are used interchangeably and refer generally to a humanized antibody or a binding portion thereof described herein. The term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." A preferred source for producing antibodies useful as starting material according to the invention is rabbits. Numerous antibody coding sequences have been described; and others may be raised by methods well-known in the art. Examples thereof include chimeric antibodies, human antibodies and other non-human mammalian antibodies, humanized antibodies, single chain antibodies (such as scFvs), camelbodies, nanobodies, IgNAR (single-chain antibodies derived from sharks), small-modular immunopharmaceuticals (SMIPs), and antibody fragments such as Fabs, Fab', F(ab')$_2$ and the like. See Streltsov V A, et al., Structure of a shark IgNAR antibody variable domain and modeling of an early-developmental isotype, Protein Sci. 2005 November; 14(11):2901-9. Epub 2005 Sep. 30; Greenberg A S, et al., A new antigen receptor gene family that undergoes rearrangement and extensive somatic diversification in sharks, Nature. 1995 Mar. 9; 374(6518):168-73; Nuttall S D, et al., Isolation of the new antigen receptor from wobbegong sharks, and use as a scaffold for the display of protein loop libraries, Mol Immunol. 2001 August; 38(4):313-26; Hamers-Casterman C, et al., Naturally occurring antibodies devoid of light chains, Nature. 1993 Jun. 3; 363(6428):446-8; Gill D S, et al., Biopharmaceutical drug discovery using novel protein scaffolds, Curr Opin Biotechnol. 2006 December; 17(6):653-8. Epub 2006 Oct. 19.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions ($V_L$ and $V_H$), obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the human constant regions of chimeric antibodies of the invention may be selected from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant regions.

Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

In addition to entire immunoglobulins (or their recombinant counterparts), immunoglobulin fragments comprising the epitope binding site (e.g., Fab', F(ab')$_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. In another embodiment of the invention, SMIPs (small molecule immunopharmaceuticals), camelbodies, nanobodies, and IgNAR are encompassed by immunoglobulin fragments.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties and the like, or specific binding moieties, such as streptavidin, avidin, or biotin, and the like may be utilized in the methods and compositions of the present invention. Examples of additional effector molecules are provided infra.

The term "polyploid yeast that stably expresses or expresses a desired secreted heterologous polypeptide for prolonged time" refers to a yeast culture that secretes said polypeptide for at least several days to a week, more preferably at least a month, still more preferably at least 1-6 months, and even more preferably for more than a year at threshold expression levels, typically at least 10-25 mg/liter and preferably substantially greater.

The term "polyploidal yeast culture that secretes desired amounts of recombinant polypeptide" refers to cultures that stably or for prolonged periods secrete at least 10-25 mg/liter of heterologous polypeptide, more preferably at least 50-500 mg/liter, and most preferably 500-1000 mg/liter or more.

A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A "coding sequence" is an in-frame sequence of codons that (in view of the genetic code) correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. Promoter sequences typically contain additional sites for binding of regulatory molecules (e.g., transcription factors) which affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence.

Vectors are used to introduce a foreign substance, such as DNA, RNA or protein, into an organism or host cell. Typical vectors include recombinant viruses (for polynucleotides) and liposomes (for polypeptides). A "DNA vector" is a replicon; such as plasmid, phage or cosmid, to which another polynucleotide segment may be attached so as to bring about the replication of the attached segment. An "expression vector" is a DNA vector which contains regulatory sequences which will direct polypeptide synthesis by an appropriate host cell. This usually means a promoter to bind RNA polymerase and initiate transcription of mRNA, as well as ribosome binding sites and initiation signals to direct translation of the mRNA into a polypeptide(s). Incorporation of a polynucleotide sequence into an expression vector at the proper site and in correct reading frame, followed by transformation of an appropriate host cell by the vector, enables the production of a polypeptide encoded by said polynucleotide sequence.

"Amplification" of polynucleotide sequences is the in vitro production of multiple copies of a particular nucleic acid sequence. The amplified sequence is usually in the form of DNA. A variety of techniques for carrying out such amplification are described in a review article by Van Brunt (1990, Bio/Technol., 8(4):291-294). Polymerase chain reaction or PCR is a prototype of nucleic acid amplification, and use of PCR herein should be considered exemplary of other suitable amplification techniques.

The general structure of antibodies in vertebrates now is well understood (Edelman, G. M., Ann. N.Y. Acad. Sci., 190: 5 (1971)). Antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the $F_C$ region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (IgG, IgM, IgA, IgD, and IgE corresponding to γ, μ, α, δ, and ε (gamma, mu, alpha, delta, or epsilon) heavy chain constant regions). The constant region or class determines subsequent effector function of the antibody, including activation of complement (Kabat, E. A., Structural Concepts in Immunology and Immunochemistry, 2nd Ed., p. 413-436, Holt, Rinehart, Winston (1976)), and other cellular responses (Andrews, D. W., et al., Clinical Immunobiology, pp 1-18, W. B. Sanders (1980); Kohl, S., et al., Immunology, 48: 187 (1983)); while the variable region determines the antigen with which it will react. Light chains are classified as either κ (kappa) or λ (lambda). Each heavy chain class can be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

The expression "variable region" or "VR" refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions (CDRs) found in the variable regions of light or heavy chains of an antibody (See Kabat, E. A. et al., Sequences of Proteins of Immunological Interest, National Institutes of Health, Bethesda, Md., (1987)). These expressions include the hypervariable regions as defined by Kabat et al. ("Sequences of Proteins of Immunological Interest," Kabat E., et al., US Dept. of Health and Human Services, 1983) or the hypervariable loops in 3-dimensional structures of antibodies (Chothia and Lesk, J Mol. Biol. 196 901-917 (1987)). The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction (Kashmiri, S., Methods, 36:25-34 (2005)).

The expressions "framework region" or "FR" refer to one or more of the framework, regions within the variable regions of the light and heavy chains of an antibody (See Kabat, E. A. et al., Sequences of Proteins of Immunological Interest, National Institutes of Health, Bethesda, Md., (1987)). These expressions include those amino acid sequence regions interposed between the CDRs within the variable regions of the light and heavy chains of an antibody.

Anti-TNF-α Antibodies and Binding Fragments Thereof

In an embodiment, the invention includes antibodies having binding specificity to TNF-α and possessing a variable light chain sequence comprising the sequence set forth below:

```
                                            (SEQ ID NO: 2)
MDTRAPTQLLGLLLLWLPGARCADIVMTQTPASVEAAVGGTVTIKCQASQ

NIRSWLAWYQQKPGQPPKLLIYGASTLASGVPSRFQGSGSGTEYTLTIID

LDCADAATYYCQSNYGSNDNSYGNG
```

The invention also includes antibodies having binding specificity to TNF-α and possessing a variable heavy chain sequence comprising the sequence set forth below:

```
                                            (SEQ ID NO: 3)
METGLRWLLLVAVLKGVQCQSVEESGGRLVTPGTPLTLTCTVSGFSLSTY

NMGWVRQAPGKGLEYIGYVLGSGITYYASWAKGRFTISKTSTTVDLEITS

PTTEDTATYFCARDAGGRASL.
```

The invention further contemplates antibodies comprising one or more of the polypeptide sequences of SEQ ID NO: 4; SEQ ID NO: 5; and SEQ ID NO: 6 which correspond to the complementarity-determining regions (CDRs, or hypervariable regions) of the variable light chain sequence of SEQ ID NO: 2, and/or one or more of the polypeptide sequences of SEQ ID NO: 7; SEQ ID NO: 8; and SEQ ID NO: 9 which correspond to the complementarity-determining regions (CDRs, or hypervariable regions) of the variable heavy chain sequence of SEQ ID NO: 3, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 4; SEQ ID NO: 5; and SEQ ID NO: 6 which correspond to the complementarity-determining regions (CDRs, or hypervariable regions) of the variable light chain sequence of SEQ ID NO: 2, and/or one or more of the polypeptide sequences of SEQ ID NO: 7; SEQ ID NO: 8; and SEQ ID NO: 9 which correspond to the complementarity-determining regions (CDRs, or hypervariable regions) of the variable heavy chain sequence of SEQ ID NO: 3, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 2. In another embodiment of the invention, antibody fragments of the invention comprise, or alternatively consist of, the polypeptide sequence of SEQ ID NO: 3.

In a further embodiment of the invention, fragments of the antibody having binding specificity to TNF-α comprise, or alternatively consist of, one or more of the polypeptide sequences of SEQ ID NO: 4; SEQ ID NO: 5; and SEQ ID NO: 6 which correspond to the complementarity-determining regions (CDRs, or hypervariable regions) of the variable light chain sequence of SEQ ID NO: 2.

In a further embodiment of the invention, fragments of the antibody having binding specificity to TNF-α comprise, or alternatively consist of, one or more of the polypeptide sequences of SEQ ID NO: 7; SEQ ID NO: 8; and SEQ ID NO: 9 which correspond to the complementarity-determining regions (CDRs, or hypervariable regions) of the variable heavy chain sequence of SEQ ID NO: 3.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 2; the variable heavy chain region of SEQ ID NO: 3; the complementarity-determining regions (SEQ ID NO: 4; SEQ ID NO: 5; and SEQ ID NO: 6) of the variable light chain region of SEQ ID NO: 2; and the complementarity-determining regions (SEQ ID NO: 7; SEQ ID NO: 8; and SEQ ID NO: 9) of the variable heavy chain region of SEQ ID NO: 3.

In a preferred embodiment of the invention, the anti-TNF-α antibody is Ab1, comprising SEQ ID NO: 2 and SEQ ID NO: 3, and having at least one of the biological activities set forth herein.

In another embodiment, the invention includes antibodies having binding specificity to TNF-α and possessing a variable light chain sequence comprising the sequence set forth below:

```
                                           (SEQ ID NO: 18)
MDTRAPTQLLGLLLLWLPGARCADIVMTQTPSSVSEPVRGTVTIKCQASQ

NIYSYLSWYQQSPGQPPKLLIYKASTLASGVPSRFKGSGSGTDFTLTISD

LECADAATYYCQSNYGSDSDSFGNA
```

The invention also includes antibodies having binding specificity to TNF-α and possessing a variable heavy chain sequence comprising the sequence set forth below:

```
                                           (SEQ ID NO: 19)
METGLRWLLLVAVLKGVQCQSVEESGGRLVTPGTPLTLTCSVSGFSLNNY

VMGWVRQAPGKGLEFIGYIAFGIGPYYASWAKGRFTISSTSSTTVDLKMT

SLTPEDTATYFCARGDYSGNDI.
```

The invention further contemplates antibodies comprising one or more of the polypeptide sequences of SEQ ID NO: 20; SEQ ID NO: 21; and SEQ ID NO: 22 which correspond to the complementarity-determining regions (CDRs, or hypervariable regions) of the variable light chain sequence of SEQ ID NO: 18, and/or one or more of the polypeptide sequences of SEQ ID NO: 23; SEQ ID NO: 24; and SEQ ID NO: 25 which correspond to the complementarity-determining regions (CDRs, or hypervariable regions) of the variable heavy chain sequence of SEQ ID NO: 19, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 20; SEQ ID NO: 21; and SEQ ID NO: 22 which correspond to the complementarity-determining regions (CDRs, or hypervariable regions) of the variable light chain sequence of SEQ ID NO: 18, and/or one or more of the polypeptide sequences of SEQ ID NO: 23; SEQ ID. NO: 24; and SEQ ID NO: 25 which correspond to the complementarity-determining regions (CDRs, or hypervariable regions) of the variable heavy chain sequence of SEQ ID NO: 19, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 18. In another embodiment of the invention, antibody fragments of the invention comprise, or alternatively consist of, the polypeptide sequence of SEQ ID NO: 19.

In a further embodiment of the invention, fragments of the antibody having binding specificity to TNF-α comprise, or alternatively consist of, one or more of the polypeptide sequences of SEQ ID NO.: 20; SEQ ID NO: 21; and SEQ ID NO: 22 which correspond to the complementarity-determining regions (CDRs, or hypervariable regions) of the variable light chain sequence of SEQ ID NO: 18.

In a further embodiment of the invention, fragments of the antibody having binding specificity to TNF-α comprise, or alternatively consist of, one or more of the polypeptide sequences of SEQ ID NO: 23; SEQ ID NO: 24; and SEQ ID NO: 25 which correspond to the complementarity-determining regions (CDRs, or hypervariable regions) of the variable heavy chain sequence of SEQ ID NO: 19.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 18; the variable heavy chain region of SEQ ID NO: 19; the complementarity-determining regions (SEQ ID NO: 20; SEQ ID NO: 21; and SEQ ID NO: 22) of the variable light chain region of SEQ ID NO: 18; and the complementarity-determining regions (SEQ ID NO: 23; SEQ ID NO: 24; and SEQ ID NO: 25) of the variable heavy chain region of SEQ ID NO: 19.

In a preferred embodiment of the invention, the anti-TNF-α antibody is Ab2, comprising SEQ ID NO: 18 and SEQ ID NO: 19, and having at least one of the biological activities set forth herein.

In another embodiment, the invention includes antibodies having binding specificity to TNF-α and possessing a variable light chain sequence comprising the sequence set forth below:

```
                                           (SEQ ID NO: 34)
MDTRAPTQLLGLLLLWLPGSTFAIKVTQTPASVSAAVGGTVSINCQASED

IESYLAWYQQKPGQPPKLLLYDASALASGVPSRFKGSGSGTEYTLTISGV

ECADAATYYCQQGYSYSNVDNS
```

The invention also includes antibodies having binding specificity to TNF-α and possessing a variable heavy chain sequence comprising the sequence set forth below:

```
                                           (SEQ ID NO: 35)
METGLRWLLLVAVLKGVQCQSVEESGGRLVTPGTPLTLTCKVSGFSLSSY

DMTWVRQAPGKGLEWIGYIWNDGSTAYASWATGRFTISKTSTTVDLKIAS

PTTEDTATYFCARGPVFATTLGYYFTI.
```

The invention further contemplates antibodies comprising one or more of the polypeptide sequences of SEQ ID NO: 36; SEQ ID NO: 37; and SEQ ID NO: 38 which correspond to the complementarity-determining regions (CDRs, or hypervariable regions) of the variable light chain sequence of SEQ ID NO: 34, and/or one or more of the polypeptide sequences of SEQ ID NO: 39; SEQ ID NO: 40; and SEQ ID NO: 41 which correspond to the complementarity-determining regions (CDRs, or hypervariable regions) of the variable heavy chain sequence of SEQ ID NO.: 35, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 36; SEQ ID NO: 37; and SEQ ID NO: 38 which correspond to the complementarity-determining regions (CDRs, or hypervariable regions) of the variable light chain sequence of SEQ ID NO: 34, and/or one or more of the polypeptide sequences of SEQ ID NO: 39; SEQ ID NO: 40; and SEQ ID NO: 41 which correspond to the complementarity-determining regions (CDRs, or hypervariable regions) of the variable heavy chain sequence of SEQ ID NO: 35, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 34. In another embodiment of the invention, antibody fragments of the invention comprise, or alternatively consist of, the polypeptide sequence of SEQ ID NO: 35.

In a further embodiment of the invention, fragments of the antibody having binding specificity to TNF-α comprise, or alternatively consist of, one or more of the polypeptide sequences of SEQ ID NO: 36; SEQ ID NO: 37; and SEQ ID NO: 38 which correspond to the complementarity-determining regions (CDRs, or hypervariable regions) of the variable light chain sequence of SEQ ID NO: 34.

In a further embodiment of the invention, fragments of the antibody having binding specificity to TNF-α comprise, or alternatively consist of, one or more of the polypeptide sequences of SEQ ID NO: 39; SEQ ID NO: 40; and SEQ ID NO: 41 which correspond to the complementarity-determining regions (CDRs, or hypervariable regions) of the variable heavy chain sequence of SEQ ID NO: 35.

The invention also contemplates antibody fragments which include one or more of the antibody fragments described herein. In one embodiment of the invention, fragments of the antibodies having binding specificity to TNF-α comprise, or alternatively consist of, one, two, three or more, including all, of the following antibody fragments: the variable light chain region of SEQ ID NO: 34; the variable heavy chain region of SEQ ID NO: 35; the complementarity-determining regions (SEQ ID NO: 36; SEQ ID NO 37; and SEQ ID NO: 38) of the variable light chain region of SEQ ID NO: 34; and the complementarity-determining regions (SEQ ID NO: 39; SEQ ID NO: 40; and SEQ ID NO: 41) of the variable heavy chain region of SEQ ID NO: 35.

In a preferred embodiment of the invention, the anti-TNF-α antibody is Ab3, comprising SEQ ID NO: 34 and SEQ NO: 35, and having at least one of the biological activities set forth herein.

In another embodiment, the invention includes antibodies having binding specificity to TNF-α and possessing a variable light chain sequence comprising the sequence set forth below:

(SEQ ID NO: 50)
MDTRAPTQLLGLLLLWLTGATFAAVLTQTPSPVSAVVGGTVSISCQSSKR

VVNSVALSWYQQKPGRSPKLLIYFASKLASGVPSRFKGSGSGTQFTLAIS

DVQCDDAATYYCAGHYTDSGDDA

The invention also includes antibodies having binding specificity to TNF-α and possessing a variable heavy chain sequence comprising the sequence set forth below:

(SEQ ID NO: 51)
METGLRWLLLVAVLKGVQCQSVEESGGRLVTPGTPLTLTCTVSGLSLSTE

TINWVRQAPGKGLEWIGYIDSSGGTGYANWARGRFTISKTSTTVDLKITS

PTTGDTATYFCARGTITTGMNI.

The invention further contemplates antibodies comprising one or more of the polypeptide sequences of SEQ ID NO: 52; SEQ ID NO: 53; and SEQ ID NO: 54 which correspond to the complementarity-determining regions (CDRs, or hypervariable regions) of the variable light chain sequence of SEQ ID NO: 50, and/or one or more of the polypeptide sequences of SEQ ID NO: 55; SEQ ID NO: 56; and SEQ ID NO: 57 which correspond to the complementarity-determining regions (CDRs, or hypervariable regions) of the variable heavy chain sequence of SEQ ID NO: 51, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 52; SEQ ID NO: 53; and SEQ ID NO: 54 which correspond to the complementarity-determining regions (CDRs, or hypervariable regions) of the variable light chain sequence of SEQ ID NO: 50, and/or one or more of the polypeptide sequences of SEQ ID NO: 55; SEQ ID NO: 56; and SEQ ID NO: 57 which correspond to the complementarity-determining regions (CDRs, or hypervariable regions) of the variable heavy chain sequence of SEQ ID NO: 51, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 50. In another embodiment of the invention, antibody fragments of the invention comprise, or alternatively consist of, the polypeptide sequence of SEQ ID NO: 51.

In a further embodiment of the invention, fragments of the antibody having binding specificity to TNF-α comprise, or alternatively consist of, one or more of the polypeptide sequences of SEQ ID NO: 52; SEQ ID NO: 53; and SEQ ID NO: 54 which correspond to the complementarity-determining regions (CDRs, or hypervariable regions) of the variable light chain sequence of SEQ ID NO: 50.

In a further embodiment of the invention, fragments of the antibody having binding specificity to TNF-α comprise, or alternatively consist of, one or more of the polypeptide sequences of SEQ ID NO: 55; SEQ ID NO: 56; and SEQ ID NO: 57 which correspond to the complementarity-determining regions (CDRs, or hypervariable regions) of the variable heavy chain sequence of SEQ ID NO: 51.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 50; the variable heavy chain region of SEQ ID NO: 51; the complementarity-determining regions (SEQ ID NO: 52; SEQ ID NO': 53; and SEQ ID NO: 54) of the variable light chain region of SEQ ID NO: 50; and the complementarity-determining regions (SEQ ID NO: 55; SEQ ID NO: 56; and SEQ ID NO: 57) of the variable heavy chain region of SEQ ID NO: 51.

In a preferred embodiment of the invention, the anti-TNF-α antibody is Ab4, comprising SEQ ID NO: 50 and SEQ ID NO: 51, and having at least one of the biological activities set forth herein.

In another embodiment, the invention includes antibodies having binding specificity to TNF-α and possessing a variable light chain sequence comprising the sequence set forth below:

(SEQ ID NO: 66)
MDTRAPTQLLGLLLLWLPGATLAQVVTQTPASVSAAVGGTVTISCQSSQN

VYNNNDLVWFQQKPGQPPKRLVYWASTLASGVSSRFRGSGSGTQFILTIS

DLQCDDAATYYCAGAYDSEIRA

The invention also includes antibodies having binding specificity to TNF-α and possessing a variable heavy chain sequence comprising the sequence set forth below:

(SEQ ID NO: 67)
METGLRWLLLVAVLKGVQCQSVEESGGRLVTPGTPLTLTCAVSGFSLSVY

WMTWVRQAPGKGLEWIGTISTDGITVYATWAKGRFTISKTSSTAVDLKLT

SPTTEDTATYFCAGGGGMDP.

The invention further contemplates antibodies comprising one or more of the polypeptide sequences of SEQ ID NO: 68; SEQ ID NO: 69; and SEQ ID NO: 70 which correspond to the complementarity-determining regions (CDRs, or hypervariable regions) of the variable light chain sequence of SEQ ID NO: 66, and/or one or more of the polypeptide sequences of SEQ ID NO: 71; SEQ ID NO: 72; and SEQ ID NO: 73 which correspond to the complementarity-determining regions (CDRs, or hypervariable regions) of the variable heavy chain sequence of SEQ ID NO: 67, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 68; SEQ ID NO: 69; and SEQ ID NO: 70 which correspond to the complementarity-determining regions (CDRs, or hypervariable regions) of the variable light chain sequence of SEQ ID NO: 66, and/or one or more of the polypeptide sequences of SEQ ID NO: 71; SEQ ID NO: 72; and SEQ ID NO: 73 which correspond to the complementarity-determining regions (CDRs, or hypervariable regions) of the variable heavy chain sequence of SEQ ID NO: 67, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 66. In another embodiment of the invention, antibody fragments of the invention comprise, or alternatively consist of, the polypeptide sequence of SEQ ID NO: 67.

In a further embodiment of the invention, fragments of the antibody having binding specificity to TNF-α comprise, or alternatively consist of, one or more of the polypeptide sequences of SEQ ID NO: 68; SEQ ID NO: 69; and SEQ ID NO: 70 which correspond to the complementarity-determining regions (CDRs, or hypervariable regions) of the variable light chain sequence of SEQ ID NO: 66.

In a further embodiment of the invention, fragments of the antibody having binding specificity to TNF-α comprise, or alternatively consist of, one or more of the polypeptide sequences of SEQ ID NO: 71; SEQ ID NO: 72; and SEQ ID NO: 73 which correspond to the complementarity-determining regions (CDRs, or hypervariable regions) of the variable heavy chain sequence of SEQ ID NO: 67.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 66; the variable heavy chain region of SEQ ID NO: 67; the complementarity-determining regions (SEQ ID NO: 68; SEQ ID NO: 69; and SEQ ID NO: 70) of the variable light chain region of SEQ ID NO: 66; and the complementarity-determining regions (SEQ ID NO: 71; SEQ ID NO: 72; and SEQ ID NO: 73) of the variable heavy chain region of SEQ ID NO: 67.

In a preferred embodiment of the invention, the anti-TNF-α antibody is Ab5, comprising SEQ ID NO: 66 and SEQ ID NO: 67, and having at least one of the biological activities set forth herein.

In another embodiment, the invention includes antibodies having binding specificity to TNF-α and possessing a variable light chain sequence comprising the sequence set forth below:

(SEQ ID NO: 82)
MDTRAPTQLLGLLLLWLPDARCAYDMTQTPASVEVAGGGTVTIKCQASQS

IANRLAWYQQKPGQPPKLLIYYASTLASGVPSRFSGSGSGTEFTLTISGV

QCDDAATYYCQQTYSDNNVDNA

The invention also includes antibodies having binding specificity to TNF-α and possessing a variable heavy chain sequence comprising the sequence set forth below:

(SEQ ID NO: 83)
METGLRWLLLVAVFKGVQCQSVEESGGRLVTPGTPLTLTCTVSGFSLSSN

TISWVRQAPGKGLEWIGYIWRGVSTYYATWAKGRFTISKTSSTTVDLKIT

GPTTEDTATYFCARDAGDGGGYSLDL.

The invention further contemplates antibodies comprising one or more of the polypeptide sequences of SEQ ID NO: 84; SEQ ID NO: 85; and SEQ ID NO: 86 which correspond to the complementarity-determining regions (CDRs, or hypervariable regions) of the variable light chain sequence of SEQ ID NO: 82, and/or one or more of the polypeptide sequences of SEQ ID NO: 87; SEQ ID NO: 88; and SEQ ID NO: 89 which correspond to the complementarity-determining regions (CDRs, or hypervariable regions) of the variable heavy chain sequence of SEQ ID NO: 83, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 84; SEQ ID NO: 85; and SEQ ID NO: 86 which correspond to the complementarity-determining regions (CDRs, or hypervariable regions) of the variable light chain sequence of SEQ ID NO: 82, and/or one or more of the polypeptide sequences of SEQ ID NO: 87; SEQ ID NO: 88; and SEQ ID NO: 89 which correspond to the complementarity-determining regions (CDRs, or hypervariable regions) of the variable heavy chain sequence of SEQ ID NO: 83, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of the polypeptide sequence of SEQ ID NO: 82. In another embodiment of the invention, antibody fragments of the invention comprise, or alternatively consist of, the polypeptide sequence of SEQ ID NO: 83.

In a further embodiment of the invention, fragments of the antibody having binding specificity to TNF-α comprise, or alternatively consist of, one or more of the polypeptide sequences of SEQ ID NO: 84; SEQ ID NO: 85; and SEQ ID NO: 86 which correspond to the complementarity-determining regions (CDRs, or hypervariable regions) of the variable light chain sequence of SEQ ID NO: 82.

In a further embodiment of the invention, fragments of the antibody having binding specificity to TNF-α comprise, or alternatively consist of, one or more of the polypeptide sequences of SEQ ID NO: 87; SEQ ID NO: 88; and SEQ ID NO: 89 which correspond to the complementarity-determining regions (CDRs, or hypervariable regions) of the variable heavy chain sequence of SEQ ID NO: 83.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 82; the variable heavy chain region of SEQ ID NO: 83; the complementarity-determining regions (SEQ ID NO: 84; SEQ ID NO: 85; and SEQ ID NO: 86) of the variable light chain region of SEQ ID NO: 82; and the complementarity-determining regions (SEQ ID NO: 87; SEQ ID NO: 88; and SEQ ID NO: 89) of the variable heavy chain region of SEQ ID NO: 83.

In a preferred embodiment of the invention, the anti-TNF-α antibody is Ab6, comprising SEQ ID NO: 82 and SEQ ID NO: 83, and having at least one of the biological activities set forth herein.

In another embodiment, the invention includes antibodies having binding specificity to TNF-α and possessing a variable light chain sequence comprising the sequence set forth below:

```
                                            (SEQ ID NO: 98)
MDTRAPTQLLGLLLLWLPGARCADIVMTQTPASVEAAVGGTVTINCQASQ

SIVSWLAWYQQKPGQPPKLLIYGASTLASGVPSRFKGSGSGTEYTLTISD

LECADAATYYCQSNYGSNSHSFGNT
```

The invention also includes antibodies having binding specificity to TNF-α and possessing a variable heavy chain sequence comprising the sequence set forth below:

```
                                            (SEQ ID NO: 99)
METGLRWLLLVAVLKGVQCQSVEESGGRLVTPGTPLTLTCTVSGFSLSSD

NMGWVRQAPGKGLEYIGYITYGGFTYYATWAKGRFTISKTSTTVDLKMTS

PTTEDTATYFCAREAGGRANV.
```

The invention further contemplates antibodies comprising one or more of the polypeptide sequences of SEQ ID NO: 100; SEQ ID NO: 101; and SEQ ID NO: 102 which correspond to the complementarity-determining regions (CDRs, or hypervariable regions) of the variable light chain sequence of SEQ ID NO: 98, and/or one or more of the polypeptide sequences of SEQ ID NO: 103; SEQ ID NO: 104; and SEQ ID NO: 105 which correspond to the complementarity-determining regions (CDRs, or hypervariable regions) of the variable heavy chain sequence of SEQ ID NO: 99, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 100; SEQ ID NO: 101; and SEQ ID NO: 102 which correspond to the complementarity-determining regions (CDRs, or hypervariable regions) of the variable light chain sequence of SEQ ID NO: 98, and/or one or more of the polypeptide sequences of SEQ ID NO: 103; SEQ ID NO: 104; and SEQ ID NO: 105 which correspond to the complementarity-determining regions (CDRs, or hypervariable regions) of the variable heavy chain sequence of SEQ ID NO: 99, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 98. In another embodiment of the invention, antibody fragments of the invention comprise, or alternatively consist of, the polypeptide sequence of SEQ ID NO: 99.

In a further embodiment of the invention, fragments of the antibody having binding specificity to TNF-α comprise, or alternatively consist of, one or more of the polypeptide sequences of SEQ ID NO: 100; SEQ ID NO: 101; and SEQ ID NO: 102 which correspond to the complementarity-determining regions (CDRs, or hypervariable regions) of the variable light chain sequence of SEQ ID NO: 98.

In a further embodiment of the invention, fragments of the antibody having binding specificity to TNF-α comprise, or alternatively consist of, one or more of the polypeptide sequences of SEQ ID NO: 103; SEQ ID NO: 104; and SEQ ID NO: 105 which correspond to the complementarity-determining regions (CDRs, or hypervariable regions) of the variable heavy chain sequence of SEQ ID NO: 99.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 98; the variable heavy chain region of SEQ ID NO: 99; the complementarity-determining regions (SEQ ID NO: 100; SEQ ID NO: 101; and SEQ ID NO: 102) of the variable light chain region of SEQ ID NO: 98; and the complementarity-determining regions (SEQ ID NO: 103; SEQ ID NO: 104; and SEQ ID NO: 105) of the variable heavy chain region of SEQ ID NO: 99.

In a preferred embodiment of the invention, the anti-TNF-α antibody is Ab7, comprising SEQ ID NO: 98 and SEQ ID NO: 99, and having at least one of the biological activities set forth herein.

In another embodiment, the invention includes antibodies having binding specificity to TNF-α and possessing a variable light chain sequence comprising the sequence set forth below:

(SEQ ID NO: 114)
MDTRAPTQLLGLLLLWLPGARCADIVMTQTPSSVSEPVGGTVTIMCQASQ

NIYSYLSWYQQKPGQPPKLLIYKASTLASGVPSRFAGSGSGTDFILTISD

LECADAATYYCQSNYGSNSDSFGNA

The invention also includes antibodies having binding specificity to TNF-α and possessing a variable heavy chain sequence comprising the sequence set forth below:

(SEQ ID NO: 115)
METGLRWLLLVAVLKGVQCQSVEESGGRLVTPGTPLTLTCTASGFSLSNY

VMGWVRQAPGKGLEFIGYIAFGIGPYYATWAKGRFSISSTSSTTVDLTMT

SLTPEDTATYFCARGDYSGNNI.

The invention further contemplates antibodies comprising one or more of the polypeptide sequences of SEQ ID NO: 116; SEQ ID NO: 117; and SEQ ID NO: 118 which correspond to the complementarity-determining regions (CDRs, or hypervariable regions) of the variable light chain sequence of SEQ ID NO: 114, and/or one or more of the polypeptide sequences of SEQ ID NO: 119; SEQ ID NO: 120; and SEQ ID NO: 121 which correspond to the complementarity-determining regions (CDRs, or hypervariable regions) of the variable heavy chain sequence of SEQ ID NO: 115, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 116; SEQ ID NO: 117; and SEQ ID NO: 118 which correspond to the complementarity-determining regions (CDRs, or hypervariable regions) of the variable light chain sequence of SEQ ID NO: 114, and/or one or more of the polypeptide sequences of SEQ ID NO: 119; SEQ ID NO: 120; and SEQ ID NO: 121 which correspond to the complementarity-determining regions (CDRs, or hypervariable regions) of the variable heavy chain sequence of SEQ ID NO: 115, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 114. In another embodiment of the invention, antibody fragments of the invention comprise, or alternatively consist of, the polypeptide sequence of SEQ ID NO: 115.

In a further embodiment of the invention, fragments of the antibody having binding specificity to TNF-α comprise, or alternatively consist of, one or more of the polypeptide sequences of SEQ ID NO: 116; SEQ ID NO: 117; and SEQ ID NO: 118 which correspond to the complementarity-determining regions (CDRs, or hypervariable regions) of the variable light chain sequence of SEQ ID NO: 114.

In a further embodiment of the invention, fragments of the antibody having binding specificity to TNF-α comprise, or alternatively consist of, one or more of the polypeptide sequences of SEQ ID NO: 119; SEQ ID NO: 120; and SEQ ID NO: 121 which correspond to the complementarity-determining regions (CDRs, or hypervariable regions) of the variable heavy chain sequence of SEQ ID NO: 115.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 114; the variable heavy chain region of SEQ ID NO: 115; the complementarity-determining regions (SEQ ID NO: 116; SEQ ID NO: 117; and SEQ ID NO: 118) of the variable light chain region of SEQ ID NO: 114; and the complementarity-determining regions (SEQ ID NO: 119; SEQ ID NO: 120; and SEQ ID NO: 121) of the variable heavy chain region of SEQ ID NO: 115.

In a preferred embodiment of the invention, the anti-TNF-α antibody is Ab8, comprising SEQ ID NO: 114 and SEQ ID NO: 115, and having at least one of the biological activities set forth herein.

In another embodiment, the invention includes antibodies having binding specificity to TNF-α and possessing a variable light chain sequence comprising the sequence set forth below:

(SEQ ID NO: 130)
MDTRAPTQLLGLLLLWLPGATFAQVLTQTPSSVSAAVGGTVTVSCQSSQN

VYNNNDFVWFQQKPGQPPKRLIYWASTLASGVPSRFKGSGSGTQFTLTIN

DLECDDAATYYCAGAYITELRT

The invention also includes antibodies having binding specificity to TNF-α and possessing a variable heavy chain sequence comprising the sequence set forth below:

(SEQ ID NO: 131)
METGLRWLLLVAVLKGVQCQSVEESGGRLVTPGTPLTLTCTVSGFSLSIY

WMTWVRQAPGKGLEWIGVISTDGSAYYATWAKGRFTISKTSSTTVDLRIT

SPTTEDTATYFCAGGGGMDP.

The invention further contemplates antibodies comprising one or more of the polypeptide sequences of SEQ ID NO: 132; SEQ ID NO: 133; and SEQ ID NO: 134 which correspond to the complementarity-determining regions (CDRs, or hypervariable regions) of the variable light chain sequence of SEQ ID NO: 130, and/or one or more of the polypeptide sequences of SEQ ID NO: 135; SEQ ID NO: 136; and SEQ ID NO: 137 which correspond to the complementarity-determining regions (CDRs, or hypervariable regions) of the variable heavy chain sequence of SEQ ID NO: 131, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 132; SEQ ID NO: 133; and SEQ ID NO: 134 which correspond to the complementarity-determining regions (CDRs, or hypervariable regions) of the variable light chain sequence of SEQ ID NO: 130, and/or one or more of the polypeptide sequences of SEQ ID NO: 135; SEQ ID NO: 136; and SEQ ID NO: 137 which correspond to the complementarity-determining regions (CDRs, or hypervariable regions) of the variable heavy chain sequence of SEQ ID NO: 131, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 130. In another embodiment of the invention, antibody fragments of the invention comprise, or alternatively consist of, the polypeptide sequence of SEQ ID NO: 131.

In a further embodiment of the invention, fragments of the antibody having binding specificity to TNF-α comprise, or alternatively consist of, one or more of the polypeptide sequences of SEQ ID NO: 132; SEQ ID NO: 133; and SEQ ID NO: 134 which correspond to the complementarity-determining regions (CDRs, or hypervariable regions) of the variable light chain sequence of SEQ ID NO: 130.

In a further embodiment of the invention, fragments of the antibody having binding specificity to TNF-α comprise, or alternatively consist of, one or more of the polypeptide sequences of SEQ ID NO: 135; SEQ ID NO: 136; and SEQ ID NO: 137 which correspond to the complementarity-determining regions (CDRs, or hypervariable regions) of the variable heavy chain sequence of SEQ ID NO: 131.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain, region of SEQ ID NO: 130; the variable heavy chain region of SEQ ID NO: 131; the complementarity-determining regions (SEQ ID NO: 132; SEQ ID NO: 133; and SEQ ID NO: 134) of the variable light chain region of SEQ ID NO: 130; and the complementarity-determining regions (SEQ ID NO: 135; SEQ ID NO: 136; and SEQ ID NO: 137) of the variable heavy chain region of SEQ ID NO: 131.

In a preferred embodiment of the invention, the anti-TNF-α antibody is Ab9, comprising SEQ ID NO: 130 and SEQ ID NO: 131, and having at least one of the biological activities set forth herein.

In another embodiment, the invention includes antibodies having binding specificity to TNF-α and possessing a variable light chain sequence comprising the sequence set forth below:

```
                                        (SEQ ID NO: 146)
MDTRAPTQLLGLLLLWLPGATFAQVLTQTASSVSAAVGGTVTISCQSSQS

VYNNNDFIWFQQKPGQPPKRLIYWASTLASGVSSRFKGSGSGTQFTLTIN

DLECDDAAVYYCAGAYDSEVRA
```

The invention also includes antibodies having binding specificity to TNF-α and possessing a variable heavy chain sequence comprising the sequence set forth below:

```
                                        (SEQ ID NO: 147)
METGLRWLLLVAVLKGVQCQSVEESGGRLVTPGTPLTLTCTVSGFSLSIY

WMTWVRQAPGRGLEWIGVISTDGTTYYANWAKGRFTISKASSTTVDLRIT

SPTTEDTATYFCAGGGGMDP.
```

The invention further contemplates antibodies comprising one or more of the polypeptide sequences of SEQ ID NO: 148; SEQ ID. NO: 149; and SEQ ID NO: 150 which correspond to the complementarity-determining regions (CDRs, or hypervariable regions) of the variable light chain sequence of SEQ ID NO: 146, and/or one or more of the polypeptide sequences of SEQ ID NO: 151; SEQ ID NO: 152; and SEQ ID NO: 153 which correspond to the complementarity-determining regions (CDRs, or hypervariable regions) of the variable heavy chain sequence of SEQ ID NO: 147, or combinations, of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 148; SEQ ID NO: 149; and SEQ ID NO: 150 which correspond to the complementarity-determining regions (CDRs, or hypervariable regions) of the variable light chain sequence of SEQ ID NO: 146, and/or one or more of the polypeptide sequences of SEQ ID NO: 151; SEQ ID NO: 152; and SEQ ID NO: 153 which correspond to the complementarity-determining regions (CDRs, or hypervariable regions) of the variable heavy chain sequence of SEQ ID NO: 147, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 146. In another embodiment of the invention, antibody fragments of the invention comprise, or alternatively consist of, the polypeptide sequence of SEQ ID NO: 147.

In a further embodiment of the invention, fragments of the antibody having binding specificity to TNF-α comprise, or alternatively consist of, one or more of the polypeptide sequences of SEQ ID NO: 148; SEQ ID NO: 149; and SEQ ID NO: 150 which correspond to the complementarity-determining regions (CDRs, or hypervariable regions) of the variable light chain sequence of SEQ ID NO: 146.

In a further embodiment of the invention, fragments of the antibody having binding specificity to TNF-α comprise, or alternatively consist of, one or more of the polypeptide sequences of SEQ ID NO: 151; SEQ ID NO: 152; and SEQ ID NO: 153 which correspond to the complementarity-determining regions (CDRs, or hypervariable regions) of the variable heavy chain sequence of SEQ ID NO: 147.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain, region of SEQ ID NO: 146; the variable heavy chain region of SEQ ID NO: 147; the complementarity-determining regions (SEQ ID NO: 148; SEQ ID NO: 149; and SEQ ID NO: 150) of the variable light chain region of SEQ ID NO: 146; and the complementarity-determining regions (SEQ ID NO: 151; SEQ ID NO: 152; and SEQ ID NO: 153) of the variable heavy chain region of SEQ ID NO: 147.

In a preferred embodiment of the invention, the anti-TNF-α antibody is Ab10, comprising SEQ ID NO: 146 and SEQ ID NO: 147, and having at least one of the biological activities set forth herein.

In another embodiment, the invention includes antibodies having binding specificity to TNF-α and possessing a variable light chain sequence comprising the sequence set forth below:

(SEQ ID NO: 162)
MDTRAPTQLLGLLLLWLPGATFAQVMTQTPASVSAAVGGTVTISCQSSES

VYNNNDLIWFRQKPGQPPKRLIYWASQLASGVSSRFKGSGSGTQFTLTIN

DLECDDAATYYCAGAYDSEIRA

The invention also includes antibodies having binding specificity to TNF-α and possessing a variable heavy chain sequence comprising the sequence set forth below:

(SEQ ID NO: 163)
METGLRWLLLVAVLKGVQCQSVEESGGRLVTPGTPLTLTCTVSGFSLSIY

WMTWVRQAPGKGLEWIGVIASDGSTYYASWAKGRFTISKASSTTVDLKIA

SPTIEDTATYFCAGGGGMDP.

The invention further contemplates antibodies comprising one or more of the polypeptide sequences of SEQ ID NO: 164; SEQ ID NO: 165; and SEQ ID NO: 166 which correspond to the complementarity-determining regions (CDRs, or hypervariable regions) of the variable light chain sequence of SEQ ID NO: 162, and/or one or more of the polypeptide sequences of SEQ ID NO: 167; SEQ ID NO: 168; and SEQ ID NO: 169 which correspond to the complementarity-determining regions (CDRs, or hypervariable regions) of the variable heavy chain sequence of SEQ ID NO: 163, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 164; SEQ ID NO: 165; and SEQ ID NO: 166 which correspond to the complementarity-determining regions (CDRs, or hypervariable regions) of the variable light chain sequence of SEQ ID NO: 162, and/or one or more of the polypeptide sequences of SEQ ID NO: 167; SEQ ID NO: 168; and SEQ ID NO: 169 which correspond to the complementarity-determining regions (CDRs, or hypervariable regions) of the variable heavy chain sequence of SEQ ID NO: 163, or combinations of these polypeptide sequences.

In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO 162. In another embodiment of the invention, antibody fragments of the invention comprise, or alternatively consist of, the polypeptide sequence of SEQ ID NO: 163.

In a further embodiment of the invention, fragments of the antibody having binding specificity to TNF-α comprise, or alternatively consist of, one or more of the polypeptide sequences of SEQ ID NO: 164; SEQ ID NO: 165; and SEQ ID NO: 166 which correspond to the complementarity-determining regions (CDRs, or hypervariable regions) of the variable light chain sequence of SEQ ID NO: 162.

In a further embodiment of the invention, fragments of the antibody having binding specificity to TNF-α comprise, or alternatively consist of, one or more of the polypeptide sequences of SEQ ID NO: 167; SEQ ID NO: 168; and SEQ ID NO: 169 which correspond to the complementarity-determining regions (CDRs, or hypervariable regions) of the variable heavy chain sequence of SEQ ID NO: 163.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 162; the variable heavy chain region of SEQ ID NO: 163; the complementarity-determining regions (SEQ ID NO: 164; SEQ ID NO: 165; and SEQ ID NO: 166) of the variable light chain region of SEQ ID NO: 162; and the complementarity-determining regions (SEQ ID NO: 167; SEQ ID NO: 168; and SEQ ID NO: 169) of the variable heavy chain region of SEQ ID NO: 163.

In a preferred embodiment of the invention, the anti-TNF-α antibody is Ab11, comprising SEQ ID NO: 162 and SEQ ID NO: 163, and having at least one of the biological activities set forth herein.

In another embodiment, the invention includes antibodies having binding specificity to TNF-α and possessing a variable light chain sequence comprising the sequence set forth below:

(SEQ ID NO: 178)
MDTRAPTQLLGLLLLWLPGARCALVMTQTPSPVSAAVGGTVTISCQSSES

VVFNNRLSWYQQKPGQPPKLLIYWASTLASGVPSRFKGSGSGTQFTLTIS

GVECDDAATYYCAGYKSYSNDDFA

The invention also includes antibodies having binding specificity to TNF-α and possessing a variable heavy chain sequence comprising the sequence set forth below:

(SEQ ID NO: 179)
METGLRWLLLVAVLKGVQCQSVEESGGRLVTPGTPLTLTCTVSGFSLSHY

AMGWVRQAPGKGLEWIGIISSNGVTYYATWASGRFTISKTSTTVDLKITS

PTTEDTATYFCARGDDTSIIYYIYAFDL.

The invention further contemplates antibodies comprising one or more of the polypeptide sequences of SEQ ID NO: 180; SEQ ID NO: 181; and SEQ ID NO: 182 which correspond to the complementarity-determining regions (CDRs, or hypervariable regions) of the variable light chain sequence of SEQ ID NO: 178, and/or one or more of the polypeptide sequences of SEQ ID NO: 183; SEQ ID NO: 184; and SEQ ID NO: 185 which correspond to the complementarity-determining regions (CDRs, or hypervariable regions) of the variable heavy chain sequence of SEQ ID. NO: 179, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 180; SEQ ID NO: 181; and SEQ ID NO: 182 which correspond to the complementarity-determining regions (CDRs, or hypervariable regions) of the variable light chain sequence of SEQ ID NO: 178, and/or one or more of the polypeptide sequences of SEQ ID NO: 183; SEQ ID NO: 184; and SEQ ID NO: 185 which correspond to the complementarity-determining regions (CDRs, or hypervariable regions) of the variable heavy chain sequence of SEQ ID NO: 179, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 178. In another embodiment of the invention, antibody fragments of the invention comprise, or alternatively consist of, the polypeptide sequence of SEQ ID NO: 179.

In a further embodiment of the invention, fragments of the antibody having binding specificity to TNF-α comprise, or alternatively consist of, one or more of the polypeptide sequences of SEQ ID NO: 180; SEQ ID NO: 181; and SEQ ID NO: 182 which correspond to the complementarity-determining regions (CDRs, or hypervariable regions) of the variable light chain sequence of SEQ ID NO: 178.

In a further embodiment of the invention, fragments of the antibody having binding specificity to TNF-α comprise, or alternatively consist of, one or more of the polypeptide sequences of SEQ ID NO: 183; SEQ ID NO: 184; and SEQ ID NO: 185 which correspond to the complementarity-determining regions (CDRs, or hypervariable regions) of the variable heavy chain sequence of SEQ ID NO: 179.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 178; the variable heavy chain region of SEQ ID NO: 179; the complementarity-determining regions (SEQ ID NO: 180; SEQ ID NO: 181; and SEQ ID NO: 182) of the variable light chain region of SEQ ID NO: 178; and the complementarity-determining regions (SEQ ID NO: 183; SEQ ID NO: 184; and SEQ ID NO: 185) of the variable heavy chain region of SEQ ID NO: 179.

In a preferred embodiment of the invention, the anti-TNF-α antibody is. Ab12, comprising SEQ ID NO: 178 and SEQ ID NO: 179, and having at least one of the biological activities set forth herein.

In another embodiment, the invention includes antibodies having binding specificity to TNF-α and possessing a variable light chain sequence comprising the sequence set forth below:

(SEQ ID NO: 194)
MDTRAPTQLLGLLLLWLPGARCADIVMTQTPASVSEPVGGTVTIKCQASQ

NIYSTLAWYQQKPGQPPKLLIYLASTLASGVPSRFKGSGSGTQFTLTISD

LECADAATYYCQTSHGSNSDSFGYA

The invention also includes antibodies having binding specificity to TNF-α and possessing a variable heavy chain sequence comprising the sequence set forth below:

(SEQ ID NO: 195)
METGLRWLLLVAVLKGVQCQSVEESGGRLVTPGTPLTLTCTVSGIDLSSY

AMGWVRQAPGKGLEYIGYILSSGITYYASWARGRFTISKTSSTTVDLKMT

SLTTEDTATYFCARNGNYNSGTDI.

The invention further contemplates antibodies comprising one or more of the polypeptide sequences of SEQ ID NO: 196; SEQ ID NO: 197; and SEQ ID NO: 198 which correspond to the complementarity-determining regions (CDRs, or hypervariable regions) of the variable light chain sequence of SEQ ID NO: 194, and/or one or more of the polypeptide sequences of SEQ ID NO: 199; SEQ ID NO: 200; and SEQ ID NO: 201 which correspond to the complementarity-determining regions (CDRs, or hypervariable regions) of the variable heavy chain sequence of SEQ ID NO: 195, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 196; SEQ ID NO: 197; and SEQ ID NO: 198 which correspond to the complementarity-determining regions (CDRs, or hypervariable regions) of the variable light chain sequence of SEQ ID NO: 194, and/or one or more of the polypeptide sequences of SEQ ID NO: 199; SEQ ID NO: 200; and SEQ ID NO: 201 which correspond to the complementarity-determining regions (CDRs, or hypervariable regions) of the variable heavy chain sequence of SEQ ID NO: 195, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 194. In another embodiment of the invention, antibody fragments of the invention comprise, or alternatively consist of, the polypeptide sequence of SEQ ID NO: 195.

In a further embodiment of the invention, fragments of the antibody having binding specificity to TNF-α comprise, or alternatively consist of, one or more of the polypeptide sequences of SEQ ID NO: 196; SEQ ID NO: 197; and SEQ ID NO: 198 which correspond to the complementarity-determining regions (CDRs, or hypervariable regions) of the variable light chain sequence of SEQ ID NO: 194.

In a further embodiment of the invention, fragments of the antibody having binding specificity to TNF-α comprise, or alternatively consist of, one or more of the polypeptide sequences of SEQ ID NO: 199; SEQ ID NO: 200; and SEQ ID NO: 201 which correspond to the complementarity-determining regions (CDRs, or hypervariable regions) of the variable heavy chain sequence of SEQ ID NO: 195.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 194; the variable heavy chain region of SEQ ID NO: 195; the complementarity-determining regions (SEQ ID NO: 196; SEQ ID NO: 197; and SEQ ID NO: 198) of the variable light chain region of SEQ ID NO: 194; and the complementarity-determining regions (SEQ ID NO: 199; SEQ ID NO: 200; and SEQ ID NO: 201) of the variable heavy chain region of SEQ ID NO: 195.

In a preferred embodiment of the invention, the anti-TNF-α antibody is. Ab13, comprising SEQ ID NO: 194 and SEQ ID NO: 195, and having at least one of the biological activities set forth herein.

In another embodiment, the invention includes antibodies having binding specificity to TNF-α and possessing a variable light chain sequence comprising the sequence set forth below:

(SEQ ID NO: 210)
MDTRAPTQLLGLLLLWLPGARCADIVMTQTPASVSEPVGGTVTIKCQASQ

NIYSTLAWYQQKPGQPPKLLIYLASTLASGVPSRFKGSGSGTQFTLTISD

LECADAATYYCQTNHGSNSDSFGYA

The invention also includes antibodies having binding specificity to TNF-α and possessing a variable heavy chain sequence comprising the sequence set forth below:

(SEQ ID NO: 211)
METGLRWLLLVAVLKGVQCQSVEESGGRLVTPGTPLTLTCTVSGFSLSSY

AMGWVRQAPGKGLEYIGYIGSSGITYYTSWARGRFTISKPSSTTVDLKMT

SLTTEDTATYFCARNGNYNSGTDI.

The invention further contemplates antibodies comprising one or more of the polypeptide sequences of SEQ ID NO: 212; SEQ ID NO: 213; and SEQ ID NO: 214 which correspond to the complementarity-determining regions (CDRs, or hypervariable regions) of the variable light chain sequence of SEQ ID NO: 210, and/or one or more of the polypeptide sequences of SEQ ID NO: 215; SEQ ID NO: 216; and SEQ ID NO: 217 which correspond to the complementarity-determining regions (CDRs, or hypervariable regions) of the variable heavy chain sequence of SEQ ID NO: 211, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 212; SEQ ID NO: 213; and SEQ ID NO: 214 which correspond to the complementarity-determining regions (CDRs, or hypervariable regions) of the variable light chain sequence of SEQ ID NO: 210, and/or one or more of the polypeptide sequences of SEQ ID NO: 215; SEQ ID NO: 216; and SEQ ID NO: 217 which correspond to the complementarity-determining regions (CDRs, or hypervariable regions) of the variable heavy chain sequence of SEQ ID NO: 211, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 210. In another embodiment of the invention, antibody fragments of the invention comprise, or alternatively consist of, the polypeptide sequence of SEQ ID NO: 211.

In a further embodiment of the invention, fragments of the antibody having binding specificity to TNF-α comprise, or alternatively consist of, one or more of the polypeptide sequences of SEQ ID NO: 212; SEQ ID NO: 213; and SEQ ID NO: 214 which correspond to the complementarity-determining regions (CDRs, or hypervariable regions) of the variable light chain sequence of SEQ ID NO: 210.

In a further embodiment of the invention, fragments of the antibody having binding specificity to TNF-α comprise, or alternatively consist of, one or more of the polypeptide sequences of SEQ ID NO: 215; SEQ ID NO: 216; and SEQ ID NO: 217 which correspond to the complementarity-determining regions (CDRs, or hypervariable regions) of the variable heavy chain sequence of SEQ ID NO: 211.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 210; the variable heavy chain region of SEQ ID NO: 211; the complementarity-determining regions (SEQ ID NO 212; SEQ ID NO: 213; and SEQ ID NO: 214) of the variable light chain region of SEQ ID NO: 210; and the complementarity-determining regions (SEQ ID NO: 215; SEQ ID NO: 216; and SEQ ID NO: 217) of the variable heavy chain region of SEQ ID NO: 211.

In a preferred embodiment of the invention, the anti-TNF-α antibody is. Ab14, comprising SEQ ID NO: 210 and SEQ ID NO: 211, and having at least one of the biological activities set forth herein.

In another embodiment, the invention includes antibodies having binding specificity to TNF-α and possessing a variable light chain sequence comprising the sequence set forth below:

(SEQ ID NO: 226)
MDTRAPTQLLGLLLLWLPGARCADIVMTQTPASVSEPVGGTVTIKCQASQ

SIYSSFSWYQQIPGQRPKLLIYYASTLASGVPSRFSGSGSGTDFTLTISD

LECADAATYYCQSNHGSNGDSFGNA

The invention also includes antibodies having binding specificity to TNF-α and possessing a variable heavy chain sequence comprising the sequence set forth below:

(SEQ ID NO: 227)
METGLRWLLLVAVLKGVQCQSVEESGGRLVSPGTPLTLTCTVSGIDLSSY

GMGWVRQAPGKGLEYIGYMIASGITYYAAWAKGRFTISKTSSTTVDLKIT

SPTTEDTATYFCARNYYGMDP.

The invention further contemplates antibodies comprising one or more of the polypeptide sequences of SEQ ID NO: 228; SEQ ID NO: 229; and SEQ ID NO: 230 which correspond to the complementarity-determining regions (CDRs, or hypervariable regions) of the variable light chain sequence of SEQ ID NO: 226, and/or one or more of the polypeptide sequences of SEQ ID NO: 231; SEQ ID NO: 232; and SEQ ID NO: 233 which correspond to the complementarity-determining regions (CDRs, or hypervariable regions) of the variable heavy chain sequence of SEQ ID NO: 227, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 228; SEQ ID NO: 229; and SEQ ID NO: 230 which correspond to the complementarity-determining regions (CDRs, or hypervariable regions) of the variable light chain sequence of SEQ ID NO: 226, and/or, one or more of the polypeptide sequences of SEQ ID NO: 231; SEQ ID NO: 232; and SEQ ID NO: 233 which correspond to the complementarity-determining regions (CDRs, or hypervariable regions) of the variable heavy chain sequence of SEQ ID NO: 227, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 226. In another embodiment of the invention, antibody, fragments of the invention comprise, or alternatively consist of, the polypeptide sequence of SEQ ID NO: 227.

In a further embodiment of the invention, fragments of the antibody having binding specificity to TNF-α comprise, or alternatively consist of, one or more of the polypeptide sequences of SEQ ID NO: 228; SEQ ID NO: 229; and SEQ ID NO: 230 which correspond to the complementarity-determining regions (CDRs, or hypervariable regions) of the variable light chain sequence of SEQ ID NO: 226.

In a further embodiment of the invention, fragments of the antibody having binding specificity to TNF-α comprise, or alternatively consist of, one or more of the polypeptide sequences of SEQ ID NO: 231; SEQ ID NO: 232; and SEQ ID NO: 233 which correspond to the complementarity-determining regions (CDRs, or hypervariable regions) of the variable heavy chain sequence of SEQ ID NO: 227.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 226; the variable heavy chain region of SEQ ID NO: 227; the complementarity-determining regions (SEQ ID NO: 228; SEQ ID NO: 229; and SEQ ID NO: 230) of the variable light chain region of SEQ ID NO: 226; and the complementarity-determining regions (SEQ ID NO: 231; SEQ ID NO: 232; and SEQ ID NO: 233) of the variable heavy chain region of SEQ ID NO: 227.

In a preferred embodiment of the invention, the anti-TNF-α antibody is. Ab15, comprising SEQ ID NO: 226 and SEQ ID NO: 227, and having at least one of the biological activities set forth herein.

In another embodiment, the invention includes antibodies having binding specificity to TNF-α and possessing a variable light chain sequence comprising the sequence set forth below:

(SEQ ID NO: 242)
MDTRAPTQLLGLLLLWLPGARCADIVMTQTPASVSEPVGGTVTIKCQASQ

TIYSSLSWYQQKPGQRPKLLIYAASTLASGVPSRFKGSGSGTDFTLTISD

LECADAATYYCQSNHGSNSDSYGNA

The invention also includes antibodies having binding specificity to TNF-α and possessing a variable heavy chain sequence comprising the sequence set forth below:

(SEQ ID NO: 243)
METGLRWLLLVAVLKGVQCQSLEESGGRLVKPDETLTITCTVSGIDLNNY

NMGWVRQAPGKGLEYIGYILGSGITYYATWAKGRFTISKTSSTTVDLKMT

SLTTEDTATYFCAGSIYYRGYGMDP.

The invention further contemplates antibodies comprising one or more of the polypeptide sequences of SEQ ID NO: 244; SEQ ID NO: 245; and SEQ ID NO: 246 which correspond to the complementarity-determining regions (CDRs, or hypervariable regions) of the variable light chain sequence of SEQ ID NO: 242, and/or one or more of the polypeptide sequences of SEQ ID NO: 247; SEQ ID NO: 248; and SEQ ID NO: 249 which correspond to the complementarity-determining regions (CDRs, or hypervariable regions) of the variable heavy chain sequence of SEQ ID NO: 243, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 244; SEQ ID NO: 245; and SEQ ID NO: 246 which correspond to the complementarity-determining regions (CDRs, or hypervariable regions) of the variable light chain sequence of SEQ ID NO: 242, and/or one or more of the polypeptide sequences of SEQ ID NO: 247; SEQ ID NO: 248; and SEQ ID NO: 249 which correspond to the complementarity-determining regions (CDRs, or hypervariable regions) of the variable heavy chain sequence of SEQ ID NO: 243, or combinations of these polypeptide sequences. In another embodiment of the invention, the antibodies of the invention include combinations of, the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 242. In another embodiment of the invention, antibody fragments of the invention comprise, or alternatively consist of, the polypeptide sequence of SEQ ID NO: 243.

In a further embodiment of the invention, fragments of the antibody having binding specificity to TNF-α comprise, or alternatively consist of, one or more of the polypeptide sequences of SEQ ID NO: 244; SEQ ID NO: 245; and SEQ ID NO: 246 which correspond to the complementarity-determining regions (CDRs, or hypervariable regions) of the variable light chain sequence of SEQ ID NO: 242.

In a further embodiment of the invention, fragments of the antibody having binding specificity to TNF-α comprise, or alternatively consist of, one or more of the polypeptide sequences of SEQ ID NO: 247; SEQ ID NO: 248; and SEQ ID NO: 249 which correspond to the complementarity-determining regions (CDRs, or hypervariable regions) of the variable heavy chain sequence of SEQ ID NO: 243.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 242; the variable heavy chain region of SEQ ID NO: 243; the complementarity-determining regions (SEQ ID NO: 244; SEQ ID NO: 245; and SEQ ID NO: 246) of the variable light chain region of SEQ ID NO: 242; and the complementarity-determining regions (SEQ ID NO: 247; SEQ ID NO: 248; and SEQ ID NO: 249) of the variable heavy chain region of SEQ ID NO: 243.

In a preferred embodiment of the invention, the anti-TNF-α antibody is. Ab16, comprising SEQ ID NO: 242 and SEQ ID NO: 243, and having at least one of the biological activities set forth herein.

In another embodiment, the invention includes antibodies having binding specificity to TNF-α and possessing a variable light chain sequence comprising the sequence set forth below:

(SEQ ID NO: 258)
MDTRAPTQLLGLLLLWLPGARCADIVMTQTPASVSEPVGGTVTIKCQASQ

SIYSTLAWYQQKPGQPPKLLISLASTLASGVPSRFKGSGSGTQFTLTISD

LECADAATYYCQTNHGSNSDSFGYA

The invention also includes antibodies having binding specificity to TNF-α and possessing a variable heavy chain sequence comprising the sequence set forth below:

(SEQ ID NO: 259)
METGLRWLLLVAVLKGVQCQSLEESGGRLVTPGGSLTLTCTVSGIDLSSY

AMGWVRQAPGKGLEYIGYVLGSGITYYASWARGRFTISKTSSTTVDLKMT

SLTTEDTATYFCVRNDNYNSGTDI.

The invention further contemplates antibodies comprising one or more of the polypeptide sequences of SEQ ID NO: 260; SEQ ID NO: 261; and SEQ ID NO: 262 which correspond to the complementarity-determining regions (CDRs, or hypervariable regions) of the variable light chain sequence of SEQ ID NO: 258, and/or one or more of the polypeptide sequences of SEQ ID NO: 263; SEQ ID NO: 264; and SEQ ID NO: 265 which correspond to the complementarity-determining regions (CDRs, or hypervariable regions) of the variable heavy chain sequence of SEQ ID NO: 259, or combinations of these polypeptide sequences. In another embodiment of the invention, the antibodies of the invention include, combinations of the CDRs and the variable heavy and light chain sequences set forth above.

In another embodiment, the invention contemplates other antibodies, such as for example chimeric antibodies, comprising one or more of the polypeptide sequences of SEQ ID NO: 260; SEQ ID NO: 261; and SEQ ID NO: 262 which correspond to the complementarity-determining regions (CDRs, or hypervariable regions) of the variable light chain sequence of SEQ ID NO: 258, and/or one or more of the polypeptide sequences of SEQ ID NO: 263; SEQ ID NO: 264; and SEQ ID NO: 265 which correspond to the complementarity-determining regions (CDRs, or hypervariable regions) of the variable heavy chain sequence of SEQ ID NO: 259, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 258. In another embodiment of the invention, antibody fragments of the invention comprise, or alternatively consist of, the polypeptide sequence of SEQ ID NO: 259.

In a further embodiment of the invention, fragments of the antibody having binding specificity to TNF-α comprise, or alternatively consist of, one or more of the polypeptide sequences of SEQ ID NO: 260; SEQ ID NO: 261; and SEQ ID NO: 262 which correspond to the complementarity-determining regions (CDRs, or hypervariable regions) of the variable light chain sequence of SEQ ID NO: 258.

In a further embodiment of the invention, fragments of the antibody having binding specificity to TNF-α comprise, or alternatively consist of, one or more of the polypeptide sequences of SEQ ID NO: 263; SEQ ID NO: 264; and SEQ ID NO: 265 which correspond to the complementarity-determining regions (CDRs, or hypervariable regions) of the variable heavy chain sequence of SEQ ID NO: 259.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 258; the variable heavy chain region of SEQ ID NO: 259; the complementarity-determining regions (SEQ ID NO: 260; SEQ ID NO: 261; and SEQ ID NO: 262) of the variable light chain region of SEQ ID NO: 258; and the complementarity-determining regions (SEQ ID NO: 263; SEQ ID NO: 264; and SEQ ID NO: 265) of the variable heavy chain region of SEQ ID NO: 259.

In a preferred embodiment of the invention, the anti-TNF-α antibody is Ab17, comprising SEQ ID NO: 258 and SEQ ID NO: 259, and having at least one of the biological activities set forth herein.

In another embodiment, the invention includes antibodies having binding specificity to TNF-α and possessing a variable light chain sequence comprising the sequence set forth below:

(SEQ ID NO: 274)
MDTRAPTQLLGLLLLWLPGARCADIVMTQTPASVSEPVGGTVTIKCQASQ

NIYSTLAWYQQKPGQPPKLLIYLASTLESGVPSRFKGSGSGTEFTLTISD

LECADAATYYCQTSHGSNSESFGYA

The invention also includes antibodies having binding specificity to TNF-α and possessing a variable heavy chain sequence comprising the sequence set forth below:

(SEQ ID NO: 275)
METGLRWLLLVAVLKGVQCQSVEESGGRLVTPGTPLTLTCTVSGIDLSSY

AMGWVRQAPGKGLEYIGYILSSGITYYASWARGRFTISKTSSTTVDLKMT

SLTTEDTATYFCVRNGNYNVGTDI.

The invention further contemplates antibodies comprising one or more of the polypeptide sequences of SEQ ID NO: 276; SEQ ID NO: 277; and SEQ ID NO: 278 which correspond to the complementarity-determining regions (CDRs, or hypervariable regions) of the variable light chain sequence of SEQ ID NO: 274, and/or one or more of the polypeptide sequences of SEQ ID NO: 279; SEQ ID NO: 280; and SEQ ID NO: 281 which correspond to the complementarity-determining regions (CDRs, or hypervariable regions) of the variable heavy chain sequence of SEQ ID NO: 275, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 276; SEQ ID NO: 277; and SEQ ID NO: 278 which correspond to the complementarity-determining regions (CDRs, or hypervariable regions) of the variable light chain sequence of SEQ ID NO: 274, and/or one or more of the polypeptide sequences of SEQ ID NO: 279; SEQ ID NO: 280; and SEQ ID NO: 281 which correspond to the complementarity-determining regions (CDRs, or hypervariable regions) of the variable heavy chain sequence of SEQ ID NO: 275, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 274. In another embodiment of the invention, antibody fragments of the invention comprise, or alternatively consist of, the polypeptide sequence of SEQ ID NO: 275.

In a further embodiment of the invention, fragments of the antibody having binding specificity to TNF-α comprise, or alternatively consist of, one or more of the polypeptide sequences of SEQ ID NO: 276; SEQ ID NO: 277; and SEQ ID NO: 278 which correspond to the complementarity-determining regions (CDRs, or hypervariable regions) of the variable light chain sequence of SEQ ID NO: 274.

In a further embodiment of the invention, fragments of the antibody having binding specificity to TNF-α comprise, or alternatively consist of, one or more of the polypeptide sequences of SEQ ID NO: 279; SEQ ID NO: 280; and SEQ ID NO: 281 which correspond to the complementarity-determining regions (CDRs, or hypervariable regions) of the variable heavy chain sequence of SEQ ID NO: 275.

The invention also contemplates antibody fragments which include one or more of the antibody fragments described herein. In one embodiment of the invention, fragments of the antibodies having binding specificity to TNF-α comprise, or alternatively consist, of, one, two, three or more, including all of the following antibody fragments: the variable light chain region of SEQ ID NO: 274; the variable heavy chain region of SEQ ID NO: 275; the complementarity-determining regions (SEQ ID NO: 276; SEQ ID NO: 277; and SEQ ID NO: 278) of the variable light chain region of SEQ ID NO: 274; and the complementarity-determining regions (SEQ ID NO: 279; SEQ ID NO: 280; and SEQ ID NO: 281) of the variable heavy chain region of SEQ ID NO: 275.

In a preferred embodiment of the invention, the anti-TNF-α antibody is. Ab18, comprising. SEQ ID NO: 274 and SEQ ID NO: 275, and having at least one of the biological activities set forth herein.

In another embodiment, the invention includes antibodies having binding specificity to TNF-α and possessing a variable light chain sequence comprising the sequence set forth below:

(SEQ ID NO: 290)
MDTRAPTQLLGLLLLWLPGARCADIVMTQTPSSVSEPVRGTVTIKCQASQ

NIYSYLSWYRQSPGQPPNLLIYKASTLASGVPSRFKGSGSGTDFTLTISD

LECADAATYYCQSNYGSNSDSFGNA

The invention also includes antibodies having binding specificity to TNF-α and possessing a variable heavy chain sequence comprising the sequence set forth below:

(SEQ ID NO: 291)
METGLRWLLLVAVLKGVQCQSVEESGGRLVTPGTPLTLTCSVSGFSLNNY

IMGWVRQAPGKGLEFIGYIAFGIGPYYASWAKGRFTSSSTSSTTVDLKMT

SLTPEDTATYFCARGDVSGNDI.

The invention further contemplates antibodies comprising one or more of the polypeptide sequences of SEQ ID NO: 292; SEQ ID NO: 293; and SEQ ID NO: 294 which correspond to the complementarity-determining regions (CDRs, or hypervariable regions) of the variable light chain sequence of SEQ ID NO: 290, and/or one or more of the polypeptide sequences of SEQ ID NO: 295; SEQ ID NO: 296; and SEQ ID NO: 297 which correspond to the complementarity-determining regions (CDRs, or hypervariable regions) of the variable heavy chain sequence of SEQ ID NO: 291, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 292; SEQ ID NO: 293; and SEQ ID NO: 294 which correspond to the complementarity-determining regions (CDRs, or hypervariable regions) of the variable light chain sequence of SEQ ID NO: 290, and/or one or more of the polypeptide sequences of SEQ ID NO: 295; SEQ ID NO: 296; and SEQ ID NO: 297 which correspond to the complementarity-determining regions (CDRs, or hypervariable regions) of the variable heavy chain sequence of SEQ ID NO: 291, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 290. In another embodiment of the invention, antibody fragments of the invention comprise, or alternatively consist of, the polypeptide sequence of SEQ ID NO: 291.

In a further embodiment of the invention, fragments of the antibody having binding specificity to TNF-α comprise, or alternatively consist of, one or more of the polypeptide sequences of SEQ ID NO: 292; SEQ ID NO: 293; and SEQ ID NO: 294 which correspond to the complementarity-determining regions (CDRs, or hypervariable regions) of the variable light chain sequence of SEQ ID NO: 290.

In a further embodiment of the invention, fragments of the antibody having binding specificity to TNF-α, comprise, or alternatively consist of, one or more of the polypeptide sequences of SEQ ID NO: 295; SEQ ID NO: 296; and SEQ ID NO: 297 which correspond to the complementarity-determining regions (CDRs, or hypervariable regions) of the variable heavy chain sequence of SEQ ID NO: 291.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 290; the variable heavy chain region of SEQ ID NO: 291; the complementarity-determining regions (SEQ ID NO: 292; SEQ ID NO: 293; and SEQ ID NO: 294) of the variable light chain region of SEQ ID NO: 290; and the complementarity-determining regions (SEQ ID NO: 295; SEQ ID NO: 296; and SEQ ID NO: 297) of the variable heavy chain region of SEQ ID NO: 291.

In a preferred embodiment of the invention, the anti-TNF-α antibody is Ab19, comprising. SEQ ID NO: 290 and SEQ ID NO: 291, and having at least one of the biological activities set forth herein.

In another embodiment, the invention includes antibodies having binding specificity to TNF-α and possessing a variable light chain sequence comprising the sequence set forth below:

```
                                           (SEQ ID NO: 306)
MDTRAPTQLLGLLLLWLPGARCADIVMTQTPASVSEPVGGTVTIKCQASQ

NIYTTLAWYQQKPGQPPKLLIYLASTLASGVPSRFKGSGSETQFTLTISD

LECADAATYYCQTSHGSNSDSFGYV
```

The invention also includes antibodies having binding specificity to TNF-α and possessing a variable heavy chain sequence comprising the sequence set forth below:

```
                                           (SEQ ID NO: 307)
METGLRWLLLVAVLKGVQCQSVEESGGRLVTPGTPLTLTCTVSGIDLNSY

AMGWVRQAPGKGLEYIGYILSSGITYYATWAKGRFTISKTSSTTVDLKMT

SLTTEDTATYFCVRNGNYNSGTDI.
```

The invention further contemplates antibodies comprising one or more of the polypeptide sequences of SEQ ID NO: 308; SEQ ID NO: 309; and SEQ ID NO: 310 which correspond to the complementarity-determining regions (CDRs, or hypervariable regions) of the variable light chain sequence of SEQ ID NO: 306, and/or one or more of the polypeptide sequences of SEQ ID NO: 311; SEQ ID NO: 312; and SEQ ID NO: 313 which correspond to the complementarity-determining regions (CDRs, or hypervariable regions) of the variable heavy chain sequence of SEQ ID NO: 307, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 308; SEQ ID NO: 309; and SEQ ID NO: 310 which correspond to the complementarity-determining regions (CDRs, or hypervariable regions) of the variable light chain sequence of SEQ ID NO: 306, and/or one or more of the polypeptide sequences of SEQ ID NO: 311; SEQ ID NO: 312; and SEQ ID NO: 313 which correspond to the complementarity-determining regions (CDRs, or hypervariable regions) of the variable heavy chain sequence of SEQ ID NO: 307, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 306. In another embodiment of the invention, antibody fragments of the invention comprise, or alternatively consist of, the polypeptide sequence of SEQ ID NO: 307.

In a further embodiment of the invention, fragments of the antibody having binding specificity to TNF-α comprise, or alternatively consist of, one or more of the polypeptide sequences of SEQ ID NO: 308; SEQ ID NO: 309; and SEQ ID NO: 310 which correspond to the complementarity-determining regions (CDRs, or hypervariable regions) of the variable light chain sequence of SEQ ID NO: 306.

In a further embodiment of the invention, fragments of the antibody having binding specificity to TNF-α comprise, or alternatively consist of, one or more of the polypeptide sequences of SEQ ID NO: 311; SEQ ID NO: 312; and SEQ ID NO: 313 which correspond to the complementarity-determining regions (CDRs, or hypervariable regions) of the variable heavy chain sequence of SEQ ID NO: 307.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 306; the variable heavy chain region of SEQ ID NO: 307; the complementarity-determining regions (SEQ ID NO: 308;

SEQ ID NO: 309; and SEQ ID NO: 310) of the variable light chain region of SEQ ID NO: 306; and the complementarity-determining regions (SEQ ID NO: 311; SEQ ID NO: 312; and SEQ ID NO: 313) of the variable heavy chain region of SEQ ID NO: 307.

In a preferred embodiment of the invention, the anti-TNF-α antibody is Ab20, comprising SEQ ID NO: 306 and SEQ ID NO: 307, and having at least one of the biological activities set forth herein.

In another embodiment, the invention includes antibodies having binding specificity to TNF-α and possessing a variable light chain sequence comprising the sequence set forth below:

```
                                       (SEQ ID NO: 322)
MDTRAPTQLLGLLLLWLPGARCADIVMTQTPSSVSAAVGGTVTIKCQASQ

SIDTYLAWYQQKPGQRPKLLIYGASNLASGVSSRFKGSGSGTEFALTISD

LECADAATYYCQSNYGSNSDSFGNG
```

The invention also includes antibodies having binding specificity to TNF-α and possessing a variable heavy chain sequence comprising the sequence set forth below:

```
                                       (SEQ ID NO: 323)
METGLRWLLLVAVFKGVQCQSVEESGGRLVTPGTPLTLTCTVSGFSLSTY

TMGWVRQAPGKGLEYIGYISYGGLAYYATWVNGRFTISKTSTTVDLKMTS

LTASDTATYFCARAASGAWGHAYGLDL.
```

The invention further contemplates antibodies comprising one or more of the polypeptide sequences of SEQ ID NO: 324; SEQ ID NO: 325; and SEQ ID NO: 326 which correspond to the complementarity-determining regions (CDRs, or hypervariable regions) of the variable light chain sequence of SEQ ID NO: 322, and/or one or more of the polypeptide sequences of SEQ ID NO: 327; SEQ ID NO: 328; and SEQ ID NO: 329 which correspond to the complementarity-determining regions (CDRs, or hypervariable regions) of the variable heavy chain sequence of SEQ ID NO: 323, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 324; SEQ ID NO: 325; and SEQ ID NO: 326 which correspond to the complementarity-determining regions (CDRs, or hypervariable regions) of the variable light chain sequence of SEQ ID NO: 322, and/or, one or more of the polypeptide sequences of SEQ ID NO: 327; SEQ ID NO: 328; and SEQ ID NO: 329 which correspond to the complementarity-determining regions (CDRs, or hypervariable regions) of the variable heavy chain sequence of SEQ ID NO: 323, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO 322. In another embodiment of the invention, antibody fragments of the invention comprise, or alternatively consist of, the polypeptide sequence of SEQ ID NO: 323.

In a further embodiment of the invention, fragments of the antibody having binding specificity to TNF-α comprise, or alternatively consist of, one or more of the polypeptide sequences of SEQ ID NO: 324; SEQ ID NO: 325; and SEQ ID NO: 326 which correspond to the complementarity-determining regions (CDRs, or hypervariable regions) of the variable light chain sequence of SEQ ID NO: 322.

In a further embodiment of the invention, fragments of the antibody having binding specificity to TNF-α comprise, or alternatively consist of, one or more of the polypeptide sequences of SEQ ID NO: 327; SEQ ID NO: 328; and SEQ ID NO: 329 which correspond to the complementarity-determining regions (CDRs, or hypervariable regions) of the variable heavy chain sequence of SEQ ID NO: 323.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 322; the variable heavy chain region of SEQ ID NO: 323; the complementarity-determining regions (SEQ ID NO: 324; SEQ ID NO: 325; and SEQ ID NO: 326) of the variable light chain region of SEQ ID NO: 322; and the complementarity-determining regions (SEQ ID NO: 327; SEQ ID NO: 328; and SEQ ID NO: 329) of the variable heavy chain region of SEQ ID NO: 323.

In a preferred embodiment of the invention, the anti-TNF-α antibody is. Ab21, comprising SEQ ID NO: 322 and SEQ ID NO: 323, and having at least one of the biological activities set forth herein.

In another embodiment, the invention includes antibodies having binding specificity to TNF-α and possessing a variable light chain sequence comprising the sequence set forth below:

```
                                       (SEQ ID NO: 338)
MDTRAPTQLLGLLLLWLPGARCADIVMTQTPASVSGPVGGTVTIKCQASQ

NIYSSFSWYQQIPGQRPKLLIYYASTLASGVPSRFSGSGSGTDFTLTISD

LECADAATYYCQSNHGSNGDSFGNA
```

The invention also includes antibodies having binding specificity to TNF-α and possessing a variable heavy chain sequence comprising the sequence set forth below:

```
                                       (SEQ ID NO: 339)
METGLRWLLLVAVLKGVQCQSVEESGGRLVSPGTPLTLTCTVSGIDLSSY

GMGWVRQAPGKGLDYIGYMLPSGITYYAAWAKGRFTISKTSSTTVDLKIT

SPTTEDTATYFCARNYYGMDP.
```

The invention further contemplates antibodies comprising one or more of the polypeptide sequences of SEQ ID NO: 340; SEQ ID NO: 341; and SEQ ID NO: 342 which correspond to the complementarity-determining regions (CDRs, or hypervariable regions) of the variable light chain sequence of SEQ ID NO: 338, and/or one or more of the polypeptide sequences of SEQ ID NO: 343; SEQ ID NO: 344; and SEQ ID NO: 345 which correspond to the complementarity-determining regions (CDRs, or hypervariable regions) of the variable heavy chain sequence of SEQ ID NO: 339, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 340; SEQ ID NO: 341; and SEQ NO: 342 which correspond to the complementarity-determining regions (CDRs, or hypervariable regions) of the variable light chain sequence of SEQ ID NO: 338, and/or one or more of the polypeptide sequences of SEQ ID NO: 343; SEQ ID NO: 344; and SEQ ID NO: 345 which correspond to the complementarity-determining regions (CDRs, or hypervariable regions) of the variable heavy chain sequence of SEQ ID NO: 339, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 338. In another embodiment of the invention, antibody fragments of the invention comprise, or alternatively consist of, the polypeptide sequence of SEQ ID NO: 339.

In a further embodiment of the invention, fragments of the antibody having binding specificity to TNF-α comprise, or alternatively consist of, one or more of the polypeptide sequences of SEQ ID NO: 340; SEQ ID NO: 341; and SEQ ID NO: 342 which correspond to the complementarity-determining regions (CDRs, or hypervariable regions) of the variable light chain sequence of SEQ ID NO: 338.

In a further embodiment of the invention, fragments of the antibody having binding specificity to TNF-α comprise, or alternatively consist of, one or more of the polypeptide sequences of SEQ ID NO: 343; SEQ ID NO: 344; and SEQ ID NO: 345 which correspond to the complementarity-determining regions (CDRs, or hypervariable regions) of the variable heavy chain sequence of SEQ ID NO: 339.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 338; the variable heavy chain region of SEQ ID NO: 339; the complementarity-determining regions (SEQ ID NO: 340; SEQ ID NO: 341; and SEQ ID NO: 342) of the variable light chain region of SEQ ID NO: 338; and the complementarity-determining regions (SEQ ID NO: 343; SEQ ID NO: 344; and SEQ ID NO: 345) of the variable heavy chain region of SEQ ID NO: 339.

In a preferred embodiment of the invention, the anti-TNF-α antibody is Ab22, comprising SEQ ID NO: 338 and SEQ ID NO: 339, and having at least one of the biological activities set forth herein.

In another embodiment, the invention includes antibodies having binding specificity to TNF-α and possessing a variable light chain sequence comprising the sequence set forth below:

```
                                          (SEQ ID NO: 354)
MDTRAPTQLLGLLLLWLPGARCADIVMTQTPASVSEPVGGTVTIKCQASQ

SIYRYLSWYHHKPGQPPKLLIYGASNLESGVPSRFKGSGSGTEYTLTISD

LECDDAATYYCQSNYGANSDSYGDA
```

The invention also includes antibodies having binding specificity to TNF-α and possessing a variable heavy chain sequence comprising the sequence set forth below:

```
                                          (SEQ ID NO: 355)
METGLRWLLLVAVLKGVQCQEQLEESGGDLVKPGASLTLTCKASGFSFSS

GYYMGWVRQAPGKGLQYIGYIDYGGSAYYASWAKGRFTISKTSSTTVTLQ

MTSLTAADTATFFCTRRDYTGGVVRGLDL.
```

The invention further contemplates antibodies comprising one or more of the polypeptide sequences of SEQ ID NO: 356; SEQ ID NO: 357; and SEQ ID NO: 358 which correspond to the complementarity-determining regions (CDRs, or hypervariable regions) of the variable light chain sequence of SEQ ID NO: 354, and/or one or more of the polypeptide sequences of SEQ ID NO: 359; SEQ ID NO: 360; and SEQ ID NO: 361 which correspond to the complementarity-determining regions (CDRs, or hypervariable regions) of the variable heavy chain sequence of SEQ ID NO: 355, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 356; SEQ ID NO: 357; and SEQ ID NO: 358 which correspond to the complementarity-determining regions (CDRs, or hypervariable regions) of the variable light chain sequence of SEQ ID NO: 354, and/or one or more of the polypeptide sequences of SEQ ID NO: 359; SEQ ID NO: 360; and SEQ ID NO: 361 which correspond to the complementarity-determining regions (CDRs, or hypervariable regions) of the variable heavy chain sequence of SEQ ID NO: 355, or combinations of these polypeptide sequences. In another embodiment of the invention, the antibodies of the invention include combinations of the CDRs and the variable heavy and light chain sequences set forth above.

The invention also, contemplates fragments of the antibody having binding specificity to TNF-α. In one embodiment of the invention, antibody fragments of the invention comprise, or alternatively consist of, the polypeptide sequence of SEQ ID NO: 354. In another embodiment of the invention, antibody fragments of the invention comprise, or alternatively consist of, the polypeptide sequence of SEQ ID NO: 355.

In a further embodiment of the invention, fragments of the antibody having binding specificity to TNF-α comprise, or alternatively consist of, one or more of the polypeptide sequences of SEQ ID NO: 356; SEQ ID NO: 357; and SEQ ID NO: 358 which correspond to the complementarity-determining regions (CDRs, or hypervariable regions) of the variable light chain sequence of SEQ ID NO: 354.

In a further embodiment of the invention, fragments of the antibody having binding specificity to TNF-α comprise, or alternatively consist of, one or more of the polypeptide sequences of SEQ ID NO: 359; SEQ ID NO: 360; and SEQ ID NO: 361 which correspond to the complementarity-determining regions (CDRs, or hypervariable regions) of the variable heavy chain sequence of SEQ ID NO: 355.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 354; the variable heavy chain region of SEQ ID NO: 355; the complementarity-determining regions (SEQ ID NO: 356; SEQ ID NO: 357; and SEQ ID NO: 358) of the variable light chain region of SEQ ID NO: 354; and the complementarity-determining regions (SEQ ID NO: 359; SEQ ID NO: 360; and SEQ ID NO: 361) of the variable heavy chain region of SEQ ID NO: 355.

In a preferred embodiment of the invention, the anti-TNF-α antibody is Ab23, comprising SEQ ID NO: 354 and SEQ ID NO: 355, and having at least one of the biological activities set forth herein.

In another embodiment, the invention includes antibodies having binding specificity to TNF-α and possessing a variable light chain sequence comprising the sequence set forth below:

(SEQ ID NO: 370)
MDTRAPTQLLGLLLLWLPGARCADIVMTQTPSSVSAAVGGTVTINCQASQ

NIYSSLAWYQQKPGQPPKLLIFGASNLESGVPSRFKGSGSGTEFTLTISD

LECADAAAYYCQSHHGSNSDSYGNA

The invention also includes antibodies having binding specificity to TNF-α and possessing a variable heavy chain sequence comprising the sequence set forth below:

(SEQ ID NO: 371)
METGLRWLLLVAVLKGVQCQSVEESGGRLVTPGTPLTLTCTASGFSLNNY

YMTWVRQAPGKGLESIGYFASGGGTYYANWAKGRFTISKTSTTVDLKITS

PTTDDTATYFCARGGAYLGTGSL.

The invention further contemplates antibodies comprising one or more of the polypeptide sequences of SEQ ID NO: 372; SEQ ID NO: 373; and SEQ ID NO: 374 which correspond to the complementarity-determining regions (CDRs, or hypervariable regions) of the variable light chain sequence of SEQ ID NO: 370, and/or one or more of the polypeptide sequences of SEQ ID NO: 375; SEQ ID NO: 376; and SEQ ID NO: 377 which correspond to the complementarity-determining regions (CDRs, or hypervariable regions) of the variable heavy chain sequence of SEQ ID NO: 371, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 372; SEQ ID NO: 373; and SEQ ID NO: 374 which correspond to the complementarity-determining regions (CDRs, or hypervariable regions) of the variable light chain sequence of SEQ ID NO: 370, and/or one or more of the polypeptide sequences of SEQ ID NO: 375; SEQ ID NO: 376; and SEQ ID NO: 377 which correspond to the complementarity-determining regions (CDRs, or hypervariable regions) of the variable heavy chain sequence of SEQ ID NO: 371, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 370. In another embodiment of the invention, antibody fragments of the invention comprise, or alternatively consist of, the polypeptide sequence of SEQ ID NO: 371.

In a further embodiment of the invention, fragments of the antibody having binding specificity to TNF-α comprise, or alternatively consist of, one or more of the polypeptide sequences of SEQ ID NO: 372; SEQ ID NO: 373; and SEQ ID NO: 374 which correspond to the complementarity-determining regions (CDRs, or hypervariable regions) of the variable light chain sequence of SEQ ID NO: 370.

In a further embodiment of the invention, fragments of the antibody having binding specificity to TNF-α comprise, or alternatively consist of, one or more of the polypeptide sequences of SEQ ID NO: 375; SEQ ID NO: 376; and SEQ ID NO: 377 which correspond to the complementarity-determining regions (CDRs, or hypervariable regions) of the variable heavy chain sequence of SEQ ID NO: 371.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 370; the variable heavy chain region of SEQ ID NO: 371; the complementarity-determining regions (SEQ ID NO: 372; SEQ ID NO: 373; and SEQ ID NO: 374) of the variable light chain region of SEQ ID NO: 370; and the complementarity-determining regions (SEQ ID NO: 375; SEQ ID NO: 376; and SEQ ID NO: 377) of the variable heavy chain region of SEQ ID NO: 371.

In a preferred embodiment of the invention, the anti-TNF-α antibody is Ab24, comprising SEQ ID NO: 370 and SEQ ID NO: 371, and having at least one of the biological activities set forth herein.

In another embodiment, the invention includes antibodies having binding specificity to TNF-α and possessing a variable light chain sequence comprising the sequence set forth below:

(SEQ ID NO: 386)
MDTRAPTQLLGLLLLWLPGARCADIVMTQTPSSVSVPVGGTVTIKCQAS

QNIYSSLAWYQQKPGQPPKRLIYYAATLASGVPSRFKGSGSGTDFTLTI

SDLECADAATYYCQSNHGSNSDSYGNP

The invention also includes antibodies having binding specificity to TNF-α and possessing a variable heavy chain sequence comprising the sequence set forth below:

(SEQ ID NO: 387)
METGLRWLLLVAVLKGVQCQSVEESGGRLVTPGTPLTLTCTVAGFSLST

YGVTWVRQAPGKGLESIGYITYGNIKYYATWAKGRFTISKTSTTVDLKM

TSPTTEDTATYFCTRYGGSGIGEDL.

The invention further contemplates antibodies comprising one or more of the polypeptide sequences of SEQ ID NO: 388; SEQ ID NO: 389; and SEQ ID NO: 390 which correspond to the complementarity-determining regions (CDRs, or hypervariable regions) of the variable light chain sequence of SEQ ID NO: 386, and/or one or more of the polypeptide sequences of SEQ ID NO: 391; SEQ ID NO: 392; and SEQ ID NO: 393 which correspond to the complementarity-determining regions (CDRs, or hypervariable regions) of the variable heavy chain sequence of SEQ ID NO: 387, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 388; SEQ ID NO: 389; and SEQ ID NO: 390 which correspond to the complementarity-determining regions (CDRs, or hypervariable regions) of the variable light chain sequence of SEQ ID NO: 386, and/or one or more of the polypeptide sequences of SEQ ID NO: 391; SEQ ID NO: 392; and SEQ ID NO: 393 which correspond to the complementarity-determining regions (CDRs, or hypervariable regions) of the variable heavy chain sequence of SEQ ID NO: 387, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 386. In another embodiment of the invention, antibody fragments of the invention comprise, or alternatively consist of, the polypeptide sequence of SEQ ID NO: 387.

In a further embodiment of the invention, fragments of the antibody having binding specificity to TNF-α comprise, or alternatively consist of, one or more of the polypeptide sequences of SEQ ID NO: 388; SEQ ID NO: 389; and SEQ ID NO: 390 which correspond to the complementarity-determining regions (CDRs, or hypervariable regions) of the variable light chain sequence of SEQ ID NO: 386.

In a further embodiment of the invention, fragments of the antibody having binding specificity to TNF-α comprise, or alternatively consist of, one or more of the polypeptide sequences of SEQ ID NO: 391; SEQ ID NO: 392; and SEQ ID NO: 393 which correspond to the complementarity-determining regions (CDRs, or hypervariable regions) of the variable heavy chain sequence of SEQ ID NO: 387.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 386; the variable heavy chain region of SEQ ID NO: 387; the complementarity-determining regions (SEQ ID NO: 388; SEQ ID NO: 389; and SEQ ID NO: 390) of the variable light chain region of SEQ ID NO: 386; and the complementarity-determining regions (SEQ ID NO: 391; SEQ ID NO: 392; and SEQ ID NO: 393) of the variable heavy chain region of SEQ ID NO: 387.

In a preferred embodiment of the invention, the anti-TNF-α antibody is. Ab25, comprising SEQ ID NO: 386 and SEQ ID NO: 387, and having at least one of the biological activities set forth herein.

In another embodiment, the invention includes antibodies having binding specificity to TNF-α and possessing a variable light chain sequence comprising the sequence set forth below:

```
                                        (SEQ ID NO: 402)
MDTRAPTQLLGLLLLWLPGARCADVVMTQTPSSVSEPVGGTVTIKCQAS

ETIGNYLSWYQQKPGQPPKRLIYYASTLSSGVPSRFKGSGSGTDFTLTI

SDLECADAATYYCQKNYGSGASSLGA
```

The invention also includes antibodies having binding specificity to TNF-α and possessing a variable heavy chain sequence comprising the sequence set forth below:

```
                                        (SEQ ID NO: 403)
METGLRWLLLVAVLKGVQCQSVEESGGRLVTPGTPLTLTCTVSGFSLSS

YYMAWVRQAPGKGLEWIGYIGFGGSTYYATWAKGRVTISRTSTTVDLQI

TSPTTEDTATYFCARGVYGDFRTGADL.
```

The invention further contemplates antibodies comprising one or more of the polypeptide sequences of SEQ ID NO: 404; SEQ ID NO: 405; and SEQ ID NO: 406 which correspond to the complementarity-determining regions (CDRs, or hypervariable regions) of the variable light chain sequence of SEQ ID NO: 402, and/or one or more of the polypeptide sequences of SEQ ID NO: 407; SEQ ID NO: 408; and SEQ ID NO: 409 which correspond to the complementarity-determining regions (CDRs, or hypervariable regions) of the variable heavy chain sequence of SEQ ID NO: 403, or combinations of these polypeptide sequences. In another embodiment of the invention, the antibodies of the invention include combinations of the CDRs and the variable heavy and light chain sequences set forth above.

In another embodiment, the invention contemplates other antibodies, such as for example chimeric antibodies, comprising one or more of the polypeptide sequences of SEQ ID NO: 404; SEQ ID NO: 405; and SEQ ID NO: 406 which correspond to the complementarity-determining regions (CDRs, or hypervariable regions) of the variable light chain sequence of SEQ ID NO: 402, and/or one or more of the polypeptide sequences of SEQ ID NO: 407; SEQ ID. NO: 408; and SEQ ID NO: 409 which correspond to the complementarity-determining regions (CDRs, or hypervariable regions) of the variable heavy chain sequence of SEQ ID NO: 403, or combinations of these polypeptide sequences. In another embodiment of the invention, the antibodies of the invention include combinations of the CDRs and the variable heavy and light chain sequences set forth above.

The invention also contemplates fragments of the antibody having binding specificity to TNF-α. In one embodiment of the invention, antibody fragments of the invention comprise, or alternatively consist of, the polypeptide sequence of SEQ ID NO: 402. In another embodiment of the invention, antibody fragments of the invention comprise, or alternatively consist of, the polypeptide sequence of SEQ ID NO: 403.

In a further embodiment of the invention, fragments of the antibody having binding specificity to TNF-α comprise, or alternatively consist of, one or more of the polypeptide sequences of SEQ ID NO: 404; SEQ ID NO: 405; and SEQ ID NO: 406 which correspond to the complementarity-determining regions (CDRs, or hypervariable regions) of the variable light chain sequence of SEQ ID NO: 402.

In a further embodiment of the invention, fragments of the antibody having binding specificity to TNF-α comprise, or alternatively consist of, one or more of the polypeptide sequences of SEQ ID NO: 407; SEQ ID NO: 408; and SEQ ID NO: 409 which correspond to the complementarity-determining regions (CDRs, or hypervariable regions) of the variable heavy chain sequence of SEQ ID NO: 403.

The invention also contemplates antibody fragments which include one or more of the antibody fragments described herein. In one embodiment of the invention, fragments of the antibodies having binding specificity to TNF-α comprise, or alternatively consist of, one, two, three or more, including all of the following antibody fragments: the variable light chain region of SEQ ID NO: 402; the variable heavy chain region of SEQ ID NO: 403; the complementarity-determining regions (SEQ ID NO: 404; SEQ ID NO: 405; and SEQ ID NO: 406) of the variable light chain region of SEQ ID NO: 402; and the complementarity-determining regions (SEQ ID NO: 407; SEQ ID NO: 408; and SEQ ID NO: 409) of the variable heavy chain region of SEQ ID NO: 403.

In a preferred embodiment of the invention, the anti-TNF-α antibody is Ab26, comprising SEQ ID NO: 402 and SEQ ID NO: 403, and having at least one of the biological activities set forth herein.

Such antibody fragments may be present in one or more of the following non-limiting forms: Fab, Fab', F(ab')₂; Fv and single chain Fv antibody forms. In a preferred embodiment, the anti-TNF-α antibodies described herein further comprises the kappa constant light chain sequence comprising the sequence set forth below:

```
                                    (SEQ ID NO: 418)
VAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTK

SFNRGEC.
```

In another preferred embodiment, the anti-TNF-α antibodies described herein further comprises and the gamma-1 constant heavy chain polypeptide sequence comprising the sequence set forth below:

```
                                    (SEQ ID NO: 420)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKRV

EPKSCDKTHTCPPCPAPELLGGPSVFLFPPKPKDTLMISRTPEVTCVVV

DVSHEDPEVKFNWYVDGVEVHNAKTKPREEQYASTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPGK.
```

In another embodiment, the invention contemplates an isolated anti-TNF-α antibody comprising a $V_H$ polypeptide sequence selected from the group consisting of: SEQ ID NO: 3, 19, 35, 51, 67, 83, 99, 115, 131, 147, 163, 179, 195, 211, 227, 243, 259, 275, 291, 307, 323, 339, 355, 371, 387 and SEQ ID NO: 403; and further comprising a $V_L$ polypeptide sequence selected from the group consisting of: SEQ ID NO: 2, 18, 34, 50, 66, 82, 98, 114, 130, 146, 162, 178, 194, 210, 226, 242, 258, 274, 290, 306, 322, 338, 354, 370, 386 and SEQ ID NO: 402 or a variant thereof, wherein one or more of the framework residues (FR residues) in said $V_H$ or $V_L$ polypeptide has been substituted with another amino acid residue resulting in an anti-TNF-α antibody that specifically binds TNF-α. The invention contemplates humanized and chimeric forms of these antibodies. The chimeric antibodies may include an Fc derived from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant regions.

In one embodiment of the invention, the antibodies or $V_H$ or $V_L$ polypeptides originate or are selected from one or more rabbit B cell populations prior to initiation of the humanization process referenced herein.

In another embodiment of the invention, the anti-TNF-α antibodies and fragments thereof have binding specificity for primate homologs of the human TNF-α protein. Non-limiting examples of primate homologs of the human TNF-α protein are TNF-α obtained from *Macaca fascicularis* (also known as the cynomolgus monkey) and the Rhesus monkey. In another embodiment of the invention, the anti-TNF-α antibodies and fragments thereof do not have binding specificity for TNF-R, either p55 TNF-R and/or p75 TNF-R. In a further embodiment of the invention, the anti-TNF-α antibodies and fragments thereof inhibit the association of TNF-α with TNF-R, either p55 TNF-R and/or p75 TNF-R. In another embodiment of the invention, the anti-TNF-α antibodies and fragments thereof inhibit the association of TNF-α with TNF-R and/or multimers thereof and/or antagonizes the biological effects thereof.

As stated in paragraph 61 herein, antibodies and fragments thereof may be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Regarding detectable moieties, further exemplary enzymes include, but are not limited to, horseradish peroxidase, acetylcholinesterase, alkaline phosphatase, beta-galactosidase and luciferase. Further exemplary fluorescent-materials include, but are not limited to, rhodamine, fluorescein, fluorescein isothiocyanate, umbelliferone, dichlorotriazinylamine, phycoerythrin and dansyl chloride. Further exemplary chemiluminescent moieties include, but are not limited to, luminol. Further exemplary bioluminescent materials include, but are not limited to, luciferin and aequorin. Further exemplary radioactive materials include, but are not limited to, Iodine 125 ($^{125}$I), Carbon 14 ($^{14}$C), Sulfur 35 ($^{35}$S), Tritium ($^{3}$H) and Phosphorus 32 ($^{32}$P).

Regarding functional moieties, exemplary cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (taxol), ricin, pseudomonas exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine and bleomycin. Toxic enzymes from plants and bacteria such as ricin, diphtheria toxin and *Pseudomonas* toxin may be conjugated to the humanized antibodies, or binding fragments thereof, to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the antibody, or binding fragments thereof, with or without the use of a complex-forming agent. Such radionuclides include beta-emitters such as Phosphorus-32 ($^{32}$P), Scandium-47 ($^{47}$Sc), Copper-67 ($^{67}$Cu), Gallium-67 ($^{67}$Ga), Yttrium-88 ($^{88}$Y), Yttrium-90 ($^{90}$Y), Iodine-125 ($^{125}$I), Iodine-131 ($^{131}$I), Samarium-153 ($^{153}$Sm), Lutetium-177 ($^{177}$Lu), Rhenium-186 ($^{186}$Re) or Rhenium-188 ($^{188}$Re), and alpha-emitters such as Astatine-211 ($^{211}$At), Lead-212 ($^{212}$Pb), Bismuth-212 ($^{212}$Bi) or -213 ($^{213}$Bi) or Actinium-225 ($^{225}$Ac).

Methods are known in the art for conjugating an antibody or binding fragment thereof to a detectable moiety and the like, such as for example those methods described by Hunter et al, Nature 144:945 (1962); David et al, Biochemistry 13:1014 (1974); Pain et al, J. Immunol. Meth. 40:219 (1981); and Nygren, J., Histochem. and Cytochem. 30:407 (1982).

Embodiments described herein further include variants and equivalents that are substantially homologous to the antibodies, antibody fragments, diabodies, SMIPs, camelbodies, nanobodies, IgNAR, polypeptides, variable regions and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid. What is intended by a conservative amino acid substitution is well known in the art.

In another embodiment, the invention contemplates polypeptide sequences having at least 90% or greater sequence homology to any one or more of the polypeptide sequences of antibody fragments, variable regions and CDRs set forth herein. More preferably, the invention contemplates polypeptide sequences having at least 95% or greater sequence homology, even more preferably at least 98% or greater sequence homology, and still more preferably at least 99% or greater sequence homology to any one or more of the polypeptide sequences of antibody fragments, variable regions and CDRs set forth herein. Methods for determining homology between nucleic acid and amino acid sequences are well known to those of ordinary skill in the art.

In another embodiment, the invention further contemplates the above-recited polypeptide homologs of the antibody fragments, variable regions and CDRs set forth herein further having anti-TNF-α activity. Non-limiting examples of anti-TNF-α activity are set forth herein.

In another embodiment, the invention further contemplates the generation and use of anti-idiotypic antibodies that bind any of the foregoing sequences. In an exemplary embodiment, such an anti-idiotypic antibody could be administered to a subject who has received an anti-TNF-α antibody to modulate, reduce, or neutralize, the effect of the anti-TNF-α antibody. Such anti-idiotypic antibodies could also be useful for treatment of an autoimmune disease characterized by the presence of anti-TNF-α antibodies. A further exemplary use of such anti-idiotypic antibodies is for detection of the anti-TNF-α antibodies of the present invention, for example to monitor the levels of the anti-TNF-α antibodies present in a subject's blood or other bodily fluids.

The present invention also contemplates anti-TNF-α antibodies comprising any of the polypeptide or polynucleotide sequences described herein substituted for any of the other polynucleotide sequences described herein. For example, without limitation thereto, the present invention contemplates antibodies comprising the combination of any of the variable light chain and variable heavy chain sequences described herein, and further contemplates antibodies resulting from substitution of any of the CDR sequences described herein for any of the other CDR sequences described herein.

Additional Exemplary Embodiments of the Invention

In another embodiment, the invention contemplates one or more anti-human TNF-α antibodies or antibody fragment which specifically bind to the same linear or conformational epitope(s) and/or competes for binding to the same linear or conformational epitope(s) on an intact human TNF-α polypeptide or fragment thereof as an anti-human TNF-α antibody selected from the group consisting of Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, and Ab26. In a preferred embodiment, the anti-human TNF-α antibody or fragment specifically binds to the same linear or conformational epitope(s) and/or competes for binding to the same linear or conformational epitope(s) on an intact human TNF-α polypeptide or a fragment thereof as Ab1 or Ab16.

In another embodiment of the invention, the anti-human TNF-α antibody which specifically binds to the same linear or conformational epitopes on an intact TNF-α polypeptide or fragment thereof that is (are) specifically bound by Ab1 binds to a TNF-α epitope(s) ascertained by epitopic mapping using overlapping linear peptide fragments which span the full length of the native human TNF-α polypeptide. In one embodiment of the invention, the TNF-α epitope comprises, or alternatively consists of, one or more residues comprised in TNF-α fragments selected from those respectively encompassing amino acid residues 118-126.

The invention is also directed to an anti-TNF-α antibody that binds with the same TNF-α epitope and/or competes with an anti-TNF-α antibody for binding to TNF-α as an antibody or antibody fragment disclosed herein, including but not limited to an anti-TNF-α antibody selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, and Ab26.

In another embodiment, the invention is also directed to an isolated anti-TNF-α antibody or antibody fragment comprising one or more of the CDRs contained in the V$_H$ polypeptide sequences selected from the group consisting of: SEQ ID NO: 3, 19, 35, 51, 67, 83, 99, 115, 131, 147, 163, 179, 195, 211, 227, 243, 259, 275, 291, 307, 323, 339, 355, 371, 387 and SEQ ID NO: 403 and/or one or more of the CDRs contained in the V$_L$ polypeptide sequence consisting of: SEQ ID NO: 2, 18, 34, 50, 66, 82, 98, 114, 130, 146, 162, 178, 194, 210, 226, 242, 258, 274, 290, 306, 322, 338, 354, 370, 386 and SEQ ID NO: 402.

In one embodiment of the invention, the anti-human TNF-α antibody discussed in the two prior paragraphs comprises at least 2 complementarity determining regions (CDRs) in each the variable light and the variable heavy regions which are identical to those contained in an anti-human TNF-α antibody selected from the group consisting of Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, and Ab26.

In a preferred embodiment, the anti-human TNF-α antibody discussed above comprises at least 2 complementarity determining regions (CDRs) in each the variable light and the variable heavy regions which are identical to those contained in Ab1 or Ab16. In another embodiment, all of the CDRs of the anti-human TNF-α antibody discussed above are identical to the CDRs contained in an anti-human TNF-α antibody selected from the group consisting of Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, and Ab26. In a preferred embodiment of the invention, all of the CDRs of the anti-human TNF-α antibody discussed above are identical to the CDRs contained in Ab1 or Ab16.

The invention further contemplates that the one or more anti-human TNF-α antibodies discussed above are aglycosylated; that contain an Fc region that has been modified to alter effector function, half-life, proteolysis, and/or glycosylation; are human, humanized, single chain or chimeric; and are a humanized antibody derived from a rabbit (parent) anti-human TNF-α antibody.

The invention further contemplates one or more anti-human TNF-α antibodies wherein the framework regions (FRs) in the variable light region and the variable heavy regions of said antibody respectively are human FRs which are unmodified or which have been modified by the substitution of at most 2 or 3 human FR residues in the variable light or heavy chain region with the corresponding FR residues of the parent rabbit antibody, and wherein said human FRs have been derived from human variable heavy and light chain antibody sequences which have been selected from a library of human germline antibody sequences based on their high level of homology to the corresponding rabbit variable heavy or light chain regions relative to other human germline antibody sequences contained in the library.

In one embodiment of the invention, the anti-human TNF-α antibody or fragment specifically binds to TNF-α expressing human cells and/or to circulating soluble TNF-α molecules in vivo, including TNF-α expressed on or by human cells in a patient with a disease associated with cells that express TNF-α.

In another embodiment, the disease is selected from Rheumatoid Arthritis, Psoriatic Arthropathy, Ankylosing Spondylitis, Juvenile Rheumatoid Arthritis, Still's Disease, Systemic Lupus Erythematosis, Sjogren's Disease, Mixed Connective Tissue Disorder, Polymyalgia Rheumatica, Giant Cell Arteritis, Wegener's Granulomatosis, Kawasaki's disease, Autoimmune vasculitis, Autoimmune Uveitis, Inflammatory Bowel Disease, Bechet's Disease, Psoriasis, Graves Disease, Hashimoto's thyroiditis, Asthma, Type 1 Diabetes, Type 2 Diabetes, Ischemic Heart Disease, Peripheral Vascular Disease, Stroke, Pyoderma gangrenosum, Sarcoidosis, Dercum's disease, toxic epidermal necrolysis, idiopathic uveitis or scleritis, birdshot retinochoroiditis, uveitic and diabetic cystoid macular edema, age-related macular degeneration, Pulmonary fibrosis, Chronic Obstructive Pulmonary Disease, Depression, Schizophrenia, Alzheimer's Disease, Vascular Dementia, glomerulonephritis, atherosclerosis, restenosis, autoimmune diseases, Crohn's disease, graft v. host (GVH) reactions (including organ transplant rejection), septic shock, cachexia, anorexia, multiple sclerosis, gram negative sepsis, endotoxic shock, neoplastic diseases, including breast cancer, ovarian cancer, bladder cancer, lung cancer, thyroid cancer, glioblastoma, stomach cancer, endometrial cancer, kidney cancer, colon and colorectal cancer, pancreatic cancer and prostate cancer, uveitis (e.g., childhood and seronegative), lupus and other diseases mediated by immune complexes such as pemphigus and glomerulonephritis, congenital hyperthyroidism (CH), delayed type hypersensitivity (DTH) such as contact hypersensitivity, sarcoidosis, chronic arthritis, adult still disease, scleroderma, giant cell arteritis, SAPHO syndrome, primary biliary cirrhosis (PBC), myelodysplastic syndromes, vasculitis, hematologic malignancies, cochleovestibular disorders, macrophage activation syndrome, interstitial lung disease, Hepatitis C, ovulation induction, and myelodysplastic syndromes. In a preferred embodiment, the disease is selected from a cancer, inflammatory disorder, or autoimmune disorder. In a particularly preferred embodiment, the disease is rheumatoid arthritis.

The invention further contemplates anti-human TNF-α antibodies or fragments directly or indirectly attached to a detectable label or therapeutic agent.

The invention also contemplates one or more nucleic acid sequences which result in the expression of an anti-human TNF-α antibody or antibody fragment as set forth above, including those comprising, or alternatively consisting of, yeast or human preferred codons. The invention also contemplates vectors (including plasmids or recombinant viral vectors) comprising said nucleic acid sequence(s). The invention also contemplates host cells or recombinant host cells expressing at least one of the antibodies set forth above, including a mammalian, yeast, bacterial, and insect cells. In a preferred embodiment, the host cell is a yeast cell. In a further preferred embodiment, the yeast cell is a diploidal yeast cell. In a more preferred embodiment, the yeast cell is a *Pichia* yeast.

The invention also contemplates a method of treatment comprising administering to a patient with a disease or condition associated with TNF-α expressing cells a therapeutically effective amount of at least one anti-human TNF-α antibody or fragment. The diseases that may be treated are presented in the non-limiting list set forth above. In a preferred embodiment, the disease is selected from a cancer, inflammatory disorder, or autoimmune disorder. In a particularly preferred embodiment, the disease is rheumatoid arthritis. In another embodiment the treatment further includes the administration of another therapeutic agent or regimen selected from chemotherapy, radiotherapy, cytokine administration or gene therapy.

The invention further contemplates a method of in vivo imaging which detects the presence of cells which express TNF-α comprising administering a diagnostically effective amount of at least one anti-human TNF-α antibody. In one embodiment, said administration further includes the administration of a radionuclide or fluorophore that facilitates detection of the antibody at TNF-α expressing disease sites. In another embodiment of the invention, the method of in vivo imaging is used to detect TNF-α expressing tumors or metastases or is used to detect the presence of sites of autoimmune disorders associated with TNF-α expressing cells. In a further embodiment, the results of said in vivo imaging method are used to facilitate design of an appropriate therapeutic regimen, including therapeutic regimens including radiotherapy, chemotherapy or a combination thereof.

Polynucleotides Encoding Anti-TNF Antibody Polypeptides

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 2:

(SEQ ID NO: 10)
ATGGACACGAGGGCCCCCACTCAGCTGCTGGGGCTCCTACTGCTCTGGC

TCCCAGGTGCCAGATGTGCTGACATTGTGATGACCCAGACTCCAGCCTC

CGTGGAGGCAGCTGTGGGAGGCACAGTCACCATCAAGTGCCAGGCCAGT

CAGAACATTCGCAGTTGGTTAGCCTGGTATCAGCAGAAACCAGGGCAGC

CTCCCAAGCTCCTGATCTATGGTGCATCCACTCTGGCATCTGGGGTCCC

ATCGCGATTCCAAGGCAGTGGATCTGGGACAGAGTACACTCTCACCATC

ATCGACCTGGACTGTGCCGATGCTGCCACTTACTACTGTCAAAGCAATT

ATGGTAGTAATGATAATAGTTATGGTAATGGT

In another embodiment of the invention, polynucleotides of the invention comprise, or alternatively consist of, the following polynucleotide sequence encoding the variable heavy chain polypeptide sequence of SEQ ID NO: 3:

(SEQ ID NO: 11)
ATGGAGACTGGGCTGCGCTGGCTTCTCCTGGTCGCTGTGCTCAAAGGTG

TCCAGTGTCAGTCGGTGGAGGAGTCCGGGGGTCGCCTGGTCACGCCTGG

GACACCCCTGACACTCACCTGCACAGTCTCTGGATTCTCCCTCAGTACC

TACAACATGGGCTGGGTCCGCCAGGCTCCAGGGAAGGGGCTGGAATACA

TCGGATACGTGTTGGGAAGTGGTATCACATACTACGCGAGCTGGGCAAA

AGGCCGATTCACCATCTCCAAAACCTCGACCACGGTGGATCTGGAGATC

ACTAGTCCGACAACCGAGGACACGGCCACCTATTTCTGTGCCAGAGATG

CTGGTGGCAGAGCTTCCTTG.

In a further embodiment of the invention, polynucleotides encoding fragments of the antibody having binding specificity to TNF-α comprise, or alternatively consist of, one or more of the polynucleotide sequences of SEQ ID NO: 12; SEQ ID NO: 13; and SEQ ID NO: 14 which correspond to polynucleotides encoding the complementarity-determining regions (CDRs, or hypervariable regions) of the light chain variable sequence of SEQ ID NO: 2.

In a further embodiment of the invention, polynucleotides encoding fragments of the antibody having binding specificity to TNF-α comprise, or alternatively consist of, one or more of the polynucleotide sequences of SEQ ID NO: 15; SEQ ID NO: 16; and SEQ ID NO: 17 which correspond to polynucleotides encoding the complementarity-determining regions (CDRs, or hypervariable regions) of the heavy chain variable sequence of SEQ ID NO: 3.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 10 encoding the light chain variable region of SEQ ID NO: 2; the polynucleotide SEQ ID NO: 11 encoding the heavy chain variable region of SEQ ID NO: 3; polynucleotides encoding the complementarity-determining regions (SEQ ID NO: 12; SEQ ID NO: 13; and SEQ ID NO: 14) of the light chain variable region of SEQ ID NO: 2; and polynucleotides encoding the complementarity-determining regions (SEQ ID NO: 15; SEQ ID NO: 16; and SEQ ID NO: 17) of the heavy chain variable region of SEQ ID NO: 3.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 18:

(SEQ ID NO: 26)
ATGGACACGAGGGCCCCCACTCAGCTGCTGGGGCTCCTGCTGCTCTGGC

TCCCAGGTGCCAGATGTGCTGACATTGTGATGACCCAGACTCCATCCTC

CGTGTCTGAACCTGTGCGAGGCACAGTCACCATCAAGTGCCAGGCCAGT

CAGAACATTTACAGCTACTTGTCCTGGTATCAACAGAGCCCAGGGCAGC

CTCCCAAGCTCCTGATCTACAAGGCATCCACTCTGGCATCTGGGGTCCC

ATCGCGGTTCAAAGGCAGTGGATCTGGGACAGATTTCACTCTCACCATC

AGCGACCTGGAGTGTGCCGATGCTGCCACTTACTACTGTCAATCCAATT

ATGGTAGTGATAGTGATAGTTTTGGGAATGCT

In another embodiment of the invention, polynucleotides of the invention comprise, or alternatively consist of, the following polynucleotide sequence encoding the variable heavy chain polypeptide sequence of SEQ ID NO: 19:

(SEQ ID NO: 27)
ATGGAGACTGGGCTGCGCTGGCTTCTCCTGGTCGCTGTGCTCAAAGGTG

TCCAGTGTCAGTCGGTGGAGGAGTCCGGGGGTCGCCTGGTCACGCCTGG

GACACCCCTGACACTCACCTGCTCAGTCTCTGGATTCTCCCTCAATAAT

TATGTAATGGGCTGGGTCCGCCAGGCTCCAGGGAAGGGGCTGGAATTCA

TCGGATACATTGCTTTTGGTATTGGCCCATACTACGCGAGCTGGGCGAA

AGGCCGATTCACCATCTCCAGCACCTCGTCGACCACGGTGGATCTGAAA

ATGACCAGTCTGACACCCGAGGACACGGCCACCTATTTCTGTGCCAGAG

GTGATTATAGTGGTAATGACATT.

In a further embodiment of the invention, polynucleotides encoding fragments of the antibody having binding specificity to TNF-α comprise, or alternatively consist of, one or more of the polynucleotide sequences of SEQ ID NO: 28; SEQ ID NO 29; and SEQ ID NO: 30 which correspond to polynucleotides encoding the complementarity-determining regions (CDRs, or hypervariable regions) of the light chain variable sequence of SEQ ID NO: 18.

In a further embodiment of the invention, polynucleotides encoding fragments of the antibody having binding specificity to TNF-α comprise, or alternatively consist of, one or more of the polynucleotide sequences of SEQ ID NO: 31; SEQ ID NO: 32; and SEQ ID NO: 33 which correspond to polynucleotides encoding the complementarity-determining regions (CDRs, or hypervariable regions) of the heavy chain variable sequence of SEQ ID NO: 19.

The invention also contemplates polynucleotide sequences including one or more of the polynucleotide sequences encoding antibody fragments described, herein. In one embodiment of the invention, polynucleotides encoding fragments of the antibody-having binding specificity to TNF-α comprise, or alternatively consist of, one, two, three or more, including all of the following polynucleotides encoding antibody fragments: the polynucleotide SEQ ID NO: 26 encoding the light chain variable region of SEQ ID NO: 18; the polynucleotide SEQ ID NO: 27 encoding the heavy chain variable region of SEQ ID NO: 19; polynucleotides encoding the complementarity-determining regions (SEQ ID NO: 28; SEQ ID NO: 29; and SEQ ID NO: 30) of the light chain variable region of SEQ ID NO: 18; and polynucleotides encoding the complementarity-determining regions (SEQ ID NO: 31; SEQ ID NO: 32; and SEQ ID NO: 33) of the heavy chain variable region of SEQ ID NO: 19.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 34:

```
                                          (SEQ ID NO: 42)
ATGGACACGAGGGCCCCCACTCAGCTGCTGGGGCTCCTGCTGCTCTGGC

TCCCAGGTTCCACATTTGCCATCAAAGTGACCCAGACACCAGCCTCCGT

GTCTGCAGCTGTGGGAGGCACAGTCAGCATCAATTGCCAGGCCAGTGAG

GACATTGAAAGCTATTTGGCCTGGTATCAGCAGAAACCAGGGCAGCCTC

CCAAACTCCTTCTCTATGATGCATCCGCTCTGGCTTCTGGGGTCCCATC

GCGGTTCAAAGGCAGTGGATCTGGGACAGAGTACACTCTCACCATCAGC

GGCGTGGAGTGTGCCGATGCTGCCACTTACTACTGTCAACAGGGTTATA

GTTATAGTAATGTTGATAATTCT
```

In another embodiment of the invention, polynucleotides of the invention comprise, or alternatively consist of, the following polynucleotide sequence encoding the variable heavy chain polypeptide sequence of SEQ ID NO: 35:

```
                                          (SEQ ID NO: 43)
ATGGAGACTGGGCTGCGCTGGCTTCTCCTGGTCGCTGTGCTCAAAGGTG

TCCAGTGTCAGTCGGTGGAGGAGTCCGGGGGTCGCCTGGTCACGCCTGG

GACACCCCTGACACTCACCTGCAAAGTCTCTGGATTCTCCCTCAGCAGC

TACGACATGACCTGGGTCCGCCAGGCTCCAGGGAAGGGGCTGGAGTGGA
```

```
-continued
TCGGATACATTTGGAATGATGGTAGTACAGCCTACGCGAGCTGGGCGAC

AGGCCGATTCACCATCTCCAAAACCTCGACCACGGTGGATCTGAAAATC

GCCAGTCCGACAACCGAGGACACGGCCACCTATTTCTGTGCCAGAGGTC

CTGTTTTTGCGACTACTCTTGGGTACTACTTTACCATC.
```

In a further embodiment of the invention, polynucleotides encoding fragments of the antibody having binding specificity to TNF-α comprise, or alternatively consist of, one or more of the polynucleotide sequences of SEQ ID NO: 44; SEQ ID NO: 45; and SEQ ID NO: 46 which correspond to polynucleotides encoding the complementarity-determining regions (CDRs, or hypervariable regions) of the light chain variable sequence of SEQ ID. NO: 34.

In a further embodiment of the invention, polynucleotides encoding fragments of the antibody having binding specificity to TNF-α comprise, or alternatively consist of, one or more of the polynucleotide sequences of SEQ ID NO: 47; SEQ ID NO: 48; and SEQ ID NO: 49 which correspond to polynucleotides encoding the complementarity-determining regions (CDRs, or hypervariable regions) of the heavy chain variable sequence of SEQ ID NO: 35.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 42 encoding the light chain variable region of SEQ ID NO: 34; the polynucleotide SEQ ID NO: 43 encoding the heavy chain variable region of SEQ ID NO: 35; polynucleotides encoding the complementarity-determining regions (SEQ ID NO: 44; SEQ ID NO: 45; and SEQ ID NO: 46) of the light chain variable region of SEQ ID NO: 34; and polynucleotides encoding the complementarity-determining regions (SEQ ID NO: 47; SEQ ID NO: 48; and SEQ ID NO: 49) of the heavy chain variable region of SEQ ID NO: 35.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 50:

```
                                          (SEQ ID NO: 58)
ATGGACACGAGGGCCCCCACTCAGCTGCTGGGGCTCCTGCTGCTCTGGC

TCACAGGTGCCACATTTGCCGCCGTGCTGACCCAGACTCCATCTCCCGT

GTCTGCAGTTGTGGGAGGCACAGTCAGCATCAGTTGCCAGTCCAGCAAG

AGAGTTGTTAATAGCGTTGCCTTATCCTGGTATCAGCAGAAACCAGGGC

GCTCTCCTAAGCTCCTGATCTATTTTGCATCCAAACTGGCATCTGGGGT

CCCATCGCGGTTCAAAGGCAGTGGATCTGGGACACAGTTCACTCTCGCC

ATTAGCGACGTGCAGTGTGACGATGCTGCCACTTACTACTGTGCAGGCC

ATTATACTGATAGTGGTGATGATGCT
```

In another embodiment of the invention, polynucleotides of the invention comprise, or alternatively consist of, the following polynucleotide sequence encoding the variable heavy chain polypeptide sequence of SEQ ID NO: 51:

(SEQ ID NO: 59)
ATGGAGACTGGGCTGCGCTGGCTTCTCCTGGTCGCTGTGCTCAAAGGTG

TCCAGTGTCAGTCGGTGGAGGAGTCCGGGGGTCGCCTGGTCACGCCTGG

GACACCCCTGACACTCACCTGCACAGTCTCTGGATTATCCCTCAGTACC

GAGACAATTAACTGGGTCCGCCAGGCTCCAGGGAAGGGACTGGAGTGGA

TCGGATACATTGATAGTTCTGGTGGCACAGGCTACGCGAACTGGGCGAG

AGGCCGATTCACCATCTCCAAAACCTCGACCACGGTGGATTTGAAAATC

ACCAGTCCGACAACCGGGGACACGGCCACCTATTTCTGTGCCAGAGGAA

CTATTACTACTGGCATGAACATC.

In a further embodiment of the invention, polynucleotides encoding fragments of the antibody having binding specificity to TNF-α comprise, or alternatively consist of, one or more of the polynucleotide sequences of SEQ ID NO: 60; SEQ ID NO: 61; and SEQ ID NO: 62 which correspond to polynucleotides encoding the complementarity-determining regions (CDRs, or hypervariable regions) of the light chain variable sequence of SEQ ID NO: 50.

In a further embodiment of the invention, polynucleotides encoding fragments of the antibody having binding specificity to TNF-α comprise, or alternatively consist of, one or more of the polynucleotide-sequences of SEQ ID NO: 63; SEQ ID NO: 64; and SEQ ID NO: 65 which correspond to polynucleotides encoding the complementarity-determining regions (CDRs, or hypervariable regions) of the heavy chain variable sequence of SEQ ID NO: 51.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 58 encoding the light chain variable region of SEQ ID NO: 50; the polynucleotide SEQ ID NO: 59 encoding the heavy chain variable region of SEQ ID NO: 51; polynucleotides encoding the complementarity-determining regions (SEQ ID NO: 60; SEQ ID NO: 61; and SEQ ID NO: 62) of the light chain variable region of SEQ ID NO: 50; and polynucleotides encoding the complementarity-determining regions (SEQ ID NO: 63; SEQ ID NO: 64; and SEQ ID NO: 65) of the heavy chain variable region of SEQ ID NO: 51.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 66:

(SEQ ID NO: 74)
ATGGACACGAGGGCCCCCACTCAGCTGCTGGGGCTCCTGCTGCTCTGGC

TCCCAGGTGCCACACTTGCGCAAGTGGTGACCCAGACTCCAGCCTCCGT

GTCTGCAGCTGTGGGAGGCACAGTCACCATCAGTTGCCAGTCCAGTCAG

AATGTTTATAATAATAATGACTTAGTCTGGTTTCAGCAGAAACCAGGTC

AGCCTCCCAAGCGCCTGGTCTACTGGGCATCCACTCTGGCATCTGGGGT

CTCATCGCGGTTCAGAGGCAGTGGATCTGGGACACAGTTCATTCTCACC

ATCAGCGACCTGCAGTGTGACGATGCTGCCACTTACTATTGTGCAGGCG

CCTATGATAGTGAAATTAGGGCT

In another embodiment of the invention, polynucleotides of the invention comprise, or alternatively consist of, the following polynucleotide sequence encoding the variable heavy chain polypeptide sequence of SEQ ID NO: 67:

(SEQ ID NO: 75)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCGCAGTCTCTGGATTCTCCCTCAGTGTTTAC

TGGATGACCTGGGTCCGCCAGGCTCCAGGGAAGGGGCTGGAATGGATCGG

AACCATTAGTACTGATGGTATCACTGTCTACGCGACCTGGGCGAAAGGCC

GATTCACCATCTCCAAAACCTCGTCGACCGCGGTGGATCTGAAACTCACC

AGTCCGACAACCGAGGACACGGCCACCTATTTCTGTGCCGGAGGGGCGG

CATGGACCCC.

In a further embodiment of the invention, polynucleotides encoding fragments of the antibody having binding specificity to TNF-α comprise, or alternatively consist of, one or more of the polynucleotide sequences of SEQ ID NO: 76; SEQ ID NO: 77; and SEQ ID NO: 78 which correspond to polynucleotides encoding the complementarity-determining regions (CDRs, or hypervariable regions) of the light chain variable sequence of SEQ ID NO: 66.

In a further embodiment of the invention, polynucleotides encoding fragments of the antibody having binding specificity to TNF-α comprise, or alternatively consist of, one or more of the polynucleotide sequences of SEQ ID NO: 79; SEQ ID NO: 80; and SEQ ID NO: 81 which correspond to polynucleotides encoding the complementarity-determining regions (CDRs, or hypervariable regions) of the heavy chain variable sequence of SEQ ID NO: 67.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two; three or more, including all of the following polynucleotides encoding antibody fragments: the polynucleotide SEQ ID NO: 74 encoding the light chain variable region of SEQ ID NO: 66; the polynucleotide SEQ ID NO: 75 encoding the heavy chain variable region of SEQ ID NO: 67; polynucleotides encoding the complementarity-determining regions (SEQ ID NO: 76; SEQ ID NO: 77; and SEQ ID NO: 78) of the light chain variable region of SEQ ID NO: 66; and polynucleotides encoding the complementarity-determining regions (SEQ ID NO: 79; SEQ ID NO: 80; and SEQ ID NO: 81) of the heavy chain variable region of SEQ ID NO: 67.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 95:

(SEQ ID NO: 90)
ATGGACACGAGGGCCCCCACTCAGCTGCTGGGGCTCCTGCTGCTCTGGCT

CCCAGATGCCAGATGTGCCTATGATATGACCCAGACTCCAGCCTCTGTGG

AGGTAGCTGGGGGAGGCACAGTCACCATCAAGTGCCAGGCCAGTCAGAGC

ATTGCTAATAGGTTAGCCTGGTATCAGCAGAAACCAGGGCAGCCTCCCAA

GCTCCTGATCTATTATGCATCCACGCTGGCATCTGGGGTCCCATCGCGGT

TCAGCGGCAGTGGATCTGGGACAGAGTTCACTCTCACCATCAGTGGCGTG

CAGTGTGACGATGCTGCCACTTACTACTGTCAGCAGACTTATAGTGATAA

TAATGTCGATAATGCT

In another embodiment of the invention, polynucleotides of the invention comprise, or alternatively consist of, the following polynucleotide sequence encoding the variable heavy chain polypeptide sequence of SEQ ID. NO: 96:

(SEQ ID NO: 91)
ATGGAGACTGGGCTGCGCTGGCTTCTCCTGGTCGCTGTGTTCAAAGGTGT

CCAGTGTCAGTCGGTGGAGGAGTCCGGGGGTCGCCTGGTCACGCCTGGGA

CACCCCTGACACTCACCTGCACAGTCTCTGGATTCTCCCTCAGTAGCAAT

ACAATAAGCTGGGTCCGCCAGGCTCCAGGGAAGGGGCTGGAGTGGATCGG

ATACATTTGGCGTGGTGTTAGCACATACTACGCGACCTGGGCGAAAGGCC

GATTCACCATCTCCAAAACCTCGTCGACGACGGTGGATCTGAAGATCACC

GGTCCGACAACCGAGGACACGGCCACCTATTTCTGTGCCAGAGATGCTGG

TGATGGTGGTGGATATTCCTTGGATCTC.

In a further embodiment of the invention, polynucleotides encoding fragments of the antibody having binding specificity to TNF-α comprise, or alternatively consist of, one or more of the polynucleotide sequences of SEQ ID NO: 92; SEQ ID NO: 93; and SEQ ID NO: 94 which correspond to polynucleotides encoding the complementarity-determining regions (CDRs, or hypervariable regions) of the light chain variable sequence of SEQ ID NO: 95.

In a further embodiment of the invention, polynucleotides encoding fragments of the antibody having binding specificity to TNF-α comprise, or alternatively consist of, one or more of the polynucleotide sequences of SEQ ID NO: 95; SEQ ID NO: 96; and SEQ ID NO: 97 which correspond to polynucleotides encoding the complementarity-determining regions (CDRs, or hypervariable regions) of the heavy chain variable sequence of SEQ ID NO: 96.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 90 encoding the light chain variable region of SEQ ID NO: 95; the polynucleotide SEQ ID NO: 91 encoding the heavy chain variable region of SEQ ID NO: 96; polynucleotides encoding the complementarity-determining regions (SEQ ID NO: 92; SEQ ID NO: 93; and SEQ ID NO: 94) of the light chain variable region of SEQ ID NO: 95; and polynucleotides encoding the complementarity-determining regions (SEQ ID NO: 95; SEQ ID NO: 96; and SEQ ID NO: 97) of the heavy chain variable region of SEQ ID NO: 96.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 98:

(SEQ ID NO: 106)
ATGGACACGAGGGCCCCCACTCAGCTGCTGGGGCTCCTACTGCTCTGGCT

CCCAGGTGCCAGATGTGCTGACATTGTGATGACCCAGACTCCAGCCTCCG

TGGAGGCAGCTGTGGGAGGCACAGTCACCATCAATTGCCAGGCCAGTCAG

AGCATTGTCAGTTGGTTAGCCTGGTATCAGCAGAAACCAGGGCAGCCTCC

CAAGCTCCTGATCTATGGTGCATCCACTCTGGCATCTGGGGTCCCATCGC

GGTTCAAAGGCAGTGGATCTGGGACAGAGTACACTCTCACCATCAGCGAC

CTGGAGTGTGCCGATGCTGCCACTTACTACTGTCAAAGCAATTATGGTAG

TAATAGTCATAGTTTTGGGAATACT

In another embodiment of the invention, polynucleotides of the invention comprise, or alternatively consist of, the following polynucleotide sequence encoding the variable heavy chain polypeptide sequence of SEQ ID NO: 99:

(SEQ ID NO: 107)
ATGGAGACTGGGCTGCGCTGGCTTCTCCTGGTCGCTGTGCTCAAAGGTGT

CCAGTGTCAGTCAGTGGAGGAGTCCGGGGGTCGCCTGGTCACGCCTGGGA

CACCCCTGACACTCACCTGCACAGTCTCTGGATTCTCCCTCAGTAGCGAC

AATATGGGCTGGGTCCGCCAGGCTCCAGGGAAGGGGCTGGAATACATCGG

ATACATTACTTATGGTGGTTTCACATACTACGCGACCTGGGCGAAAGGCC

GATTCACCATCTCCAAGACCTCGACCACGGTGGATCTGAAAATGACCAGT

CCGACAACCGAGGACACGGCCACCTATTTCTGTGCCAGAGAAGCTGGTGG

TAGGGCTAATGTC.

In a further embodiment of the invention, polynucleotides encoding fragments of the antibody having binding specificity to TNF-α comprise, or alternatively consist of, one or more of the polynucleotide sequences of SEQ ID NO: 108; SEQ ID NO: 109; and SEQ ID NO: 110 which correspond to polynucleotides encoding the complementarity-determining regions (CDRs, or hypervariable regions) of the light chain variable sequence of SEQ ID NO: 98.

In a further embodiment of the invention, polynucleotides encoding fragments of the antibody having binding specificity to TNF-α comprise, or alternatively consist of, one or more of the polynucleotide sequences of SEQ ID NO: 111; SEQ ID NO: 112; and SEQ ID NO: 113 which correspond to polynucleotides encoding the complementarity-determining regions (CDRs, or hypervariable regions) of the heavy chain variable sequence of SEQ ID NO: 99.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 106 encoding the light chain variable region of SEQ ID NO: 98; the polynucleotide SEQ ID NO: 107 encoding the heavy chain variable region of SEQ. ID NO: 99; polynucleotides encoding the complementarity-determining regions (SEQ ID NO: 108; SEQ ID NO: 109; and SEQ ID NO: 110) of the light chain variable region of SEQ ID NO: 98; and polynucleotides encoding the complementarity-determining regions (SEQ ID NO: 111; SEQ ID NO: 112; and SEQ ID NO: 113) of the heavy chain variable region of SEQ ID NO: 99.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 114:

(SEQ ID NO: 122)
ATGGACACGAGGGCCCCCACTCAGCTGCTGGGGCTCCTGCTGCTCTGGCT

CCCAGGTGCCAGATGTGCTGACATTGTGATGACCCAGACTCCATCCTCCG

TGTCTGAACCTGTGGGAGGCACAGTCACCATCATGTGCCAGGCCAGTCAG

AACATTTACAGCTACTTATCCTGGTATCAGCAGAAACCAGGGCAGCCTCC

CAAGCTCCTGATCTACAAGGCATCCACTCTGGCATCTGGGGTCCCATCGC

GGTTCGCAGGCAGTGGATCTGGGACAGATTTCACTCTCACCATCAGCGAC

CTGGAGTGTGCCGATGCTGCCACTTACTACTGTCAAAGCAATTATGGTAG

TAATAGTGATAGTTTTGGGAATGCT

In another embodiment of the invention, polynucleotides of the invention comprise, or alternatively consist of, the following polynucleotide sequence encoding the variable heavy chain polypeptide sequence of SEQ ID NO: 115:

(SEQ ID NO: 123)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGCCTCTGGATTCTCCCTCAGTAATTAT

GTAATGGGCTGGGTCCGCCAGGCTCCAGGGAAGGGGCTGGAATTCATCGG

ATACATTGCTTTTGGTATTGGCCCATACTACGCGACCTGGGCGAAAGGCC

GATTCTCCATCTCCAGCACCTCGTCGACCACGGTGGATCTGACAATGACC

AGTCTGACACCCGAGGACACGGCCACCTATTTCTGTGCCAGAGGTGATTA

TAGTGGTAATAACATT.

In a further embodiment of the invention, polynucleotides encoding fragments of the antibody having binding specificity to TNF-α comprise, or alternatively consist of, one or more of the polynucleotide sequences of SEQ ID NO: 124; SEQ ID NO: 125; and SEQ ID NO: 126 which correspond to polynucleotides encoding the complementarity-determining regions (CDRs, or hypervariable regions) of the light chain variable sequence of SEQ ID NO: 114.

In a further embodiment of the invention, polynucleotides encoding fragments of the antibody having binding specificity to TNF-α comprise, or alternatively consist of, one or more of the polynucleotide sequences of SEQ ID NO: 127; SEQ ID NO: 128; and SEQ ID NO: 129 which correspond to polynucleotides encoding the complementarity-determining regions (CDRs, or hypervariable regions) of the heavy chain variable sequence of SEQ ID NO: 115.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 122 encoding the light chain variable region of SEQ ID NO: 114; the polynucleotide SEQ ID NO: 123 encoding the heavy chain variable region of SEQ ID NO: 115; polynucleotides encoding the complementarity-determining regions (SEQ ID NO: 124; SEQ ID NO: 125; and SEQ ID. NO: 126) of the light chain variable region of SEQ ID NO: 114; and polynucleotides encoding the complementarity-determining regions (SEQ ID NO: 127; SEQ ID NO: 128; and SEQ ID NO: 129) of the heavy chain variable region of SEQ ID NO: 115.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 130:

(SEQ ID NO: 138)
ATGGACACGAGGGCCCCCACTCAGCTGCTGGGGCTCCTGCTGCTCTGGCT

CCCAGGTGCCACATTTGCGCAAGTGCTGACCCAGACTCCATCCTCCGTGT

CTGCAGCTGTGGGAGGCACAGTCACCGTCAGTTGCCAGTCCAGTCAGAAT

GTTTATAATAACAACGACTTCGTCTGGTTTCAGCAGAAACCAGGGCAGCC

TCCCAAGCGCCTAATCTACTGGGCATCCACTCTGGCATCTGGGGTCCCAT

CGCGGTTCAAAGGCAGTGGATCTGGGACACAGTTCACTCTCACCATCAAC

GACCTGGAATGTGACGATGCTGCCACTTACTACTGTGCAGGCGCTTATAT

TACTGAGCTTAGGACT

In another embodiment of the invention, polynucleotides of the invention comprise, or alternatively consist of, the following polynucleotide sequence encoding the variable heavy chain polypeptide sequence of SEQ ID NO: 131:

(SEQ ID NO: 139)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTCTCTGGATTCTCCCTCAGTATCTAC

TGGATGACCTGGGTCCGCCAGGCTCCAGGGAAGGGGCTGGAATGGATCGG

AGTCATTAGTACTGATGGTAGCGCATACTACGCGACCTGGGCGAAAGGCC

GATTCACCATCTCCAAAACCTCGTCGACCACGGTGGATCTGAGGATCACC

AGTCCGACAACCGAGGACACGGCCACCTATTTCTGTGCCGGAGGGGCGG

CATGGACCCC.

In a further embodiment of the invention, polynucleotides encoding fragments of the antibody having binding specificity to TNF-α comprise, or alternatively consist of, one or more of the polynucleotide sequences of SEQ ID NO: 140; SEQ ID NO: 141; and SEQ ID NO: 142 which correspond to polynucleotides encoding the complementarity-determining regions (CDRs, or hypervariable regions) of the light chain variable sequence of SEQ ID NO: 130.

In a further embodiment of the invention, polynucleotides encoding fragments of the antibody having binding specificity to TNF-α comprise, or alternatively consist of, one or more of the polynucleotide sequences of SEQ ID NO: 143; SEQ ID NO: 144; and SEQ ID NO: 145 which correspond to polynucleotides encoding the complementarity-determining regions (CDRs, or hypervariable regions) of the heavy chain variable sequence of SEQ ID NO: 131.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 138 encoding the light chain variable region of SEQ ID NO: 130; the polynucleotide SEQ ID NO: 139 encoding the heavy chain variable region of SEQ ID NO: 131; polynucleotides encoding the complementarity-determining regions (SEQ ID NO: 140; SEQ ID NO: 141; and SEQ ID NO: 142) of the light chain variable region of SEQ ID NO: 130; and polynucleotides encoding the complementarity-determining regions (SEQ ID NO: 143; SEQ ID NO: 144; and SEQ ID NO: 145) of the heavy chain variable region of SEQ ID NO: 131.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 146:

```
                                        (SEQ ID NO: 154)
ATGGACACGAGGGCCCCCACTCAGCTGCTGGGGCTCCTGCTGCTCTGGCT

CCCAGGTGCCACATTTGCGCAAGTGCTGACCCAGACTGCATCGTCCGTGT

CTGCAGCTGTGGGAGGCACAGTCACCATCAGTTGCCAGTCCAGTCAGAGT

GTTTATAATAATAACGACTTCATCTGGTTTCAGCAGAAACCAGGGCAGCC

TCCCAAGCGCCTCATCTACTGGGCATCCACTCTGGCATCTGGGGTCTCAT

CGCGGTTCAAAGGCAGTGGATCTGGGACACAGTTCACTCTCACCATCAAC

GACCTGGAGTGTGACGATGCTGCCGTTTACTATTGTGCAGGCGCTTATGA

TAGTGAGGTTAGGGCT
```

In another embodiment of the invention, polynucleotides of the invention comprise, or alternatively consist of, the following polynucleotide sequence encoding the variable heavy chain polypeptide sequence of SEQ ID NO: 147:

```
                                        (SEQ ID NO: 155)
ATGGAGACTGGGCTGCGCTGGCTTCTCCTGGTCGCTGTGCTCAAAGGTGT

CCAGTGTCAGTCGGTGGAGGAGTCTGGGGGTCGCCTGGTCACGCCTGGGA

CACCCCTGACACTCACCTGCACAGTCTCTGGATTCTCCCTCAGTATCTAC

TGGATGACCTGGGTCCGCCAGGCTCCAGGGAGGGGGCTGGAATGGATCGG

GGTCATTAGTACTGATGGTACCACATACTACGCGAACTGGGCGAAAGGCC

GATTCACCATCTCCAAAGCCTCGTCGACCACGGTGGATCTGAGAATCACC

AGTCCGACAACCGAGGACACGGCCACCTATTTCTGTGCCGGAGGGGCGG

CATGGACCCC.
```

In a further embodiment of the invention, polynucleotides encoding fragments of the antibody having binding specificity to TNF-α comprise, or alternatively consist of, one or more of the polynucleotide sequences of SEQ ID NO: 156; SEQ ID NO: 157; and SEQ ID NO: 158 which correspond to polynucleotides encoding the complementarity-determining regions (CDRs, or hypervariable regions) of the light chain variable sequence of SEQ ID NO: 146.

In a further embodiment of the invention, polynucleotides encoding fragments of the antibody having binding specificity to TNF-α comprise, or alternatively consist of, one or more of the polynucleotide sequences of SEQ ID NO: 159; SEQ ID NO: 160; and SEQ ID NO: 161 which correspond to polynucleotides encoding the complementarity-determining regions (CDRs, or hypervariable regions) of the heavy chain variable sequence of SEQ ID NO: 147.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 154 encoding the light chain variable region of SEQ ID NO: 146; the polynucleotide SEQ ID NO: 155 encoding the heavy chain variable region of SEQ ID NO: 147; polynucleotides encoding the complementarity-determining regions (SEQ ID NO: 156; SEQ ID NO: 157; and SEQ ID NO: 158) of the light chain variable region of SEQ ID NO: 146; and polynucleotides encoding the complementarity-determining regions (SEQ ID NO: 159; SEQ ID NO: 160; and SEQ ID NO: 161) of the heavy chain variable region of SEQ ID NO: 147.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 162:

```
                                        (SEQ ID NO: 170)
ATGGACACGAGGGCCCCCACTCAGCTGCTGGGGCTCCTGCTGCTCTGGCT

CCCAGGTGCCACATTTGCGCAAGTGATGACCCAGACTCCAGCCTCCGTGT

CTGCAGCTGTGGGAGGCACAGTCACCATCAGTTGCCAGTCCAGTGAGAGT

GTTTATAATAATAATGACTTAATCTGGTTCCGGCAGAAACCAGGGCAGCC

TCCCAAGCGCCTAATTTACTGGGCATCCCAACTGGCATCTGGGGTCTCAT

CGCGGTTCAAAGGCAGTGGATCTGGGACACAGTTCACTCTCACCATCAAC

GACCTGGAGTGTGACGATGCTGCCACTTACTACTGTGCAGGCGCTTATGA

TAGTGAGATTAGGGCT
```

In another embodiment of the invention, polynucleotides of the invention comprise, or alternatively consist of, the following polynucleotide sequence encoding the variable heavy chain polypeptide sequence of SEQ ID NO: 163:

```
                                              (SEQ ID NO: 171)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTCTCTGGATTCTCCCTCAGTATCTAC

TGGATGACCTGGGTCCGCCAGGCTCCAGGGAAGGGGCTGGAATGGATCGG

AGTCATTGCTTCTGATGGTAGCACATACTACGGGAGCTGGGCGAAAGGCC

GATTCACCATCTCCAAAGCCTCGTCGACCACGGTGGATCTGAAGATTGCC

AGCCCGACAATTGAGGACACGGCCACCTATTTCTGTGCCGGAGGGGCGG

CATGGACCCC.
```

In a further embodiment of the invention, polynucleotides encoding fragments of the antibody having binding specificity to TNF-α comprise, or alternatively consist of, one or more of the polynucleotide sequences of SEQ ID NO: 172; SEQ ID NO: 173; and SEQ ID NO: 174 which correspond to polynucleotides encoding the complementarity-determining regions (CDRs, or hypervariable regions) of the light chain variable sequence of SEQ ID NO: 162.

In a further embodiment of the invention, polynucleotides encoding fragments of the antibody having binding specificity to TNF-α comprise, or alternatively consist of, one or more of the polynucleotide sequences of SEQ ID NO: 175; SEQ ID NO: 176; and SEQ ID NO: 177 which correspond to polynucleotides encoding the complementarity-determining regions (CDRs, or hypervariable regions) of the heavy chain variable sequence of SEQ ID NO: 163.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 170 encoding the light chain variable region of SEQ ID NO: 162; the polynucleotide SEQ ID NO: 171 encoding the heavy chain variable region of SEQ ID NO: 163; polynucleotides encoding the complementarity-determining regions (SEQ ID NO: 172; SEQ ID NO: 173; and SEQ ID NO: 174) of the light chain variable region of SEQ ID NO: 162; and polynucleotides encoding the complementarity-determining regions (SEQ ID NO: 175; SEQ ID NO: 176; and SEQ ID NO: 177) of the heavy chain variable region of SEQ ID NO: 163.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 178:

```
                                              (SEQ ID NO: 186)
ATGGACACGAGGGCCCCCACTCAGCTGCTGGGGCTCCTGCTGCTCTGGCT

CCCAGGTGCCAGATGTGCGCTTGTGATGACCCAGACTCCATCCCCTGTGT

CTGCAGCTGTGGGAGGCACAGTCACCATCAGTTGCCAGTCTAGTGAGAGC

GTTGTTTTTAACAACCGCTTATCCTGGTATCAGCAGAAACCAGGGCAGCC

TCCCAAGCTCCTGATCTACTGGGCATCCACTCTGGCATCTGGGGTCCCAT

CGCGGTTCAAAGGCAGTGGATCTGGGACACAGTTCACTCTCACCATCAGT

GGCGTGGAGTGTGACGATGCTGCCACTTACTACTGTGCAGGATATAAAAG

TTATAGTAATGATGATTTTGCT
```

In another embodiment of the invention, polynucleotides of the invention comprise, or alternatively consist of, the following polynucleotide sequence encoding the variable heavy chain polypeptide sequence of SEQ ID NO: 179:

```
                                              (SEQ ID NO: 187)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTCTCTGGATTCTCCCTCAGTCACTAT

GCAATGGGCTGGGTCCGCCAGGCTCCAGGGAAGGGGCTGGAATGGATCGG

AATCATTAGTAGTAATGGTGTCACATACTACGCGACCTGGGCGAGCGGCC

GATTCACCATCTCCAAAACCTCGACCACGGTGGATCTGAAAATCACCAGT

CCGACAACCGAGGACACGGCCACCTATTTCTGTGCCAGAGGAGATGATAC

TAGTATTATTTATTACATTTACGCCTTTGATCTC.
```

In a further embodiment of the invention, polynucleotides encoding fragments of the antibody having binding specificity to TNF-α comprise, or alternatively consist of, one or more of the polynucleotide sequences of SEQ ID NO: 188; SEQ ID NO: 189; and SEQ ID NO: 190 which correspond to polynucleotides encoding the complementarity-determining regions (CDRs, or hypervariable regions) of the light chain variable sequence of SEQ ID NO: 178.

In a further embodiment of the invention, polynucleotides encoding fragments of the antibody having binding specificity to TNF-α comprise, or alternatively consist of, one or more of the polynucleotide sequences of SEQ ID NO: 191; SEQ ID NO: 192; and SEQ ID NO: 193 which correspond to polynucleotides encoding the complementarity-determining regions (CDRs, or hypervariable regions) of the heavy chain variable sequence of SEQ ID NO: 179.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 186 encoding the light chain variable region of SEQ ID NO: 178; the polynucleotide SEQ ID NO: 187 encoding the heavy chain variable region of SEQ ID NO: 179; polynucleotides encoding the complementarity-determining regions (SEQ ID NO: 188; SEQ ID NO: 189; and SEQ ID NO: 190) of the light chain variable region of SEQ ID NO: 178; and polynucleotides encoding the complementarity-determining regions (SEQ ID NO: 191; SEQ ID NO: 192; and SEQ ID NO: 193) of the heavy chain variable region of SEQ ID NO: 179.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 194:

(SEQ ID NO: 202)
ATGGACACGAGGGCCCCCACTCAGCTGCTGGGGCTCCTGCTGCTCTGGCT

CCCAGGTGCCAGATGTGCTGACATTGTGATGACCCAGACTCCAGCCTCCG

TGTCTGAACCTGTGGGAGGCACAGTCACCATCAAGTGCCAGGCCAGTCAG

AACATTTACAGCACCTTAGCCTGGTATCAGCAGAAACCAGGGCAGCCTCC

CAAGCTCCTGATCTATCTGGCATCCACTCTGGCATCTGGGGTCCCATCGC

GGTTCAAAGGCAGTGGATCTGGGACACAGTTCACTCTCACCATCAGCGAC

CTGGAGTGTGCCGATGCTGCCACTTATTACTGTCAAACCAGTCATGGTAG

TAATAGTGATAGTTTTGGTTATGCT

In another embodiment of the invention, polynucleotides of the invention comprise, or alternatively consist of, the following polynucleotide sequence encoding the variable heavy chain polypeptide sequence of SEQ ID NO: 195:

(SEQ ID NO: 203)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACTTGCACAGTCTCTGGAATCGACCTCAGTAGCTAT

GCAATGGGCTGGGTCCGCCAGGCTCCAGGGAAGGGGCTGGAATACATCGG

ATACATTCTTAGTAGTGGTATCACATACTACGCGAGTTGGGCGAGAGGCC

GATTCACCATCTCCAAAACCTCGTCGACCACGGTGGATCTGAAAATGACC

AGTCTGACAACCGAGGACACGGCCACCTATTTCTGTGCCAGAAATGGTAA

TTATAATAGTGGTACGGACATC.

In a further embodiment of the invention, polynucleotides encoding fragments of the antibody having binding specificity to TNF-α comprise, or alternatively consist of, one or more of the polynucleotide sequences of SEQ ID NO: 204; SEQ ID NO: 205; and SEQ ID NO: 206 which correspond to polynucleotides encoding the complementarity-determining regions (CDRs, or hypervariable regions) of the light chain variable sequence of SEQ ID NO: 194.

In a further embodiment of the invention, polynucleotides encoding, fragments of the antibody having binding specificity to TNF-α comprise, or alternatively consist of, one or more of the polynucleotide sequences of SEQ ID NO: 207; SEQ ID NO: 208; and SEQ ID NO: 209 which correspond to polynucleotides encoding the complementarity-determining regions (CDRs, or hypervariable regions) of the heavy chain variable sequence of SEQ ID NO: 195.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 202 encoding the light chain variable region of SEQ ID NO: 194; the polynucleotide SEQ ID NO: 203 encoding the heavy chain variable region of SEQ ID NO: 195; polynucleotides encoding the complementarity-determining regions (SEQ ID NO: 204; SEQ ID NO: 205; and SEQ ID NO: 206) of the light chain variable region of SEQ ID NO: 194; and polynucleotides encoding the complementarity-determining regions (SEQ ID NO: 207; SEQ ID NO: 208; and SEQ ID NO: 209) of the heavy chain variable region of SEQ ID NO: 195.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 210:

(SEQ ID NO: 218)
ATGGACACGAGGGCCCCCACTCAGCTGCTGGGGCTCCTGCTGCTCTGGCT

CCCAGGTGCCAGATGTGCTGACATTGTGATGACCCAGACTCCAGCCTCCG

TGTCTGAACCTGTGGGAGGCACAGTCACCATCAAGTGCCAGGCCAGTCAG

AACATTTACAGCACCTTAGCCTGGTATCAGCAGAAACCAGGGCAGCCTCC

CAAGCTCCTGATCTATCTGGCATCCACTCTGGCATCTGGGGTCCCATCGC

GGTTCAAAGGCAGTGGATCTGGGACACAGTTCACTCTCACCATCAGCGAC

CTGGAGTGTGCCGATGCTGCCACCTATTACTGTCAAACCAATCATGGTAG

TAATAGTGATAGTTTTGGTTATGCT

In another embodiment of the invention, polynucleotides of the invention comprise, or alternatively consist of, the following polynucleotide sequence encoding the variable heavy chain polypeptide sequence of SEQ ID NO: 211:

(SEQ ID NO: 219)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTCTCTGGATTCTCCCTCAGTAGCTAT

GCAATGGGCTGGGTCCGCCAGGCTCCAGGGAAGGGGCTGGAATACATCGG

ATACATTGGTAGTAGTGGTATCACATACTACACGAGTTGGGCGAGAGGCC

GTTTCACCATCTCCAAACCCTCGTCGACCACGGTGGATCTGAAAATGACC

AGTCTGACAACCGAGGACACGGCCACCTATTTCTGTGCCAGAAATGGTAA

TTATAATAGTGGTACGGACATC.

In a further embodiment of the invention, polynucleotides encoding fragments of the antibody having binding specificity to TNF-α comprise, or alternatively consist of, one or more of the polynucleotide sequences of SEQ ID NO: 220; SEQ ID NO: 221; and SEQ ID NO: 222 which correspond to polynucleotides encoding the complementarity-determining regions (CDRs, or hypervariable regions) of the light chain variable sequence of SEQ ID NO: 210.

In a further embodiment of the invention, polynucleotides encoding fragments of the antibody having binding specificity to TNF-α comprise, or alternatively consist of, one or more of the polynucleotide, sequences of SEQ ID NO: 223; SEQ ID NO: 224; and SEQ ID NO: 225 which correspond to polynucleotides encoding the complementarity-determining regions (CDRs, or hypervariable regions) of the heavy chain variable sequence of SEQ ID NO: 211.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 218 encoding the light chain variable region of SEQ ID NO: 210; the polynucleotide SEQ ID NO: 219 encoding the heavy chain variable region of SEQ ID NO: 211; polynucleotides encoding the complementarity-determining regions (SEQ ID NO: 220; SEQ ID NO: 221; and SEQ ID NO: 222) of the light chain variable region of SEQ ID NO: 210; and polynucleotides encoding the complementarity-determining regions (SEQ ID NO: 223; SEQ ID NO: 224; and SEQ ID NO: 225) of the heavy chain variable region of SEQ ID NO: 211.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 226:

(SEQ ID NO: 234)
ATGGACACGAGGGCCCCCACTCAGCTGCTGGGGCTCCTGCTGGTGTGGCT

CCCAGGTGCCAGATGTGCTGACATTGTGATGACCCAGACTCCAGCCTCCG

TGTCTGAACCTGTGGGAGGCACAGTCACCATCAAGTGCCAGGCCAGTCAG

AGCATTTACAGCTCCTTTTCCTGGTATCAACAGATACCAGGCCAGCGTCC

CAAGCTCCTGATCTATTATGCATCCACTCTGGCCTCTGGGGTCCCATCGC

GATTCAGCGGCAGTGGATCTGGGACAGATTTCACTCTCACCATCAGCGAC

CTGGAGTGTGCCGATGCTGCCACTTACTACTGTCAAAGCAATCATGGTAG

TAATGGTGATAGTTTTGGTAATGCT

In another embodiment of the invention, polynucleotides of the invention comprise, or alternatively consist of, the following polynucleotide sequence encoding the variable heavy chain polypeptide sequence of SEQ ID NO: 227:

(SEQ ID NO: 235)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTGTCGCCTGGGA

CACCCCTGACACTCACCTGCACAGTCTCTGGAATCGACCTCAGTAGTTAT

GGAATGGGCTGGGTCCGCCAGGCTCCAGGGAAGGGGCTGGAATACATCGG

ATACATGATTGCTAGTGGTATCACATATTACGCGGCCTGGGCGAAAGGCC

GATTCACCATCTCCAAAACCTCGTCGACCACGGTGGATCTGAAAATCACC

AGTCCGACAACCGAGGACACGGCCACCTATTTCTGTGCCAGAAATTACTA

CGGCATGGACCCC.

In a further embodiment of the invention, polynucleotides encoding fragments of the antibody having binding specificity to TNF-α comprise, or alternatively consist of, one or more of the polynucleotide sequences of SEQ ID NO: 236; SEQ ID NO: 237; and SEQ ID NO: 238 which correspond to polynucleotides encoding the complementarity-determining regions (CDRs, or hypervariable regions) of the light chain variable sequence of SEQ ID NO: 226.

In a further embodiment of the invention, polynucleotides encoding fragments of the antibody having binding specificity to TNF-α comprise, or alternatively consist of, one or more of the polynucleotide sequences of SEQ ID NO: 239; SEQ ID NO: 240; and SEQ ID NO: 241 which correspond to polynucleotides encoding the complementarity-determining regions (CDRs, or hypervariable regions) of the heavy chain variable sequence of SEQ ID NO: 227.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 234 encoding the light chain variable region of SEQ ID NO: 226; the polynucleotide SEQ ID NO: 235 encoding the heavy chain variable region of SEQ ID NO: 227; polynucleotides encoding the complementarity-determining regions (SEQ ID NO: 236; SEQ ID NO: 237; and SEQ ID NO: 238) of the light chain variable region of SEQ ID NO: 226; and polynucleotides encoding the complementarity-determining regions (SEQ ID NO: 239; SEQ ID NO: 240; and SEQ ID NO: 241) of the heavy chain variable region of SEQ ID. NO: 227.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 242:

(SEQ ID NO: 250)
ATGGACACGAGGGCCCCCACTCAGCTGCTGGGGCTCCTGCTGCTCTGGCT

CCCAGGTGCCAGATGTGCTGACATTGTGATGACGCAGACTCCAGCCTCCG

TGTCCGAACCTGTGGGAGGCACAGTCACCATCAAGTGTCAGGCCAGTCAG

ACCATTTACAGTAGCTTATCCTGGTATCAGCAGAAACCAGGGCAGCGTCC

CAAGCTCCTGATCTATGCTGCATCCACTCTGGCATCTGGGGTCCCATCGC

GGTTCAAAGGCAGTGGATCTGGGACAGATTTCACTCTCACCATAAGCGAC

CTGGAGTGTGCCGATGCTGCCACTTACTACTGTCAAAGTAATCATGGTAG

TAATAGTGATAGTTATGGCAATGCT

In another embodiment of the invention, polynucleotides of the invention comprise, or alternatively consist of, the following polynucleotide sequence encoding the variable heavy chain polypeptide sequence of ID NO: 243:

(SEQ ID NO: 251)
ATGGAGACTGGGCTGCGCTGGCTTCTCCTGGTCGCTGTGCTCAAAGGTGT

CCAGTGTCAGTCGCTGGAGGAGTCCGGGGGTCGCCTGGTCAAGCCTGACG

AAACCCTGACAATCACCTGCACAGTCTCTGGAATCGACCTCAATAACTAC

AACATGGGCTGGGTCCGCCAGGCTCCAGGGAAGGGGCTGGAATACATCGG

ATACATTCTTGGTAGTGGTATCACATACTACGCGACCTGGGCGAAAGGCC

GATTCACCATCTCGAAAACCTCGTCGACCACGGTGGATCTGAAAATGACC

AGTCTGACAACCGAGGACACGGCCACGTATTTCTGTGCTGGTAGTATTTA

TTATAGGGGGTACGGCATGGACCCC.

In a further embodiment of the invention, polynucleotides encoding fragments of the antibody having binding specificity to TNF-α comprise, or alternatively consist of, one or more of the polynucleotide sequences of SEQ ID NO: 252; SEQ ID NO: 253; and SEQ ID NO: 254 which correspond to polynucleotides encoding the complementarity-determining regions (CDRs, or hypervariable regions) of the light chain variable sequence of SEQ ID NO: 242.

In a further embodiment of the invention, polynucleotides encoding fragments of the antibody having binding specificity to TNF-α comprise, or alternatively consist of, one or more of the polynucleotide sequences of SEQ ID NO: 255; SEQ ID NO: 256; and SEQ ID NO: 257 which correspond to polynucleotides encoding the complementarity-determining regions (CDRs, or hypervariable regions) of the heavy chain variable sequence of SEQ ID NO: 243.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 250 encoding the light chain variable region of SEQ ID NO: 242; the polynucleotide SEQ ID NO: 251 encoding the heavy chain variable region of SEQ ID NO: 243; polynucleotides encoding the complementarity-determining regions (SEQ ID NO: 252; SEQ ID NO: 253; and SEQ ID NO: 254) of the light chain variable region of SEQ ID NO: 242; and polynucleotides encoding the complementarity-determining regions (SEQ ID NO: 255; SEQ ID NO: 256; and SEQ ID NO: 257) of the heavy chain variable region of SEQ ID NO: 243.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 258:

(SEQ ID NO: 266)
ATGGACACGAGGGCCCCCACTCAGCTGCTGGGGCTCCTGCTGCTCTGGCT

CCCAGGTGCCAGATGTGCTGACATTGTGATGACCCAGACTCCAGCCTCCG

TGTCTGAACCTGTGGGAGGCACAGTCACCATCAAGTGCCAGGCCAGTCAG

AGCATTTACAGCACCTTAGCCTGGTATCAGCAGAAACCAGGGCAGCCTCC

CAAACTCCTGATCTCGCTGGCATCCACTCTGGCATCTGGGGTCCCATCGC

GGTTCAAAGGCAGTGGATCTGGGACACAGTTCACTCTCACCATCAGCGAC

CTGGAGTGTGCCGATGCTGCCACTTATTACTGTCAAACCAATCATGGTAG

TAATAGTGATAGTTTTGGTTATGCT

In another embodiment of the invention, polynucleotides of the invention comprise, or alternatively consist of, the following polynucleotide sequence encoding the variable heavy chain polypeptide sequence of SEQ ID NO: 259:

(SEQ ID NO: 267)
ATGGAGACTGGGCTGCGCTGGCTTCTCCTGGTCGCTGTGCTCAAAGGTGT

CCAGTGTCAGTCGCTGGAGGAGTCCGGGGGTCGCCTGGTAACGCCTGGAG

GATCCCTGACACTCACCTGCACAGTCTCTGGAATCGACCTCAGTAGCTAT

GCAATGGGCTGGGTCCGCCAGGCTCCAGGGAAGGGGCTGGAATACATCGG

ATACGTTCTTGGTAGTGGTATCACATACTACGCGAGTTGGGCGAGAGGCC

GATTCACCATCTCCAAAACCTCGTCGACCACGGTGGATCTGAAGATGACC

AGTCTGACAACCGAGGACACGGCCACCTATTTCTGTGTCAGAAATGATAA

TTATAATAGTGGCACGGACATC.

In a further embodiment of the invention, polynucleotides encoding fragments of the antibody having binding specificity to TNF-α comprise, or alternatively consist of, one or more of the polynucleotide sequences of SEQ ID NO: 268; SEQ ID NO: 269; and SEQ ID NO: 270 which correspond to polynucleotides encoding the complementarity-determining regions (CDRs, or hypervariable regions) of the light chain variable sequence of SEQ ID NO: 258.

In a further embodiment of the invention, polynucleotides encoding fragments of the antibody having binding specificity to TNF-α comprise, or alternatively consist of, one or more of the polynucleotide sequences of SEQ ID NO: 271; SEQ ID NO: 272; and SEQ ID NO: 273 which correspond to polynucleotides encoding the complementarity-determining regions (CDRs, or hypervariable regions) of the heavy chain variable sequence of SEQ ID NO: 259.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 266 encoding the light chain variable region of SEQ ID NO: 258; the polynucleotide SEQ ID NO: 267 encoding the heavy chain variable region of SEQ ID NO: 259; polynucleotides encoding the complementarity-determining regions (SEQ ID NO: 268; SEQ ID NO: 269; and SEQ ID NO: 270) of the light chain variable region of SEQ ID NO: 258; and polynucleotides encoding the complementarity-determining regions (SEQ ID NO: 271; SEQ ID NO: 272; and SEQ ID NO: 273) of the heavy chain variable region of SEQ ID NO: 259.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 274:

(SEQ ID NO: 282)
ATGGACACGAGGGCCCCCACTCAGCTGCTGGGGCTCCTGCTGCTCTGGCT

CCCAGGTGCCAGATGTGCTGACATTGTGATGACCCAGACTCCAGCCTCCG

TGTCTGAACCTGTGGGAGGCACAGTCACCATCAAGTGCCAGGCCAGTCAG

AACATTTACAGCACCTTAGCCTGGTATCAGCAGAAACCAGGGCAGCCTCC

CAAGCTCCTGATCTATCTGGCATCCACTCTGGAATCTGGGGTCCCATCGC

GGTTCAAAGGCAGTGGATCTGGGACAGAGTTCACTCTCACCATCAGCGAC

CTGGAGTGTGCCGATGCTGCCACTTATTACTGTCAAACCAGTCATGGTAG

TAATAGTGAAAGTTTTGGTTATGCT

In another embodiment of the invention, polynucleotides of the invention comprise, or alternatively consist of, the following polynucleotide sequence encoding the variable heavy chain polypeptide sequence of SEQ ID NO: 275:

(SEQ ID NO: 283)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACTTGCACGGTCTCTGGAATCGACCTCAGTAGCTAT

GCAATGGGCTGGGTCCGCCAGGCTCCAGGGAAGGGGCTGGAATACATCGG

ATACATTCTTAGTAGTGGTATCACATACTACGCGAGTTGGGCGAGAGGCC

GATTCACCATCTCCAAAACCTCGTCGACCACGGTGGATCTGAAAATGACC

AGTCTGACAACCGAGGACACGGCCACCTATTTCTGTGTCAGAAATGGTAA

TTATAATGTTGGTACGGACATC.

In a further embodiment of the invention, polynucleotides encoding fragments of the antibody having binding specificity to TNF-α comprise, or alternatively consist of, one or more of the polynucleotide sequences of SEQ ID NO: 284; SEQ ID NO: 285; and SEQ ID NO: 286 which correspond to polynucleotides encoding the complementarity-determining regions (CDRs, or hypervariable regions) of the light chain variable sequence of SEQ ID NO: 274.

In a further embodiment of the invention, polynucleotides encoding fragments of the antibody having binding specificity to TNF-α comprise, or alternatively consist of, one or more of the polynucleotide sequences of SEQ ID NO: 287; SEQ ID NO: 288; and SEQ ID NO: 289 which correspond to polynucleotides encoding the complementarity-determining regions (CDRs, or hypervariable regions) of the heavy chain variable sequence of SEQ ID NO: 275.

The invention also contemplates polynucleotide sequences including one or more of the polynucleotide sequences encoding antibody fragments described, herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 282 encoding the light chain variable region of SEQ ID NO: 274; the polynucleotide SEQ ID NO: 283 encoding the heavy chain variable region of SEQ ID NO: 275; polynucleotides encoding the complementarity-determining regions (SEQ ID NO: 284; SEQ ID NO: 285; and SEQ ID NO: 286) of the light chain variable region of SEQ ID NO: 274; and polynucleotides encoding the complementarity-determining regions (SEQ ID NO: 287; SEQ ID NO: 288; and SEQ ID NO: 289) of the heavy chain variable region of SEQ ID NO: 275.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 290:

(SEQ ID NO: 298)
ATGGACACGAGGGCCCCCACTCAGCTGCTGGGGCTCCTGCTGCTCTGGCT

CCCAGGTGCCAGATGTGCTGACATTGTGATGACCCAGACTCCATCCTCCG

TGTCTGAACCTGTGCGAGGCACAGTCACCATCAAGTGCCAGGCCAGTCAG

AACATTTACAGCTACTTGTCCTGGTATCGACAGAGCCCAGGGCAGCCTCC

CAACCTCCTGATCTACAAGGCATCCACTCTGGCATCTGGGGTCCCATCGC

GGTTCAAAGGCAGTGGATCTGGGACAGATTTCACTCTCACCATCAGCGAC

CTGGAGTGTGCCGATGCTGCCACTTACTACTGTCAAAGCAATTATGGTAG

TAATAGTGATAGTTTTGGGAATGCT

In another embodiment of the invention, polynucleotides of the invention comprise, or alternatively consist of, the following polynucleotide sequence encoding the variable heavy chain polypeptide sequence of SEQ ID NO: 291:

(SEQ ID NO: 299)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCTCAGTCTCTGGATTCTCCCTCAATAACTAT

ATAATGGGCTGGGTCCGCCAGGCTCCAGGGAAGGGGCTGGAATTCATCGG

ATACATTGCTTTTGGTATTGGCCCATACTACGCGAGCTGGGCGAAAGGCC

GATTCACCAGCTCCAGCACCTCGTCGACCACGGTGGATCTGAAAATGACC

AGTCTGACACCCGAGGACACGGCCACCTATTTCTGTGCCAGAGGTGATGT

TAGTGGTAATGACATT.

In a further embodiment of the invention, polynucleotides encoding fragments of the antibody having binding specificity to TNF-α comprise, or alternatively consist of, one or more of the polynucleotide sequences of SEQ ID NO: 300; SEQ ID NO: 301; and SEQ ID NO: 302 which correspond to polynucleotides encoding the complementarity-determining regions (CDRs, or hypervariable regions) of the light chain variable sequence of SEQ ID NO: 290.

In a further embodiment of the invention, polynucleotides encoding fragments of the antibody having binding specificity to TNF-α comprise, or alternatively consist of, one or more of the polynucleotide sequences of SEQ ID NO: 303; SEQ ID NO: 304; and SEQ ID NO: 305 which correspond to polynucleotides encoding the complementarity-determining regions (CDRs, or hypervariable regions) of the heavy chain variable sequence of SEQ ID NO: 291.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 298 encoding the light chain variable region of SEQ ID NO: 290; the polynucleotide SEQ ID NO: 299 encoding the heavy chain variable region of SEQ ID NO: 291; polynucleotides encoding the complementarity-determining regions (SEQ ID NO: 300; SEQ ID NO: 301; and SEQ ID NO: 302) of the light chain variable region of SEQ ID NO: 290; and polynucleotides encoding the complementarity-determining regions (SEQ ID NO: 303; SEQ ID NO: 304; and SEQ ID NO: 305) of the heavy, chain variable region of SEQ ID NO: 291.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 306:

(SEQ ID NO: 314)
ATGGACACGAGGGCCCCCACTCAGCTGCTGGGGCTCCTGCTGCTCTGGCT

CCCAGGTGCCAGATGTGCTGACATTGTGATGACCCAGACTCCAGCCTCCG

TGTCTGAACCTGTGGGAGGCACAGTCACCATCAAATGCCAGGCCAGTCAG

AACATTTACACCACCTTAGCCTGGTATCAGCAGAAACCAGGGCAGCCTCC

CAAGCTCCTGATCTATCTGGCATCCACTCTGGCATCTGGGGTCCCATCGC

GGTTCAAAGGCAGTGGATCTGAGACACAGTTCACTCTCACCATCAGCGAC

CTGGAGTGTGCCGATGCTGCCACTTATTACTGTCAAACCAGTCATGGTAG

TAATAGTGATAGTTTTGGTTATGTT

In another embodiment of the invention, polynucleotides of the invention comprise, or alternatively consist of, the following polynucleotide sequence encoding the variable heavy chain polypeptide sequence of SEQ ID NO: 307:

(SEQ ID NO: 315)
ATGGAGACTGGGCTGCGCTGGCTTCTCCTGGTCGCTGTGCTCAAAGGTGT

CCAGTGTCAGTCAGTGGAGGAGTCCGGGGGTCGCCTGGTCACGCCTGGGA

CACCCCTGACACTCACTTGCACAGTCTCTGGAATCGACCTCAATAGCTAT

GCAATGGGCTGGGTCCGCCAGGCTCCAGGGAAGGGGCTGGAATACATCGG

ATACATTCTTAGTAGTGGTATCACATACTACGCGACCTGGGCGAAAGGCC

GATTCACCATCTCCAAAACCTCGTCGACCACGGTGGATCTGAAAATGACC

AGTCTGACAACCGAGGACACGGCCACCTATTTCTGTGTCAGGAATGGTAA

TTATAATAGTGGTACGGACATC.

In a further embodiment of the invention, polynucleotides encoding fragments of the antibody having binding specificity to TNF-α comprise, or alternatively consist of, one or more of the polynucleotide sequences of SEQ ID NO: 316; SEQ ID NO: 317; and SEQ ID NO: 318 which correspond to polynucleotides encoding the complementarity-determining regions (CDRs, or hypervariable regions) of the light chain variable sequence of SEQ ID NO: 306.

In a further embodiment of the invention, polynucleotides encoding fragments of the antibody having binding specificity to TNF-α comprise, or alternatively consist of, one or more of the polynucleotide sequences of SEQ ID NO: 319; SEQ ID NO: 320; and SEQ ID NO: 321 which correspond to polynucleotides encoding the complementarity-determining regions (CDRs, or hypervariable regions) of the heavy chain variable sequence of SEQ ID NO: 307.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 314 encoding the light chain variable region of SEQ ID NO: 306; the polynucleotide SEQ ID NO: 315 encoding the heavy chain variable region of SEQ ID NO: 307; polynucleotides encoding the complementarity-determining regions (SEQ ID NO: 316; SEQ ID NO: 317; and SEQ ID NO: 318) of the light chain variable region of SEQ ID NO: 306; and polynucleotides encoding the complementarity-determining regions (SEQ ID NO: 319; SEQ ID NO: 320; and SEQ ID NO: 321) of the heavy chain variable region of SEQ ID NO: 307.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 322:

(SEQ ID NO: 330)
ATGGACACGAGGGCCCCCACTCAGCTGCTGGGGCTCCTGCTGCTCTGGCT

CCCAGGTGCCAGATGTGCTGACATTGTGATGACCCAGACTCCATCCTCCG

TGTCTGCAGCTGTGGGAGGCACAGTCACCATCAAGTGCCAGGCCAGTCAG

AGCATTGATACCTACTTAGCCTGGTATCAGCAGAAACCAGGGCAGCGTCC

CAAGCTCCTGATCTATGGTGCATCCAATCTGGCATCTGGGGTCTCATCGC

GGTTCAAAGGCAGTGGATCTGGGACAGAATTCGCTCTCACCATCAGCGAC

CTGGAGTGTGCCGATGCTGCCACTTACTACTGTCAAAGCAATTATGGTAG

TAATAGTGATAGTTTTGGTAATGGT

In another embodiment of the invention, polynucleotides of the invention comprise, or alternatively consist of, the following polynucleotide sequence encoding the variable heavy chain polypeptide sequence of SEQ ID NO: 323:

(SEQ ID NO: 331)
ATGGAGACTGGGCTGCGCTGGCTTCTCCTGGTCGCTGTGTTCAAAGGTGT

CCAGTGTCAGTCGGTGGAGGAGTCCGGGGGTCGCCTGGTCACGCCTGGGA

CACCCCTGACACTCACCTGCACAGTCTCTGGATTCTCCCTCAGTACCTAT

ACAATGGGCTGGGTCCGCCAGGCTCCAGGGAAGGGGCTGGAATACATCGG

GTACATTAGTTATGGTGGTCTCGCATACTACGCGACCTGGGTGAATGCC

GATTCACCATCTCCAAAACCTCGACCACGGTGGATCTGAAAATGACCAGT

CTGACAGCTTCAGACACGGCCACCTATTTCTGTGCCAGAGCGGCTAGTGG

TGCCTGGGGTCATGCCTACGGCTTGGACCTC.

In a further embodiment of the invention, polynucleotides encoding fragments of the antibody having binding specificity to TNF-α comprise, or alternatively consist of, one or more of the polynucleotide sequences of SEQ ID NO: 332; SEQ ID NO: 333; and SEQ ID NO: 334 which correspond to polynucleotides encoding the complementarity-determining regions (CDRs, or hypervariable regions) of the light chain variable sequence of SEQ ID NO: 322.

In a further embodiment of the invention, polynucleotides encoding fragments of the antibody having binding specificity to TNF-α comprise, or alternatively consist of, one or more of the polynucleotide sequences of SEQ ID NO: 335; SEQ ID NO: 336; and SEQ ID NO: 337 which correspond to polynucleotides encoding the complementarity-determining regions (CDRs, or hypervariable regions) of the heavy chain variable sequence of SEQ ID NO: 323.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 330 encoding the light chain variable region of SEQ ID NO: 322; the polynucleotide SEQ ID NO: 331 encoding the heavy chain variable region of SEQ ID NO: 323; polynucleotides encoding the complementarity-determining regions (SEQ ID NO: 332; SEQ ID NO: 333; and SEQ ID NO: 334) of the light chain variable region of SEQ ID NO: 322; and polynucleotides encoding the complementarity-determining regions (SEQ ID NO: 335; SEQ ID NO: 336; and SEQ ID NO: 337) of the heavy chain variable region of SEQ ID NO: 323.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 338:

(SEQ ID NO: 346)
ATGGACACGAGGGCCCCCACTCAGCTGCTGGGGCTCCTGCTGCTCTGGCT

CCCAGGTGCCAGATGTGCTGACATTGTGATGACCCAGACTCCAGCCTCCG

TGTCTGGACCTGTGGGAGGCACAGTCACCATCAAGTGCCAGGCCAGTCAG

AACATTTACAGCTCCTTTTCCTGGTATCAACAAATACCAGGCCAGCGTCC

CAAGCTCCTGATCTATTATGCATCCACTCTGGCCTCTGGGGTCCCATCGC

GGTTCAGCGGCAGTGGATCTGGGACAGATTTCACTCTCACCATCAGCGAC

CTGGAGTGTGCCGATGCTGCCACTTACTACTGTCAAAGCAATCATGGTAG

TAATGGTGATAGTTTTGGTAATGCT

In another embodiment of the invention, polynucleotides of the invention comprise, or alternatively consist of, the following polynucleotide sequence encoding the variable heavy chain polypeptide sequence of SEQ ID. NO: 339:

(SEQ ID NO: 347)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTGTCGCCTGGGA

CACCCCTGACACTCACCTGCACAGTCTCTGGAATCGACCTCAGTAGCTAT

GGAATGGGCTGGGTCCGCCAGGCTCCAGGGAAGGGGCTGGATTACATCGG

ATACATGCTTCCTAGTGGTATCACATATTACGCGGCCTGGGCGAAAGGCC

GATTCACCATCTCCAAAACCTCGTCGACCACGGTGGATCTGAAAATCACC

AGTCCGACAACCGAGGACACGGCCACCTATTTCTGTGCCAGAAATTACTA

CGGCATGGACCCC.

In a further embodiment of the invention, polynucleotides encoding fragments of the antibody having binding specificity to TNF-α comprise, or alternatively consist of, one or more of the polynucleotide sequences of SEQ ID NO: 348; SEQ ID NO: 349; and SEQ ID NO: 350 which correspond to polynucleotides encoding the complementarity-determining regions (CDRs, or hypervariable regions) of the light chain variable sequence of SEQ ID NO: 338.

In a further embodiment of the invention, polynucleotides encoding fragments of the antibody having binding specificity to TNF-α comprise, or alternatively consist of, one or more of the polynucleotide sequences of SEQ ID NO: 351; SEQ ID NO: 352; and SEQ ID NO: 353 which correspond to polynucleotides encoding the complementarity-determining regions (CDRs, or hypervariable regions) of the heavy chain variable sequence of SEQ ID NO: 339.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 346 encoding the light chain variable region of SEQ ID NO: 338; the polynucleotide SEQ ID NO: 347 encoding the heavy chain variable region of SEQ ID NO: 339; polynucleotides encoding the complementarity-determining regions (SEQ ID NO: 348; SEQ ID NO: 349; and SEQ ID NO: 350) of the light chain variable region of SEQ ID NO: 338; and polynucleotides encoding the complementarity-determining regions (SEQ ID NO: 351; SEQ ID NO: 352; and SEQ ID NO: 353) of the heavy chain variable region of SEQ ID NO: 339.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 354:

(SEQ ID NO: 362)
ATGGACACGAGGGCCCCCACTCAGCTGCTGGGGCTCCTGCTGCTCTGGCT

CCCAGGTGCCAGATGTGCTGACATTGTGATGACCCAGACTCCAGCCTCCG

TGTCTGAACCTGTGGGAGGCACAGTCACCATCAAGTGCCAGGCCAGTCAG

AGCATTTACAGGTACTTATCCTGGTATCACCACAAACCAGGGCAGCCTCC

CAAGCTCCTGATCTATGGTGCATCCAATCTGGAATCTGGGGTCCCATCGC

GGTTCAAAGGCAGTGGATCTGGGACAGAGTACACTCTCACCATCAGCGAC

CTGGAGTGTGACGATGCTGCCACTTATTACTGTCAGAGCAATTATGGTGC

TAATAGTGATAGTTATGGGGATGCT

In another embodiment of the invention, polynucleotides of the invention comprise, or alternatively consist of, the following polynucleotide sequence encoding the variable heavy chain polypeptide sequence of SEQ ID NO: 355:

(SEQ ID NO: 363)
ATGGAGACTGGGCTGCGCTGGCTTCTCCTGGTCGCTGTGCTCAAAGGTGT

CCAGTGTCAGGAGCAGCTGGAGGAGTCCGGGGGAGACCTGGTCAAGCCTG

GGGCATCCCTGACACTCACCTGCAAAGCCTCTGGATTCTCCTTCAGTAGC

GGCTACTACATGGGCTGGGTCCGCCAGGCTCCAGGGAAAGGGCTGCAATA

CATCGGTTACATTGATTATGGTGGTAGCGCATACTACGCGAGCTGGGCGA

AAGGCCGATTCACCATCTCCAAAACCTCGTCGACCACGGTGACTCTGCAA

ATGACCAGTCTGACAGCCGCGGACACGGCCACCTTTTTCTGTGTACGAGACG

TGACTATACTGGTGGTGTTGTCAGAGGGCTGGATCTC.

In a further embodiment of the invention, polynucleotides encoding fragments of the antibody having binding specificity to TNF-α comprise, or alternatively consist of, one or more of the polynucleotide sequences of SEQ ID NO: 364; SEQ ID NO: 365; and SEQ ID NO: 366 which correspond to polynucleotides encoding the complementarity-determining regions (CDRs, or hypervariable regions)' of the light chain variable sequence of SEQ NO: 354.

In a further embodiment of the invention, polynucleotides encoding fragments of the antibody having binding specificity to TNF-α comprise, or alternatively consist of, one or more of the polynucleotide sequences of SEQ ID NO: 367; SEQ ID NO: 368; and SEQ ID NO: 369 which correspond to polynucleotides encoding the complementarity-determining regions (CDRs, or hyper-variable regions) of the heavy chain variable sequence of SEQ ID NO: 355.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 362 encoding the light chain variable region of SEQ ID NO: 354; the polynucleotide SEQ ID NO: 363 encoding the heavy chain variable region of SEQ. ID NO 355; polynucleotides encoding the complementarity-determining regions (SEQ ID NO: 364; SEQ ID NO: 365; and SEQ ID NO: 366) of the light chain variable region of SEQ ID NO: 354; and polynucleotides encoding the complementarity-determining regions (SEQ ID NO: 367; SEQ ID NO: 368; and SEQ ID NO: 369) of the heavy chain variable region of SEQ ID NO: 355.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 370:

(SEQ ID NO: 378)
ATGGACACGAGGGCCCCCACTCAGCTGCTGGGGCTCCTGCTGCTCTGGCT

CCCAGGTGCCAGATGTGCCGACATTGTGATGACCCAGACTCCATCCTCCG

TGTCTGCAGCTGTGGGAGGCACAGTCACCATCAATTGCCAGGCCAGTCAG

AACATTTACAGCTCTTTAGCCTGGTATCAGCAGAAACCAGGGCAGCCTCC

CAAGCTCCTGATCTTTGGTGCATCCAATCTGGAATCTGGGGTCCCATCGC

GGTTCAAAGGCAGTGGATCTGGGACAGAGTTCACTCTCACCATCAGCGAC

CTGGAGTGTGCCGATGCTGCCGCTTACTACTGTCAGAGCCATCATGGTAG

TAATAGTGATAGTTATGGTAATGCT

In another embodiment of the invention, polynucleotides of the invention comprise, or alternatively consist of, the following polynucleotide sequence encoding the variable heavy chain polypeptide sequence of SEQ ID NO: 371:

(SEQ ID NO: 379)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGCCTCTGGATTCTCCCTTAATAACTAC

TACATGACCTGGGTCCGCCAGGCTCCAGGGAAGGGGCTGGAATCCATCGG

ATATTTTGCTTCTGGTGGTGGCACATACTACGCGAACTGGGCGAAAGGCC

GATTCACCATCTCCAAAACCTCGACCACGGTGGATCTGAAGATCACCAGT

CCGACAACCGACGATACGGCCACCTATTTCTGTGCCAGGGGTGGTGCTTA

TTTGGGTACTGGGAGTTTG.

In a further embodiment of the invention, polynucleotides encoding fragments of the antibody having binding specificity to TNF-α comprise, or alternatively consist of, one or more of the polynucleotide sequences of SEQ ID NO: 380; SEQ ID NO: 381; and SEQ ID NO: 382 which correspond to polynucleotides encoding the complementarity-determining regions (CDRs, or hypervariable regions) of the light chain variable sequence of SEQ ID NO: 370.

In a further embodiment of the invention, polynucleotides encoding fragments of the antibody having binding specificity to TNF-α comprise, or alternatively consist of, one or more of the polynucleotide sequences of SEQ ID NO: 383; SEQ ID NO: 384; and SEQ ID NO: 385 which correspond to polynucleotides encoding the complementarity-determining regions (CDRs, or hypervariable regions) of the heavy chain variable sequence of SEQ ID NO: 371.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 378 encoding the light chain variable region of SEQ ID NO: 370; the polynucleotide SEQ ID NO: 379 encoding the heavy chain variable region of SEQ ID NO: 371; polynucleotides encoding the complementarity-determining regions (SEQ ID NO: 380; SEQ ID NO: 381; and SEQ ID NO: 382) of the light chain variable region of SEQ ID NO: 370; and polynucleotides encoding the complementarity-determining regions (SEQ ID NO: 383; SEQ ID NO: 384; and SEQ ID NO: 385) of the heavy chain variable region of SEQ ID NO: 371.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 386:

(SEQ ID NO: 394)
ATGGACACGAGGGCCCCCACTCAGCTGCTGGGGCTCCTGCTGCTCTGGCT

CCCAGGTGCCAGATGTGCTGACATTGTGATGACCCAGACTCCATCCTCCG

TGTCTGTACCTGTGGGAGGCACAGTCACCATCAAGTGCCAGGCCAGTCAG

AACATTTACAGCTCTTTAGCCTGGTATCAGCAGAAACCAGGACAGCCTCC

CAAGCGCCTGATCTATTATGCCGCCACTCTGGCATCTGGGGTCCCATCGC

GGTTCAAAGGCAGTGGATCTGGGACAGATTTCACTCTCACCATCAGCGAC

CTGGAGTGTGCCGATGCTGCCACTTACTATTGTCAAAGCAATCATGGTAG

TAATAGTGATAGTTATGGTAATCCT

In another embodiment of the invention, polynucleotides of the invention comprise, or alternatively consist of, the following polynucleotide sequence encoding the variable heavy chain polypeptide sequence of SEQ ID NO: 387:

(SEQ ID NO: 395)
ATGGAGACTGGGCTGCGCTGGCTTCTCCTGGTCGCTGTGCTCAAGGGTGT

CCAGTGTCAGTCGGTGGAGGAGTCCGGGGGTCGCCTGGTCACGCCTGGGA

CACCCCTGACACTCACCTGCACAGTCGCTGGATTCTCCCTCAGTACCTAT

GGAGTGACCTGGGTCCGCCAGGCTCCAGGGAAGGGGCTGGAATCCATCGG

ATACATTACTTATGGTAATATTAAATACTACGCGACCTGGGCGAAAGGCC

GATTCACCATCTCCAAAACCTCGACCACGGTGGATCTGAAAATGACCAGT

CCGACAACCGAGGACACGGCCACCTATTTCTGTACCAGATATGGTGGTAG

TGGGATTGGTGAGGACTTG.

In a further embodiment of the invention, polynucleotides encoding fragments of the antibody having binding specificity to TNF-α comprise, or alternatively consist of, one or more of the polynucleotide sequences of SEQ ID NO: 396; SEQ ID NO: 397; and SEQ ID NO: 398 which correspond to polynucleotides encoding the complementarity-determining regions (CDRs, or hypervariable regions) of the light chain variable sequence of SEQ ID NO: 386.

In a further embodiment of the invention, polynucleotides encoding fragments of the antibody having binding specificity to TNF-α comprise, or alternatively consist of, one or more of the polynucleotide sequences of SEQ ID NO: 399; SEQ ID NO: 400; and SEQ ID NO: 401 which correspond to polynucleotides encoding the complementarity-determining regions (CDRs, or hypervariable regions) of the heavy chain variable sequence of SEQ ID NO: 387.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 394 encoding the light chain variable region of SEQ ID NO: 386; the polynucleotide SEQ ID NO: 395 encoding the heavy chain variable region of SEQ ID NO: 387; polynucleotides encoding the complementarity-determining regions (SEQ ID NO: 396; SEQ ID NO: 397; and SEQ ID NO: 398) of the light chain variable region of SEQ ID NO: 386; and polynucleotides encoding the complementarity-determining regions (SEQ ID NO: 399; SEQ ID NO: 400; and SEQ ID NO: 401) of the heavy chain variable region of SEQ ID NO: 387.

The invention is further directed to polynucleotides encoding polypeptides of the antibodies having binding specificity to TNF-α. In one embodiment of the invention, polynucleotides of the invention comprise, or alternatively consist of, the following polynucleotide sequence encoding the variable light chain polypeptide sequence of SEQ ID NO: 402:

(SEQ ID NO: 410)
ATGGACACGAGGGCCCCCACTCAGCTGCTGGGGCTCCTGCTGCTCTGGCT

CCCAGGTGCCAGATGTGCCGACGTCGTGATGACCCAGACTCCATCCTCCG

TGTCTGAACCTGTGGGAGGCACAGTCACCATCAAGTGCCAGGCCAGTGAA

ACCATTGGTAACTACTTATCCTGGTATCAGCAGAAACCAGGGCAGCCTCC

CAAGCGCCTGATCTATTATGCATCCACTCTGTCATCTGGGGTCCCATCGC

GGTTCAAAGGCAGTGGATCTGGGACAGATTTCACTCTCACCATCAGCGAC

CTGGAGTGTGCCGATGCTGCCACTTACTACTGCCAAAAGAATTATGGTAG

TGGTGCTAGTAGTTTGGGTGCT

In another embodiment of the invention, polynucleotides of the invention comprise, or alternatively consist of, the following polynucleotide sequence encoding the variable heavy chain polypeptide sequence of SEQ ID NO: 403:

(SEQ ID NO: 411)
ATGGAGACTGGGCTGCGCTGGCTTCTCCTGGTCGCTGTGCTCAAAGGTGT

CCAGTGTCAGTCGGTGGAGGAGTCCGGGGGTCGCCTGGTCACGCCTGGGA

CACCCCTGACACTCACCTGCACAGTCTCTGGATTCTCCCTCAGTAGCTAC

TACATGGCCTGGGTCCGCCAGGCTCCAGGGAAGGGGCTGGAGTGGATCGG

ATATATTGGTTTTGGTGGTAGCACATACTACGCGACCTGGGCGAAAGGCC

GGGTCACCATCTCCAGGACCTCGACCACGGTGGATCTGCAAATCACCAGT

CCGACAACCGAGGACACGGCCACCTATTTCTGTGCCAGAGGAGTTTATGG

TGATTTTCGTACTGGTGCCGACTTG.

In a further embodiment of the invention, polynucleotides encoding fragments of the antibody having binding specificity to TNF-α comprise, or alternatively consist of, one or more of the polynucleotide sequences of SEQ ID NO: 412; SEQ ID NO: 413; and SEQ ID NO: 414 which correspond to polynucleotides encoding the complementarity-determining regions (CDRs, or hypervariable regions) of the light chain variable sequence of SEQ ID NO: 402.

In a further embodiment of the invention, polynucleotides encoding fragments of the antibody having binding specificity to TNF-α comprise, or alternatively consist of, one or more of the polynucleotide sequences of SEQ ID NO: 415; SEQ ID NO: 416; and SEQ ID NO: 417 which correspond to polynucleotides encoding the complementarity-determining regions (CDRs, or hypervariable regions) of the heavy chain variable sequence of SEQ ID NO: 403.

The invention also contemplates polynucleotide sequences including one or more of the polynucleotide sequences encoding antibody fragments described herein. In one embodiment of the invention, polynucleotides encoding fragments of the antibody having binding specificity to TNF-α comprise, or alternatively consist of, one, two, three or more, including all of the following polynucleotides encoding antibody fragments: the polynucleotide SEQ ID NO: 410 encoding the light chain variable region of SEQ ID NO: 402; the polynucleotide SEQ ID NO: 411 encoding the heavy chain variable region of SEQ ID NO: 403; polynucleotides encoding the complementarity-determining regions (SEQ ID NO: 412; SEQ ID NO: 413; and SEQ ID NO: 414) of the light chain variable region of SEQ ID NO: 402; and polynucleotides encoding the complementarity-determining regions (SEQ ID NO: 415; SEQ ID NO: 416; and SEQ ID NO: 417) of the heavy chain variable region of SEQ ID NO: 403.

In another embodiment of the invention, polynucleotides of the invention further comprise, the following polynucleotide sequence encoding the kappa constant light chain sequence of SEQ ID NO: 418:

```
                                                (SEQ ID NO: 419)
GTGGCTGCACCATCTGTCTTCATCTTCCCGCCATCTGATGAGCAGTTGAA

ATCTGGAACTGCCTCTGTTGTGTGCCTGCTGAATAACTTCTATCCCAGAG

AGGCCAAAGTACAGTGGAAGGTGGATAACGCCCTCCAATCGGGTAACTCC

CAGGAGAGTGTCACAGAGCAGGACAGCAAGGACAGCACCTACAGCCTCAG

CAGCACCCTGACGCTGAGCAAAGCAGACTACGAGAAACACAAAGTCTACG

CCTGCGAAGTCACCCATCAGGGCCTGAGCTCGCCCGTCACAAAGAGCTTC

AACAGGGGAGAGTGT.
```

In another embodiment of the invention, polynucleotides of the invention further comprise, the following polynucleotide sequence encoding the gamma-1 constant heavy chain polypeptide sequence of SEQ ID NO: 420:

```
                                                (SEQ ID NO: 421)
GCCTCCACCAAGGGCCCATCGGTCTTCCCCCTGGCACCCTCCTCCAAGAG

CACCTCTGGGGGCACAGCGGCCCTGGGCTGCCTGGTCAAGGACTACTTCC

CCGAACCGGTGACGGTGTCGTGGAACTCAGGCGCCCTGACCAGCGGCGTG

CACACCTTCCCGGCTGTCCTACAGTCCTCAGGACTCTACTCCCTCAGCAG

CGTGGTGACCGTGCCCTCCAGCAGCTTGGGCACCCAGACCTACATCTGCA

ACGTGAATCACAAGCCCAGCAACACCAAGGTGGACAAGAGAGTTGAGCCC

AAATCTTGTGACAAAACTCACACATGCCCACCGTGCCCAGCACCTGAACT

CCTGGGGGACCGTCAGTCTTCCTCTTCCCCCCAAAACCCAAGGACACCC

TCATGATCTCCCGGACCCCTGAGGTCACATGCGTGGTGGTGGACGTGAGC

CACGAAGACCCTGAGGTCAAGTTCAACTGGTACGTGGACGGCGTGGAGGT

GCATAATGCCAAGACAAAGCCGCGGGAGGAGCAGTACGCCAGCACGTACC

GTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAA

AACCATCTCCAAAGCCAAAGGGCAGCCCCGAGAACCACAGGTGTACACCC

TGCCCCCATCCCGGGAGGAGATGACCAAGAACCAGGTCAGCCTGACCTGC

CTGGTCAAAGGCTTCTATCCCAGCGACATCGCCGTGGAGTGGGAGAGCAA

TGGGCAGCCGGAGAACAACTACAAGACCACGCCTCCCGTGCTGGACTCCG

ACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAA

CCACTACACGCAGAAGAGCCTCTCCCTGTCTCCGGGTAAA.
```

In one embodiment, the invention is directed to an isolated polynucleotide comprising a polynucleotide encoding an anti-TNF-α $V_H$ antibody amino acid sequence selected from SEQ ID NO: 3, 19, 35, 51, 67, 83, 99, 115, 131, 147, 163, 179, 195, 211, 227, 243, 259, 275, 291, 307, 323, 339, 355, 371, 387 and SEQ ID NO: 403 or encoding a variant thereof wherein at least one framework residue (FR residue) has been substituted with an amino acid present at the corresponding position in a rabbit anti-TNF-α antibody $V_H$ polypeptide or a conservative amino acid substitution.

In another embodiment, the invention is directed to an isolated polynucleotide comprising the polynucleotide sequence encoding an anti-TNF-α $V_L$ antibody amino acid sequence of 2, 18, 34, 50, 66, 82, 98, 114, 130, 146, 162, 178, 194, 210, 226, 242, 258, 274, 290, 306, 322, 338, 354, 370, 386 and SEQ ID NO: 402 or encoding a variant thereof wherein at least one framework residue (FR residue) has been substituted with an amino acid present at the corresponding position in a rabbit anti-TNF-α antibody $V_L$ polypeptide or a conservative amino acid substitution:

In yet another embodiment, the invention is directed to one or more heterologous polynucleotides comprising a sequence encoding the polypeptides contained in SEQ ID NO:2 and SEQ ID NO:3; SEQ ID NO:18 and SEQ ID NO:19; SEQ ID NO:34 and SEQ ID NO:35; SEQ ID NO:50 and SEQ ID NO:51; SEQ ID NO:66 and SEQ ID NO:67; SEQ ID NO:82 and SEQ ID NO:83; SEQ ID NO:98 and SEQ ID NO:99; SEQ ID NO:114 and SEQ ID NO:115; SEQ ID NO:130 and SEQ ID NO:131; SEQ ID NO:146 and SEQ ID NO:147; SEQ ID NO:162 and SEQ ID NO:163; SEQ ID NO:178 and SEQ ID NO:179; SEQ ID NO:194 and SEQ ID NO:195; SEQ ID NO:210 and SEQ ID NO:211; SEQ ID NO:226 and SEQ ID NO:227; SEQ ID NO:242 and SEQ ID NO:243; SEQ ID NO:258 and SEQ ID NO:259; SEQ ID NO:274 and SEQ ID NO:275; SEQ ID NO:290 and SEQ ID NO:291; SEQ ID NO:306 and SEQ ID NO:307; SEQ ID NO:322 and SEQ ID NO:323; SEQ ID NO:338 and SEQ ID NO:339; SEQ ID NO:354 and SEQ ID NO:355; SEQ ID NO:370 and SEQ ID NO:371; SEQ ID NO:386 and SEQ ID NO:387; or SEQ ID NO:402 and SEQ ID NO:403.

In another embodiment, the invention is directed to an isolated polynucleotide that expresses a polypeptide containing at least one CDR polypeptide derived from an anti-TNF-α antibody wherein said expressed polypeptide alone specifically binds TNF-α or specifically binds TNF-α when expressed in association with another polynucleotide sequence that expresses a polypeptide containing at least one CDR polypeptide derived from an anti-TNF-α antibody wherein said at least one CDR is selected from those contained in the $V_L$ or $V_H$ polypeptides contained in SEQ ID NO: 3, 19, 35, 51, 67, 83, 99, 115, 131, 147, 163, 179, 195, 211, 227, 243, 259, 275, 291, 307, 323, 339, 355, 371, 387, 2, 18, 34, 50, 66, 82, 98, 114, 130, 146, 162, 178, 194, 210, 226, 242, 258, 274, 290, 306, 322, 338, 354, 370, 386 and SEQ ID NO: 402.

Host cells and vectors comprising said polynucleotides, are also contemplated.

The invention further contemplates vectors comprising the polynucleotide sequences encoding the variable heavy and light chain polypeptide sequences, as well as the individual complementarity-determining regions (CDRs, or hypervariable regions), as set forth herein, as well as host cells comprising said sequences. In one embodiment of the invention, the host cell is a yeast cell. In another embodiment of the invention, the yeast host cell belongs to the genus *Pichia*.

Anti-TNF-α Activity

The anti-TNF-α activity of the anti-TNF-α antibody of the present invention, and fragments thereof having binding specificity to TNF-α, may also be described by their strength of binding or their affinity for TNF-α. In one embodiment of the invention, the anti-TNF-α antibodies of the present invention, and fragments thereof having binding specificity to TNF-α, bind to TNF-α with a dissociation constant ($K_D$) of less than or equal to $5\times10^{-7}$, $10^{-7}$, $5\times10^{-8}$, $10^{-8}$, $5\times10^{-9}$, $10^{-9}$, $5\times10^{-10}$, $10^{-10}$, $5\times10^{-11}$, $10^{-11}$, $5\times10^{-12}$, $10^{-12}$, $5\times10^{-13}$, $10^{-13}$, $5\times10^{-14}$, $10^{-14}$, $5\times10^{-15}$ or $10^{-15}$. Preferably, the anti-TNF-α antibodies and fragments thereof bind TNF-α with a dissociation constant of less than or equal to $5\times10^{-10}$. In another embodiment of the invention, the anti-TNF-α antibodies of the present invention, and fragments thereof having binding specificity to TNF-α, bind to a linear or conformational TNF-α epitope.

In another embodiment of the invention, the anti-TNF-α activity of the anti-TNF-α antibodies of the present invention, and fragments thereof having binding specificity to TNF-α, bind to TNF-α with an off-rate of less than or equal to $10^{-4}$ $S^{-1}$, $5\times10^{-5}$ $S^{-1}$, $10^{-5}$ $S^{-1}$, $5\times10^{-6}$ $S^{-1}$, $10^{-6}$ $S^{-1}$, $5\times10^{-7}$ $S^{-1}$, or $10^{-7}$ $S^{-1}$.

In a further embodiment of the invention, the anti-TNF-α activity of the anti-TNF-α antibodies of the present invention, and fragments thereof having binding specificity to TNF-α, exhibit anti-TNF-α activity by preventing, ameliorating or reducing the symptoms of, or alternatively treating, diseases and disorders associated with TNF-α. Non-limiting examples of diseases and disorders associated with TNF-α are set forth infra.

B-Cell Screening and Isolation

In one embodiment, the present invention provides methods of isolating a clonal population of antigen-specific B cells that may be used for isolating at least one antigen-specific cell. As described and exemplified infra, these methods contain a series of culture and selection steps that can be used separately, in combination, sequentially, repetitively, or periodically. Preferably, these methods are used for isolating at least one antigen-specific cell, which can be used to produce a monoclonal antibody, which is specific to a desired antigen, or a nucleic acid sequence corresponding to such an antibody.

In one embodiment, the present invention provides a method comprising the steps of:

a. preparing a cell population comprising at least one antigen-specific B cell;

b. enriching the cell population, e.g., by chromatography, to form an enriched cell population comprising at least one antigen-specific B cell;

c. isolating a single B cell from the enriched B cell population; and d. determining whether the single B cell produces an antibody specific to the antigen.

In another embodiment, the present invention provides an improvement to a method of isolating a single, antibody-producing B cell, the improvement comprising enriching a B cell population obtained from a host that has been immunized or naturally exposed to an antigen, wherein the enriching step precedes any selection steps, comprises at least one culturing step, and results in a clonal population of B cells that produces a single monoclonal antibody specific to said antigen.

Throughout this application, a "clonal population of B cells" refers to a population of B cells that only secrete a single antibody specific to a desired antigen. That is to say that these cells produce only one type of monoclonal antibody specific to the desired antigen.

In the present application, "enriching" a cell population cells means increasing the frequency of desired cells, typically antigen-specific cells, contained in a mixed cell population, e.g., a B cell-containing isolate derived from a host that is immunized against a desired antigen. Thus, an enriched cell population encompasses a cell population having a higher frequency of antigen-specific cells as a result of an enrichment step, but this population of cells may contain and produce different antibodies.

The general term "cell population" encompasses pre- and post-enrichment cell populations, keeping in mind that when multiple enrichment steps are performed, a cell population can be both pre- and post-enrichment. For example, in one embodiment, the present invention provides a method:

a. harvesting a cell population from an immunized host to obtain a harvested cell population;

b. creating at least one single cell suspension from the harvested cell population;

c. enriching at least one single cell suspension to form a first enriched cell population;

d. enriching the first enriched cell population to form a second enriched cell population;

e. enriching the second enriched cell population to form a third enriched cell population; and f. selecting an antibody produced by an antigen-specific cell of the third enriched cell population.

Each cell population may be used directly in the next step, or it can be partially or wholly frozen for long- or short-term storage or for later steps. Also, cells from a cell population can be individually suspended to yield single cell suspensions. The single cell suspension can be enriched, such that a single cell suspension serves as the pre-enrichment cell population. Then, one or more antigen-specific single cell suspensions together form the enriched cell population; the antigen-specific single cell suspensions can be grouped together, e.g., re-plated for further analysis and/or antibody production.

In one embodiment, the present invention provides a method of enriching a cell population to yield an enriched cell population having an antigen-specific cell frequency that is about 50% to about 100%, or increments therein. Preferably; the enriched cell population has an antigen-specific cell frequency greater than or equal to about 50%, 60%, 70%, 75%, 80%, 90%, 95%, 99%, or 100%.

In another embodiment, the present invention provides a method of enriching a cell population whereby the frequency of antigen-specific cells is increased by at least about 2-fold, 5-fold, 10-fold, 20-fold, 50-fold, 100-fold, or increments therein.

Throughout this application, the term "increment" is used to define a numerical value in varying degrees of precision, e.g., to the nearest 10, 1, 0.1, 0.01, etc. The increment can be rounded to any measurable degree of precision, and the increment need not be rounded to the same degree of precision on both sides of a range. For example, the range 1 to 100 or increments therein includes ranges such as 20 to 80, 5 to 50, and 0.4 to 98. When a range is open-ended, e.g., a range of less than 100, increments therein means increments between 100 and the measurable limit. For example, less than 100 or increments therein means 0 to 100 or increments therein unless the feature, e.g., temperature, is not limited by 0.

Antigen-specificity can be measured with respect to any antigen. The antigen can be any substance to which an antibody can bind including, but not limited to, peptides, proteins or fragments thereof; carbohydrates; organic and inorganic molecules; receptors produced by animal cells, bacterial cells, and viruses; enzymes; agonists and antagonists of biological pathways; hormones; and cytokines. Exemplary antigens include, but are not limited to, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF) and Hepcidin. Preferred antigens include IL-6, IL-13, TNF-α, VEGF-α, Hepatocyte Growth Factor (HGF) and Hepcidin. In a method utilizing more than one enrichment step, the antigen used in each enrichment step can be the same as or different from one another. Multiple enrichment steps with the same antigen may yield a large and/or diverse population of antigen-specific cells;

multiple enrichment steps with different antigens may yield an enriched cell population with cross-specificity to the different antigens.

Enriching a cell population can be performed by any cell-selection means known in the art for isolating antigen-specific cells. For example, a cell population can be enriched by chromatographic techniques, e.g., Miltenyi bead or magnetic bead technology. The beads can be directly or indirectly attached to the antigen of interest. In a preferred embodiment, the method of enriching a cell population, includes at least, one chromatographic enrichment step.

A cell population can also be enriched by performed by any antigen-specificity assay technique known in the art, e.g., an ELISA assay or a halo assay. ELISA assays include, but are not limited to, selective antigen immobilization (e.g., biotinylated antigen capture by streptavidin, avidin, or neutravidin coated plate), non-specific antigen plate coating, and through an antigen build-up strategy (e.g., selective antigen capture followed by binding partner addition to generate a heteromeric protein-antigen complex). The antigen can be directly or indirectly attached to a solid matrix or support, e.g., a column. A halo assay comprises contacting the cells with antigen-loaded beads and labeled anti-host antibody specific to the host used to harvest the B cells. The label can be, e.g., a fluorophore. In one embodiment, at least one assay enrichment step is performed on at least one single cell suspension. In another embodiment, the method of enriching a cell population includes at least one chromatographic enrichment step and at least one assay enrichment step.

Methods of "enriching" a cell population by size or density are known in the art. See, e.g., U.S. Pat. No. 5,627,052. These steps can be used in the present method in addition to enriching the cell population by antigen-specificity.

The cell populations of the present invention contain at least one cell capable of recognizing an antigen. Antigen-recognizing cells include, but are not limited to, B cells, plasma cells, and progeny thereof. In one embodiment, the present invention provides a clonal cell population containing a single type of antigen-specific B-cell, i.e., the cell population produces a single monoclonal antibody specific to a desired antigen.

In such embodiment, it is believed that the clonal antigen-specific population of B cells consists predominantly of antigen-specific, antibody-secreting cells, which are obtained by the novel culture and selection protocol provided herein. Accordingly, the present invention also provides methods for obtaining an enriched cell population containing at least one antigen-specific, antibody-secreting cell. In one embodiment, the present invention provides an enriched cell population containing about 50% to about 100%, or increments therein, or greater than or equal to about 60%, 70%, 80%, 90%, or 100% of antigen-specific, antibody-secreting cells.

In one embodiment, the present invention provides a method of isolating a single B cell by enriching a cell population obtained from a host before any selection steps, e.g., selecting a particular B cell from a cell population and/or selecting an antibody produced by a particular cell. The enrichment step can be performed as one, two, three, or more steps. In one embodiment, a single B cell is isolated from an enriched cell population before confirming whether the single B cell secretes an antibody with antigen-specificity and/or a desired property.

In one embodiment, a method of enriching a cell population is used in a method for antibody production and/or selection. Thus, the present invention provides a method comprising enriching a cell population before selecting an antibody. The method can include the steps of: preparing a cell population comprising at least one antigen-specific cell, enriching the cell population by isolating at least one antigen-specific cell to form an enriched cell population, and inducing antibody production from at least one antigen-specific cell. In a preferred embodiment, the enriched cell population contains more than one antigen-specific cell. In one embodiment, each antigen-specific cell of the enriched population is cultured under conditions that yield a clonal antigen-specific B cell population before isolating an antibody producing cell therefrom and/or producing an antibody using said B cell, or a nucleic acid sequence corresponding to such an antibody. In contrast to prior techniques where antibodies are produced from a cell population with a low frequency of antigen-specific cells, the present invention allows antibody selection from among a high frequency of antigen-specific cells. Because an enrichment step is used prior to antibody selection, the majority of the cells, preferably virtually all of the cells, used for antibody production are antigen-specific. By producing antibodies from a population of cells with an increased frequency of antigen specificity, the quantity and variety of antibodies are increased.

In the antibody selection methods of the present invention, an antibody is preferably selected after an enrichment step and a culture step that results in a clonal population of antigen-specific B cells. The methods can further comprise a step of sequencing a selected antibody or portions thereof from one or more isolated, antigen-specific cells. Any method known in the art for sequencing can be employed and can include sequencing the heavy chain, light chain, variable region(s), and/or complementarity determining region(s) (CDR).

In addition to the enrichment step, the method for antibody selection can also include one or more steps of screening a cell population for antigen recognition and/or antibody functionality. For example, the desired antibodies may have specific structural features, such as binding to a particular epitope or mimicry of a particular structure; antagonist or agonist activity; or neutralizing activity, e.g., inhibiting binding between the antigen and a ligand. In one embodiment, the antibody functionality screen is ligand-dependent. Screening for antibody functionality includes, but is not limited to, an in vitro protein-protein interaction assay that recreates the natural interaction of the antigen ligand with recombinant receptor protein; and a cell-based response that is ligand dependent and easily monitored (e.g., proliferation response). In one embodiment, the method for antibody selection includes a step of screening the cell population for antibody functionality by measuring the inhibitory concentration (IC50). In one embodiment, at least one of the isolated, antigen-specific cells produces an antibody having an IC50 of less than about 100, 50, 30, 25, 10 µg/mL, or increments therein.

In addition to the enrichment step, the method for antibody selection can also include one or more steps of screening a cell population for antibody binding strength. Antibody binding strength can be measured by any method known in the art (e.g., Biacore). In one embodiment, at least one of the isolated, antigen-specific cells produces an antibody having a high antigen affinity, e.g., a dissociation constant (Kd) of less than about $5\times10^{-10}$ $M^{-1}$, preferably about $1\times10^{-13}$ to $5\times10^{-10}$, $1\times10^{-12}$ to $1\times10^{-10}$, $1\times10^{-12}$ to $7.5\times10^{11}$, $1\times10^{-11}$ to $2\times10^{-11}$, about $1.5\times10^{-11}$ or less, or increments therein. In this embodiment, the antibodies are said to be affinity mature. In a preferred embodiment, the affinity of the antibodies is comparable to or higher than the affinity of any one of Panorex® (edrecolomab), Rituxan® (rituximab), Herceptin® (traztuzumab), Mylotarg® (gentuzumab), Campath® (alemtuzumab), Zevalin™ (ibritumomab), Erbitux™ (cetuximab), Avastin™ (bevicizumab), Raptiva™ (efalizumab), Remicade® (infliximab), Humira™ (adalimumab), and Xolair™ (omalizumab). Preferably, the affinity of the antibodies is comparable to or higher than the affinity of Humira™. The affinity of an antibody can also be increased by known affinity maturation techniques. In one embodiment, at least one cell population is screened for at least one of, preferably both, antibody functionality and antibody binding strength.

In addition to the enrichment step, the method for antibody selection can also include one or more steps of screening a cell population for antibody sequence homology, especially human homology. In one embodiment, at least one of the isolated, antigen-specific cells produces an antibody that has a homology to a human antibody of about 50% to about 100%, or increments therein, or greater than about 60%, 70%, 80%, 85%, 90%, or 95% homologous. The antibodies can be humanized to increase the homology to a human sequence by techniques known in the art such as CDR grafting or selectivity determining residue grafting (SDR).

In another embodiment, the present invention also provides the antibodies themselves according to any of the embodiments described above in terms of IC50, Kd, and/or homology.

The B cell selection protocol disclosed herein has a number of intrinsic advantages versus other methods for obtaining antibody-secreting B cells and monoclonal antibodies specific to desired target antigens. These advantages include, but are not restricted to, the following:

First, it has been found that when these selection procedures are utilized with a desired antigen such as IL-6 or TNF-α, the methods reproducibly result in antigen-specific B cells capable of generating what appears to be a substantially comprehensive complement of antibodies, i.e., antibodies that bind to the various different epitopes of the antigen. Without being bound by theory, it is hypothesized that the comprehensive complement is attributable to the antigen enrichment step that is performed prior to initial B cell recovery. Moreover, this advantage allows for the isolation and selection of antibodies with different properties as these properties may vary depending on the epitope specificity of the particular antibody.

Second, it has been found that the B cell selection protocol reproducibly yields a clonal B cell culture containing a single B cell, or its progeny, secreting a single monoclonal antibody that generally binds to the desired antigen with a relatively high binding affinity, i.e. picomolar or better antigen binding affinities. By contrast, prior antibody selection methods tend to yield relatively few high affinity antibodies and therefore require extensive screening procedures to isolate an antibody with therapeutic potential. Without being, bound by theory, it is hypothesized that the protocol results in both in vivo B cell immunization of the host (primary immunization) followed by a second in vitro B cell stimulation (secondary antigen priming step) that may enhance the ability and propensity of the recovered clonal B cells to secrete a single high affinity monoclonal antibody specific to the antigen target.

Third, it has been observed (as shown herein with TNF-α specific B cells) that the B cell selection protocol reproducibly yields enriched B cells producing IgG's that are, on average, highly selective (antigen specific) to the desired target. Antigen-enriched B cells recovered by these methods are believed to contain B cells capable of yielding the desired full complement of epitopic specificities as discussed above.

Fourth, it has been observed that the B cell selection protocols, even when used with small antigens, i.e., peptides of 100 amino acids or less, e.g., 5-50 amino acids long, reproducibly give rise to a clonal B cell culture that secretes a single high affinity antibody to the small antigen, e.g., a peptide. This is highly surprising as it is generally quite difficult, labor intensive, and sometimes not even feasible to produce high affinity antibodies to small peptides. Accordingly, the invention can be used to produce therapeutic antibodies to desired peptide targets, e.g., viral, bacterial or autoantigen peptides, thereby allowing for the production of monoclonal antibodies with very discrete binding properties or even the production of a cocktail of monoclonal antibodies to different peptide targets, e.g., different viral strains. This advantage may especially be useful in the context of the production of a therapeutic or prophylactic vaccine having a desired valency, such as an HPV vaccine that induces protective immunity to different HPV strains.

Fifth, the B cell selection protocol, particularly when used with B cells derived from rabbits, tends to reproducibly yield antigen-specific antibody sequences that are very similar to endogenous human immunoglobulins (around 90% similar at the amino acid level) and that contain CDRs that possess a length very analogous to human immunoglobulins and therefore require little or no sequence modification (typically at most only a few CDR residues may be modified in the parent antibody sequence and no framework exogenous residues introduced) in order to eliminate potential immunogenicity concerns. In particular, preferably the recombinant antibody will contain only the host (rabbit) CDR1 and CDR2 residues required for antigen recognition and the entire CDR3. Thereby, the high antigen binding affinity of the recovered antibody sequences produced according to the B cell and antibody selection protocol remains intact or substantially intact even with humanization.

In sum, these methods can be used, to produce antibodies exhibiting higher binding affinities to more distinct epitopes by the use of a more efficient protocol than was previously known.

In a specific embodiment, the present invention provides a method for identifying a single B cell that secretes an antibody specific to a desired antigen and that optionally possesses at least one desired functional property such as affinity, avidity, cytolytic activity, and the like by a process including the following steps:

a. immunizing a host against an antigen;
   b. harvesting B cells from the host;
   c. enriching the harvested B cells to increase the frequency of antigen-specific cells;
   d. creating at least one single cell suspension;
   e. culturing a sub-population from the single cell suspension under conditions that favor the survival of a single antigen-specific B cell per culture well;
   f. isolating B cells from the sub-population; and
   g. determining whether the single B cell produces an antibody specific to the antigen.

Typically, these methods will further comprise an additional step of isolating and sequencing, in whole or in part, the polypeptide and nucleic acid sequences encoding the desired antibody. These sequences or modified versions or portions thereof can be expressed in desired host cells in order to produce recombinant antibodies to a desired antigen.

As noted previously, it is believed that the clonal population of B cells predominantly comprises antibody-secreting B cells producing antibody against the desired antigen. It is also believed based on experimental results obtained with several antigens and with different B cell populations that the clonally produced B cells and the isolated antigen-specific B cells derived therefrom produced according to the invention secrete a monoclonal antibody that is typically of relatively high affinity and moreover is capable of efficiently and reproducibly producing a selection of monoclonal antibodies of greater epitopic variability as compared to other methods of deriving monoclonal antibodies from cultured antigen-specific B cells. In an exemplary embodiment the population of immune cells used in such B cell selection methods will be derived from a rabbit. However, other hosts that produce antibodies, including non-human and human hosts, can alternatively be used as a source of immune B cells. It is believed that the use of rabbits as a source of B cells may enhance the diversity of monoclonal antibodies that may be derived by the methods. Also, the antibody sequences derived from rabbits according to the invention typically possess sequences having a high degree of sequence identity to human antibody sequences making them favored for use in humans since they should possess little antigenicity. In the course of humanization, the final humanized antibody contains a much lower foreign/host residue content, usually restricted to a subset of the host CDR residues that differ dramatically due to their nature versus the human target sequence used in the grafting. This enhances the probability of complete activity recovery in the humanized antibody protein.

The methods of antibody selection using an enrichment step disclosed herein include a step of obtaining a immune cell-containing cell population from an immunized host. Methods of obtaining an immune cell-containing cell population from an immunized host are known in the art and generally include inducing an immune response in a host and harvesting cells from the host to obtain one or more cell populations. The response can be elicited by immunizing the host against a desired antigen. Alternatively, the host used as a source of such immune cells can be naturally exposed to the desired antigen such as an individual who has been infected with a particular pathogen such as a bacterium or virus or alternatively has mounted a specific antibody response to a cancer that the individual is afflicted with.

Host animals are well-known in the art and include, but are not limited to, guinea pig, rabbit, mouse, rat, non-human primate, human, as well as other mammals and rodents, chicken, cow, pig, goat, and sheep. Preferably the host is a mammal, more preferably, rabbit, mouse, rat, or human. When exposed to an antigen, the host produces antibodies as part of the native immune response to the antigen. As mentioned, the immune response can occur naturally, as a result of disease, or it can be induced by immunization with the antigen. Immunization can be performed by any method known in the art, such as, by one or more injections of the antigen with or without an agent to enhance immune response, such as complete or incomplete Freund's adjuvant. In another embodiment, the invention also contemplates intrasplenic immunization. As an alternative to immunizing a host animal in vivo, the method can comprise immunizing a host cell culture in vitro.

After allowing time for the immune response (e.g., as measured by serum antibody detection), host animal cells are harvested to obtain one or more cell populations. In a preferred embodiment, a harvested cell population is screened for antibody binding strength and/or antibody functionality. A harvested cell population is preferably from at least one of the spleen, lymph nodes, bone marrow, and/or peripheral blood mononuclear cells (PBMCs). The cells can be harvested from more than one source and pooled. Certain sources may be preferred for certain antigens. For example, the spleen, lymph nodes, and PBMCs are preferred for IL-6; and the lymph nodes are preferred for TNF. The cell population is harvested about 20 to about 90 days or increments therein after immunization, preferably about 50 to about 60 days. A harvested cell population and/or a single cell suspension therefrom can be enriched, screened, and/or cultured for antibody selection. The frequency of antigen-specific cells within a harvested cell population is usually about 1% to about 5%, or increments therein.

In one embodiment, a single cell suspension from a harvested cell population is enriched, preferably by using Miltenyi beads. From the harvested cell population having a frequency of antigen-specific cells of about 1% to about 5%, an enriched cell population is thus derived having a frequency of antigen-specific cells approaching 100%.

The method of antibody selection using an enrichment step includes a step of producing antibodies from at least one antigen-specific cell from an enriched cell population. Methods of producing antibodies in vitro are well known in the art, and any suitable method can be employed. In one embodiment, an enriched cell population, such as an antigen-specific single cell suspension from a harvested cell population, is plated at various cell densities, such as 50, 100, 250, 0.500, or other increments between 1 and 1000 cells per well. Preferably, the sub-population comprises no more than about 10,000-antigen-specific, antibody-secreting cells, more preferably about 50-10,000, about 50-5,000, about 50-1,000, about 50-500, about 50-250 antigen-specific, antibody-secreting cells, or increments therein. Then, these sub-populations are cultured with suitable medium (e.g., an activated T cell conditioned medium, particularly 1-5% activated rabbit T cell conditioned medium) on a feeder layer, preferably under conditions that favor the survival of a single proliferating antibody-secreting cell per culture well. The feeder layer, generally comprised of irradiated cell matter, e.g., EL4B cells, does not constitute part of the cell population. The cells are cultured in a suitable media for a time sufficient for antibody production, for example about 1 day to about 2 weeks, about 1 day to about 10 days, at least about 3 days, about 3 to about 5 days, about 5 days to about 7 days, at least about 7 days, or other increments therein. In one embodiment, more than one sub-population is cultured simultaneously. Preferably, a single antibody-producing cell and progeny thereof survives in each well, thereby providing a clonal population of antigen-specific B cells in each well. At this stage, the immunoglobulin G (IgG) produced by the clonal population is highly correlative with antigen specificity. In a preferred embodiment, the IgGs exhibit a correlation with antigen specificity that is greater than about 50%, more preferably greater than 70%, 85%, 90%, 95%, 99%, or increments therein. See FIG. 3, which demonstrates an exemplary correlation for huTNF-α. The correlations were demonstrated by setting up B cell cultures under limiting conditions to establish, single antigen-specific antibody products per well. Antigen-specific versus general IgG synthesis was compared. Three populations were observed: IgG that recognized a single formate of antigen (biotinylated and direct coating), detectable IgG and antigen recognition irrespective of immobilization, and IgG production alone. IgG production was highly correlated with antigen-specificity.

A supernatant containing the antibodies is optionally collected, which can be enriched, screened, and/or cultured for antibody selection according to the steps described above. In one embodiment, the supernatant is enriched (preferably by an antigen-specificity assay, especially an ELISA assay) and/or screened for antibody functionality.

In another embodiment, the enriched, preferably clonal, antigen-specific B cell population from which a supernatant described above is optionally screened in order to detect the presence of the desired secreted monoclonal antibody is used for the isolation of a few B cells, preferably a single B cell, which is then tested in an appropriate assay in order to confirm the presence of a single antibody-producing B cell in the clonal B cell population. In one embodiment about 1 to about 20 cells are isolated from the clonal B cell population, preferably less than about 15, 12, 10, 5, or 3 cells, or increments therein, most preferably a single cell. The screen is preferably effected by an antigen-specificity assay, especially a halo assay. The halo assay can be performed with the full length protein, or a fragment thereof. The antibody-containing supernatant can also be screened for at least one of: antigen binding affinity; agonism or antagonism of antigen-ligand binding, induction or inhibition of the proliferation of a specific target cell type; induction or inhibition of lysis of a target cell, and induction or inhibition of a biological pathway involving the antigen.

The identified antigen-specific cell can be used to derive the corresponding nucleic acid sequences encoding the desired monoclonal antibody. (An AluI digest can confirm that only a single monoclonal antibody type is produced per well.) As mentioned above, these sequences can be mutated, such as by humanization, in order to render them suitable for use in human medicaments.

As mentioned, the enriched B cell population used in the process can also be further enriched, screened, and/or cultured for antibody selection according to the steps described above which can be repeated or performed in a different order. In a preferred embodiment, at least one cell of an enriched, preferably clonal, antigen-specific cell population is isolated, cultured, and used for antibody selection.

Thus, in one embodiment, the present invention provides a method comprising:

a. harvesting a cell population from an immunized host to obtain a harvested cell population;

b. creating at least one single cell suspension from a harvested cell population;

c. enriching at least one single cell suspension, preferably by chromatography, to form a first enriched cell population;

d. enriching the first enriched cell population, preferably by ELISA assay, to form a second enriched cell population which preferably is clonal, i.e., it contains only a single type of antigen-specific B cell;

e. enriching the second enriched cell population, preferably by halo assay, to form a third enriched cell population containing a single, or a few number of B cells that produce an antibody specific to a desired antigen; and f. selecting an antibody produced by an antigen-specific cell isolated from the third enriched cell population.

The method can further include one or more steps of screening the harvested cell population for antibody binding strength (affinity, avidity) and/or antibody functionality. Suitable screening steps include, but are not limited to, assay methods that detect: whether the antibody produced by the identified antigen-specific B cell produces an antibody possessing a minimal antigen binding affinity, whether the antibody agonizes or antagonizes the binding of a desired antigen to a ligand; whether the antibody induces or inhibits the proliferation of a specific cell type; whether the antibody induces or elicits a cytolytic reaction against target cells; whether the antibody binds to a specific epitope; and whether the antibody modulates (inhibits or agonizes) a specific biological pathway or pathways involving the antigen.

Similarly, the method can include one or more steps of screening the second enriched cell population for antibody binding strength and/or antibody functionality.

The method can further include a step of sequencing the polypeptide sequence or the corresponding nucleic acid sequence of the selected antibody. The method can also include a step of producing a recombinant antibody using the sequence, a fragment thereof, or a genetically modified version of the selected antibody. Methods for mutating antibody sequences in order to retain desired properties are well known to those skilled in the art and include humanization, chimerisation, production of single chain antibodies; these mutation methods can yield recombinant antibodies possessing desired effector function, immunogenicity, stability, removal or addition of glycosylation, and the like. The recombinant antibody can be produced by any suitable recombinant cell, including, but not limited to mammalian cells such as CHO, COS, BHK, HEK-293, bacterial cells, yeast cells, plant cells, insect cells, and amphibian cells. In one embodiment, the antibodies are expressed in polyploidal yeast cells, i.e., diploid yeast cells, particularly *Pichia*.

In one embodiment, the method comprises:

a. immunizing a host against an antigen to yield host antibodies;

b. screening the host antibodies for antigen specificity and neutralization;

c. harvesting B cells from the host;

d. enriching the harvested B cells to create an enriched cell population having an increased frequency of antigen-specific cells;

e. culturing one or more sub-populations from the enriched cell population under conditions that favor the survival of a single B cell to produce a clonal population in at least one culture well;

f. determining whether the clonal population produces an antibody specific to the antigen;

g. isolating a single B cell; and h. sequencing the nucleic acid sequence of the antibody produced by the single B cell.

Methods of Humanizing Antibodies

In another embodiment of the invention, there is provided a method for humanizing antibody heavy and light chains. In this embodiment, the following method is followed for the humanization of the heavy and light chains:

Light Chain

1. Identify the amino acid that is the first one following the signal peptide sequence. This is the start of Framework 1. The signal peptide starts at the first initiation methionine and is typically, but not necessarily 22 amino acids in length for rabbit light chain protein sequences. The start of the mature polypeptide can also be determined experimentally by N-terminal protein sequencing, or can be predicted using a prediction algorithm. This is also the start of Framework 1 as classically defined by those in the field.

Example: RbtVL Amino Acid residue 1 in FIG. 2, starting 'AYDM . . . '

2. Identify the end of Framework 3. This is typically 86-90 amino acids following the start of Framework I and is typically a cysteine residue preceded by two tyrosine residues. This is the end of the Framework 3 as classically defined by those in the field.

Example: RbtVL amino acid residue 88 in FIG. 2, ending as 'TYYC'

3. Use the rabbit light chain sequence of the polypeptide starting from the beginning of Framework 1 to the end of Framework 3 as defined above and perform a sequence homology search for the most similar human antibody protein sequences. This will typically be a search against human germline sequences prior to antibody maturation in order to reduce the possibility of immunogenicity, however any human sequences can be used. Typically a program like BLAST can be used to search a database of sequences for the most homologous. Databases of human antibody sequences can be found from various sources such as NCBI (National Center for Biotechnology Information).

Example: RbtVL amino acid sequence from residues numbered 1 through 88 in FIG. 2 is BLASTed against a human antibody germline database. The top three unique returned sequences are shown in FIG. 2 as L12A, V1 and Vx02.

4. Generally the most homologous human germline variable light chain' sequence is then used as the basis for humanization. However those skilled in the art may decide to use another sequence that wasn't the highest homology as determined by the homology algorithm, based on other factors including sequence gaps and framework similarities.

Example: In FIG. 2, L12A was the most homologous human germline variable light chain sequence and is used as the basis for the humanization of RbtVL.

5. Determine the framework and CDR arrangement (FR1, FR2, FR3, CDR1 & CDR2) for the human homolog being used for the light chain humanization. This is using the traditional layout as described in the field. Align the rabbit variable light chain sequence with the human homolog, while maintaining the layout of the framework and CDR regions.

Example: In FIG. 2, the RbtVL sequence is aligned with the human homologous sequence L12A, and the framework and CDR domains are indicated.

6. Replace the human homologous light chain sequence CDR1 and CDR2 regions with the CDR1 and CDR2 sequences from the rabbit sequence. If there are differences in length between the rabbit and human CDR sequences then use the entire rabbit CDR sequences and their lengths. It is possible that the specificity, affinity, and/or immunogenicity of the resulting humanized antibody may be unaltered if smaller or larger sequence exchanges are performed, or if specific residue(s) are altered, however the exchanges as described have been used successfully, but do not exclude the possibility that other changes may be permitted.

Example: In FIG. 2, the CDR1 and CDR2 amino acid residues of the human homologous variable light chain L12A are replaced with the CDR1 and CDR2 amino acid sequences from the RbtVL rabbit antibody light chain sequence. The human L12A frameworks 1, 2 and 3 are unaltered. The resulting humanized sequence is shown below as VLh from residues numbered 1 through 88. Note that the only residues that are different from the L12A human sequence are underlined, and are thus rabbit-derived amino acid residues. In this example only 8 of the 88 residues are different than the human sequence.

7. After framework 3 of the new hybrid sequence created in Step 6, attach the entire CDR3 of the rabbit light chain antibody sequence. The CDR3 sequence can be of various lengths, but is typically 9 to 15 amino acid residues in length. The CDR3 region and the beginning of the following framework 4 region are defined classically and identifiable by those skilled in the art. Typically the beginning of Framework 4, and thus after the end of CDR3 consists of the sequence 'FGGG . . . ', however some variation may exist in these residues.

Example: In FIG. 2, the CDR3 of RbtVL (amino acid residues numbered 89-100) is added after the end of framework 3 in the humanized sequence indicated as VLh.

8. The rabbit light chain framework 4, which is typically the final 11 amino acid residues of the variable light chain and begins as indicated in Step 7 above and typically ends with the amino acid sequence ' . . . VVKR' is replaced with the nearest human light chain framework 4 homolog, usually from germline sequence. Frequently this human light chain framework 4 is of the sequence 'FGGGTKVE1KR'. It is possible that other human light chain framework 4 sequences that are not the most homologous or otherwise different may be used without affecting the specificity, affinity and/or immunogenicity of the resulting humanized antibody. This human light chain framework 4 sequence is added to the end of the variable light chain humanized sequence immediately following the CDR3 sequence from Step 7 above. This is now the end of the variable light chain humanized amino acid sequence.

Example: In FIG. 2, Framework 4 (FR4) of the RbtVL rabbit light chain sequence is shown above a homologous human FR4 sequence. The human FR4 sequence is added to the humanized variable light chain sequence (VLh) right after the end of the CD3 region added in Step 7 above.

Heavy Chain

1. Identify the amino acid that is the first one following the signal peptide sequence. This is the start of Framework 1. The signal peptide starts at the first initiation methionine and is typically 19 amino acids in length for rabbit heavy chain protein sequences. Typically, but not necessarily always, the final 3 amino acid residues of a rabbit heavy chain signal peptide are ' . . . VQC', followed by the start of Framework 1. The start of the mature polypeptide can also be determined experimentally by N-terminal protein sequencing, or can be predicted using a prediction algorithm. This is also the start of Framework 1 as classically defined by those in the field.

Example: RbtVH Amino acid residue 1 in FIG. 2, starting 'QEQL . . . '

2. Identify the end of Framework 3. This is typically 95-100 amino acids following the start of Framework 1 and typically has the final sequence of ' . . . CAR' (although the alanine can also be a valine). This is the end of the Framework 3 as classically defined by those in the field.

Example: RbtVH amino acid residue 98 in FIG. 2, ending as ' . . . FCVR'.

3. Use the rabbit heavy chain sequence of the polypeptide starting from the beginning of Framework 1 to the end of Framework 3 as defined above and perform a sequence homology search for the most similar human antibody protein sequences. This will typically be against a database of human germline sequences prior to antibody maturation in order to reduce the possibility of immunogenicity, however any human sequences can be used. Typically a program like BLAST can be used to search a database of sequences for the most homologous. Databases of human antibody sequences can be found from various sources such as NCBI (National Center for Biotechnology Information).

Example: RbtVH amino acid sequence from residues numbered 1 through 98 in FIG. 2 is BLASTed against a human antibody germline database. The top three unique returned sequences are shown in FIG. 2 as 3-64-04, 3-66-04, and 3-53-02.

4. Generally the most homologous human germline variable heavy chain sequence is then used as the basis for humanization. However those skilled in the art may decide to use another sequence that wasn't the most homologous as determined by the homology algorithm, based on other factors including sequence gaps and framework similarities.

Example: 3-64-04 in FIG. 2 was the most homologous human germline variable heavy chain sequence and is used as the basis for the humanization of RbtVH.

5. Determine the framework and CDR arrangement (FR1, FR2, FR3, CDR1 & CDR2) for the human homolog being used for the heavy chain humanization. This is using the traditional layout as described in the field. Align the rabbit variable heavy chain sequence with the human homolog, while maintaining the layout of the framework and CDR regions.

Example: In FIG. 2, the RbtVH sequence is aligned with the human homologous sequence 3-64-04, and the framework and CDR domains are indicated.

6. Replace the human homologous heavy chain sequence CDR1 and CDR2 regions with the CDR1 and CDR2 sequences from the rabbit sequence. If there are differences in length between the rabbit and human CDR sequences then use the entire rabbit CDR sequences and their lengths. In addition, it may be necessary to replace the final three amino acids of the human heavy chain Framework 1 region with the final three amino acids of the rabbit heavy chain Framework 1. Typically but not always, in rabbit heavy chain Framework 1 these three residues follow a Glycine residue preceded by a Serine residue. In addition, it may be necessary replace the final amino acid of the human heavy chain Framework 2 region with the final amino acid of the rabbit heavy chain Framework 2. Typically, but not necessarily always, this is a Glycine residue preceded by an Isoleucine residue in the rabbit heavy chain Framework 2. It is possible that the specificity, affinity and/or immunogenicity of the resulting humanized antibody may be unaltered if smaller or larger sequence exchanges are performed, or if specific residue(s) are altered, however the exchanges as described have been used successfully, but do not exclude the possibility that other changes may be permitted. For example; a tryptophan amino acid residue typically occurs four residues prior to the end of the rabbit heavy chain CDR2 region, whereas in human heavy chain CDR2 this residue is typically a Serine residue. Changing this rabbit tryptophan residue to a the human Serine residue at this position has been demonstrated to have minimal to no effect on the humanized antibody's specificity or affinity, and thus further minimizes the content of rabbit sequence-derived amino acid residues in the humanized sequence.

Example: In FIG. 2, The CDR1 and CDR2 amino acid residues of the human homologous variable heavy chain are replaced with the CDR1 and CDR2 amino acid sequences from the RbtVH rabbit antibody light chain sequence, except for the boxed residue, which is tryptophan in the rabbit sequence (position number 63) and Serine at the same position in the human sequence, and is kept as the human Serine residue. In addition to the CDR1 and CDR2 changes, the final three amino acids of Framework 1 (positions 28-30) as well as the final residue of Framework 2 (position 49) are retained as rabbit, amino acid residues instead of human. The resulting humanized sequence is shown below as VHh from residues numbered 1 through 98. Note that the only residues that are different from the 3-64-04 human sequence are underlined, and are thus rabbit-derived amino acid residues. In this example only 15 of the 98 residues are different than the human sequence.

7. After framework 3 of the new hybrid sequence created in Step 6, attach the entire CDR3 of the rabbit heavy chain antibody sequence. The CDR3 sequence can be of various lengths, but is typically 5 to 19 amino acid residues in length. The CDR3 region and the beginning of the following framework 4 region are defined classically and are identifiable by those skilled in the art. Typically the beginning of framework 4, and thus after the end of CDR3 consists of the sequence WGXG . . . (where X is usually Q or P), however some variation may exist in these residues.

Example: The CDR3 of RbtVH (amino acid residues numbered 99-110) is added after the end of framework 3 in the humanized sequence indicated as VHh.

8. The rabbit heavy chain framework 4, which is typically the final 11 amino acid residues of the variable heavy chain and begins as indicated in Step 7 above and typically ends with the amino acid sequence ' . . . TVSS' is replaced with the nearest human heavy chain framework 4 homolog, usually from germline sequence. Frequently this human heavy chain framework 4 is of the sequence 'WGQGTLVT-VSS'. It is possible that other human heavy chain framework 4 sequences that are not the most homologous or otherwise different may be used without affecting the specificity, affinity and/or immunogenicity of the resulting humanized antibody. This human heavy chain framework 4 sequence is added to the end of the variable heavy chain humanized sequence immediately following the CDR3 sequence from Step 7 above. This is now the end of the variable heavy chain humanized amino acid sequence.

Example: In FIG. 2, framework 4 (FR4) of the RbtVH rabbit heavy chain sequence is shown above a homologous human heavy FR4 sequence. The human FR4 sequence is added to the humanized variable heavy chain sequence (VHh) right after the end of the CD3 region added in Step 7 above.

Methods of Producing Antibodies and Fragments Thereof

The invention is also directed to the production of the antibodies described herein or fragments thereof. Recombinant polypeptides corresponding to the antibodies described herein or fragments thereof are secreted from polyploidal, preferably diploid or tetraploid strains of mating competent yeast. In an exemplary embodiment, the invention is directed to methods for producing these recombinant polypeptides in secreted form for prolonged periods using cultures comprising polyploid yeast, i.e., at least several days to a week, more preferably at least a month or several months, and even more preferably at least 6 months to a year or longer. These polyploid yeast cultures will express at least 10-25 mg/liter of the polypeptide, more preferably at least 50-250 mg/liter, still more preferably at least 500-1000 mg/liter, and most preferably a gram per liter or more of the recombinant polypeptide(s).

In one embodiment of the invention a pair of genetically marked yeast haploid cells are transformed with expression vectors comprising subunits of a desired heteromultimeric protein. One haploid cell comprises a first expression vector, and a second haploid cell comprises a second expression vector. In another embodiment diploid yeast cells will be transformed with one or more expression vectors that provide for the expression and secretion of one or more of the recombinant polypeptides. In still another embodiment a single haploid cell may be transformed with one or more vectors and used to produce a polyploidal yeast by fusion or mating strategies. In yet another embodiment a diploid yeast culture may be transformed with one or more vectors providing for the expression and secretion of a desired polypeptide or polypeptides. These vectors may comprise vectors e.g., linearized plasmids or other linear DNA products that integrate into the yeast cell's genome randomly through homologous recombination, or using a recombinase such as Cre/Lox or Flp/Frt. Optionally, additional expression vectors may be introduced into the haploid or diploid cells; or the first or second expression vectors may comprise additional coding sequences; for the synthesis of heterotrimers; heterotetramers; etc. The expression levels of the non-identical polypeptides may be individually calibrated, and adjusted through appropriate selection, vector copy number, promoter strength and/or induction and the like. The transformed haploid cells are genetically crossed or fused. The resulting diploid or tetraploid strains are utilized to produce and secrete fully assembled and biologically functional proteins, humanized antibodies described herein or fragments thereof.

The use of diploid or tetraploid cells for protein production provides for unexpected benefits. The cells can be grown for production purposes, i.e. scaled up, and for extended periods of time, in conditions that can be deleterious to the growth of haploid cells, which conditions may include high cell density; growth in minimal media; growth at low temperatures; stable growth in the absence of selective pressure; and which may provide for maintenance of heterologous gene sequence integrity and maintenance of high level expression over time. Indeed the inventors have achieved expression yields in excess of about 1 g/liter and these yields may be enhanced by further optimization. Without wishing to be bound thereby, the inventors theorize that these benefits may arise, at least in part, from the creation of diploid strains from two distinct parental haploid strains. Such haploid strains can comprise numerous minor autotrophic mutations, which mutations are complemented in the diploid or tetraploid, enabling growth and enhanced production under highly selective conditions.

Transformed mating competent haploid yeast cells provide a genetic method that enables subunit pairing of a desired protein. Haploid yeast strains are transformed with each of two expression vectors, a first vector to direct the synthesis of one polypeptide chain and a second vector to direct the synthesis of a second, non-identical polypeptide chain. The two haploid strains are mated to provide a diploid host where optimized target protein production can be obtained.

Optionally, additional non-identical coding sequence(s) are provided. Such sequences may be present on additional expression vectors or in the first or the second expression vectors. As is known in the art, multiple coding sequences may be independently expressed from individual promoters; or may be coordinately expressed through the inclusion of an "internal ribosome entry site" or "IRES", which is an element that promotes direct internal ribosome entry to the initiation codon, such as ATG, of a cistron (a protein encoding region), thereby leading to the cap-independent translation of the gene. IRES elements functional in yeast are described by Thompson et al. (2001) *P.N.A.S.* 98:12866-12868.

In one embodiment of the invention, antibody sequences are produced in combination with a secretory. J chain, which provides for enhanced stability of IgA (see U.S. Pat. Nos. 5,959,177; and 5,202,422).

In a preferred embodiment the two haploid yeast strains are each auxotrophic, and require supplementation of media for growth of the haploid cells. The pair of auxotrophs are complementary, such that the diploid product will grow in the absence of the supplements required for the haploid cells. Many such genetic markers are known in yeast, including requirements for amino acids (e.g. met, lys, his, arg, etc.), nucleosides (e.g. ura3, ade1, etc.); and the like. Amino acid markers may be preferred for the methods of the invention. Alternatively diploid cells which contain the desired vectors can be selected by other means, e.g., by use of other markers, such as green fluorescent protein, antibiotic resistance genes, various dominant selectable markers, and the like.

Two transformed haploid cells may be genetically crossed and diploid strains arising from this mating event selected by their hybrid nutritional requirements and/or antibiotic resistance spectra. Alternatively, populations of the two transformed haploid strains are spheroplasted and fused, and diploid progeny regenerated and selected. By either method, diploid strains can be identified and selectively grown based on their ability to grow in different media than their parents. For example, the diploid cells may be grown in minimal medium that may include antibiotics. The diploid synthesis strategy has certain advantages. Diploid strains have the potential to produce enhanced levels of heterologous protein through broader complementation to underlying mutations, which may impact the production and/or secretion of recombinant protein. Furthermore, once stable strains have been obtained, any antibiotics used to select those strains do not necessarily need to be continuously present in the growth media.

As noted above, in some embodiments a haploid yeast may be transformed with a single or multiple vectors and mated or fused with a non-transformed cell to produce a diploid cell containing the vector or vectors. In other embodiments, a diploid yeast cell may be transformed with one or more vectors that provide for the expression and secretion of a desired heterologous polypeptide by the diploid yeast cell.

In one embodiment of the invention, two haploid strains are transformed with a library of polypeptides, e.g. a library of antibody heavy or light chains. Transformed haploid cells that synthesize the polypeptides are mated with the complementary haploid cells. The resulting diploid cells are screened for functional protein. The diploid cells provide a means of rapidly, conveniently and inexpensively bringing together a large number of combinations of polypeptides for functional testing. This technology is especially applicable for the generation of heterodimeric protein products, where optimized subunit synthesis levels are critical for functional protein expression and secretion.

In another embodiment of the invention, the expression level ratio of the two subunits is regulated in order to maximize product generation. Heterodimer subunit protein levels have been shown previously to impact the final product generation (Simmons L C, J Immunol Methods. 2002 May 1; 263(1-2):133-47). Regulation can be achieved prior to the mating step by selection for a marker present on the expression vector. By stably increasing the copy number of the vector, the expression level can be increased. In some cases, it may be desirable to increase the level of one chain relative to the other, so as to reach a balanced proportion between the subunits of the polypeptide. Antibiotic resistance markers are useful for this purpose, e.g. Zeocin resistance marker, G418 resistance, etc. and provide a means of enrichment for strains that contain multiple integrated copies of an expression vector in a strain by selecting for transformants that are resistant to higher levels of Zeocin or G418. The proper ratio, e.g. 1:1; 1:2; etc. of the subunit genes may be important for efficient protein production. Even when the same promoter is used to transcribe both subunits, many other factors contribute to the final level of protein expressed and therefore, it can be useful to increase the number of copies of one encoded gene relative to the other. Alternatively, diploid strains that produce higher levels of a polypeptide, relative to single copy vector strains, are created by mating two haploid strains, both of which have multiple copies of the expression vectors.

Host cells are transformed with the above-described expression vectors, mated to form diploid strains, and cultured in conventional nutrient media modified as appropriate for inducing promoters, selecting transformants or amplifying the genes encoding the desired sequences. A number of minimal media suitable for the growth of yeast are known in the art. Any of these media may be supplemented as necessary with salts (such as sodium chloride, calcium, magnesium, and phosphate), buffers (such as phosphate, HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

Secreted proteins are recovered from the culture medium. A protease inhibitor, such as phenyl methyl sulfonyl fluoride (PMSF) may be useful to inhibit proteolytic degradation during purification, and antibiotics may be included to prevent the growth of adventitious contaminants. The composition may be concentrated, filtered, dialyzed, etc., using methods known in the art.

The diploid cells of the invention are grown for production purposes. Such production purposes desirably include growth in minimal media, which media lacks pre-formed amino acids and other complex biomolecules, e.g., media comprising ammonia as a nitrogen source, and glucose as an energy and carbon source, and salts as a source of phosphate, calcium and the like. Preferably such production media lacks selective agents such as antibiotics, amino acids, purines, pyrimidines, etc. The diploid cells can be grown to high cell density, for example at least about 50 g/L; more usually at least about 100 g/L; and may be at least about 300, about 400, about 500 g/L or more.

In one embodiment of the invention, the growth of the subject cells for production purposes is performed at low temperatures, which temperatures may be lowered during log phase, during stationary phase, or both. The term "low temperature" refers to temperatures of at least about 15° C., more usually at least about 17° C., and may be about 20° C., and is usually not more than about 25° C., more usually not more than about 22° C. In another embodiment of the invention, the low temperature is usually not more than about 28° C. Growth temperature can impact the production of full-length secreted proteins in production cultures, and decreasing the culture growth temperature can strongly enhance the intact product yield. The decreased temperature appears to assist intracellular trafficking through the folding and post-translational processing pathways used by the host to generate the target product, along with reduction of cellular protease degradation.

The methods of the invention provide for expression of secreted, active protein, preferably a mammalian protein. In one embodiment, secreted, "active antibodies", as used herein, refers to a correctly folded multimer of at least two properly paired chains, which accurately binds to its cognate antigen. Expression levels of active protein are usually at least about 10-50 mg/liter culture, more usually at least about 100 mg/liter, preferably at least about 500 mg/liter, and may be 1000 mg/liter or more.

The methods of the invention can provide for increased stability of the host and heterologous coding sequences during production. The stability is evidenced, for example, by maintenance of high levels of expression of time, where the starting level of expression is decreased by not more than about 20%, usually not more than 10%, and may be decreased by not more than about 5% over about 20 doublings, 50 doublings, 100 doublings, or more.

The strain stability also provides for maintenance of heterologous gene sequence integrity over time, where the sequence of the active coding sequence and requisite transcriptional regulatory elements are maintained in at least about 99% of the diploid cells, usually in at least about 99.9% of the diploid cells, and preferably in at least about 99.99% of the diploid cells over about 20 doublings, 50 doublings, 100 doublings, or more. Preferably, substantially all of the diploid cells maintain the sequence of the active coding sequence and requisite transcriptional regulatory elements.

Other methods of producing antibodies are well known to those of ordinary skill in the art. For example, methods of producing chimeric antibodies are now well known in the art (See, for example, U.S. Pat. No. 4,816,567 to Cabilly et al.; Morrison et al., P.N.A.S. USA, 81:8651-55 (1984); Neuberger, M. S. et al., Nature, 314:268-270 (1985); Boulianne, G. L. et al., Nature, 312:643-46 (1984), the disclosures of each of which are herein incorporated by reference in their entireties).

Likewise, other methods of producing humanized antibodies are now well known in the art (See, for example, U.S. Pat. Nos. 5,530,101, 5,585,089, 5,693,762, and 6,180,370 to Queen et al; U.S. Pat. Nos. 5,225,539 and 6,548,640 to Winter; U.S. Pat. Nos. 6,054,297, 6,407,213 and 6,639,055 to Carter et al; U.S. Pat. No. 6,632,927 to Adair; Jones, P. T. et al, Nature, 321:522-525 (1986); Reichmann, L., et al, Nature, 332:323-327 (1988); Verhoeyen, M, et al, Science, 239:1534-36 (1988), the disclosures of each of which are herein incorporated by reference in their entireties).

Antibody polypeptides of the invention having TNF-α binding specificity may also be produced by constructing, using conventional techniques well known to those of ordinary skill in the art, an expression vector containing an operon and a DNA sequence encoding an antibody heavy chain in which the DNA sequence encoding the CDRs required for antibody specificity is derived from a non-human cell source, preferably a rabbit B-cell source, while the DNA sequence encoding the remaining parts of the antibody chain is derived from a human cell source.

A second expression vector is produced using the same conventional means well known to those of ordinary skill in the art, said expression vector containing an operon and a DNA sequence encoding an antibody light chain in which the DNA sequence encoding the CDRs required for antibody specificity is derived from a non-human cell source, preferably a rabbit B-cell source, while the DNA sequence encoding the remaining parts of the antibody chain is derived from a human cell source.

The expression vectors are transfected into a host cell by convention techniques well known to those of ordinary skill in the art to produce a transfected host cell, said transfected host cell cultured by conventional techniques well known to those of ordinary skill in the art to produce said antibody polypeptides.

The host cell may be co-transfected with the two expression vectors described above, the first expression vector containing DNA encoding an operon and a light chain-derived polypeptide and the second vector containing DNA encoding an operon and a heavy chain-derived polypeptide. The two vectors contain different selectable markers, but preferably achieve substantially equal expression of the heavy and light chain polypeptides. Alternatively, a single vector may be used, the vector including DNA encoding both the heavy and light chain polypeptides. The coding sequences for the heavy and light chains may comprise cDNA, genomic DNA, or both.

The host cells used to express the antibody polypeptides may be either a bacterial cell such as E. coli, or a eukaryotic cell. In a particularly preferred embodiment of the invention, a mammalian cell of a well-defined type for this purpose, such as a myeloma cell or a Chinese hamster ovary (CHO) cell line may be used.

The general methods by which the vectors may be constructed, transfection methods required to produce the host cell and culturing methods required to produce the antibody polypeptides from said host cells all include conventional techniques. Although preferably the cell line used to produce the antibody is a mammalian cell line, any other suitable cell line, such as a bacterial cell line such as an E. coli-derived bacterial strain, or a yeast cell line, may, alternatively be used.

Similarly, once produced the antibody polypeptides may be purified according to standard procedures in the art, such as for example cross-flow filtration, ammonium sulphate precipitation, affinity column chromatography and the like.

The antibody polypeptides described herein may also be used for the design and synthesis of either peptide or non-peptide mimetics that would be useful for the same therapeutic applications as the antibody polypeptides of the invention. See, for example, Saragobi et al, Science, 253: 792-795 (1991), the contents of which is herein incorporated by reference in its entirety.

Screening Assays

The invention also includes screening assays designed to assist in the identification of diseases and disorders associated with TNF-α in patients exhibiting symptoms of an TNF-α associated disease or disorder.

In one embodiment of the invention, the anti-TNF-α antibodies of the invention, or TNF-α binding fragments thereof, are used to detect the presence of TNF-α in a biological sample obtained from a patient exhibiting symptoms of a disease or disorder associated with TNF-α. The presence of TNF-α, or elevated levels thereof when compared to pre-disease levels of TNF-α in a comparable biological sample, may be beneficial in diagnosing a disease or disorder associated with TNF-α.

Another embodiment of the invention provides a diagnostic or screening assay to assist in diagnosis of diseases or disorders associated with TNF-α in patients exhibiting symptoms of an TNF-α associated disease or disorder identified herein, comprising assaying the level of TNF-α expression in a biological sample from said patient using a post-translationally modified anti-TNF-α antibody or binding fragment thereof. The anti-TNF-α antibody or binding fragment thereof may be post-translationally modified to include a detectable moiety such as set forth previously in the disclosure.

The TNF-α level in the biological sample is determined using a modified anti-TNF-α antibody or binding fragment thereof as set forth herein, and comparing the level of TNF-α in the biological sample against a standard level of TNF-α (e.g., the level in normal biological samples). The skilled clinician would understand that some variability may exist between normal biological samples, and would take that into consideration when evaluating results.

The above-recited assay may also be useful in monitoring a disease or disorder, where the level of TNF-α obtained in a biological sample from a patient believed to have a TNF-α associated disease or disorder is compared with the level of TNF-α in prior biological samples from the same patient, in order to ascertain whether the TNF-α level in said patient has changed with, for example, a treatment regimen.

The invention is also directed to a method of in vivo imaging which detects the presence of cells which express TNF-α comprising administering a diagnostically effective amount of a diagnostic composition. Said in vivo imaging is useful for the detection or imaging of TNF-α expressing tumors or metastases and TNF-α expressing inflammatory sites, for example, and can be useful as part of a planning regimen for the design of an effective cancer or arthritis treatment protocol. The treatment protocol may include, for example, one or more of radiation, chemotherapy, cytokine therapy, gene therapy, and antibody therapy, as well as an anti-TNF-α antibody or fragment thereof.

A skilled clinician would understand that a biological sample includes, but is not limited to, sera, plasma, urine, saliva, mucous, pleural fluid, synovial fluid and spinal fluid.

Methods of Ameliorating or Reducing Symptoms of, or Treating, or Preventing, Diseases and Disorders Associated with, TNF-α

In another embodiment of the invention, anti-TNF-α antibodies described herein, or fragments thereof, are useful for ameliorating or reducing the symptoms of, or treating, or preventing, diseases and disorders associated with TNF-α. Anti-TNF-α antibodies described herein, or fragments thereof, can also be administered in a therapeutically effective amount to patients in need of treatment of, diseases and disorders associated with TNF-α in the form of a pharmaceutical composition as described in greater detail below.

In one embodiment of the invention, anti-TNF-α antibodies described herein, or fragments thereof, are useful for ameliorating or reducing the symptoms of, or treating, or preventing, the following non-limiting listing of diseases and disorders: Rheumatoid Arthritis, Psoriatic Arthropathy, Ankylosing Spondylitis, Juvenile Rheumatoid Arthritis, Still's Disease, Systemic Lupus Erythematosis, Sjogren's Disease, Mixed Connective Tissue Disorder, Polymyalgia Rheumatica, Giant Cell Arteritis, Wegener's Granulomatosis, Kawasaki's disease, Autoimmune vasculitis, Autoimmune Uveitis, Inflammatory Bowel Disease, Bechet's Disease, Psoriasis, Graves Disease, Hashimoto's thyroiditis, Asthma, Type 1 Diabetes; Type 2 Diabetes, Ischemic Heart Disease, Peripheral Vascular Disease, Stroke, Pyoderma gangrenosum, Sarcoidosis, Dercum's disease, toxic epidermal necrolysis, idiopathic uveitis or scleritis, birdshot retinochoroiditis, uveitic and diabetic cystoid macular edema, age-related macular degeneration, Pulmonary fibrosis, Chronic Obstructive Pulmonary Disease, Depression, Schizophrenia, Alzheimer's Disease, Vascular Dementia.

In another embodiment of the invention, anti-TNF-α antibodies described herein, or fragments thereof, are useful for ameliorating or reducing the symptoms of, or treating, or preventing, the following non-limiting listing of diseases and disorders: glomerulonephritis, atherosclerosis, restenosis, autoimmune diseases, Crohn's disease, graft v. host (GVH) reactions (including organ transplant rejection), septic shock, cachexia, anorexia, multiple sclerosis, gram negative sepsis, and endotoxic shock.

In another embodiment of the invention, anti-TNF-α antibodies described herein, or fragments thereof, are useful for ameliorating or reducing the symptoms of, or treating, or preventing, the following non-limiting listing of diseases and disorders: neoplastic diseases, including breast cancer, ovarian cancer, bladder cancer, lung cancer, thyroid cancer, glioblastoma, stomach cancer, endometrial cancer, kidney cancer, colon and colorectal cancer, pancreatic cancer and prostate cancer.

In another embodiment of the invention, anti-TNF-α antibodies described herein, or fragments thereof, are useful for ameliorating or reducing the symptoms of, or treating, or preventing, the following non-limiting listing of diseases and disorders: uveitis (e.g., childhood and seronegative), lupus and other diseases mediated by immune complexes such as pemphigus and glomerulonephritis, congenital hyperthyroidism (CH), delayed type hypersensitivity (DTH) such as contact hypersensitivity, sarcoidosis, chronic arthritis, adult still disease, scleroderma, giant cell arteritis, SAPHO syndrome, primary biliary cirrhosis (PBC), myelodysplastic syndromes, vasculitis, hematologic malignancies, cochleovestibular disorders, macrophage activation syndrome, interstitial lung disease, Hepatitis C, ovulation induction, and myelodysplastic syndromes. Other TNF-α related diseases and disorders are disclosed in U.S. Pat. No. 6,090,382 to Salfeld et al, and U.S. Pat. No. 5,436,154 to Barbanti et al, both of which are incorporated by reference in their entireties.

Administration

In one embodiment of the invention, the anti-TNF-α antibodies described herein, or TNF-α binding fragments thereof, as well as combinations of said antibody fragments, are administered to a subject at a concentration of between about 0.1 and 10.0 mg/kg of body weight of recipient subject. In a preferred embodiment of the invention, the anti-TNF-α antibodies described herein, or TNF-α binding fragments thereof, as well as combinations of said antibody fragments, are administered to a subject at a concentration of about 0.4 mg/kg of body weight of recipient subject. In a preferred embodiment of the invention, the anti-TNF-α antibodies described herein, or TNF-α binding fragments thereof, as well as combinations of said antibody fragments, are administered to a recipient subject with a frequency of once every twenty-six weeks or less, such as once every sixteen weeks or less, once every eight weeks or less, or once every four weeks or less.

A person of skill in the art would be able to determine an effective dosage and frequency of administration through routine experimentation, for example guided by the disclosure herein and the teachings in Goodman, L. S., Gilman, A., Brunton, L. L., Lazo, J. S., & Parker, K. L. (2006). Goodman & Gilman's the pharmacological basis of therapeutics. New York: McGraw-Hill; Howland, R. D., Mycek, M. J., Harvey, R. A., Champe, P. C., & Mycek, M. J. (2006). Pharmacology. Lippincott's illustrated reviews. Philadelphia: Lippincott Williams & Wilkins; and Golan, D. E. (2008). Principles of pharmacology: the pathophysiologic basis of drug therapy. Philadelphia, Pa., [etc.]: Lippincott Williams & Wilkins.

In another embodiment of the invention, the anti-TNF-α antibodies described herein, or TNF-α binding fragments thereof, as well as combinations of said antibody fragments, are administered to a subject in a pharmaceutical formulation.

A "pharmaceutical composition" refers to a chemical or biological composition suitable for administration to a mammal. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, powder, liquid, gel, drops, or other means of administration.

In one embodiment of the invention, the anti-TNF-α antibodies described herein, or TNF-α binding fragments thereof, as well as combinations of said antibody fragments, may be optionally administered in combination with one or more active agents. Such active agents include analgesic, antipyretic, anti-inflammatory, antibiotic, antiviral, and anti-cytokine agents. Active agents include agonists, antagonists, and modulators of TNF-α, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors. Active agents also include 2-Arylpropionic acids, Aceclofenac, Acemetacin, Acetylsalicylic acid (Aspirin), Alclofenac, Alminoprofen, Amoxiprin, Ampyrone, Arylalkanoic acids, Azapropazone, Benorylate/Benorilate, Benoxaprofen, Bromfenac, Carprofen, Celecoxib, Choline magnesium salicylate, Clofezone, COX-2 inhibitors, Dexibuprofen, Dexketoprofen, Diclofenac, Diflunisal, Droxicam, Ethenzamide, Etodolac, Etoricoxib, Faislamine, fenamic acids, Fenbufen, Fenoprofen, Flufenamic acid, Flunoxaprofen, Flurbiprofen, Ibuprofen, Ibuproxam, Indometacin, Indoprofen, Kebuzone, Ketoprofen, Ketorolac, Lornoxicam, Loxoprofen, Lumiracoxib, Magnesium salicylate, Meclofenamic acid, Mefenamic acid, Meloxicam, Metamizole, Methyl salicylate, Mofebutazone, Nabumetone, Naproxen, N-Arylanthranilic acids, Oxametacin, Oxaprozin, Oxicams, Oxyphenbutazone, Parecoxib, Phenazone, Phenylbutazone, Phenylbutazone, Piroxicam, Pirprofen, profens, Proglumetacin, Pyrazolidine derivatives, Rofecoxib, Salicyl salicylate, Salicylamide, Salicylates, Sulfinpyrazone, Sulindac, Suprofen, Tenoxicam, Tiaprofenic acid, Tolfenamic acid, Tolmetin, and Valdecoxib. Antibiotics include Amikacin, Aminoglycosides, Amoxicillin, Ampicillin, Ansamycins, Arsphenamine, Azithromycin, Azlocillin, Aztreonam, Bacitracin, Carbacephem, Carbapenems, Carbenicillin, Cefaclor, Cefadroxil, Cefalexin, Cefalothin, Cefalotin, Cefamandole, Cefazolin, Cefdinir, Cefditoren, Cefepime, Cefixime, Cefoperazone, Cefotaxime, Cefoxitin, Cefpodoxime, Cefprozil, Ceftazidime, Ceftibuten, Ceftizoxime, Ceftobiprole, Ceftriaxone, Cefuroxime, Cephalosporins, Chloramphenicol, Cilastatin, Ciprofloxacin, Clarithromycin, Clindamycin, Cloxacillin, Colistin, Co-trimoxazole, Dalfopristin, Demeclocycline, Dicloxacillin, Dirithromycin, Doripenem, Doxycycline, Enoxacin, Ertapenem, Erythromycin, Ethambutol, Flucloxacillin, Fosfomycin, Furazolidone, Fusidic acid, Gatifloxacin, Geldanamycin, Gentamicin, Glycopeptides, Herbimycin, Imipenem, Isoniazid, Kanamycin, Levofloxacin, Lincomycin, Linezolid, Lomefloxacin, Loracarbef, Macrolides, Mafenide, Meropenem, Meticillin, Metronidazole, Mezlocillin, Minocycline, Monobactams, Moxifloxacin, Mupirocin, Nafcillin, Neomycin, Netilmicin, Nitrofurantoin, Norfloxacin, Ofloxacin, Oxacillin, Oxytetracycline, Paromomyciri, Penicillin, Penicillins, Piperacillin, Platensimycin, Polymyxin B, Polypeptides, Prontosil, Pyrazinamide, Quinolones, Quinupristin, Rifampicin, Rifampin, Roxithromycin, Spectinomycin, Streptomycin, Sulfacetamide, Sulfamethizole, Sulfanilimide, Sulfasalazine, Sulfisoxazole, Sulfonamides, Teicoplanin, Telithromycin, Tetracycline, Tetracyclines, Ticarcillin, Tinidazole, Tobramycin, Trimethoprim, Trimethoprim-Sulfamethoxazole, Troleandomycin, Trovafloxacin, and Vancomycin. Active agents also include Aldosterone, Beclometasone, Betamethasone, Corticosteroids, Cortisol, Cortisone acetate, Deoxycorticosterone acetate, Dexamethasone, Fludrocortisone acetate, Glucocorticoids, Hydrocortisone, Methylprednisolone, Prednisolone, Prednisone, Steroids, and Triamcinolone. Any suitable combination of these active agents is also contemplated.

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity to the formulation, though it may provide chemical and/or biological stability, and release characteristics. Exemplary formulations can be found; for example, in Remington's Pharmaceutical Sciences, 19$^{th}$ Ed., Grennaro, A., Ed., 1995 which is incorporated by reference.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions and sterile powders for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The invention contemplates that the pharmaceutical composition is present in lyophilized form. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the alkaline polypeptide can be formulated in a time release formulation, for example: in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

For each of the recited embodiments, the compounds can be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

Certain teachings related to methods for obtaining a clonal population of antigen-specific B cells were disclosed in U.S. Provisional patent application No. 60/801,412, filed May 19, 2006, the disclosure of which is herein incorporated by reference in its entirety.

Certain teachings related to humanization of rabbit-derived monoclonal antibodies and preferred sequence modifications to maintain antigen binding affinity were disclosed in International Application No. PCT/US2008/064414, entitled "Novel Rabbit Antibody Humanization Method and Humanized Rabbit Antibodies", filed May 21, 2008, the disclosure of which is herein incorporated by reference in its entirety.

Certain teachings related to producing antibodies or fragments thereof using mating competent yeast and corresponding methods were disclosed in U.S. patent application Ser. No. 11/429,053, filed May 8, 2006, (U.S. Patent Application Publication No. US2006/0270045), the disclosure of which is herein incorporated by reference in its entirety.

Certain teachings related to anti-TNF-α antibodies, methods of producing antibodies or fragments thereof using mating competent yeast and corresponding methods were disclosed in U.S. provisional patent application No. 60/924,551, filed May 21, 2007, the disclosure of which is herein incorporated by reference in its entirety.

Certain TNF-α antibody polynucleotides and polypeptides are disclosed in the sequence listing accompanying this patent application filing, and the disclosure of said sequence listing is herein incorporated by reference in its entirety.

The entire disclosure of each document cited (including patents, patent applications, journal articles, abstracts, manuals, books, or other disclosures) in the Background of the Invention, Detailed Description, and Examples is herein incorporated by reference in their entireties.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1 Production of Enriched Antigen-Specific B Cell Antibody Culture

Panels of antibodies are derived by immunizing traditional antibody host animals to exploit the native immune response to a target antigen of interest. Typically, the host used for immunization is a rabbit or other host that produces antibodies using a similar maturation process and provides for a population of antigen-specific B cells producing antibodies of comparable diversity, e.g., epitopic diversity. The initial antigen immunization can be conducted using complete Freund's adjuvant (CFA), and the subsequent boosts effected with incomplete adjuvant. At about 50-60 days after immunization, preferably at day 55, antibody titers are tested, and the Antibody Selection (ABS) process is initiated if appropriate titers are established. The two key criteria for ABS initiation are potent antigen recognition and function-modifying activity in the polyclonal sera.

At the time positive antibody titers are established, animals are sacrificed and B cell sources isolated. These sources include: the spleen, lymph nodes, bone marrow, and peripheral blood mononuclear cells (PBMCs). Single cell suspensions are generated, and the cell suspensions are washed to make them compatible for low temperature long term storage. The cells are then typically frozen.

To initiate the antibody identification process, a small fraction of the frozen cell suspensions are thawed, washed, and placed in tissue culture media. These suspensions are then mixed with a biotinylated form of the antigen that was used to generate the animal immune response, and antigen-specific cells are recovered using the Miltenyi magnetic bead cell selection methodology. Specific enrichment is conducted using streptavidin beads. The enriched population is recovered and progressed in the next phase of specific B cell isolation.

Example 2 Production of Clonal, Antigen-Specific B Cell-Containing Culture

Enriched B cells produced according to Example 1 are then plated at varying cell densities per well in a 96 well microtiter plate. Generally, this is at 50, 100, 250, or 500 cells per well with 10 plates per group. The media is supplemented with 4% activated rabbit T cell conditioned media along with 50K frozen irradiated EL4B feeder cells. These cultures are left undisturbed for 5-7 days at which time supernatant-containing secreted antibody is collected and evaluated for target properties in a separate assay setting. The remaining supernatant is left intact, and the plate is frozen at −70° C. Under these conditions, the culture process typically results in wells containing a mixed cell population that comprises a clonal population of antigen-specific B cells, i.e., a single well will only contain a single monoclonal antibody specific to the desired antigen.

Example 3 Screening of Antibody Supernatants for Monoclonal Antibody of Desired Specificity and/or Functional Properties Antibody-containing supernatants derived from the well containing a clonal antigen-specific B cell population produced according to Example 2 are initially screened for antigen recognition using ELISA methods. This includes selective antigen immobilization (e.g., biotinylated antigen capture by streptavidin coated plate), non-specific antigen plate coating, or alternatively, through an antigen build-up strategy (e.g., selective antigen capture followed by binding partner addition to generate a heteromeric protein-antigen complex). Antigen-positive well supernatants are then optionally tested in a function-modifying assay that is strictly dependant on the ligand. One such example is an in vitro protein-protein interaction assay that recreates the natural interaction of the antigen ligand with recombinant receptor protein. Alternatively, a cell-based response that is ligand dependent and easily monitored (e.g., proliferation response) is utilized. Supernatant that displays significant antigen recognition and potency is deemed a positive well. Cells derived from the original positive well are then transitioned to the antibody recovery phase.

Example 4 Recovery of Single, Antibody-Producing B Cell of Desired Antigen Specificity A few number of cells are isolated from a well that contains a clonal population of antigen-specific B cells (produced according to Example 2 or 3), which secrete a single antibody sequence. The isolated cells are then assayed to isolate a single, antibody-secreting cell. Dynal streptavidin beads are coated with biotinylated target antigen under buffered medium to prepare antigen-containing microbeads compatible with cell viability. Next antigen-loaded beads, antibody-producing cells from the positive well, and a fluorescein isothiocyanate (FITC)-labeled anti-host H&L IgG antibody (as noted, the host can be any mammalian host, e.g., rabbit, mouse, rat, etc.) are incubated together at 37° C. This mixture is then re-pipetted in aliquots onto a glass slide such that each aliquot has on average a single, antibody-producing B-cell. The antigen-specific, antibody-secreting cells are then detected through fluorescence microscopy. Secreted antibody is locally concentrated onto the adjacent beads due to the bound antigen and provides localization information based on the strong fluorescent signal. Antibody-secreting cells are identified via FITC detection of antibody-antigen complexes formed adjacent to the secreting cell. The single cell found in the center of this complex is then recovered using a micromanipulator. The cell is snap-frozen in an eppendorf PCR tube for storage at −80° C. until antibody sequence recovery is initiated.

Example 5 Isolation of Antibody Sequences from Antigen-Specific B Cell

Antibody sequences are recovered using a combined RT-PCR based method from a single isolated B-cell produced according to Example 4 or an antigenic specific B cell isolated from the clonal B cell population obtained according to Example 2. Primers are designed to anneal in conserved and constant regions of the target immunoglobulin genes (heavy and light), such as rabbit immunoglobulin sequences, and a two-step nested PCR recovery step is used to obtain the antibody sequence. Amplicons from each well are analyzed for recovery and size integrity. The resulting fragments are then digested with AluI to fingerprint the sequence clonality. Identical sequences display a common fragmentation pattern in their electrophoretic analysis. Significantly, this common fragmentation pattern which proves cell clonality is generally observed even in the wells originally plated up to 1000 cells/well. The original heavy and light chain amplicon fragments are then restriction enzyme digested with HindIII and XhoI or HindIII and BsiwI to prepare the respective pieces of DNA for cloning. The resulting digestions are then ligated into an expression vector and transformed into bacteria for plasmid propagation and production. Colonies are selected for sequence characterization.

Example 6 Recombinant Production of Monoclonal Antibody of Desired Antigen Specificity and/or Functional Properties Correct full-length antibody sequences for each well containing a single monoclonal antibody is established and miniprep DNA is prepared using Qiagen solid-phase methodology. This DNA is then used to transfect mammalian cells to produce recombinant full-length antibody. Crude antibody product is tested for antigen recognition and functional properties to confirm the original characteristics are found in the recombinant antibody protein. Where appropriate, large-scale transient mammalian transfections are completed, and antibody is purified through Protein A affinity chromatography. Kd is assessed using standard methods (e.g., Biacore) as well as 1050 in a potency assay.

Example 7 Preparation of Antibodies that Bind HuTNF-α

By using the antibody selection protocol described herein, one can generate a collection of antibodies that exhibit potent functional antagonism of TNF-α. The antibodies elucidate a variety of TNF-α epitopes and thus may provide useful alternatives to, or adjunctives with, antibodies that target previously identified TNF-α epitopes, such as Remicade® (infliximab).

A screening method can be employed to identify antibodies that bind alternative TNF-α epitopes, while retaining significant functional antagonism. After the primary antigen-recognition screen, positive BCC wells were tested for functional antagonism towards TNF-α as well as for epitope competition, e.g., competition with infliximab. Unique epitope recognition was established by ForteBio Octet antibody-TNF-α binding competition studies. See FIG. 1. BCC wells that displayed functional activity as well as lack of competition were pursued, and the coding sequences for the antibody present in these wells recovered. The majority of the recovered sequences displayed the original target characteristics: potent antigen recognition, functional antagonism, and distinct epitope recognition. Thus, the resulting antibody collection established multiple novel epitope regions associated with potent functional antagonism.

Immunization Strategy:

Rabbits were immunized with TNF-α (R&D #210-TA). Immunization consisted of a first subcutaneous (sc) injection of 100 μg in complete Freund's adjuvant (CFA) (Sigma) followed by two boosts, two weeks apart, of 50 μg each in incomplete Freund's adjuvant (IFA) (Sigma). Animals were bled on day 55, and serum titers were determined by ELISA (antigen recognition) and by non-radioactive proliferation assay (Promega) using the WEHI cell line.

Antibody Selection Titer Assessment

Antigen recognition was determined by coating Immulon 4 plates (Thermo) with 1 μg/ml of huTNF-α (50 μl/well) in phosphate buffered saline (PBS, Hyclone) overnight at 4° C. On the day of the assay, plates were washed 3 times with PBS/Tween 20 (PBST tablets, Calbiochem). Plates were then blocked with 200 μl/well of 0.5% fish skin gelatin (FSG, Sigma) in PBS for 30 minutes at 37° C. Blocking solution was removed, and plates were blotted. Serum samples were made (bleeds and pre-bleeds) at a starting dilution of 1:100 (all dilutions were made in FSG 50 μl/well) followed by 1:10 dilutions across the plate (column 12 was left blank for background control). Plates were incubated for 30 minutes at 37° C. Plates were washed 3 times with PBS/Tween 20. Goat anti-rabbit FC-HRP (Pierce) diluted 1:5000 was added to all wells (50 μl/well), and plates were incubated for 30 minutes at 37° C. Plates were washed as described above. 50 μl/well of TMB-Stable stop (Fitzgerald Industries) was added to plates, and color was allowed to develop, generally for 3 to 5 minutes. The development reaction was stopped with 50 μl/well 0.5 M HCl. Plates were read at 450 nm. Optical density (OD) versus dilution was plotted using Graph Pad Prizm software, and titers were determined.

Functional Titer Assessment

The functional activities of the samples were determined by a TNF-α stimulated WEHI cytotoxic assay. WEHI cells were routinely maintained in the medium described above without huIL-6. On the day of the assay, cell density was determined by trypan blue. Cells were resuspended at 1E06 cells/ml and plated at 50 μl/well (volume was adjusted to number of samples and replicates) in sterile flat-bottom 96-well tissue culture plates. Plates were incubated for 2 h at 37° C.

Separately, in a round-bottom 96-well plate, serum samples were added at a 1:100 dilution (in the described media) followed by 1:10 dilution across the plate (columns 2-10, column 11 was media only for TNF-α control), 50 μl/well in replicates of 5 (rows B-F, row G was media only for background control). 50 μl/well of media containing TNF-α at a concentration 4 times the final EC50 (concentration was previously determined for each lot) and 1 μg/ml of Actinomycin D was added to all sample wells except row F. Plates were incubated for 1 h at 37° C.

At 1 h, 50 μl of the Serum/Ag complex and controls were transferred to the 96-well flat-bottom plates containing 50 μl/well of responder cells at a fixed density (final volume: 100 μl/well) and incubated for 24 h at 37° C. (Columns 1 and 12 and rows A and H were filled with 200 μl of media to prevent evaporation and cause edge effect.)

At 24 h, 20 μl/well of CellTiter96 reagent (Promega) was added to all test wells per the manufacturer protocol, and plates were incubated for 2 h at 37° C. After 2 h, plates were gently shaken to allow homogeneity in the test wells. Plates were read at 490 nm wavelength. OD versus dilution were plotted using Graph Pad Prizm (non-linear sigmoid dose/response curve was used), and functional titer was determined.

Tissue Harvesting Rabbit spleen, lymph nodes, and whole blood were harvested, processed, and frozen as follows:

Spleen and lymph nodes were processed into a single cell suspension by disassociating the tissue and pushing through sterile wire mesh at 70 µm (Fisher) with a plunger of a 20 cc syringe. Cells were collected in the modified RPMI medium described above without huIL-6, but with low glucose. Cells were washed twice by centrifugation. After the last wash, cell density was determined by trypan blue. Cells were centrifuged at 1500 rpm for 10 minutes; the supernatant was discarded. Cells were, resuspended in the appropriate volume of 10% dimethyl sulfoxide (DMSO, Sigma) in FBS (Hyclone) and dispensed at 1 ml/vial. Vials were then stored at −70° C. for 24 h prior to being placed in a liquid nitrogen (LN2) tank for long-term storage.

Peripheral blood mononuclear cells (PBMCs) were isolated by mixing whole blood with equal parts of the low glucose medium described above without FBS. 35 ml of the whole blood mixture was carefully layered onto 8 ml of Lympholyte Rabbit (Cedarlane) into a 45 ml conical tube (Corning) and centrifuged 30 minutes at 2500 rpm at room temperature without brakes. After centrifugation, the PBMC layers were carefully removed using a glass Pasteur pipette (VWR), combined, and placed into a clean-50 ml vial. Cells were washed twice with the modified medium described above by centrifugation at 1500 rpm for 10 minutes at room temperature, and cell density was determined by trypan blue staining. After the last wash, cells were resuspended in an appropriate volume of 10% DMSO/FBS medium and frozen as described above.

B Cell Culture (BCC)

On the day of setting up B cell culture, PBMC, splenocyte, or lymph node vials were thawed for use. Vials were removed from LN2 tank and placed in a 37° C. water bath until thawed. Contents of vials were transferred into 15 ml conical centrifuge tube (Corning) and 10 ml of modified RPMI described above was slowly added to the tube. Cells were centrifuged for 5 minutes at 1.5K rpm, and the supernatant was discarded. Cells were resuspended in 10 ml of fresh media. Cell density and viability was determined by trypan blue. Cells were washed again and resuspended at 1E07 cells/80 µl medium. Biotinylated huTNF-α was added to the cell suspension at a final concentration of 3 µg/ml and incubated for 30 minutes at 4° C. Unbound Biotinylated huTNF-α was removed with two 10 ml washes of phosphate-buffered saline free of Ca/Mg (PBF), 2 mM ethylenediamine tetraacetic acid (EDTA), 0.5% bovine serum albumin (BSA) (Sigma-biotin free). After the second wash, cells were resuspended at 1E07 cells/80 µl PBF. 20 µl of MACS® streptavidin beads (Milteni)/10E7 cells were added to the cell suspension. Cells were incubated at 4° C. for 15 minutes. Cells were washed once with 2 ml of PBF/10E7 cells. After washing, the cells were resuspended at 1E08 cells/500 µl of PBF and set aside. A MACS® MS column (Milteni) was pre-rinsed with 500 ml of PBF, on a magnetic stand (Milteni). Cell suspension was applied to the column through a pre-filter, and unbound fraction was collected. The column was washed with 1.5 ml of PBF buffer. The column was removed from the magnet stand and placed onto a clean, sterile 5 ml Polypropylene Falcon tube. 1 ml of PBF buffer was added to the top of the column, and positive selected cells were collected. The yield and viability of positive and negative cell fraction was determined by trypan blue staining. Positive selection yielded an average of 1% of the starting cell concentration.

A pilot cell screen was established to provide information on seeding levels for the culture. Three 10-plate groups (a total of 30 plates) were seeded at 50, 100, and 200 enriched B cells/well. In addition, each well contained 50K cells/well of irradiated EL-4.B5 cells (5,000 Rads) and an appropriate level of T cell supernatant (ranging from 1-5% depending on preparation) in high glucose modified RPMI medium at a final volume of 250 µl/well. Cultures were incubated for 5 to 7 days at 37° C. in 4% CO2 and tested for rabbit IgG production.

Antigen Recognition Screening

Antigen recognition screening was performed as described above as single points. The ELISA format used is as described above except 50 µl of supernatant from the B cell cultures (BCC) wells (all 30 plates) was used as the source of the antibody. The conditioned medium was transferred to antigen-coated plates. After positive wells were identified, the supernatant was removed and transferred to a 96-well master plate(s). The original culture plates were then frozen by removing all the supernatant except 40 µl/well and adding 60 µl/well of 16% DMSO in FBS. Plates were wrapped in paper towels to slow freezing and placed at −70° C.

Functional Activity Screening

Functional activity screening was performed by a WEHI cytotoxic assay. Supernatant from master plate(s) was tested in the TNF-α stimulated WEHI cytotoxic assay (as described above) as single points. Supernatants were tested as neat according to the following template:

Row F is media only for background control (50 µl/well).

Row G is media+TNF-α for positive cytotoxic control.

Rows B-E and columns 2-11 are the wells from the BCC (40 µl/well, single points).

40 µl of TNF-α+Actinomycin D was added to all wells (except the media row) at 4 times the EC50 concentration determined for the assay. After 1 h incubation, the Ab/Ag complex was transferred to a TC-treated 96-well flat-bottom plate. 20 µl of cell suspension (WEHI at 1E06 cells/ml) was added to all wells (final volume: 100 µl/well), and the plates were incubated for 24 h at 37° C. At 24 h, CellTiter96 reagent was added per manufacturer instructions. Plates were read at 490 nm wavelength, background was subtracted from wells, and OD values were transformed into % inhibition.

Secondary Functional Activity Assay for Recombinant Antibodies: Blocking of IL-6 Expression by HUVEC Cells Treated with huTNF-α

Human umbilical vein endothelial cells (HUVECs) were routinely maintained in endothelial growth medium (EGM) medium and appropriate HUVEC supplements (Cambrex). On the day of the assay, HUVEC viability was determined by trypan blue. The cells were resuspended at 5E05/ml in the appropriate volume of medium necessary for the assay (100 µl/well). Cells were plated in middle wells of 96-well flat-bottom culture plates, and 200 µl medium was added to all outside perimeter wells to prevent evaporation. The plate was incubated for 24 h at 37° C.

At 24 h, the appropriate antibody dilutions are made in EGM at 4 times the desired final concentration. (Starting antibody concentration was 1 µg/ml; a 1:3 dilution was performed across the plate, except for last row.) The same volume of rhuTNF-α in EGM (4 times the desired final concentration) was added to the wells. The plate was incubated for 1 h at 37° C. to form the antibody/antigen complex. At 1 h, 50 µl of media from the HUVEC culture plate was removed and discarded. 50 µl Ab-Ag mixture was added, and the plate was incubated for 48 h at 37° C. Standard positive and negative controls were included: huTNF-α only (column 11), medium only (No Ab/No TNF) for background growth (row G).

At 48 h, conditioned medium IL-6 levels were assessed by ELISA. An Immulon plate was coated with 1 μg/ml goat anti-huIL-6 at 50 μl/well, overnight at 4° C., or room temperature for 1 hour. The plate was washed in PBS+0.5% Tween 20 in a plate washer (200 μl/well; 3 times). The plate was blocked with 200 μl/well FSG for 1 hour at room temperature. The blocking solution was aspirated, and the plate was blotted. The huIL-6 standard was set on rows A and B (duplicates), starting at 1 μg/ml and diluted 1:3 across the plate (all dilutions made in FSG) leaving column 12 as blank. Samples from HUVEC culture were added to the wells below standard curve and incubated for 1 hour at room temperature, aspirated and wash repeated. 1 μg/ml ALD515v5 (anti-huIL-6) was added at 50 μl/well to the plate and incubated for 1 hour at room temperature. The wash protocol was repeated. Secondary anti-human IgG Fc HRP at 1:5000 dilution was added at 50 μl/well and incubated for 45 minutes at room temperature. Wash was repeated. Assay was developed with 50 μl/well 3,3',5,5' tetramethylbenzidine (TMB) for a minimum of 5 minutes. Unbound secondary antibody was removed and the wash repeated. Data was analyzed using Graph Pad Prizm.

B Cell Recovery

Plates containing wells of interest were removed from −70° C., and the cells from each well were recovered with 5-200 μl washes of medium/well. The washes were pooled in a 1.5 ml sterile centrifuge tube, and cells were pelleted for 2 minutes at 1500 rpm.

The tube was inverted, the spin repeated, and the supernatant carefully removed. Cells were resuspended in 100 μl/tube of medium. 100 μl biotinylated TNF-α coated streptavidin M280 dynabeads (Invitrogen) and 16 μl of goat anti-rabbit H&L IgG-FITC diluted 1:100 in medium was added to the cell suspension.

20 μl of cell/beads/FITC suspension was removed, and 5 μl droplets were prepared on a glass slide (Corning) previously treated with sigmacote (Sigma) and an impermeable barrier (approximately 35 to 40 droplets/slide). Parafin oil (JT Baker) was added to submerge the droplets, and the slide was incubated for 90 minutes at 37° C., 4% CO2 in the dark.

Specific B cells that produce antibody can be identified by the fluorescent ring around them due to antibody secretion, recognition of the bead-associated biotinylated antigen, and subsequent detection by the fluorescent-IgG detection reagent. Once a cell of interest was identified, the cell in the center of the fluorescent ring was recovered via a micromanipulator (Eppendorf). The single cell synthesizing and exporting the antibody was transferred into a 250 μl microcentrifuge tube and placed in dry ice. After recovering all cells of interest, these were transferred to −70° C. for long-term storage.

Example 8 Competitive Binding Experiments

In order to demonstrate that the binding nature of the antibodies to TNF-α set forth in this experiment displayed unique epitope recognition versus REMICADE®, a stericheinderance competition assay was developed using biolayer interferometry on an Octet QK instrument (ForteBio; Menlo Park, Calif.). Lack of binding competition establishes distinct binding epitopes on TNF-α.

Briefly, a biotinylated sample of Remicade® (Centocor, Malvern Pa., biotinylated using Pierce EZ-link sulfo-NHS-LC-LC-biotin product number 21338 according to manufacturer's recommendation) was used to immobilize TNF-α (R&D systems, Minneapolis, Minn., product number 210-TA-CF) onto a set of streptavidin biosensors (product number 18-502, ForteBio, Menlo Park, Calif.). Binding was measured by an increase in signal.

To ensure that all Remicade binding sites on TNF-α were saturated, these sensors were further incubated with non-biotinylated (unlabeled) Remicade®. Sensors were then incubated in the presence of the test antibody, or as a control, with Remicade®. An increase in signal with a test antibody demonstrated that both Remicade® and the antibody in question were able to bind TNF-α simultaneously and therefore Remicade® and the test antibody did not compete for the same topographical space on TNF.

Figure 6A:
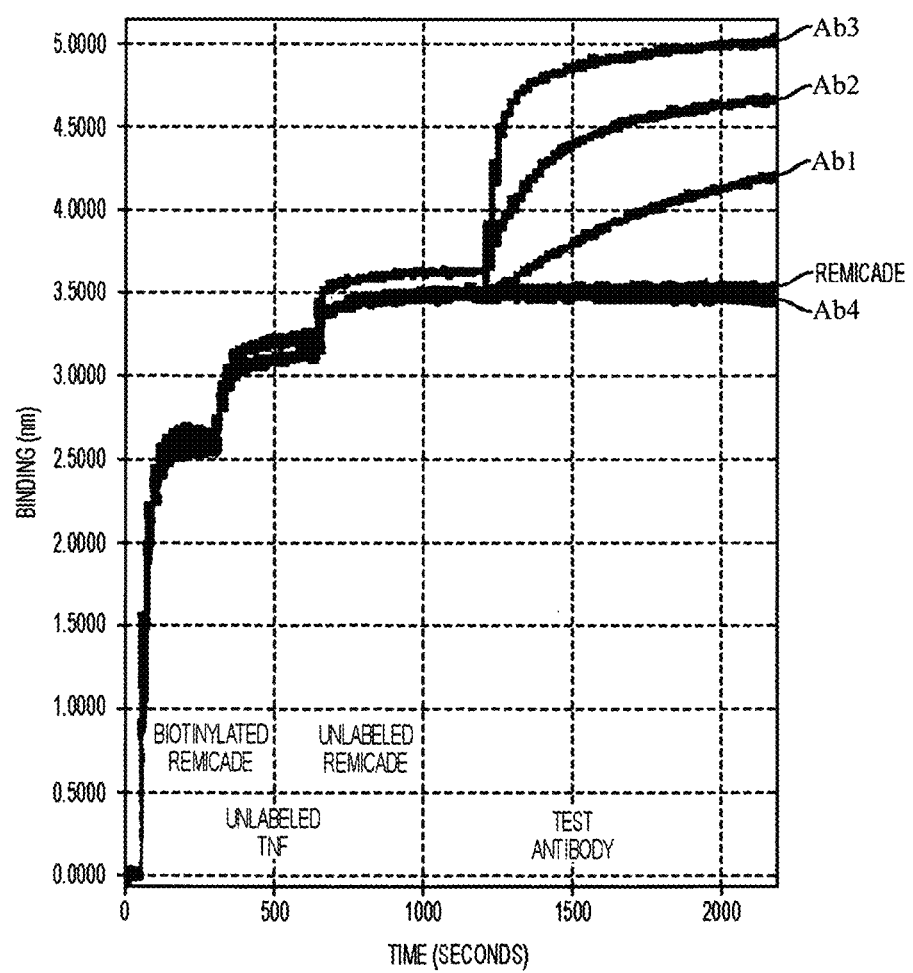
FIG. 6A provides data corresponding to competitive binding experiments between antibodies Ab1, Ab2, Ab3, and Ab4 and Remicade®, a commercially available anti-TNF-α antibody.

FIG. 6A provides data corresponding to competitive binding experiments between antibodies Ab1, Ab2, Ab3, and Ab4 and Remicade®, a commercially available anti-TNF-α antibody.

Figure 6B:
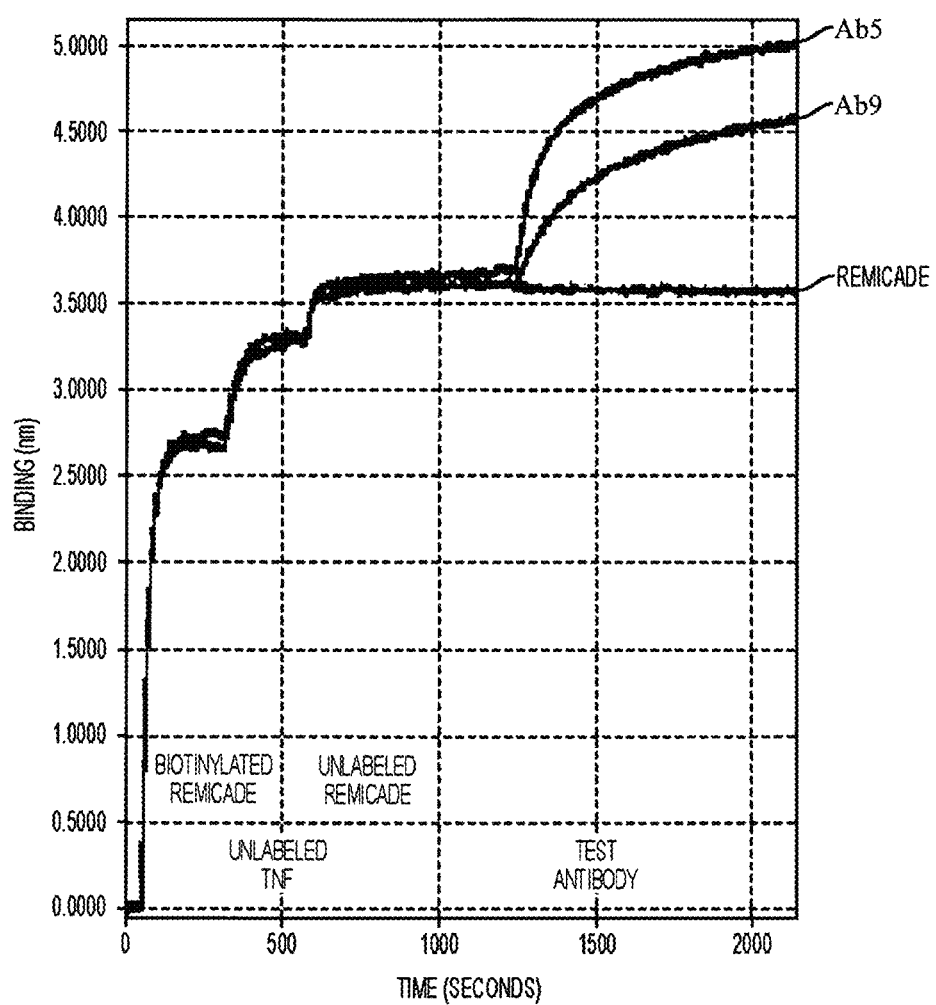
FIG. 6B provides data corresponding to competitive binding experiments between antibodies. Ab5, Ab9 and Remicade®, a commercially available anti-TNF-α antibody.

FIG. 6B provides data corresponding to competitive binding experiments between antibodies Ab5, Ab9 and Remicade®, a commercially available anti-TNF-α antibody.

Figure 6C:
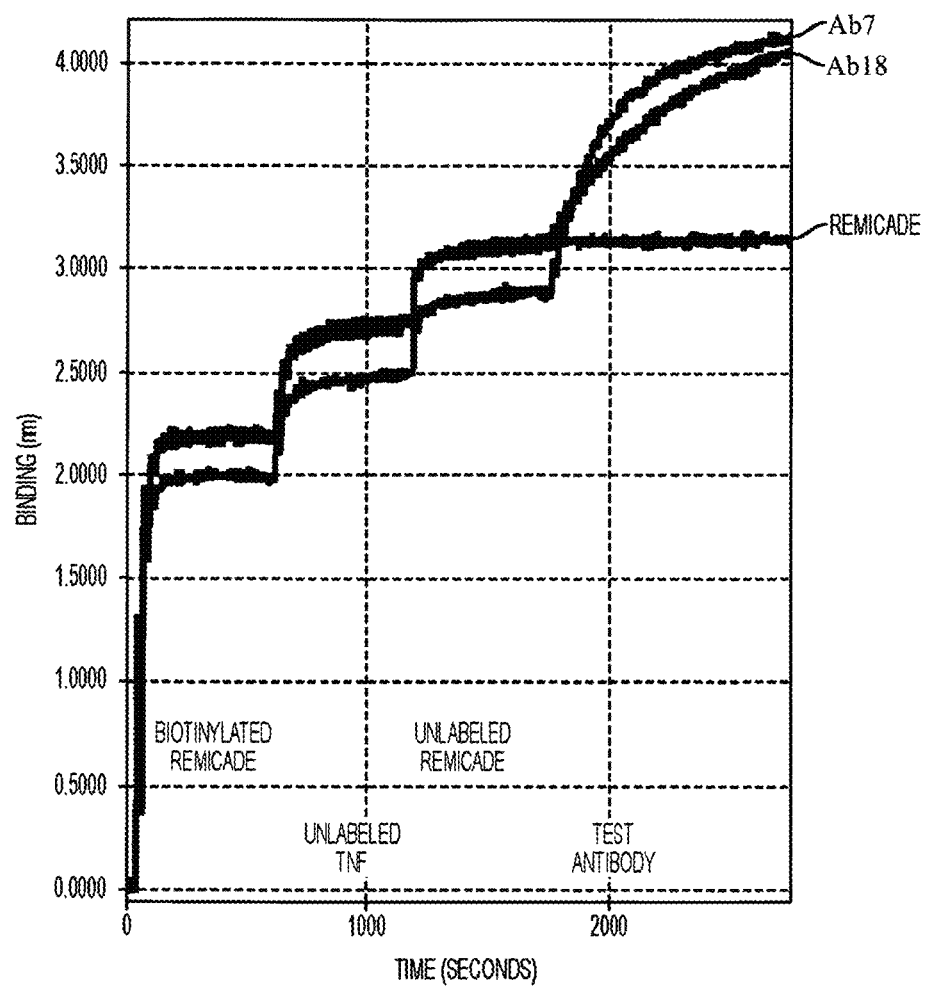
FIG. 6C provides data corresponding to competitive binding experiments between antibodies Ab7, Ab18 and Remicade®, a commercially available anti-TNF-α antibody.

FIG. 6C provides data corresponding to competitive binding experiments between antibodies Ab7, Ab18 and Remicade®, a commercially available anti-TNF-α antibody.

Figure 6D:
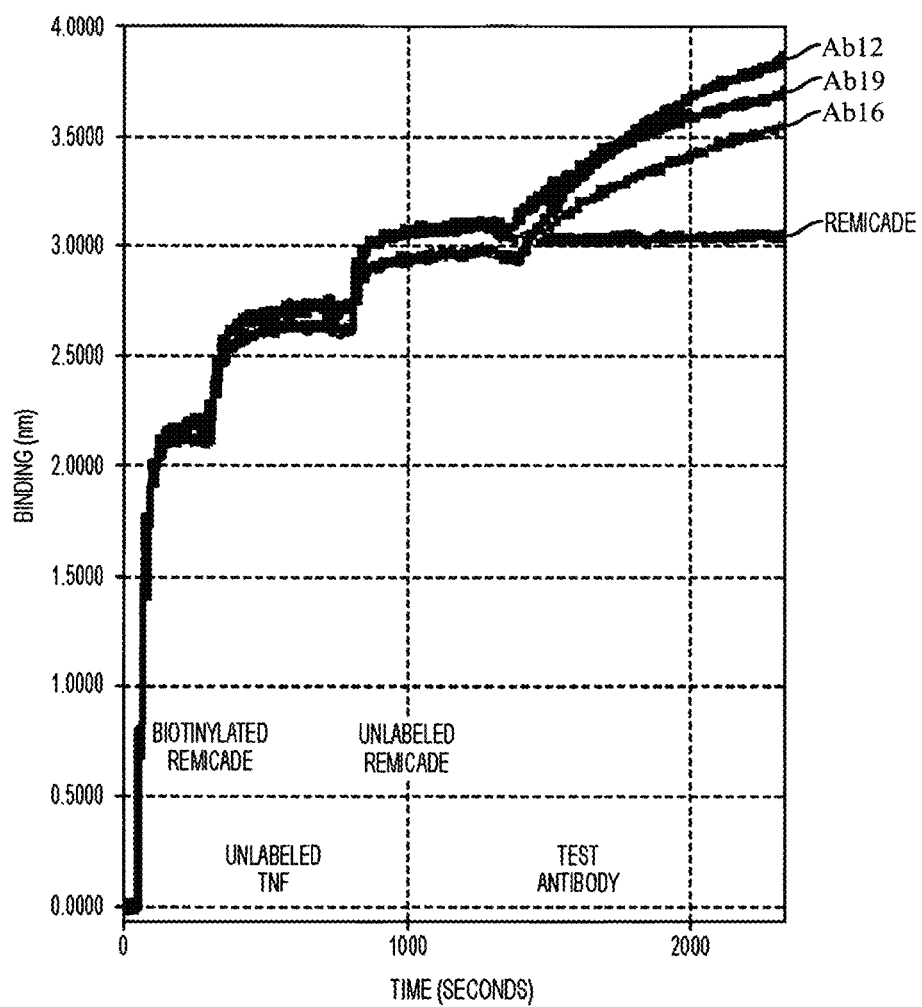
FIG. 6D provides data corresponding to competitive binding experiments between antibodies Ab12, Ab16, Ab19 and Remicade®, a commercially available anti-TNF-α antibody.

FIG. 6D provides data corresponding to competitive binding experiments between antibodies Ab12, Ab16, Ab19 and Remicade®, a commercially available anti-TNF-α antibody.

Example 9 Epitope Mapping

A. Anti-TNF-α Antibody Ab1

The following epitope mapping experiment was conducted to identify the epitope to which the anti-TNF-α antibody Ab1 binds to TNF-α. The TNF-α sequence utilized (NCBI#P01375) was 158 Amino Acids long representing V77 through L233 with an N-terminal Methionine added. A 49-member library of linear overlapping peptides of 12 amino acids in length encompassing this sequence was commercially synthesized and covalently bound to a Pep-Spots nitrocellulose membrane (JPT Peptide technologies, Berlin, Germany). Blots were prepared and probed according to manufacturer's recommendations.

Anti-TNF-α antibodies were used at 1 μg/ml final dilution, and the HRP-conjugated Goat Anti-Human H+L secondary antibody (Jackson ImmunoResearch Laboratories, Inc., West Grove, Pa.; product number 109-035-088) was used at a 1:1000 dilution. Blocking steps and antibody incubations were performed in 10% non-fat milk in PBS/0.05% Tween 20 (Bio-Rad, Hercules, Calif.; part number 170-6531). Blots were developed using ECL advance western blotting detection kit (GE Healthcare, Piscataway N.J., product number RPN2135) and chemiluminescence was detected using a CCD camera (AlphaInnotec, San Leandro, Calif.).

The results of the blot for anti-TNF-α antibody Ab1 are presented in FIG. 7(A). The blot shows that anti-TNF-α antibody Ab1 binds to the following epitope on TNF-α: ELRDNQLVV.

B. Anti-TNF-α Antibody Ab5

The experiment performed above for anti-TNF-α antibody Ab1 was repeated for anti-TNF-α antibody Ab5. The results of the blot for anti-TNF-α antibody Ab5 are presented in FIG. 7(A). The blot shows that anti-TNF-α antibody Ab5 binds to the following epitope on TNF-α: VRSSSRTPSDKPVA.

Example 10 Affinity Constant Determinations

Binding kinetics of certain Anti-TNF-α antibodies referenced in this experiment were determined using biolayer Interferometry on an Octet QK instrument (ForteBio, Menlo Park, Calif.). Biotinylated TNF-α (R&D systems part number 210-TA, biotinylated using Pierce EZ-link sulfo-NHS-LC-LC-biotin product number 21338 according to manufacturer's protocols) was initially bound onto a streptavidin coated biosensor (ForteBio, Menlo Park, Calif. part number 18-5006). TNF-α coated sensors were then incubated with the Anti-TNF-α antibodies at concentrations ranging from 8 nM to 1 nM. Binding was monitored as an increase in signal over a period of 900 seconds.

Sensors removed from the antibody dilutions and immediately incubated in diluent were monitored for a dissociation phase over an 1800 second time period. For these studies, all proteins were diluted using ForteBio's sample diluent buffer (ForteBio, Menlo Park, Calif. part number 18-5028). Analysis of Kinetic data was performed using ForteBio Software utilizing full dissociation modeling.

The affinity constant determinations for antibodies Ab1-Ab19 are set forth below in Table 1:

TABLE 1

| Antibody | $K_D$ |
|---|---|
| Ab1 | 10 pM |
| Ab2 | 10 pM |
| Ab3 | 20-40 pM |
| Ab4 | 10 pM |
| Ab5 | 25-50 pM |
| Ab6 | 10 pM |
| Ab7 | 10 pM |
| Ab8 | 10 pM |
| Ab9 | 25-50 pM |
| Ab10 | 15-30 pM |
| Ab11 | 20 pM |
| Ab12 | 10-25 pM |
| Ab13 | 10-50 pM |
| Ab14 | 10 pM |
| Ab15 | 10 pM |
| Ab16 | 10 pM |
| Ab17 | 10 pM |
| Ab18 | 10 pM |
| Ab19 | 60 pM |

What is claimed is:

1. An anti-human TNF-.alpha. antibody or antibody fragment which comprises the identical CDR polypeptides as the anti-human TNFα antibody comprising the variable light polypeptide of SEQ ID NO:34 and the variable heavy polypeptide of SEQ ID NO:35.

2. The anti-human TNF-α antibody or fragment of claim 1 which is aglycosylated.

3. The anti-human TNF-α antibody of claim 1 which contains an Fc region that has been modified to alter effector function, half-life, proteolysis, and/or glycosylation.

4. The anti-human TNF-α antibody or fragment of claim 1 which is a human, humanized, single chain or chimeric antibody.

5. The anti-human TNF-α antibody or fragment of claim 1 which is directly or indirectly attached to a detectable label or therapeutic agent.

6. A method of treatment comprising administering to a patient with a disease or condition associated with TNF-α expressing cells a therapeutically effective amount of at least one anti-human TNF-α antibody or fragment according to claim 1, wherein the disease is selected from Rheumatoid Arthritis, Psoriatic Arthropathy, Ankylosing Spondylitis, Juvenile Rheumatoid Arthritis, Still's Disease, Systemic Lupus Erythematosus, Autoimmune Uveitis, Inflammatory Bowel Disease, Behçet's Disease, Psoriasis, Crohn's disease, lupus, pemphigus, glomerulonephritis and adult Still's disease.

7. The method of claim 6 wherein the Rheumatoid Arthritis occurs as a side effect of an autoimmune disorder.

8. A method of in vivo imaging which detects the presence of cells which express TNF-α comprising administering a diagnostically effective amount of at least one anti-human TNFα antibody according to claim 1.

* * * * *

SEQUENCE LISTING

```
<160> NUMBER OF SEQ ID NOS: 421

<210> SEQ ID NO 1
<211> LENGTH: 233
<212> TYPE: PRT
<213> ORGANISM: Homo sapiens

<400> SEQUENCE: 1

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
```

```
    210                 215                 220
Gln Val Tyr Phe Gly Ile Ile Ala Leu
225                 230

<210> SEQ ID NO 2
<211> LENGTH: 125
<212> TYPE: PRT
<213> ORGANISM: Oryctolagus cuniculus

<400> SEQUENCE: 2

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ala
            20                  25                  30

Ser Val Glu Ala Val Gly Gly Thr Val Thr Ile Lys Cys Gln Ala
        35                  40                  45

Ser Gln Asn Ile Arg Ser Trp Leu Ala Trp Tyr Gln Gln Lys Pro Gly
    50                  55                  60

Gln Pro Pro Lys Leu Leu Ile Tyr Gly Ala Ser Thr Leu Ala Ser Gly
65                  70                  75                  80

Val Pro Ser Arg Phe Gln Gly Ser Gly Ser Gly Thr Glu Tyr Thr Leu
                85                  90                  95

Thr Ile Ile Asp Leu Asp Cys Ala Asp Ala Ala Thr Tyr Tyr Cys Gln
            100                 105                 110

Ser Asn Tyr Gly Ser Asn Asp Asn Ser Tyr Gly Asn Gly
        115                 120                 125

<210> SEQ ID NO 3
<211> LENGTH: 121
<212> TYPE: PRT
<213> ORGANISM: Oryctolagus cuniculus

<400> SEQUENCE: 3

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Thr Tyr Asn Met Gly Trp Val Arg Gln Ala Pro Gly Lys Gly Leu Glu
    50                  55                  60

Tyr Ile Gly Tyr Val Leu Gly Ser Gly Ile Thr Tyr Tyr Ala Ser Trp
65                  70                  75                  80

Ala Lys Gly Arg Phe Thr Ile Ser Lys Thr Ser Thr Thr Val Asp Leu
                85                  90                  95

Glu Ile Thr Ser Pro Thr Thr Glu Asp Thr Ala Thr Tyr Phe Cys Ala
            100                 105                 110

Arg Asp Ala Gly Gly Arg Ala Ser Leu
        115                 120

<210> SEQ ID NO 4
<211> LENGTH: 11
<212> TYPE: PRT
<213> ORGANISM: Oryctolagus cuniculus

<400> SEQUENCE: 4

Gln Ala Ser Gln Asn Ile Arg Ser Trp Leu Ala
1               5                   10
```

<210> SEQ ID NO 5
<211> LENGTH: 7
<212> TYPE: PRT
<213> ORGANISM: Oryctolagus cuniculus

<400> SEQUENCE: 5

Gly Ala Ser Thr Leu Ala Ser
1               5

<210> SEQ ID NO 6
<211> LENGTH: 14
<212> TYPE: PRT
<213> ORGANISM: Oryctolagus cuniculus

<400> SEQUENCE: 6

Gln Ser Asn Tyr Gly Ser Asn Asp Asn Ser Tyr Gly Asn Gly
1               5                   10

<210> SEQ ID NO 7
<211> LENGTH: 5
<212> TYPE: PRT
<213> ORGANISM: Oryctolagus cuniculus

<400> SEQUENCE: 7

Thr Tyr Asn Met Gly
1               5

<210> SEQ ID NO 8
<211> LENGTH: 16
<212> TYPE: PRT
<213> ORGANISM: Oryctolagus cuniculus

<400> SEQUENCE: 8

Tyr Val Leu Gly Ser Gly Ile Thr Tyr Tyr Ala Ser Trp Ala Lys Gly
1               5                   10                  15

<210> SEQ ID NO 9
<211> LENGTH: 8
<212> TYPE: PRT
<213> ORGANISM: Oryctolagus cuniculus

<400> SEQUENCE: 9

Asp Ala Gly Gly Arg Ala Ser Leu
1               5

<210> SEQ ID NO 10
<211> LENGTH: 375
<212> TYPE: DNA
<213> ORGANISM: Oryctolagus cuniculus

<400> SEQUENCE: 10

```
atggacacga gggcccccac tcagctgctg ggctcctac  tgctctggct cccaggtgcc      60
agatgtgctg acattgtgat gacccagact ccagcctccg tggaggcagc tgtgggaggc     120
acagtcacca tcaagtgcca ggccagtcag aacattcgca gttggttagc ctggtatcag     180
cagaaaccag gcagcctcc  caagctcctg atctatggtg catccactct ggcatctggg     240
gtcccatcgc gattccaagg cagtggatct gggacagagt acactctcac catcatcgac     300
ctggactgtg ccgatgctgc cacttactac tgtcaaagca attatggtag taatgataat     360
agttatggta atggt                                                      375
```

<210> SEQ ID NO 11
<211> LENGTH: 363
<212> TYPE: DNA
<213> ORGANISM: Oryctolagus cuniculus

<400> SEQUENCE: 11

```
atggagactg ggctgcgctg gcttctcctg gtcgctgtgc tcaaaggtgt ccagtgtcag    60
tcggtggagg agtccggggg tcgcctggtc acgcctggga caccctgac actcacctgc    120 acagtctctg gattctccct cagtacctac aacatgggct gggtccgcca ggctccaggg    180
aaggggctgg aatacatcgg atacgtgttg ggaagtggta tcacatacta cgcgagctgg    240
gcaaaaggcc gattcaccat ctccaaaacc tcgaccacgg tggatctgga gatcactagt    300
ccgacaaccg aggacacggc cacctatttc tgtgccagag atgctggtgg cagagcttcc    360
ttg                                                                   363
```

<210> SEQ ID NO 12
<211> LENGTH: 33
<212> TYPE: DNA
<213> ORGANISM: Oryctolagus cuniculus

<400> SEQUENCE: 12

```
caggccagtc agaacattcg cagttggtta gcc                                  33
```

<210> SEQ ID NO 13
<211> LENGTH: 21
<212> TYPE: DNA
<213> ORGANISM: Oryctolagus cuniculus

<400> SEQUENCE: 13

```
ggtgcatcca ctctggcatc t                                               21
```

<210> SEQ ID NO 14
<211> LENGTH: 42
<212> TYPE: DNA
<213> ORGANISM: Oryctolagus cuniculus

<400> SEQUENCE: 14

```
caaagcaatt atggtagtaa tgataatagt tatggtaatg gt                        42
```

<210> SEQ ID NO 15
<211> LENGTH: 15
<212> TYPE: DNA
<213> ORGANISM: Oryctolagus cuniculus

<400> SEQUENCE: 15

```
acctacaaca tgggc                                                      15
```

<210> SEQ ID NO 16
<211> LENGTH: 48
<212> TYPE: DNA
<213> ORGANISM: Oryctolagus cuniculus

<400> SEQUENCE: 16

```
tacgtgttgg gaagtggtat cacatactac gcgagctggg caaaaggc                  48
```

<210> SEQ ID NO 17
<211> LENGTH: 24
<212> TYPE: DNA
<213> ORGANISM: Oryctolagus cuniculus

<400> SEQUENCE: 17
gatgctggtg gcagagcttc cttg    24

<210> SEQ ID NO 18
<211> LENGTH: 125
<212> TYPE: PRT
<213> ORGANISM: Oryctolagus cuniculus

<400> SEQUENCE: 18

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ser
                20                  25                  30

Ser Val Ser Glu Pro Val Arg Gly Thr Val Thr Ile Lys Cys Gln Ala
            35                  40                  45

Ser Gln Asn Ile Tyr Ser Tyr Leu Ser Trp Tyr Gln Gln Ser Pro Gly
        50                  55                  60

Gln Pro Pro Lys Leu Leu Ile Tyr Lys Ala Ser Thr Leu Ala Ser Gly
65                  70                  75                  80

Val Pro Ser Arg Phe Lys Gly Ser Gly Ser Gly Thr Asp Phe Thr Leu
                85                  90                  95

Thr Ile Ser Asp Leu Glu Cys Ala Asp Ala Ala Thr Tyr Tyr Cys Gln
            100                 105                 110

Ser Asn Tyr Gly Ser Asp Ser Asp Ser Phe Gly Asn Ala
        115                 120                 125

<210> SEQ ID NO 19
<211> LENGTH: 122
<212> TYPE: PRT
<213> ORGANISM: Oryctolagus cuniculus

<400> SEQUENCE: 19

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
                20                  25                  30

Gly Thr Pro Leu Thr Leu Thr Cys Ser Val Ser Gly Phe Ser Leu Asn
            35                  40                  45

Asn Tyr Val Met Gly Trp Val Arg Gln Ala Pro Gly Lys Gly Leu Glu
        50                  55                  60

Phe Ile Gly Tyr Ile Ala Phe Gly Ile Gly Pro Tyr Tyr Ala Ser Trp
65                  70                  75                  80

Ala Lys Gly Arg Phe Thr Ile Ser Ser Thr Ser Thr Thr Val Asp
                85                  90                  95

Leu Lys Met Thr Ser Leu Thr Pro Glu Asp Thr Ala Thr Tyr Phe Cys
            100                 105                 110

Ala Arg Gly Asp Tyr Ser Gly Asn Asp Ile
        115                 120

<210> SEQ ID NO 20
<211> LENGTH: 11
<212> TYPE: PRT
<213> ORGANISM: Oryctolagus cuniculus

<400> SEQUENCE: 20

Gln Ala Ser Gln Asn Ile Tyr Ser Tyr Leu Ser
1               5                   10

<210> SEQ ID NO 21

```
<211> LENGTH: 7
<212> TYPE: PRT
<213> ORGANISM: Oryctolagus cuniculus

<400> SEQUENCE: 21

Lys Ala Ser Thr Leu Ala Ser
1               5

<210> SEQ ID NO 22
<211> LENGTH: 14
<212> TYPE: PRT
<213> ORGANISM: Oryctolagus cuniculus

<400> SEQUENCE: 22

Gln Ser Asn Tyr Gly Ser Asp Ser Asp Ser Phe Gly Asn Ala
1               5                   10

<210> SEQ ID NO 23
<211> LENGTH: 5
<212> TYPE: PRT
<213> ORGANISM: Oryctolagus cuniculus

<400> SEQUENCE: 23

Asn Tyr Val Met Gly
1               5

<210> SEQ ID NO 24
<211> LENGTH: 16
<212> TYPE: PRT
<213> ORGANISM: Oryctolagus cuniculus

<400> SEQUENCE: 24

Tyr Ile Ala Phe Gly Ile Gly Pro Tyr Tyr Ala Ser Trp Ala Lys Gly
1               5                   10                  15

<210> SEQ ID NO 25
<211> LENGTH: 8
<212> TYPE: PRT
<213> ORGANISM: Oryctolagus cuniculus

<400> SEQUENCE: 25

Gly Asp Tyr Ser Gly Asn Asp Ile
1               5

<210> SEQ ID NO 26
<211> LENGTH: 375
<212> TYPE: DNA
<213> ORGANISM: Oryctolagus cuniculus

<400> SEQUENCE: 26
atggacacga gggcccccac tcagctgctg gggctcctgc tgctctggct cccaggtgcc      60
agatgtgctg acattgtgat gacccagact ccatcctccg tgtctgaacc tgtgcgaggc     120
acagtcacca tcaagtgcca ggccagtcag aacatttaca gctacttgtc ctggtatcaa     180
cagagcccag gcagcctcc caagctcctg atctacaagg catccactct ggcatctggg     240
gtcccatcgc ggttcaaagg cagtggatct gggacagatt tcactctcac catcagcgac     300
ctggagtgtg ccgatgctgc cacttactac tgtcaatcca attatggtag tgatagtgat     360
agttttggga atgct                                                     375

<210> SEQ ID NO 27
<211> LENGTH: 366
<212> TYPE: DNA
```

<213> ORGANISM: Oryctolagus cuniculus

<400> SEQUENCE: 27

```
atggagactg ggctgcgctg gcttctcctg gtcgctgtgc tcaaaggtgt ccagtgtcag    60
tcggtggagg agtccggggg tcgcctggtc acgcctggga cccccctgac actcacctgc   120
tcagtctctg gattctccct caataattat gtaatgggct gggtccgcca ggctccaggg   180
aaggggctgg aattcatcgg atacattgct tttggtattg gcccatacta cgcgagctgg   240
gcgaaaggcc gattcaccat ctccagcacc tcgtcgacca cggtggatct gaaaatgacc   300
agtctgacac ccgaggacac ggccacctat ttctgtgcca gaggtgatta tagtggtaat   360
gacatt                                                              366
```

<210> SEQ ID NO 28
<211> LENGTH: 33
<212> TYPE: DNA
<213> ORGANISM: Oryctolagus cuniculus

<400> SEQUENCE: 28

```
caggccagtc agaacattta cagctacttg tcc                                 33
```

<210> SEQ ID NO 29
<211> LENGTH: 21
<212> TYPE: DNA
<213> ORGANISM: Oryctolagus cuniculus

<400> SEQUENCE: 29

```
aaggcatcca ctctggcatc t                                              21
```

<210> SEQ ID NO 30
<211> LENGTH: 42
<212> TYPE: DNA
<213> ORGANISM: Oryctolagus cuniculus

<400> SEQUENCE: 30

```
caatccaatt atggtagtga tagtgatagt tttgggaatg ct                       42
```

<210> SEQ ID NO 31
<211> LENGTH: 15
<212> TYPE: DNA
<213> ORGANISM: Oryctolagus cuniculus

<400> SEQUENCE: 31

```
aattatgtaa tgggc                                                     15
```

<210> SEQ ID NO 32
<211> LENGTH: 48
<212> TYPE: DNA
<213> ORGANISM: Oryctolagus cuniculus

<400> SEQUENCE: 32

```
tacattgctt ttggtattgg cccatactac gcgagctggg cgaaaggc                 48
```

<210> SEQ ID NO 33
<211> LENGTH: 24
<212> TYPE: DNA
<213> ORGANISM: Oryctolagus cuniculus

<400> SEQUENCE: 33

```
ggtgattata gtggtaatga catt                                           24
```

```
<210> SEQ ID NO 34
<211> LENGTH: 122
<212> TYPE: PRT
<213> ORGANISM: Oryctolagus cuniculus

<400> SEQUENCE: 34

Met Asp Thr Arg Ala Pro Thr Gln Leu Leu Gly Leu Leu Leu Leu Trp
1               5                   10                  15

Leu Pro Gly Ser Thr Phe Ala Ile Lys Val Thr Gln Thr Pro Ala Ser
            20                  25                  30

Val Ser Ala Ala Val Gly Gly Thr Val Ser Ile Asn Cys Gln Ala Ser
        35                  40                  45

Glu Asp Ile Glu Ser Tyr Leu Ala Trp Tyr Gln Gln Lys Pro Gly Gln
    50                  55                  60

Pro Pro Lys Leu Leu Leu Tyr Asp Ala Ser Ala Leu Ala Ser Gly Val
65                  70                  75                  80

Pro Ser Arg Phe Lys Gly Ser Gly Ser Gly Thr Glu Tyr Thr Leu Thr
                85                  90                  95

Ile Ser Gly Val Glu Cys Ala Asp Ala Ala Thr Tyr Tyr Cys Gln Gln
            100                 105                 110

Gly Tyr Ser Tyr Ser Asn Val Asp Asn Ser
        115                 120

<210> SEQ ID NO 35
<211> LENGTH: 127
<212> TYPE: PRT
<213> ORGANISM: Oryctolagus cuniculus

<400> SEQUENCE: 35

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Lys Val Ser Gly Phe Ser Leu Ser
        35                  40                  45

Ser Tyr Asp Met Thr Trp Val Arg Gln Ala Pro Gly Lys Gly Leu Glu
    50                  55                  60

Trp Ile Gly Tyr Ile Trp Asn Asp Gly Ser Thr Ala Tyr Ala Ser Trp
65                  70                  75                  80

Ala Thr Gly Arg Phe Thr Ile Ser Lys Thr Ser Thr Thr Val Asp Leu
                85                  90                  95

Lys Ile Ala Ser Pro Thr Thr Glu Asp Thr Ala Thr Tyr Phe Cys Ala
            100                 105                 110

Arg Gly Pro Val Phe Ala Thr Thr Leu Gly Tyr Tyr Phe Thr Ile
        115                 120                 125

<210> SEQ ID NO 36
<211> LENGTH: 11
<212> TYPE: PRT
<213> ORGANISM: Oryctolagus cuniculus

<400> SEQUENCE: 36

Gln Ala Ser Glu Asp Ile Glu Ser Tyr Leu Ala
1               5                   10

<210> SEQ ID NO 37
<211> LENGTH: 7
<212> TYPE: PRT
<213> ORGANISM: Oryctolagus cuniculus
```

<400> SEQUENCE: 37

Asp Ala Ser Ala Leu Ala Ser
1               5

<210> SEQ ID NO 38
<211> LENGTH: 12
<212> TYPE: PRT
<213> ORGANISM: Oryctolagus cuniculus

<400> SEQUENCE: 38

Gln Gln Gly Tyr Ser Tyr Ser Asn Val Asp Asn Ser
1               5                   10

<210> SEQ ID NO 39
<211> LENGTH: 5
<212> TYPE: PRT
<213> ORGANISM: Oryctolagus cuniculus

<400> SEQUENCE: 39

Ser Tyr Asp Met Thr
1               5

<210> SEQ ID NO 40
<211> LENGTH: 16
<212> TYPE: PRT
<213> ORGANISM: Oryctolagus cuniculus

<400> SEQUENCE: 40

Tyr Ile Trp Asn Asp Gly Ser Thr Ala Tyr Ala Ser Trp Ala Thr Gly
1               5                   10                  15

<210> SEQ ID NO 41
<211> LENGTH: 14
<212> TYPE: PRT
<213> ORGANISM: Oryctolagus cuniculus

<400> SEQUENCE: 41

Gly Pro Val Phe Ala Thr Thr Leu Gly Tyr Tyr Phe Thr Ile
1               5                   10

<210> SEQ ID NO 42
<211> LENGTH: 366
<212> TYPE: DNA
<213> ORGANISM: Oryctolagus cuniculus

<400> SEQUENCE: 42

```
atggacacga gggcccccac tcagctgctg gggctcctgc tgctctggct cccaggttcc    60
acatttgcca tcaaagtgac ccagacacca gcctccgtgt ctgcagctgt gggaggcaca   120
gtcagcatca attgccaggc cagtgaggac attgaaagct atttggcctg gtatcagcag   180
aaaccagggc agcctcccaa actccttctc tatgatgcat ccgctctggc ttctggggtc   240
ccatcgcggt tcaaaggcag tggatctggg acagagtaca ctctcaccat cagcggcgtg   300
gagtgtgccg atgctgccac ttactactgt caacagggtt atagttatag taatgttgat   360
aattct                                                              366
```

<210> SEQ ID NO 43
<211> LENGTH: 381
<212> TYPE: DNA
<213> ORGANISM: Oryctolagus cuniculus

<400> SEQUENCE: 43

```
atggagactg ggctgcgctg gcttctcctg gtcgctgtgc tcaaaggtgt ccagtgtcag      60
tcggtggagg agtccggggg tcgcctggtc acgcctggga caccccctgac actcacctgc    120 aaagtctctg gattctccct cagcagctac gacatgacct gggtccgcca ggctccaggg    180
aaggggctgg agtggatcgg atacatttgg aatgatggta gtacagccta cgcgagctgg    240
gcgacaggcc gattcaccat ctccaaaacc tcgaccacgg tggatctgaa aatcgccagt    300
ccgacaaccg aggacacggc cacctatttc tgtgccagag gtcctgtttt tgcgactact    360
cttgggtact actttaccat c                                              381
```

`<210>` SEQ ID NO 44
`<211>` LENGTH: 33
`<212>` TYPE: DNA
`<213>` ORGANISM: Oryctolagus cuniculus

`<400>` SEQUENCE: 44

```
caggccagtg aggacattga aagctatttg gcc                                  33
```

`<210>` SEQ ID NO 45
`<211>` LENGTH: 21
`<212>` TYPE: DNA
`<213>` ORGANISM: Oryctolagus cuniculus

`<400>` SEQUENCE: 45

```
gatgcatccg ctctggcttc t                                               21
```

`<210>` SEQ ID NO 46
`<211>` LENGTH: 36
`<212>` TYPE: DNA
`<213>` ORGANISM: Oryctolagus cuniculus

`<400>` SEQUENCE: 46

```
caacagggtt atagttatag taatgttgat aattct                               36
```

`<210>` SEQ ID NO 47
`<211>` LENGTH: 15
`<212>` TYPE: DNA
`<213>` ORGANISM: Oryctolagus cuniculus

`<400>` SEQUENCE: 47

```
agctacgaca tgacc                                                      15
```

`<210>` SEQ ID NO 48
`<211>` LENGTH: 48
`<212>` TYPE: DNA
`<213>` ORGANISM: Oryctolagus cuniculus

`<400>` SEQUENCE: 48

```
tacatttgga atgatggtag tacagcctac gcgagctggg cgacaggc                  48
```

`<210>` SEQ ID NO 49
`<211>` LENGTH: 42
`<212>` TYPE: DNA
`<213>` ORGANISM: Oryctolagus cuniculus

`<400>` SEQUENCE: 49

```
ggtcctgttt ttgcgactac tcttgggtac tactttacca tc                        42
```

`<210>` SEQ ID NO 50
`<211>` LENGTH: 123
`<212>` TYPE: PRT

<213> ORGANISM: Oryctolagus cuniculus

<400> SEQUENCE: 50

Met Asp Thr Arg Ala Pro Thr Gln Leu Leu Gly Leu Leu Leu Leu Trp
1               5                   10                  15
Leu Thr Gly Ala Thr Phe Ala Ala Val Leu Thr Gln Thr Pro Ser Pro
                20                  25                  30
Val Ser Ala Val Val Gly Gly Thr Val Ser Ile Ser Cys Gln Ser Ser
                35                  40                  45
Lys Arg Val Val Asn Ser Val Ala Leu Ser Trp Tyr Gln Gln Lys Pro
        50                  55                  60
Gly Arg Ser Pro Lys Leu Leu Ile Tyr Phe Ala Ser Lys Leu Ala Ser
65                  70                  75                  80
Gly Val Pro Ser Arg Phe Lys Gly Ser Gly Ser Gly Thr Gln Phe Thr
                85                  90                  95
Leu Ala Ile Ser Asp Val Gln Cys Asp Asp Ala Ala Thr Tyr Tyr Cys
                100                 105                 110
Ala Gly His Tyr Thr Asp Ser Gly Asp Ala
            115                 120

<210> SEQ ID NO 51
<211> LENGTH: 122
<212> TYPE: PRT
<213> ORGANISM: Oryctolagus cuniculus

<400> SEQUENCE: 51

Met Glu Thr Gly Leu Arg Trp Leu Leu Leu Val Ala Val Leu Lys Gly
1               5                   10                  15
Val Gln Cys Gln Ser Val Glu Glu Ser Gly Gly Arg Leu Val Thr Pro
                20                  25                  30
Gly Thr Pro Leu Thr Leu Thr Cys Thr Val Ser Gly Leu Ser Leu Ser
                35                  40                  45
Thr Glu Thr Ile Asn Trp Val Arg Gln Ala Pro Gly Lys Gly Leu Glu
        50                  55                  60
Trp Ile Gly Tyr Ile Asp Ser Ser Gly Gly Thr Gly Tyr Ala Asn Trp
65                  70                  75                  80
Ala Arg Gly Arg Phe Thr Ile Ser Lys Thr Ser Thr Thr Val Asp Leu
                85                  90                  95
Lys Ile Thr Ser Pro Thr Thr Gly Asp Thr Ala Thr Tyr Phe Cys Ala
                100                 105                 110
Arg Gly Thr Ile Thr Thr Gly Met Asn Ile
            115                 120

<210> SEQ ID NO 52
<211> LENGTH: 13
<212> TYPE: PRT
<213> ORGANISM: Oryctolagus cuniculus

<400> SEQUENCE: 52

Gln Ser Ser Lys Arg Val Val Asn Ser Val Ala Leu Ser
1               5                   10

<210> SEQ ID NO 53
<211> LENGTH: 7
<212> TYPE: PRT
<213> ORGANISM: Oryctolagus cuniculus

<400> SEQUENCE: 53

```
Phe Ala Ser Lys Leu Ala Ser
1               5

<210> SEQ ID NO 54
<211> LENGTH: 11
<212> TYPE: PRT
<213> ORGANISM: Oryctolagus cuniculus

<400> SEQUENCE: 54

Ala Gly His Tyr Thr Asp Ser Gly Asp Asp Ala
1               5                   10

<210> SEQ ID NO 55
<211> LENGTH: 5
<212> TYPE: PRT
<213> ORGANISM: Oryctolagus cuniculus

<400> SEQUENCE: 55

Thr Glu Thr Ile Asn
1               5

<210> SEQ ID NO 56
<211> LENGTH: 16
<212> TYPE: PRT
<213> ORGANISM: Oryctolagus cuniculus

<400> SEQUENCE: 56

Tyr Ile Asp Ser Ser Gly Gly Thr Gly Tyr Ala Asn Trp Ala Arg Gly
1               5                   10                  15

<210> SEQ ID NO 57
<211> LENGTH: 9
<212> TYPE: PRT
<213> ORGANISM: Oryctolagus cuniculus

<400> SEQUENCE: 57

Gly Thr Ile Thr Thr Gly Met Asn Ile
1               5

<210> SEQ ID NO 58
<211> LENGTH: 369
<212> TYPE: DNA
<213> ORGANISM: Oryctolagus cuniculus

<400> SEQUENCE: 58
atggacacga gggcccccac tcagctgctg gggctcctgc tgctctggct cacaggtgcc      60
acatttgccg ccgtgctgac ccagactcca tctcccgtgt ctgcagttgt gggaggcaca     120
gtcagcatca gttgccagtc cagcaagaga gttgttaata gcgttgcctt atcctggtat     180
cagcagaaac cagggcgctc tcctaagctc ctgatctatt tgcatccaa actggcatct      240 ggggtcccat cgcggttcaa aggcagtgga tctgggacac agttcactct cgccattagc     300
gacgtgcagt gtgacgatgc tgccacttac tactgtgcag ccattatac tgatagtggt      360 gatgatgct                                                             369

<210> SEQ ID NO 59
<211> LENGTH: 366
<212> TYPE: DNA
<213> ORGANISM: Oryctolagus cuniculus

<400> SEQUENCE: 59
atggagactg ggctgcgctg gcttctcctg gtcgctgtgc tcaaaggtgt ccagtgtcag      60
```

```
tcggtggagg agtccggggg tcgcctggtc acgcctggga caccccTgac actcacctgc    120
acagtctctg gattatccct cagtaccgag acaattaact gggtccgcca ggctccaggg    180
aagggactgg agtggatcgg atacattgat agttctggtg cacaggcta cgcgaactgg     240 gcgagaggcc gattcaccat ctccaaaacc tcgaccacgg tggatttgaa aatcaccagt    300
ccgacaaccg gggacacggc cacctatttc tgtgccagag aactattac tactggcatg     360 aacatc                                                               366

<210> SEQ ID NO 60
<211> LENGTH: 39
<212> TYPE: DNA
<213> ORGANISM: Oryctolagus cuniculus

<400> SEQUENCE: 60
cagtccagca agagagttgt taatagcgtt gccttatcc                            39

<210> SEQ ID NO 61
<211> LENGTH: 21
<212> TYPE: DNA
<213> ORGANISM: Oryctolagus cuniculus

<400> SEQUENCE: 61
tttgcatcca aactggcatc t                                               21

<210> SEQ ID NO 62
<211> LENGTH: 33
<212> TYPE: DNA
<213> ORGANISM: Oryctolagus cuniculus

<400> SEQUENCE: 62
gcaggccatt atactgatag tggtgatgat gct                                  33

<210> SEQ ID NO 63
<211> LENGTH: 15
<212> TYPE: DNA
<213> ORGANISM: Oryctolagus cuniculus

<400> SEQUENCE: 63
accgagacaa ttaac                                                      15

<210> SEQ ID NO 64
<211> LENGTH: 48
<212> TYPE: DNA
<213> ORGANISM: Oryctolagus cuniculus

<400> SEQUENCE: 64
tacattgata gttctggtgg cacaggctac gcgaactggg cgagaggc                  48

<210> SEQ ID NO 65
<211> LENGTH: 27
<212> TYPE: DNA
<213> ORGANISM: Oryctolagus cuniculus

<400> SEQUENCE: 65
ggaactatta ctactggcat gaacatc                                         27

<210> SEQ ID NO 66
<211> LENGTH: 122
<212> TYPE: PRT
<213> ORGANISM: Oryctolagus cuniculus

<400> SEQUENCE: 66
```

Met Asp Thr Arg Ala Pro Thr Gln Leu Leu Gly Leu Leu Leu Trp
1               5                   10                  15

Leu Pro Gly Ala Thr Leu Ala Gln Val Val Thr Gln Thr Pro Ala Ser
                20                  25                  30

Val Ser Ala Ala Val Gly Gly Thr Val Thr Ile Ser Cys Gln Ser Ser
            35                  40                  45

Gln Asn Val Tyr Asn Asn Asp Leu Val Trp Phe Gln Gln Lys Pro
    50                  55                  60

Gly Gln Pro Pro Lys Arg Leu Val Tyr Trp Ala Ser Thr Leu Ala Ser
65              70                  75                  80

Gly Val Ser Ser Arg Phe Arg Gly Ser Gly Ser Gly Thr Gln Phe Ile
                85                  90                  95

Leu Thr Ile Ser Asp Leu Gln Cys Asp Asp Ala Ala Thr Tyr Tyr Cys
            100                 105                 110

Ala Gly Ala Tyr Asp Ser Glu Ile Arg Ala
        115                 120

<210> SEQ ID NO 67
<211> LENGTH: 120
<212> TYPE: PRT
<213> ORGANISM: Oryctolagus cuniculus

<400> SEQUENCE: 67

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
                20                  25                  30

Gly Thr Pro Leu Thr Leu Thr Cys Ala Val Ser Gly Phe Ser Leu Ser
            35                  40                  45

Val Tyr Trp Met Thr Trp Val Arg Gln Ala Pro Gly Lys Gly Leu Glu
    50                  55                  60

Trp Ile Gly Thr Ile Ser Thr Asp Gly Ile Thr Val Tyr Ala Thr Trp
65              70                  75                  80

Ala Lys Gly Arg Phe Thr Ile Ser Lys Thr Ser Ser Thr Ala Val Asp
                85                  90                  95

Leu Lys Leu Thr Ser Pro Thr Thr Glu Asp Thr Ala Thr Tyr Phe Cys
            100                 105                 110

Ala Gly Gly Gly Gly Met Asp Pro
        115                 120

<210> SEQ ID NO 68
<211> LENGTH: 13
<212> TYPE: PRT
<213> ORGANISM: Oryctolagus cuniculus

<400> SEQUENCE: 68

Gln Ser Ser Gln Asn Val Tyr Asn Asn Asp Leu Val
1               5                   10

<210> SEQ ID NO 69
<211> LENGTH: 7
<212> TYPE: PRT
<213> ORGANISM: Oryctolagus cuniculus

<400> SEQUENCE: 69

Trp Ala Ser Thr Leu Ala Ser
1               5

<210> SEQ ID NO 70
<211> LENGTH: 10
<212> TYPE: PRT
<213> ORGANISM: Oryctolagus cuniculus

<400> SEQUENCE: 70

Ala Gly Ala Tyr Asp Ser Glu Ile Arg Ala
1               5                   10

<210> SEQ ID NO 71
<211> LENGTH: 5
<212> TYPE: PRT
<213> ORGANISM: Oryctolagus cuniculus

<400> SEQUENCE: 71

Val Tyr Trp Met Thr
1               5

<210> SEQ ID NO 72
<211> LENGTH: 16
<212> TYPE: PRT
<213> ORGANISM: Oryctolagus cuniculus

<400> SEQUENCE: 72

Thr Ile Ser Thr Asp Gly Ile Thr Val Tyr Ala Thr Trp Ala Lys Gly
1               5                   10                  15

<210> SEQ ID NO 73
<211> LENGTH: 6
<212> TYPE: PRT
<213> ORGANISM: Oryctolagus cuniculus

<400> SEQUENCE: 73

Gly Gly Gly Met Asp Pro
1               5

<210> SEQ ID NO 74
<211> LENGTH: 366
<212> TYPE: DNA
<213> ORGANISM: Oryctolagus cuniculus

<400> SEQUENCE: 74

```
atggacacga gggcccccac tcagctgctg gggctcctgc tgctctggct cccaggtgcc      60
acacttgcgc aagtggtgac ccagactcca gcctccgtgt ctgcagctgt gggaggcaca     120
gtcaccatca gttgccagtc cagtcagaat gtttataata ataatgactt agtctggttt     180
cagcagaaac aggtcagcc tcccaagcgc ctggtctact gggcatccac tctggcatct     240
ggggtctcat cgcggttcag aggcagtgga tctgggacac agttcattct caccatcagc     300
gacctgcagt gtgacgatgc tgccacttac tattgtgcag cgcctatga tagtgaaatt     360
agggct                                                                366
```

<210> SEQ ID NO 75
<211> LENGTH: 360
<212> TYPE: DNA
<213> ORGANISM: Oryctolagus cuniculus

<400> SEQUENCE: 75

```
atggagactg ggctgcgctg gcttctcctg gtcgctgtgc tcaaaggtgt ccagtgtcag      60
tcggtggagg agtccggggg tcgcctggtc acgcctggga caccctgac actcacctgc     120
gcagtctctg gattctccct cagtgtttac tggatgacct gggtccgcca ggctccaggg     180
```

```
aaggggctgg aatggatcgg aaccattagt actgatggta tcactgtcta cgcgacctgg    240
gcgaaaggcc gattcaccat ctccaaaacc tcgtcgaccg cggtggatct gaaactcacc    300
agtccgacaa ccgaggacac ggccacctat ttctgtgccg agggggcgg catggacccc     360
```

<210> SEQ ID NO 76
<211> LENGTH: 39
<212> TYPE: DNA
<213> ORGANISM: Oryctolagus cuniculus

<400> SEQUENCE: 76

```
cagtccagtc agaatgttta taataataat gacttagtc                            39
```

<210> SEQ ID NO 77
<211> LENGTH: 21
<212> TYPE: DNA
<213> ORGANISM: Oryctolagus cuniculus

<400> SEQUENCE: 77

```
tgggcatcca ctctggcatc t                                               21
```

<210> SEQ ID NO 78
<211> LENGTH: 30
<212> TYPE: DNA
<213> ORGANISM: Oryctolagus cuniculus

<400> SEQUENCE: 78

```
gcaggcgcct atgatagtga aattagggct                                      30
```

<210> SEQ ID NO 79
<211> LENGTH: 15
<212> TYPE: DNA
<213> ORGANISM: Oryctolagus cuniculus

<400> SEQUENCE: 79

```
gtttactgga tgacc                                                      15
```

<210> SEQ ID NO 80
<211> LENGTH: 48
<212> TYPE: DNA
<213> ORGANISM: Oryctolagus cuniculus

<400> SEQUENCE: 80

```
accattagta ctgatggtat cactgtctac gcgacctggg cgaaaggc                  48
```

<210> SEQ ID NO 81
<211> LENGTH: 18
<212> TYPE: DNA
<213> ORGANISM: Oryctolagus cuniculus

<400> SEQUENCE: 81

```
gggggcggca tggacccc                                                   18
```

<210> SEQ ID NO 82
<211> LENGTH: 122
<212> TYPE: PRT
<213> ORGANISM: Oryctolagus cuniculus

<400> SEQUENCE: 82

```
Met Asp Thr Arg Ala Pro Thr Gln Leu Leu Gly Leu Leu Leu Leu Trp
1               5                   10                  15

Leu Pro Asp Ala Arg Cys Ala Tyr Asp Met Thr Gln Thr Pro Ala Ser
```

-continued

```
                20                  25                  30
Val Glu Val Ala Gly Gly Thr Val Thr Ile Lys Cys Gln Ala Ser
             35                  40                  45
Gln Ser Ile Ala Asn Arg Leu Ala Trp Tyr Gln Gln Lys Pro Gly Gln
 50                  55                  60
Pro Pro Lys Leu Leu Ile Tyr Tyr Ala Ser Thr Leu Ala Ser Gly Val
 65                  70                  75                  80
Pro Ser Arg Phe Ser Gly Ser Gly Ser Gly Thr Glu Phe Thr Leu Thr
                 85                  90                  95
Ile Ser Gly Val Gln Cys Asp Asp Ala Ala Thr Tyr Tyr Cys Gln Gln
             100                 105                 110
Thr Tyr Ser Asp Asn Asn Val Asp Asn Ala
             115                 120
```

<210> SEQ ID NO 83
<211> LENGTH: 126
<212> TYPE: PRT
<213> ORGANISM: Oryctolagus cuniculus

<400> SEQUENCE: 83

```
Met Glu Thr Gly Leu Arg Trp Leu Leu Leu Val Ala Val Phe Lys Gly
 1               5                  10                  15
Val Gln Cys Gln Ser Val Glu Glu Ser Gly Arg Leu Val Thr Pro
             20                  25                  30
Gly Thr Pro Leu Thr Leu Thr Cys Thr Val Ser Gly Phe Ser Leu Ser
             35                  40                  45
Ser Asn Thr Ile Ser Trp Val Arg Gln Ala Pro Gly Lys Gly Leu Glu
 50                  55                  60
Trp Ile Gly Tyr Ile Trp Arg Gly Val Ser Thr Tyr Tyr Ala Thr Trp
 65                  70                  75                  80
Ala Lys Gly Arg Phe Thr Ile Ser Lys Thr Ser Ser Thr Thr Val Asp
                 85                  90                  95
Leu Lys Ile Thr Gly Pro Thr Thr Glu Asp Thr Ala Thr Tyr Phe Cys
             100                 105                 110
Ala Arg Asp Ala Gly Asp Gly Gly Tyr Ser Leu Asp Leu
             115                 120                 125
```

<210> SEQ ID NO 84
<211> LENGTH: 11
<212> TYPE: PRT
<213> ORGANISM: Oryctolagus cuniculus

<400> SEQUENCE: 84

```
Gln Ala Ser Gln Ser Ile Ala Asn Arg Leu Ala
 1               5                  10
```

<210> SEQ ID NO 85
<211> LENGTH: 7
<212> TYPE: PRT
<213> ORGANISM: Oryctolagus cuniculus

<400> SEQUENCE: 85

```
Tyr Ala Ser Thr Leu Ala Ser
 1               5
```

<210> SEQ ID NO 86
<211> LENGTH: 12
<212> TYPE: PRT
<213> ORGANISM: Oryctolagus cuniculus

<400> SEQUENCE: 86

Gln Gln Thr Tyr Ser Asp Asn Asn Val Asp Asn Ala
1               5                   10

<210> SEQ ID NO 87
<211> LENGTH: 5
<212> TYPE: PRT
<213> ORGANISM: Oryctolagus cuniculus

<400> SEQUENCE: 87

Ser Asn Thr Ile Ser
1               5

<210> SEQ ID NO 88
<211> LENGTH: 16
<212> TYPE: PRT
<213> ORGANISM: Oryctolagus cuniculus

<400> SEQUENCE: 88

Tyr Ile Trp Arg Gly Val Ser Thr Tyr Tyr Ala Thr Trp Ala Lys Gly
1               5                   10                  15

<210> SEQ ID NO 89
<211> LENGTH: 12
<212> TYPE: PRT
<213> ORGANISM: Oryctolagus cuniculus

<400> SEQUENCE: 89

Asp Ala Gly Asp Gly Gly Gly Tyr Ser Leu Asp Leu
1               5                   10

<210> SEQ ID NO 90
<211> LENGTH: 366
<212> TYPE: DNA
<213> ORGANISM: Oryctolagus cuniculus

<400> SEQUENCE: 90

| | | | | | | |
|---|---|---|---|---|---|---|
| atggacacga | gggcccccac | tcagctgctg | gggctcctgc | tgctctggct | cccagatgcc | 60 |
| agatgtgcct | atgatatgac | ccagactcca | gcctctgtgg | aggtagctgg | gggaggcaca | 120 |
| gtcaccatca | gtgccaggc | cagtcagagc | attgctaata | ggttagcctg | gtatcagcag | 180 |
| aaaccagggc | agcctcccaa | gctcctgatc | tattatgcat | ccacgctggc | atctggggtc | 240 |
| ccatcgcggt | tcagcggcag | tggatctggg | acagagttca | ctctcaccat | cagtggcgtg | 300 |
| cagtgtgacg | atgctgccac | ttactactgt | cagcagactt | atagtgataa | taatgtcgat | 360 |
| aatgct | | | | | | 366 |

<210> SEQ ID NO 91
<211> LENGTH: 378
<212> TYPE: DNA
<213> ORGANISM: Oryctolagus cuniculus

<400> SEQUENCE: 91

| | | | | | | |
|---|---|---|---|---|---|---|
| atggagactg | ggctgcgctg | gcttctcctg | gtcgctgtgt | tcaaaggtgt | ccagtgtcag | 60 |
| tcggtggagg | agtccggggg | tcgcctggtc | acgcctggga | cacccctgac | actcacctgc | 120 |
| acagtctctg | gattctccct | cagtagcaat | acaataagct | gggtccgcca | ggctccaggg | 180 |
| aaggggctgg | agtggatcgg | atacatttgg | cgtggtgtta | gcacatacta | cgcgacctgg | 240 |
| gcgaaaggcc | gattcaccat | ctccaaaacc | tcgtcgacga | cggtggatct | gaagatcacc | 300 |

```
ggtccgacaa ccgaggacac ggccacctat ttctgtgcca gagatgctgg tgatggtggt        360
ggatattcct tggatctc                                                      378
```

<210> SEQ ID NO 92
<211> LENGTH: 33
<212> TYPE: DNA
<213> ORGANISM: Oryctolagus cuniculus

<400> SEQUENCE: 92

```
caggccagtc agagcattgc taataggtta gcc                                      33
```

<210> SEQ ID NO 93
<211> LENGTH: 21
<212> TYPE: DNA
<213> ORGANISM: Oryctolagus cuniculus

<400> SEQUENCE: 93

```
tatgcatcca cgctggcatc t                                                   21
```

<210> SEQ ID NO 94
<211> LENGTH: 36
<212> TYPE: DNA
<213> ORGANISM: Oryctolagus cuniculus

<400> SEQUENCE: 94

```
cagcagactt atagtgataa taatgtcgat aatgct                                   36
```

<210> SEQ ID NO 95
<211> LENGTH: 15
<212> TYPE: DNA
<213> ORGANISM: Oryctolagus cuniculus

<400> SEQUENCE: 95

```
agcaatacaa taagc                                                          15
```

<210> SEQ ID NO 96
<211> LENGTH: 48
<212> TYPE: DNA
<213> ORGANISM: Oryctolagus cuniculus

<400> SEQUENCE: 96

```
tacatttggc gtggtgttag cacatactac gcgacctggg cgaaaggc                      48
```

<210> SEQ ID NO 97
<211> LENGTH: 36
<212> TYPE: DNA
<213> ORGANISM: Oryctolagus cuniculus

<400> SEQUENCE: 97

```
gatgctggtg atggtggtgg atattccttg gatctc                                   36
```

<210> SEQ ID NO 98
<211> LENGTH: 125
<212> TYPE: PRT
<213> ORGANISM: Oryctolagus cuniculus

<400> SEQUENCE: 98

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ala
            20                  25                  30

Ser Val Glu Ala Ala Val Gly Gly Thr Val Thr Ile Asn Cys Gln Ala

```
            35                  40                  45
Ser Gln Ser Ile Val Ser Trp Leu Ala Trp Tyr Gln Gln Lys Pro Gly
     50                  55                  60

Gln Pro Pro Lys Leu Leu Ile Tyr Gly Ala Ser Thr Leu Ala Ser Gly
 65                  70                  75                  80

Val Pro Ser Arg Phe Lys Gly Ser Gly Ser Gly Thr Glu Tyr Thr Leu
                 85                  90                  95

Thr Ile Ser Asp Leu Glu Cys Ala Asp Ala Ala Thr Tyr Tyr Cys Gln
                100                 105                 110

Ser Asn Tyr Gly Ser Asn Ser His Ser Phe Gly Asn Thr
                115                 120                 125

<210> SEQ ID NO 99
<211> LENGTH: 121
<212> TYPE: PRT
<213> ORGANISM: Oryctolagus cuniculus

<400> SEQUENCE: 99

Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Thr Pro
                 20                  25                  30

Gly Thr Pro Leu Thr Leu Thr Cys Thr Val Ser Gly Phe Ser Leu Ser
             35                  40                  45

Ser Asp Asn Met Gly Trp Val Arg Gln Ala Pro Gly Lys Gly Leu Glu
     50                  55                  60

Tyr Ile Gly Tyr Ile Tyr Gly Gly Phe Thr Tyr Tyr Ala Thr Trp
 65                  70                  75                  80

Ala Lys Gly Arg Phe Thr Ile Ser Lys Thr Ser Thr Thr Val Asp Leu
                 85                  90                  95

Lys Met Thr Ser Pro Thr Thr Glu Asp Thr Ala Thr Tyr Phe Cys Ala
                100                 105                 110

Arg Glu Ala Gly Gly Arg Ala Asn Val
                115                 120

<210> SEQ ID NO 100
<211> LENGTH: 11
<212> TYPE: PRT
<213> ORGANISM: Oryctolagus cuniculus

<400> SEQUENCE: 100

Gln Ala Ser Gln Ser Ile Val Ser Trp Leu Ala
 1               5                  10

<210> SEQ ID NO 101
<211> LENGTH: 7
<212> TYPE: PRT
<213> ORGANISM: Oryctolagus cuniculus

<400> SEQUENCE: 101

Gly Ala Ser Thr Leu Ala Ser
 1               5

<210> SEQ ID NO 102
<211> LENGTH: 14
<212> TYPE: PRT
<213> ORGANISM: Oryctolagus cuniculus

<400> SEQUENCE: 102
```

Gln Ser Asn Tyr Gly Ser Asn Ser His Ser Phe Gly Asn Thr
1               5                   10

<210> SEQ ID NO 103
<211> LENGTH: 5
<212> TYPE: PRT
<213> ORGANISM: Oryctolagus cuniculus

<400> SEQUENCE: 103

Ser Asp Asn Met Gly
1               5

<210> SEQ ID NO 104
<211> LENGTH: 16
<212> TYPE: PRT
<213> ORGANISM: Oryctolagus cuniculus

<400> SEQUENCE: 104

Tyr Ile Thr Tyr Gly Gly Phe Thr Tyr Tyr Ala Thr Trp Ala Lys Gly
1               5                   10                  15

<210> SEQ ID NO 105
<211> LENGTH: 8
<212> TYPE: PRT
<213> ORGANISM: Oryctolagus cuniculus

<400> SEQUENCE: 105

Glu Ala Gly Gly Arg Ala Asn Val
1               5

<210> SEQ ID NO 106
<211> LENGTH: 375
<212> TYPE: DNA
<213> ORGANISM: Oryctolagus cuniculus

<400> SEQUENCE: 106

```
atggacacga gggcccccac tcagctgctg gggctcctac tgctctggct cccaggtgcc    60
agatgtgctg acattgtgat gacccagact ccagcctccg tggaggcagc tgtgggaggc   120
acagtcacca tcaattgcca ggccagtcag agcattgtca gttggttagc ctggtatcag   180
cagaaaccag gcagcctcc  caagctcctg atctatggtg catccactct ggcatctggg   240
gtcccatcgc ggttcaaagg cagtggatct gggacagagt acactctcac catcagcgac   300
ctggagtgtg ccgatgctgc cacttactac tgtcaaagca attatggtag taatagtcat   360
agttttggga atact                                                    375
```

<210> SEQ ID NO 107
<211> LENGTH: 363
<212> TYPE: DNA
<213> ORGANISM: Oryctolagus cuniculus

<400> SEQUENCE: 107

```
atggagactg ggctgcgctg gcttctcctg gtcgctgtgc tcaaaggtgt ccagtgtcag    60
tcagtggagg agtccggggg tcgcctggtc acgcctggga cacccctgac actcacctgc   120
acagtctctg gattctccct cagtagcgac aatatgggct gggtccgcca ggctccaggg   180
aaggggctgg aatacatcgg atacattact tatggtggtt tcacatacta cgcgacctgg   240
gcgaaaggcc gattcaccat ctccaagacc tcgaccacgg tggatctgaa aatgaccagt   300
ccgacaaccg aggacacggc cacctatttc tgtgccagag aagctggtgg tagggctaat   360
gtc                                                                 363
```

<210> SEQ ID NO 108
<211> LENGTH: 33
<212> TYPE: DNA
<213> ORGANISM: Oryctolagus cuniculus

<400> SEQUENCE: 108
caggccagtc agagcattgt cagttggtta gcc                          33

<210> SEQ ID NO 109
<211> LENGTH: 21
<212> TYPE: DNA
<213> ORGANISM: Oryctolagus cuniculus

<400> SEQUENCE: 109
ggtgcatcca ctctggcatc t                                       21

<210> SEQ ID NO 110
<211> LENGTH: 42
<212> TYPE: DNA
<213> ORGANISM: Oryctolagus cuniculus

<400> SEQUENCE: 110
caaagcaatt atggtagtaa tagtcatagt tttgggaata ct                42

<210> SEQ ID NO 111
<211> LENGTH: 15
<212> TYPE: DNA
<213> ORGANISM: Oryctolagus cuniculus

<400> SEQUENCE: 111
agcgacaata tgggc                                              15

<210> SEQ ID NO 112
<211> LENGTH: 48
<212> TYPE: DNA
<213> ORGANISM: Oryctolagus cuniculus

<400> SEQUENCE: 112
tacattactt atggtggttt cacatactac gcgacctggg cgaaaggc          48

<210> SEQ ID NO 113
<211> LENGTH: 24
<212> TYPE: DNA
<213> ORGANISM: Oryctolagus cuniculus

<400> SEQUENCE: 113
gaagctggtg gtagggctaa tgtc                                    24

<210> SEQ ID NO 114
<211> LENGTH: 125
<212> TYPE: PRT
<213> ORGANISM: Oryctolagus cuniculus

<400> SEQUENCE: 114

Met Asp Thr Arg Ala Pro Thr Gln Leu Leu Gly Leu Leu Leu Trp
1               5                   10                  15

Leu Pro Gly Ala Arg Cys Ala Asp Ile Val Met Thr Gln Thr Pro Ser
                20                  25                  30

Ser Val Ser Glu Pro Val Gly Gly Thr Val Thr Ile Met Cys Gln Ala
            35                  40                  45

Ser Gln Asn Ile Tyr Ser Tyr Leu Ser Trp Tyr Gln Gln Lys Pro Gly

```
                        50                  55                  60
Gln Pro Pro Lys Leu Leu Ile Tyr Lys Ala Ser Thr Leu Ala Ser Gly
 65                  70                  75                  80

Val Pro Ser Arg Phe Ala Gly Ser Gly Ser Gly Thr Asp Phe Thr Leu
                 85                  90                  95

Thr Ile Ser Asp Leu Glu Cys Ala Asp Ala Ala Thr Tyr Tyr Cys Gln
            100                 105                 110

Ser Asn Tyr Gly Ser Asn Ser Asp Ser Phe Gly Asn Ala
        115                 120                 125

<210> SEQ ID NO 115
<211> LENGTH: 122
<212> TYPE: PRT
<213> ORGANISM: Oryctolagus cuniculus

<400> SEQUENCE: 115

Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Thr Pro
                20                  25                  30

Gly Thr Pro Leu Thr Leu Thr Cys Thr Ala Ser Gly Phe Ser Leu Ser
             35                  40                  45

Asn Tyr Val Met Gly Trp Val Arg Gln Ala Pro Gly Lys Gly Leu Glu
 50                  55                  60

Phe Ile Gly Tyr Ile Ala Phe Gly Ile Gly Pro Tyr Tyr Ala Thr Trp
 65                  70                  75                  80

Ala Lys Gly Arg Phe Ser Ile Ser Ser Thr Ser Thr Thr Val Asp
                 85                  90                  95

Leu Thr Met Thr Ser Leu Thr Pro Glu Asp Thr Ala Thr Tyr Phe Cys
            100                 105                 110

Ala Arg Gly Asp Tyr Ser Gly Asn Asn Ile
        115                 120

<210> SEQ ID NO 116
<211> LENGTH: 11
<212> TYPE: PRT
<213> ORGANISM: Oryctolagus cuniculus

<400> SEQUENCE: 116

Gln Ala Ser Gln Asn Ile Tyr Ser Tyr Leu Ser
 1               5                  10

<210> SEQ ID NO 117
<211> LENGTH: 7
<212> TYPE: PRT
<213> ORGANISM: Oryctolagus cuniculus

<400> SEQUENCE: 117

Lys Ala Ser Thr Leu Ala Ser
 1               5

<210> SEQ ID NO 118
<211> LENGTH: 14
<212> TYPE: PRT
<213> ORGANISM: Oryctolagus cuniculus

<400> SEQUENCE: 118

Gln Ser Asn Tyr Gly Ser Asn Ser Asp Ser Phe Gly Asn Ala
 1               5                  10
```

<210> SEQ ID NO 119
<211> LENGTH: 5
<212> TYPE: PRT
<213> ORGANISM: Oryctolagus cuniculus

<400> SEQUENCE: 119

Asn Tyr Val Met Gly
1               5

<210> SEQ ID NO 120
<211> LENGTH: 16
<212> TYPE: PRT
<213> ORGANISM: Oryctolagus cuniculus

<400> SEQUENCE: 120

Tyr Ile Ala Phe Gly Ile Gly Pro Tyr Tyr Ala Thr Trp Ala Lys Gly
1               5                   10                  15

<210> SEQ ID NO 121
<211> LENGTH: 8
<212> TYPE: PRT
<213> ORGANISM: Oryctolagus cuniculus

<400> SEQUENCE: 121

Gly Asp Tyr Ser Gly Asn Asn Ile
1               5

<210> SEQ ID NO 122
<211> LENGTH: 375
<212> TYPE: DNA
<213> ORGANISM: Oryctolagus cuniculus

<400> SEQUENCE: 122

```
atggacacga gggcccccac tcagctgctg gggctcctgc tgctctggct cccaggtgcc    60
agatgtgctg acattgtgat gacccagact ccatcctccg tgtctgaacc tgtgggaggc   120
acagtcacca tcatgtgcca ggccagtcag aacatttaca gctacttatc ctggtatcag   180
cagaaaccag gcagcctcc caagctcctg atctacaagg catccactct ggcatctggg   240
gtcccatcgc ggttcgcagg cagtggatct gggacagatt tcactctcac catcagcgac   300
ctggagtgtg ccgatgctgc cacttactac tgtcaaagca attatggtag taatagtgat   360
agttttggga atgct                                                    375
```

<210> SEQ ID NO 123
<211> LENGTH: 366
<212> TYPE: DNA
<213> ORGANISM: Oryctolagus cuniculus

<400> SEQUENCE: 123

```
atggagactg ggctgcgctg cttctcctg gtcgctgtgc tcaaaggtgt ccagtgtcag    60
tcggtggagg agtccggggg tcgcctggtc acgcctggga cacccctgac actcacctgc   120
acagcctctg gattctcct cagtaattat gtaatgggct gggtccgcca ggctccaggg   180
aaggggctgg aattcatcgg atacattgct tttggtattg gcccatacta cgcgacctgg   240
gcgaaaggcc gattctccat ctccagcacc tcgtcgacca cggtggatct gacaatgacc   300
agtctgacac ccgaggacac ggccacctat ttctgtgcca gaggtgatta gtggtaat    360
aacatt                                                              366
```

<210> SEQ ID NO 124

```
<211> LENGTH: 33
<212> TYPE: DNA
<213> ORGANISM: Oryctolagus cuniculus

<400> SEQUENCE: 124
caggccagtc agaacattta cagctactta tcc                              33

<210> SEQ ID NO 125
<211> LENGTH: 21
<212> TYPE: DNA
<213> ORGANISM: Oryctolagus cuniculus

<400> SEQUENCE: 125
aaggcatcca ctctggcatc t                                           21

<210> SEQ ID NO 126
<211> LENGTH: 42
<212> TYPE: DNA
<213> ORGANISM: Oryctolagus cuniculus

<400> SEQUENCE: 126
caaagcaatt atggtagtaa tagtgatagt tttgggaatg ct                    42

<210> SEQ ID NO 127
<211> LENGTH: 15
<212> TYPE: DNA
<213> ORGANISM: Oryctolagus cuniculus

<400> SEQUENCE: 127
aattatgtaa tgggc                                                  15

<210> SEQ ID NO 128
<211> LENGTH: 48
<212> TYPE: DNA
<213> ORGANISM: Oryctolagus cuniculus

<400> SEQUENCE: 128
tacattgctt ttggtattgg cccatactac gcgacctggg cgaaaggc              48

<210> SEQ ID NO 129
<211> LENGTH: 24
<212> TYPE: DNA
<213> ORGANISM: Oryctolagus cuniculus

<400> SEQUENCE: 129
ggtgattata gtggtaataa catt                                        24

<210> SEQ ID NO 130
<211> LENGTH: 122
<212> TYPE: PRT
<213> ORGANISM: Oryctolagus cuniculus

<400> SEQUENCE: 130

Met Asp Thr Arg Ala Pro Thr Gln Leu Leu Gly Leu Leu Leu Leu Trp
  1               5                  10                  15

Leu Pro Gly Ala Thr Phe Ala Gln Val Leu Thr Gln Thr Pro Ser Ser
             20                  25                  30

Val Ser Ala Ala Val Gly Gly Thr Val Thr Val Ser Cys Gln Ser Ser
         35                  40                  45

Gln Asn Val Tyr Asn Asn Asn Asp Phe Val Trp Phe Gln Gln Lys Pro
     50                  55                  60

Gly Gln Pro Pro Lys Arg Leu Ile Tyr Trp Ala Ser Thr Leu Ala Ser
```

```
                 65                  70                  75                  80
Gly Val Pro Ser Arg Phe Lys Gly Ser Gly Ser Gly Thr Gln Phe Thr
                 85                  90                  95

Leu Thr Ile Asn Asp Leu Glu Cys Asp Asp Ala Ala Thr Tyr Tyr Cys
                100                 105                 110

Ala Gly Ala Tyr Ile Thr Glu Leu Arg Thr
            115                 120

<210> SEQ ID NO 131
<211> LENGTH: 120
<212> TYPE: PRT
<213> ORGANISM: Oryctolagus cuniculus

<400> SEQUENCE: 131

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ile Tyr Trp Met Thr Trp Val Arg Gln Ala Pro Gly Lys Gly Leu Glu
50                  55                  60

Trp Ile Gly Val Ile Ser Thr Asp Gly Ser Ala Tyr Tyr Ala Thr Trp
65                  70                  75                  80

Ala Lys Gly Arg Phe Thr Ile Ser Lys Thr Ser Ser Thr Thr Val Asp
                85                  90                  95

Leu Arg Ile Thr Ser Pro Thr Thr Glu Asp Thr Ala Thr Tyr Phe Cys
            100                 105                 110

Ala Gly Gly Gly Gly Met Asp Pro
        115                 120

<210> SEQ ID NO 132
<211> LENGTH: 13
<212> TYPE: PRT
<213> ORGANISM: Oryctolagus cuniculus

<400> SEQUENCE: 132

Gln Ser Ser Gln Asn Val Tyr Asn Asn Asn Asp Phe Val
1               5                   10

<210> SEQ ID NO 133
<211> LENGTH: 7
<212> TYPE: PRT
<213> ORGANISM: Oryctolagus cuniculus

<400> SEQUENCE: 133

Trp Ala Ser Thr Leu Ala Ser
1               5

<210> SEQ ID NO 134
<211> LENGTH: 10
<212> TYPE: PRT
<213> ORGANISM: Oryctolagus cuniculus

<400> SEQUENCE: 134

Ala Gly Ala Tyr Ile Thr Glu Leu Arg Thr
1               5                   10

<210> SEQ ID NO 135
<211> LENGTH: 5
```

```
<212> TYPE: PRT
<213> ORGANISM: Oryctolagus cuniculus

<400> SEQUENCE: 135

Ile Tyr Trp Met Thr
1               5

<210> SEQ ID NO 136
<211> LENGTH: 16
<212> TYPE: PRT
<213> ORGANISM: Oryctolagus cuniculus

<400> SEQUENCE: 136

Val Ile Ser Thr Asp Gly Ser Ala Tyr Tyr Ala Thr Trp Ala Lys Gly
1               5                   10                  15

<210> SEQ ID NO 137
<211> LENGTH: 6
<212> TYPE: PRT
<213> ORGANISM: Oryctolagus cuniculus

<400> SEQUENCE: 137

Gly Gly Gly Met Asp Pro
1               5

<210> SEQ ID NO 138
<211> LENGTH: 366
<212> TYPE: DNA
<213> ORGANISM: Oryctolagus cuniculus

<400> SEQUENCE: 138
atggacacga gggcccccac tcagctgctg ggctcctgc tgctctggct cccaggtgcc      60
acatttgcgc aagtgctgac ccagactcca tcctccgtgt ctgcagctgt gggaggcaca    120
gtcaccgtca gttgccagtc cagtcagaat gtttataata caacgacttt cgtctggttt    180
cagcagaaac cagggcagcc tcccaagcgc ctaatctact gggcatccac tctggcatct    240
ggggtcccat cgcggttcaa aggcagtgga tctgggacac agttcactct caccatcaac    300
gacctggaat gtgacgatgc tgccacttac tactgtgcag gcgcttatat tactgagctt    360
aggact                                                               366

<210> SEQ ID NO 139
<211> LENGTH: 360
<212> TYPE: DNA
<213> ORGANISM: Oryctolagus cuniculus

<400> SEQUENCE: 139
atggagactg ggctgcgctg gcttctcctg gtcgctgtgc tcaaaggtgt ccagtgtcag     60
tcggtggagg agtccggggg tcgcctggtc acgcctggga caccctgac actcacctgc    120 acagtctctg gattctccct cagtatctac tggatgacct gggtccgcca ggctccaggg   180
aagggactgg aatggatcgg agtcattagt actgatggta cgcatacta cgcgacctgg    240 gcgaaaggcc gattcaccat ctccaaaacc tcgtcgacca cggtggatct gaggatcacc    300
agtccgacaa ccgaggacac ggccacctat ttctgtgccg agggggcgg catggacccc    360

<210> SEQ ID NO 140
<211> LENGTH: 39
<212> TYPE: DNA
<213> ORGANISM: Oryctolagus cuniculus

<400> SEQUENCE: 140
```

```
cagtccagtc agaatgttta taataacaac gacttcgtc                                    39
```

<210> SEQ ID NO 141
<211> LENGTH: 21
<212> TYPE: DNA
<213> ORGANISM: Oryctolagus cuniculus

<400> SEQUENCE: 141

```
tgggcatcca ctctggcatc t                                                       21
```

<210> SEQ ID NO 142
<211> LENGTH: 30
<212> TYPE: DNA
<213> ORGANISM: Oryctolagus cuniculus

<400> SEQUENCE: 142

```
gcaggcgctt atattactga gcttaggact                                              30
```

<210> SEQ ID NO 143
<211> LENGTH: 15
<212> TYPE: DNA
<213> ORGANISM: Oryctolagus cuniculus

<400> SEQUENCE: 143

```
atctactgga tgacc                                                              15
```

<210> SEQ ID NO 144
<211> LENGTH: 48
<212> TYPE: DNA
<213> ORGANISM: Oryctolagus cuniculus

<400> SEQUENCE: 144

```
gtcattagta ctgatggtag cgcatactac gcgacctggg cgaaaggc                          48
```

<210> SEQ ID NO 145
<211> LENGTH: 18
<212> TYPE: DNA
<213> ORGANISM: Oryctolagus cuniculus

<400> SEQUENCE: 145

```
gggggcggca tggacccc                                                           18
```

<210> SEQ ID NO 146
<211> LENGTH: 122
<212> TYPE: PRT
<213> ORGANISM: Oryctolagus cuniculus

<400> SEQUENCE: 146

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Ser
            20                  25                  30

Val Ser Ala Ala Val Gly Gly Thr Val Thr Ile Ser Cys Gln Ser Ser
        35                  40                  45

Gln Ser Val Tyr Asn Asn Asn Asp Phe Ile Trp Phe Gln Gln Lys Pro
    50                  55                  60

Gly Gln Pro Pro Lys Arg Leu Ile Tyr Trp Ala Ser Thr Leu Ala Ser
65                  70                  75                  80

Gly Val Ser Ser Arg Phe Lys Gly Ser Gly Ser Gly Thr Gln Phe Thr
                85                  90                  95

```
Leu Thr Ile Asn Asp Leu Glu Cys Asp Asp Ala Ala Val Tyr Tyr Cys
                100                 105                 110

Ala Gly Ala Tyr Asp Ser Glu Val Arg Ala
        115                 120

<210> SEQ ID NO 147
<211> LENGTH: 120
<212> TYPE: PRT
<213> ORGANISM: Oryctolagus cuniculus

<400> SEQUENCE: 147

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ile Tyr Trp Met Thr Trp Val Arg Gln Ala Pro Gly Arg Gly Leu Glu
    50                  55                  60

Trp Ile Gly Val Ile Ser Thr Asp Gly Thr Thr Tyr Tyr Ala Asn Trp
65                  70                  75                  80

Ala Lys Gly Arg Phe Thr Ile Ser Lys Ala Ser Ser Thr Thr Val Asp
                85                  90                  95

Leu Arg Ile Thr Ser Pro Thr Thr Glu Asp Thr Ala Thr Tyr Phe Cys
                100                 105                 110

Ala Gly Gly Gly Gly Met Asp Pro
        115                 120

<210> SEQ ID NO 148
<211> LENGTH: 13
<212> TYPE: PRT
<213> ORGANISM: Oryctolagus cuniculus

<400> SEQUENCE: 148

Gln Ser Ser Gln Ser Val Tyr Asn Asn Asn Asp Phe Ile
1               5                   10

<210> SEQ ID NO 149
<211> LENGTH: 7
<212> TYPE: PRT
<213> ORGANISM: Oryctolagus cuniculus

<400> SEQUENCE: 149

Trp Ala Ser Thr Leu Ala Ser
1               5

<210> SEQ ID NO 150
<211> LENGTH: 10
<212> TYPE: PRT
<213> ORGANISM: Oryctolagus cuniculus

<400> SEQUENCE: 150

Ala Gly Ala Tyr Asp Ser Glu Val Arg Ala
1               5                   10

<210> SEQ ID NO 151
<211> LENGTH: 5
<212> TYPE: PRT
<213> ORGANISM: Oryctolagus cuniculus

<400> SEQUENCE: 151
```

Ile Tyr Trp Met Thr
1               5

<210> SEQ ID NO 152
<211> LENGTH: 16
<212> TYPE: PRT
<213> ORGANISM: Oryctolagus cuniculus

<400> SEQUENCE: 152

Val Ile Ser Thr Asp Gly Thr Thr Tyr Tyr Ala Asn Trp Ala Lys Gly
1               5                   10                  15

<210> SEQ ID NO 153
<211> LENGTH: 6
<212> TYPE: PRT
<213> ORGANISM: Oryctolagus cuniculus

<400> SEQUENCE: 153

Gly Gly Gly Met Asp Pro
1               5

<210> SEQ ID NO 154
<211> LENGTH: 366
<212> TYPE: DNA
<213> ORGANISM: Oryctolagus cuniculus

<400> SEQUENCE: 154
atggacacga gggcccccac tcagctgctg gggctcctgc tgctctggct cccaggtgcc      60
acatttgcgc aagtgctgac ccagactgca tcgtccgtgt ctgcagctgt gggaggcaca     120
gtcaccatca gttgccagtc cagtcagagt gttttataata taacgacttt catctggttt    180
cagcagaaac cagggcagcc tcccaagcgc ctcatctact gggcatccac tctggcatct    240
ggggtctcat cgcggttcaa aggcagtgga tctgggacac agttcactct caccatcaac    300
gacctggagt gtgacgatgc tgccgtttac tattgtgcag gcgcttatga tagtgaggtt    360
agggct                                                              366

<210> SEQ ID NO 155
<211> LENGTH: 360
<212> TYPE: DNA
<213> ORGANISM: Oryctolagus cuniculus

<400> SEQUENCE: 155
atggagactg ggctgcgctg gcttctcctg gtcgctgtgc tcaaaggtgt ccagtgtcag      60
tcggtggagg agtctggggg tcgcctggtc acgcctggga caccccctgac actcacctgc   120 acagtctctg gattctcccct cagtatctac tggatgacct gggtccgcca ggctccaggg   180 aggggggctgg aatggatcgg ggtcattagt actgatggta ccacatacta cgcgaactgg   240
gcgaaaggcc gattcaccat ctccaaagcc tcgtcgacca cggtggatct gagaatcacc   300
agtccgacaa ccgaggacac ggccacctat ttctgtgccg agggggcgg catggacccc     360

<210> SEQ ID NO 156
<211> LENGTH: 39
<212> TYPE: DNA
<213> ORGANISM: Oryctolagus cuniculus

<400> SEQUENCE: 156
cagtccagtc agagtgttta taataataac gacttcatc                             39

<210> SEQ ID NO 157

-continued

<210> SEQ ID NO 157
<211> LENGTH: 21
<212> TYPE: DNA
<213> ORGANISM: Oryctolagus cuniculus

<400> SEQUENCE: 157
tgggcatcca ctctggcatc t                                           21

<210> SEQ ID NO 158
<211> LENGTH: 30
<212> TYPE: DNA
<213> ORGANISM: Oryctolagus cuniculus

<400> SEQUENCE: 158
gcaggcgctt atgatagtga ggttagggct                                  30

<210> SEQ ID NO 159
<211> LENGTH: 15
<212> TYPE: DNA
<213> ORGANISM: Oryctolagus cuniculus

<400> SEQUENCE: 159
atctactgga tgacc                                                  15

<210> SEQ ID NO 160
<211> LENGTH: 48
<212> TYPE: DNA
<213> ORGANISM: Oryctolagus cuniculus

<400> SEQUENCE: 160
gtcattagta ctgatggtac cacatactac gcgaactggg cgaaaggc              48

<210> SEQ ID NO 161
<211> LENGTH: 18
<212> TYPE: DNA
<213> ORGANISM: Oryctolagus cuniculus

<400> SEQUENCE: 161
gggggcggca tggacccc                                               18

<210> SEQ ID NO 162
<211> LENGTH: 122
<212> TYPE: PRT
<213> ORGANISM: Oryctolagus cuniculus

<400> SEQUENCE: 162

Met Asp Thr Arg Ala Pro Thr Gln Leu Leu Gly Leu Leu Leu Leu Trp
1               5                   10                  15

Leu Pro Gly Ala Thr Phe Ala Gln Val Met Thr Gln Thr Pro Ala Ser
                20                  25                  30

Val Ser Ala Ala Val Gly Gly Thr Val Thr Ile Ser Cys Gln Ser Ser
            35                  40                  45

Glu Ser Val Tyr Asn Asn Asn Asp Leu Ile Trp Phe Arg Gln Lys Pro
        50                  55                  60

Gly Gln Pro Pro Lys Arg Leu Ile Tyr Trp Ala Ser Gln Leu Ala Ser
65                  70                  75                  80

Gly Val Ser Ser Arg Phe Lys Gly Ser Gly Ser Gly Thr Gln Phe Thr
                85                  90                  95

Leu Thr Ile Asn Asp Leu Glu Cys Asp Asp Ala Ala Thr Tyr Tyr Cys
            100                 105                 110

Ala Gly Ala Tyr Asp Ser Glu Ile Arg Ala
        115                 120

<210> SEQ ID NO 163
<211> LENGTH: 120
<212> TYPE: PRT
<213> ORGANISM: Oryctolagus cuniculus

<400> SEQUENCE: 163

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ile Tyr Trp Met Thr Trp Val Arg Gln Ala Pro Gly Lys Gly Leu Glu
    50                  55                  60

Trp Ile Gly Val Ile Ala Ser Asp Gly Ser Thr Tyr Tyr Ala Ser Trp
65                  70                  75                  80

Ala Lys Gly Arg Phe Thr Ile Ser Lys Ala Ser Ser Thr Thr Val Asp
                85                  90                  95

Leu Lys Ile Ala Ser Pro Thr Ile Glu Asp Thr Ala Thr Tyr Phe Cys
            100                 105                 110

Ala Gly Gly Gly Gly Met Asp Pro
        115                 120

<210> SEQ ID NO 164
<211> LENGTH: 13
<212> TYPE: PRT
<213> ORGANISM: Oryctolagus cuniculus

<400> SEQUENCE: 164

Gln Ser Ser Glu Ser Val Tyr Asn Asn Asn Asp Leu Ile
1               5                   10

<210> SEQ ID NO 165
<211> LENGTH: 7
<212> TYPE: PRT
<213> ORGANISM: Oryctolagus cuniculus

<400> SEQUENCE: 165

Trp Ala Ser Gln Leu Ala Ser
1               5

<210> SEQ ID NO 166
<211> LENGTH: 10
<212> TYPE: PRT
<213> ORGANISM: Oryctolagus cuniculus

<400> SEQUENCE: 166

Ala Gly Ala Tyr Asp Ser Glu Ile Arg Ala
1               5                   10

<210> SEQ ID NO 167
<211> LENGTH: 5
<212> TYPE: PRT
<213> ORGANISM: Oryctolagus cuniculus

<400> SEQUENCE: 167

Ile Tyr Trp Met Thr
1               5

<210> SEQ ID NO 168

```
<211> LENGTH: 16
<212> TYPE: PRT
<213> ORGANISM: Oryctolagus cuniculus

<400> SEQUENCE: 168

Val Ile Ala Ser Asp Gly Ser Thr Tyr Tyr Ala Ser Trp Ala Lys Gly
1               5                   10                  15

<210> SEQ ID NO 169
<211> LENGTH: 6
<212> TYPE: PRT
<213> ORGANISM: Oryctolagus cuniculus

<400> SEQUENCE: 169

Gly Gly Gly Met Asp Pro
1               5

<210> SEQ ID NO 170
<211> LENGTH: 366
<212> TYPE: DNA
<213> ORGANISM: Oryctolagus cuniculus

<400> SEQUENCE: 170
atggacacga gggcccccac tcagctgctg gggctcctgc tgctctggct cccaggtgcc      60
acatttgcgc aagtgatgac ccagactcca gcctccgtgt ctgcagctgt gggaggcaca     120
gtcaccatca gttgccagtc cagtgagagt gtttataata ataatgactt aatctggttc     180
cggcagaaac cagggcagcc tcccaagcgc ctaatttact gggcatccca actggcatct     240
ggggtctcat cgcggttcaa aggcagtgga tctgggacac agttcactct caccatcaac     300
gacctggagt gtgacgatgc tgccacttac tactgtgcag gcgcttatga tagtgagatt     360
agggct                                                                366

<210> SEQ ID NO 171
<211> LENGTH: 360
<212> TYPE: DNA
<213> ORGANISM: Oryctolagus cuniculus

<400> SEQUENCE: 171
atggagactg ggctgcgctg gcttctcctg gtcgctgtgc tcaaaggtgt ccagtgtcag      60
tcggtggagg agtccggggg tcgcctggtc acgcctggga cacccctgac actcacctgc     120
acagtctctg gattctcccc tcagtatctac tggatgacct gggtccgcca ggctccaggg     180
aaggggctgg aatggatcgg agtcattgct tctgatggta gcacatacta cgcgagctgg     240
gcgaaaggcc gattcaccat ctccaaagcc tcgtcgacca cggtggatct gaagattgcc     300
agcccgacaa ttgaggacac ggccacctat ttctgtgccg aggggggcgg catggacccc     360

<210> SEQ ID NO 172
<211> LENGTH: 39
<212> TYPE: DNA
<213> ORGANISM: Oryctolagus cuniculus

<400> SEQUENCE: 172
cagtccagtg agagtgttta ataataataat gacttaatc                            39

<210> SEQ ID NO 173
<211> LENGTH: 21
<212> TYPE: DNA
<213> ORGANISM: Oryctolagus cuniculus

<400> SEQUENCE: 173
```

-continued

```
tgggcatccc aactggcatc t                                              21

<210> SEQ ID NO 174
<211> LENGTH: 30
<212> TYPE: DNA
<213> ORGANISM: Oryctolagus cuniculus

<400> SEQUENCE: 174
gcaggcgctt atgatagtga gattagggct                                     30

<210> SEQ ID NO 175
<211> LENGTH: 15
<212> TYPE: DNA
<213> ORGANISM: Oryctolagus cuniculus

<400> SEQUENCE: 175
atctactgga tgacc                                                     15

<210> SEQ ID NO 176
<211> LENGTH: 48
<212> TYPE: DNA
<213> ORGANISM: Oryctolagus cuniculus

<400> SEQUENCE: 176
gtcattgctt ctgatggtag cacatactac gcgagctggg cgaaaggc                 48

<210> SEQ ID NO 177
<211> LENGTH: 18
<212> TYPE: DNA
<213> ORGANISM: Oryctolagus cuniculus

<400> SEQUENCE: 177
gggggcggca tggacccc                                                  18

<210> SEQ ID NO 178
<211> LENGTH: 124
<212> TYPE: PRT
<213> ORGANISM: Oryctolagus cuniculus

<400> SEQUENCE: 178

Met Asp Thr Arg Ala Pro Thr Gln Leu Leu Gly Leu Leu Leu Leu Trp
1               5                   10                  15

Leu Pro Gly Ala Arg Cys Ala Leu Val Met Thr Gln Thr Pro Ser Pro
                20                  25                  30

Val Ser Ala Ala Val Gly Gly Thr Val Thr Ile Ser Cys Gln Ser Ser
            35                  40                  45

Glu Ser Val Val Phe Asn Asn Arg Leu Ser Trp Tyr Gln Gln Lys Pro
        50                  55                  60

Gly Gln Pro Pro Lys Leu Leu Ile Tyr Trp Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Glu Cys Asp Asp Ala Ala Thr Tyr Tyr Cys
            100                 105                 110

Ala Gly Tyr Lys Ser Tyr Ser Asn Asp Asp Phe Ala
        115                 120

<210> SEQ ID NO 179
<211> LENGTH: 128
<212> TYPE: PRT
```

<213> ORGANISM: Oryctolagus cuniculus

<400> SEQUENCE: 179

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

His Tyr Ala Met Gly Trp Val Arg Gln Ala Pro Gly Lys Gly Leu Glu
    50                  55                  60

Trp Ile Gly Ile Ile Ser Ser Asn Gly Val Thr Tyr Tyr Ala Thr Trp
65                  70                  75                  80

Ala Ser Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Gly Asp Asp Thr Ser Ile Ile Tyr Tyr Ile Tyr Ala Phe Asp Leu
        115                 120                 125

<210> SEQ ID NO 180
<211> LENGTH: 13
<212> TYPE: PRT
<213> ORGANISM: Oryctolagus cuniculus

<400> SEQUENCE: 180

Gln Ser Ser Glu Ser Val Val Phe Asn Asn Arg Leu Ser
1               5                   10

<210> SEQ ID NO 181
<211> LENGTH: 7
<212> TYPE: PRT
<213> ORGANISM: Oryctolagus cuniculus

<400> SEQUENCE: 181

Trp Ala Ser Thr Leu Ala Ser
1               5

<210> SEQ ID NO 182
<211> LENGTH: 12
<212> TYPE: PRT
<213> ORGANISM: Oryctolagus cuniculus

<400> SEQUENCE: 182

Ala Gly Tyr Lys Ser Tyr Ser Asn Asp Asp Phe Ala
1               5                   10

<210> SEQ ID NO 183
<211> LENGTH: 5
<212> TYPE: PRT
<213> ORGANISM: Oryctolagus cuniculus

<400> SEQUENCE: 183

His Tyr Ala Met Gly
1               5

<210> SEQ ID NO 184
<211> LENGTH: 16
<212> TYPE: PRT
<213> ORGANISM: Oryctolagus cuniculus

<400> SEQUENCE: 184

```
Ile Ile Ser Ser Asn Gly Val Thr Tyr Tyr Ala Thr Trp Ala Ser Gly
 1               5                  10                  15
```

<210> SEQ ID NO 185
<211> LENGTH: 15
<212> TYPE: PRT
<213> ORGANISM: Oryctolagus cuniculus

<400> SEQUENCE: 185

```
Gly Asp Asp Thr Ser Ile Ile Tyr Tyr Ile Tyr Ala Phe Asp Leu
 1               5                  10                  15
```

<210> SEQ ID NO 186
<211> LENGTH: 372
<212> TYPE: DNA
<213> ORGANISM: Oryctolagus cuniculus

<400> SEQUENCE: 186

| | | | | | |
|---|---|---|---|---|---|
| atggacacga | gggcccccac | tcagctgctg | gggctcctgc | tgctctggct | cccaggtgcc | 60 |
| agatgtgcgc | ttgtgatgac | ccagactcca | tccctgtgt | ctgcagctgt | gggaggcaca | 120 |
| gtcaccatca | gttgccagtc | tagtgagagc | gttgttttta | caaccgctt | atcctggtat | 180 |
| cagcagaaac | cagggcagcc | tcccaagctc | ctgatctact | gggcatccac | tctggcatct | 240 |
| ggggtcccat | cgcggttcaa | aggcagtgga | tctgggacac | agttcactct | caccatcagt | 300 |
| ggcgtggagt | gtgacgatgc | tgccacttac | tactgtgcag | atataaaag | ttatagtaat | 360 |
| gatgattttg | ct | | | | | 372 |

<210> SEQ ID NO 187
<211> LENGTH: 384
<212> TYPE: DNA
<213> ORGANISM: Oryctolagus cuniculus

<400> SEQUENCE: 187

| | | | | | |
|---|---|---|---|---|---|
| atggagactg | ggctgcgctg | gcttctcctg | gtcgctgtgc | tcaaaggtgt | ccagtgtcag | 60 |
| tcggtggagg | agtccggggg | tcgcctggtc | acgcctggga | cacccctgac | actcacctgc | 120 |
| acagtctctg | gattctccct | cagtcactat | gcaatgggct | gggtccgcca | ggctccaggg | 180 |
| aaggggctgg | aatggatcgg | aatcattagt | agtaatggtg | tcacatacta | cgcgacctgg | 240 |
| gcgagcggcc | gattcaccat | ctccaaaacc | tcgaccacgg | tggatctgaa | aatcaccagt | 300 |
| ccgacaaccg | aggacacggc | cacctatttc | tgtgccagag | agatgatac | tagtattatt | 360 |
| tattacattt | acgcctttga | tctc | | | | 384 |

<210> SEQ ID NO 188
<211> LENGTH: 39
<212> TYPE: DNA
<213> ORGANISM: Oryctolagus cuniculus

<400> SEQUENCE: 188
cagtctagtg agagcgttgt ttttaacaac cgcttatcc         39

<210> SEQ ID NO 189
<211> LENGTH: 21
<212> TYPE: DNA
<213> ORGANISM: Oryctolagus cuniculus

<400> SEQUENCE: 189
tgggcatcca ctctggcatc t         21

<210> SEQ ID NO 190
<211> LENGTH: 36
<212> TYPE: DNA
<213> ORGANISM: Oryctolagus cuniculus

<400> SEQUENCE: 190
gcaggatata aaagttatag taatgatgat tttgct                     36

<210> SEQ ID NO 191
<211> LENGTH: 15
<212> TYPE: DNA
<213> ORGANISM: Oryctolagus cuniculus

<400> SEQUENCE: 191
cactatgcaa tgggc                                            15

<210> SEQ ID NO 192
<211> LENGTH: 48
<212> TYPE: DNA
<213> ORGANISM: Oryctolagus cuniculus

<400> SEQUENCE: 192
atcattagta gtaatggtgt cacatactac gcgacctggg cgagcggc        48

<210> SEQ ID NO 193
<211> LENGTH: 45
<212> TYPE: DNA
<213> ORGANISM: Oryctolagus cuniculus

<400> SEQUENCE: 193
ggagatgata ctagtattat ttattacatt tacgcctttg atctc           45

<210> SEQ ID NO 194
<211> LENGTH: 125
<212> TYPE: PRT
<213> ORGANISM: Oryctolagus cuniculus

<400> SEQUENCE: 194

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ala
            20                  25                  30

Ser Val Ser Glu Pro Val Gly Gly Thr Val Thr Ile Lys Cys Gln Ala
        35                  40                  45

Ser Gln Asn Ile Tyr Ser Thr Leu Ala Trp Tyr Gln Gln Lys Pro Gly
    50                  55                  60

Gln Pro Pro Lys Leu Leu Ile Tyr Leu Ala Ser Thr Leu Ala Ser Gly
65                  70                  75                  80

Val Pro Ser Arg Phe Lys Gly Ser Gly Ser Gly Thr Gln Phe Thr Leu
                85                  90                  95

Thr Ile Ser Asp Leu Glu Cys Ala Asp Ala Ala Thr Tyr Tyr Cys Gln
            100                 105                 110

Thr Ser His Gly Ser Asn Ser Asp Ser Phe Gly Tyr Ala
        115                 120                 125

<210> SEQ ID NO 195
<211> LENGTH: 124
<212> TYPE: PRT
<213> ORGANISM: Oryctolagus cuniculus

<400> SEQUENCE: 195

```
Met Glu Thr Gly Leu Arg Trp Leu Leu Leu Val Ala Val Leu Lys Gly
1               5                   10                  15

Val Gln Cys Gln Ser Val Glu Ser Gly Gly Arg Leu Val Thr Pro
                20                  25                  30

Gly Thr Pro Leu Thr Leu Thr Cys Thr Val Ser Gly Ile Asp Leu Ser
            35                  40                  45

Ser Tyr Ala Met Gly Trp Val Arg Gln Ala Pro Gly Lys Gly Leu Glu
    50                  55                  60

Tyr Ile Gly Tyr Ile Leu Ser Ser Gly Ile Thr Tyr Ala Ser Trp
65                  70                  75                  80

Ala Arg Gly Arg Phe Thr Ile Ser Lys Thr Ser Thr Thr Val Asp
                85                  90                  95

Leu Lys Met Thr Ser Leu Thr Thr Glu Asp Thr Ala Thr Tyr Phe Cys
                100                 105                 110

Ala Arg Asn Gly Asn Tyr Asn Ser Gly Thr Asp Ile
            115                 120
```

<210> SEQ ID NO 196
<211> LENGTH: 11
<212> TYPE: PRT
<213> ORGANISM: Oryctolagus cuniculus

<400> SEQUENCE: 196

```
Gln Ala Ser Gln Asn Ile Tyr Ser Thr Leu Ala
1               5                   10
```

<210> SEQ ID NO 197
<211> LENGTH: 7
<212> TYPE: PRT
<213> ORGANISM: Oryctolagus cuniculus

<400> SEQUENCE: 197

```
Leu Ala Ser Thr Leu Ala Ser
1               5
```

<210> SEQ ID NO 198
<211> LENGTH: 14
<212> TYPE: PRT
<213> ORGANISM: Oryctolagus cuniculus

<400> SEQUENCE: 198

```
Gln Thr Ser His Gly Ser Asn Ser Asp Ser Phe Gly Tyr Ala
1               5                   10
```

<210> SEQ ID NO 199
<211> LENGTH: 5
<212> TYPE: PRT
<213> ORGANISM: Oryctolagus cuniculus

<400> SEQUENCE: 199

```
Ser Tyr Ala Met Gly
1               5
```

<210> SEQ ID NO 200
<211> LENGTH: 16
<212> TYPE: PRT
<213> ORGANISM: Oryctolagus cuniculus

<400> SEQUENCE: 200

```
Tyr Ile Leu Ser Ser Gly Ile Thr Tyr Ala Ser Trp Ala Arg Gly
1               5                   10                  15
```

<210> SEQ ID NO 201
<211> LENGTH: 10
<212> TYPE: PRT
<213> ORGANISM: Oryctolagus cuniculus

<400> SEQUENCE: 201

Asn Gly Asn Tyr Asn Ser Gly Thr Asp Ile
1               5                   10

<210> SEQ ID NO 202
<211> LENGTH: 375
<212> TYPE: DNA
<213> ORGANISM: Oryctolagus cuniculus

<400> SEQUENCE: 202

```
atggacacga gggcccccac tcagctgctg gggctcctgc tgctctggct cccaggtgcc      60
agatgtgctg acattgtgat gacccagact ccagcctccg tgtctgaacc tgtgggaggc     120
acagtcacca tcaagtgcca ggccagtcag aacatttaca gcaccttagc ctggtatcag     180
cagaaaccag gcagcctcc caagctcctg atctatctgg catccactct ggcatctggg      240
gtcccatcgc ggttcaaagg cagtggatct gggacacagt tcactctcac catcagcgac     300
ctggagtgtg ccgatgctgc cacttattac tgtcaaacca gtcatggtag taatagtgat     360
agttttggtt atgct                                                      375
```

<210> SEQ ID NO 203
<211> LENGTH: 372
<212> TYPE: DNA
<213> ORGANISM: Oryctolagus cuniculus

<400> SEQUENCE: 203

```
atggagactg ggctgcgctg gcttctcctg gtcgctgtgc tcaaaggtgt ccagtgtcag      60
tcggtggagg agtccggggg tcgcctggtc acgcctggga caccctgac actcacttgc      120 acagtctctg gaatcgacct cagtagctat gcaatgggct gggtccgcca ggctccaggg     180
aaggggctgg aatacatcgg atacattctt agtagtggta tcacatacta cgcgagttgg     240
gcgagaggcc gattcaccat ctccaaaacc tcgtcgacca cggtggatct gaaaatgacc     300
agtctgacaa ccgaggacac ggccacctat ttctgtgcca gaaatggtaa ttataatagt     360
ggtacggaca tc                                                         372
```

<210> SEQ ID NO 204
<211> LENGTH: 33
<212> TYPE: DNA
<213> ORGANISM: Oryctolagus cuniculus

<400> SEQUENCE: 204

```
caggccagtc agaacattta cagcaccta gcc                                    33
```

<210> SEQ ID NO 205
<211> LENGTH: 21
<212> TYPE: DNA
<213> ORGANISM: Oryctolagus cuniculus

<400> SEQUENCE: 205

```
ctggcatcca ctctggcatc t                                                21
```

<210> SEQ ID NO 206
<211> LENGTH: 42

```
<212> TYPE: DNA
<213> ORGANISM: Oryctolagus cuniculus

<400> SEQUENCE: 206
caaaccagtc atggtagtaa tagtgatagt tttggttatg ct                              42

<210> SEQ ID NO 207
<211> LENGTH: 15
<212> TYPE: DNA
<213> ORGANISM: Oryctolagus cuniculus

<400> SEQUENCE: 207
agctatgcaa tgggc                                                           15

<210> SEQ ID NO 208
<211> LENGTH: 48
<212> TYPE: DNA
<213> ORGANISM: Oryctolagus cuniculus

<400> SEQUENCE: 208
tacattctta gtagtggtat cacatactac gcgagttggg cgagaggc                       48

<210> SEQ ID NO 209
<211> LENGTH: 30
<212> TYPE: DNA
<213> ORGANISM: Oryctolagus cuniculus

<400> SEQUENCE: 209
aatggtaatt ataatagtgg tacggacatc                                           30

<210> SEQ ID NO 210
<211> LENGTH: 125
<212> TYPE: PRT
<213> ORGANISM: Oryctolagus cuniculus

<400> SEQUENCE: 210

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ala
            20                  25                  30

Ser Val Ser Glu Pro Val Gly Gly Thr Val Thr Ile Lys Cys Gln Ala
        35                  40                  45

Ser Gln Asn Ile Tyr Ser Thr Leu Ala Trp Tyr Gln Gln Lys Pro Gly
    50                  55                  60

Gln Pro Pro Lys Leu Leu Ile Tyr Leu Ala Ser Thr Leu Ala Ser Gly
65                  70                  75                  80

Val Pro Ser Arg Phe Lys Gly Ser Gly Ser Gly Thr Gln Phe Thr Leu
                85                  90                  95

Thr Ile Ser Asp Leu Glu Cys Ala Asp Ala Ala Thr Tyr Tyr Cys Gln
            100                 105                 110

Thr Asn His Gly Ser Asn Ser Asp Ser Phe Gly Tyr Ala
        115                 120                 125

<210> SEQ ID NO 211
<211> LENGTH: 124
<212> TYPE: PRT
<213> ORGANISM: Oryctolagus cuniculus

<400> SEQUENCE: 211

Met Glu Thr Gly Leu Arg Trp Leu Leu Leu Val Ala Val Leu Lys Gly
1               5                   10                  15
```

```
Val Gln Cys Gln Ser Val Glu Ser Gly Gly Arg Leu Val Thr Pro
            20                  25                  30
Gly Thr Pro Leu Thr Leu Thr Cys Thr Val Ser Gly Phe Ser Leu Ser
        35                  40                  45
Ser Tyr Ala Met Gly Trp Val Arg Gln Ala Pro Gly Lys Gly Leu Glu
    50                  55                  60
Tyr Ile Gly Tyr Ile Gly Ser Ser Gly Ile Thr Tyr Tyr Thr Ser Trp
65                  70                  75                  80
Ala Arg Gly Arg Phe Thr Ile Ser Lys Pro Ser Ser Thr Thr Val Asp
                85                  90                  95
Leu Lys Met Thr Ser Leu Thr Thr Glu Asp Thr Ala Thr Tyr Phe Cys
            100                 105                 110
Ala Arg Asn Gly Asn Tyr Asn Ser Gly Thr Asp Ile
        115                 120
```

```
<210> SEQ ID NO 212
<211> LENGTH: 11
<212> TYPE: PRT
<213> ORGANISM: Oryctolagus cuniculus

<400> SEQUENCE: 212

Gln Ala Ser Gln Asn Ile Tyr Ser Thr Leu Ala
1               5                   10

<210> SEQ ID NO 213
<211> LENGTH: 7
<212> TYPE: PRT
<213> ORGANISM: Oryctolagus cuniculus

<400> SEQUENCE: 213

Leu Ala Ser Thr Leu Ala Ser
1               5

<210> SEQ ID NO 214
<211> LENGTH: 14
<212> TYPE: PRT
<213> ORGANISM: Oryctolagus cuniculus

<400> SEQUENCE: 214

Gln Thr Asn His Gly Ser Asn Ser Asp Ser Phe Gly Tyr Ala
1               5                   10

<210> SEQ ID NO 215
<211> LENGTH: 5
<212> TYPE: PRT
<213> ORGANISM: Oryctolagus cuniculus

<400> SEQUENCE: 215

Ser Tyr Ala Met Gly
1               5

<210> SEQ ID NO 216
<211> LENGTH: 16
<212> TYPE: PRT
<213> ORGANISM: Oryctolagus cuniculus

<400> SEQUENCE: 216

Tyr Ile Gly Ser Ser Gly Ile Thr Tyr Tyr Thr Ser Trp Ala Arg Gly
1               5                   10                  15

<210> SEQ ID NO 217
```

```
<211> LENGTH: 10
<212> TYPE: PRT
<213> ORGANISM: Oryctolagus cuniculus

<400> SEQUENCE: 217

Asn Gly Asn Tyr Asn Ser Gly Thr Asp Ile
1               5                   10

<210> SEQ ID NO 218
<211> LENGTH: 375
<212> TYPE: DNA
<213> ORGANISM: Oryctolagus cuniculus

<400> SEQUENCE: 218
atggacacga gggcccccac tcagctgctg gggctcctgc tgctctggct cccaggtgcc      60
agatgtgctg acattgtgat gacccagact ccagcctccg tgtctgaacc tgtgggaggc     120
acagtcacca tcaagtgcca ggccagtcag aacatttaca gcaccttagc ctggtatcag     180
cagaaaccag ggcagcctcc caagctcctg atctatctgg catccactct ggcatctggg     240
gtcccatcgc ggttcaaagg cagtggatct gggacacagt tcactctcac catcagcgac     300
ctggagtgtg ccgatgctgc cacctattac tgtcaaacca atcatggtag taatagtgat     360
agttttggtt atgct                                                      375

<210> SEQ ID NO 219
<211> LENGTH: 372
<212> TYPE: DNA
<213> ORGANISM: Oryctolagus cuniculus

<400> SEQUENCE: 219
atggagactg ggctgcgctg gcttctcctg gtcgctgtgc tcaaaggtgt ccagtgtcag      60
tcggtggagg agtccggggg tcgcctggtc acgcctggga cacccctgac actcacctgc     120
acagtctctg gattctccct cagtagctat gcaatgggct gggtccgcca ggctccaggg     180
aaggggctgg aatacatcgg atacattggt agtagtggta tcacatacta cacgagttgg     240
gcgagaggcc gtttcaccat ctccaaaccc tcgtcgacca cggtggatct gaaaatgacc     300
agtctgacaa ccgaggacac ggccacctat ttctgtgcca gaaatggtaa ttataatagt     360
ggtacggaca tc                                                         372

<210> SEQ ID NO 220
<211> LENGTH: 33
<212> TYPE: DNA
<213> ORGANISM: Oryctolagus cuniculus

<400> SEQUENCE: 220
caggccagtc agaacattta cagcaccttacc gcc                                33

<210> SEQ ID NO 221
<211> LENGTH: 21
<212> TYPE: DNA
<213> ORGANISM: Oryctolagus cuniculus

<400> SEQUENCE: 221
ctggcatcca ctctggcatc t                                               21

<210> SEQ ID NO 222
<211> LENGTH: 42
<212> TYPE: DNA
<213> ORGANISM: Oryctolagus cuniculus
```

```
<400> SEQUENCE: 222
caaaccaatc atggtagtaa tagtgatagt tttggttatg ct                              42

<210> SEQ ID NO 223
<211> LENGTH: 15
<212> TYPE: DNA
<213> ORGANISM: Oryctolagus cuniculus

<400> SEQUENCE: 223
agctatgcaa tgggc                                                           15

<210> SEQ ID NO 224
<211> LENGTH: 48
<212> TYPE: DNA
<213> ORGANISM: Oryctolagus cuniculus

<400> SEQUENCE: 224
tacattggta gtagtggtat cacatactac acgagttggg cgagaggc                       48

<210> SEQ ID NO 225
<211> LENGTH: 30
<212> TYPE: DNA
<213> ORGANISM: Oryctolagus cuniculus

<400> SEQUENCE: 225
aatggtaatt ataatagtgg tacggacatc                                           30

<210> SEQ ID NO 226
<211> LENGTH: 125
<212> TYPE: PRT
<213> ORGANISM: Oryctolagus cuniculus

<400> SEQUENCE: 226
```

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ala
            20                  25                  30

Ser Val Ser Glu Pro Val Gly Gly Thr Val Thr Ile Lys Cys Gln Ala
        35                  40                  45

Ser Gln Ser Ile Tyr Ser Ser Phe Ser Trp Tyr Gln Gln Ile Pro Gly
    50                  55                  60

Gln Arg Pro Lys Leu Leu Ile Tyr Tyr Ala Ser Thr Leu Ala Ser Gly
65                  70                  75                  80

Val Pro Ser Arg Phe Ser Gly Ser Gly Ser Gly Thr Asp Phe Thr Leu
                85                  90                  95

Thr Ile Ser Asp Leu Glu Cys Ala Asp Ala Ala Thr Tyr Tyr Cys Gln
            100                 105                 110

Ser Asn His Gly Ser Asn Gly Asp Ser Phe Gly Asn Ala
        115                 120                 125

```
<210> SEQ ID NO 227
<211> LENGTH: 121
<212> TYPE: PRT
<213> ORGANISM: Oryctolagus cuniculus

<400> SEQUENCE: 227
```

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Ser Pro
            20                  25                  30

```
Gly Thr Pro Leu Thr Leu Thr Cys Thr Val Ser Gly Ile Asp Leu Ser
            35                  40                  45

Ser Tyr Gly Met Gly Trp Val Arg Gln Ala Pro Gly Lys Gly Leu Glu
        50                  55                  60

Tyr Ile Gly Tyr Met Ile Ala Ser Gly Ile Thr Tyr Tyr Ala Ala Trp
65                  70                  75                  80

Ala Lys Gly Arg Phe Thr Ile Ser Lys Thr Ser Ser Thr Val Asp
                85                  90                  95

Leu Lys Ile Thr Ser Pro Thr Thr Glu Asp Thr Ala Thr Tyr Phe Cys
            100                 105                 110

Ala Arg Asn Tyr Tyr Gly Met Asp Pro
            115                 120

<210> SEQ ID NO 228
<211> LENGTH: 11
<212> TYPE: PRT
<213> ORGANISM: Oryctolagus cuniculus

<400> SEQUENCE: 228

Gln Ala Ser Gln Ser Ile Tyr Ser Ser Phe Ser
1               5                   10

<210> SEQ ID NO 229
<211> LENGTH: 7
<212> TYPE: PRT
<213> ORGANISM: Oryctolagus cuniculus

<400> SEQUENCE: 229

Tyr Ala Ser Thr Leu Ala Ser
1               5

<210> SEQ ID NO 230
<211> LENGTH: 14
<212> TYPE: PRT
<213> ORGANISM: Oryctolagus cuniculus

<400> SEQUENCE: 230

Gln Ser Asn His Gly Ser Asn Gly Asp Ser Phe Gly Asn Ala
1               5                   10

<210> SEQ ID NO 231
<211> LENGTH: 5
<212> TYPE: PRT
<213> ORGANISM: Oryctolagus cuniculus

<400> SEQUENCE: 231

Ser Tyr Gly Met Gly
1               5

<210> SEQ ID NO 232
<211> LENGTH: 16
<212> TYPE: PRT
<213> ORGANISM: Oryctolagus cuniculus

<400> SEQUENCE: 232

Tyr Met Ile Ala Ser Gly Ile Thr Tyr Tyr Ala Ala Trp Ala Lys Gly
1               5                   10                  15

<210> SEQ ID NO 233
<211> LENGTH: 7
<212> TYPE: PRT
<213> ORGANISM: Oryctolagus cuniculus
```

<400> SEQUENCE: 233

Asn Tyr Tyr Gly Met Asp Pro
1               5

<210> SEQ ID NO 234
<211> LENGTH: 375
<212> TYPE: DNA
<213> ORGANISM: Oryctolagus cuniculus

<400> SEQUENCE: 234

```
atggacacga gggcccccac tcagctgctg gggctcctgc tgctctggct cccaggtgcc    60
agatgtgctg acattgtgat gacccagact ccagcctccg tgtctgaacc tgtgggaggc   120
acagtcacca tcaagtgcca ggccagtcag agcatttaca ctccttttc ctggtatcaa    180
cagataccag gccagcgtcc caagctcctg atctattatg catccactct ggcctctggg   240
gtcccatcgc gattcagcgg cagtggatct gggacagatt tcactctcac catcagcgac   300
ctggagtgtg ccgatgctgc cacttactac tgtcaaagca tcatggtag taatggtgat    360
agttttggta atgct                                                    375
```

<210> SEQ ID NO 235
<211> LENGTH: 363
<212> TYPE: DNA
<213> ORGANISM: Oryctolagus cuniculus

<400> SEQUENCE: 235

```
atggagactg ggctgcgctg gcttctcctg gtcgctgtgc tcaaaggtgt ccagtgtcag    60
tcggtggagg agtccggggg tcgcctggtg tcgcctggga caccctgac actcacctgc    120
acagtctctg gaatcgacct cagtagttat ggaatgggct gggtccgcca ggctccaggg   180
aaggggctgg aatacatcgg atacatgatt gctagtggta tcacatatta cgcggcctgg   240
gcgaaaggcc gattcaccat ctccaaaacc tcgtcgacca cggtggatct gaaaatcacc   300
agtccgacaa ccgaggacac ggccacctat ttctgtgcca gaattactta cggcatggac   360
ccc                                                                 363
```

<210> SEQ ID NO 236
<211> LENGTH: 33
<212> TYPE: DNA
<213> ORGANISM: Oryctolagus cuniculus

<400> SEQUENCE: 236

```
caggccagtc agagcattta cagctccttt tcc                                 33
```

<210> SEQ ID NO 237
<211> LENGTH: 21
<212> TYPE: DNA
<213> ORGANISM: Oryctolagus cuniculus

<400> SEQUENCE: 237

```
tatgcatcca ctctggcctc t                                              21
```

<210> SEQ ID NO 238
<211> LENGTH: 42
<212> TYPE: DNA
<213> ORGANISM: Oryctolagus cuniculus

<400> SEQUENCE: 238

```
caaagcaatc atggtagtaa tggtgatagt tttggtaatg ct                       42
```

<210> SEQ ID NO 239
<211> LENGTH: 15
<212> TYPE: DNA
<213> ORGANISM: Oryctolagus cuniculus

<400> SEQUENCE: 239
agttatggaa tgggc                                                    15

<210> SEQ ID NO 240
<211> LENGTH: 48
<212> TYPE: DNA
<213> ORGANISM: Oryctolagus cuniculus

<400> SEQUENCE: 240
tacatgattg ctagtggtat cacatattac gcggcctggg cgaaaggc                48

<210> SEQ ID NO 241
<211> LENGTH: 21
<212> TYPE: DNA
<213> ORGANISM: Oryctolagus cuniculus

<400> SEQUENCE: 241
aattactacg gcatggaccc c                                             21

<210> SEQ ID NO 242
<211> LENGTH: 125
<212> TYPE: PRT
<213> ORGANISM: Oryctolagus cuniculus

<400> SEQUENCE: 242

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ala
                20                  25                  30

Ser Val Ser Glu Pro Val Gly Gly Thr Val Thr Ile Lys Cys Gln Ala
            35                  40                  45

Ser Gln Thr Ile Tyr Ser Ser Leu Ser Trp Tyr Gln Gln Lys Pro Gly
        50                  55                  60

Gln Arg Pro Lys Leu Leu Ile Tyr Ala Ala Ser Thr Leu Ala Ser Gly
65                  70                  75                  80

Val Pro Ser Arg Phe Lys Gly Ser Gly Ser Gly Thr Asp Phe Thr Leu
                85                  90                  95

Thr Ile Ser Asp Leu Glu Cys Ala Asp Ala Ala Thr Tyr Tyr Cys Gln
            100                 105                 110

Ser Asn His Gly Ser Asn Ser Asp Ser Tyr Gly Asn Ala
        115                 120                 125

<210> SEQ ID NO 243
<211> LENGTH: 125
<212> TYPE: PRT
<213> ORGANISM: Oryctolagus cuniculus

<400> SEQUENCE: 243

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Lys Pro
                20                  25                  30

Asp Glu Thr Leu Thr Ile Thr Cys Thr Val Ser Gly Ile Asp Leu Asn
            35                  40                  45

```
Asn Tyr Asn Met Gly Trp Val Arg Gln Ala Pro Gly Lys Gly Leu Glu
         50                   55                  60

Tyr Ile Gly Tyr Ile Leu Gly Ser Gly Ile Thr Tyr Tyr Ala Thr Trp
 65                  70                  75                  80

Ala Lys Gly Arg Phe Thr Ile Ser Lys Thr Ser Ser Thr Val Asp
                 85                  90                  95

Leu Lys Met Thr Ser Leu Thr Thr Glu Asp Thr Ala Thr Tyr Phe Cys
            100                 105                 110

Ala Gly Ser Ile Tyr Tyr Arg Gly Tyr Gly Met Asp Pro
            115                 120                 125
```

<210> SEQ ID NO 244
<211> LENGTH: 11
<212> TYPE: PRT
<213> ORGANISM: Oryctolagus cuniculus

<400> SEQUENCE: 244

```
Gln Ala Ser Gln Thr Ile Tyr Ser Ser Leu Ser
 1               5                   10
```

<210> SEQ ID NO 245
<211> LENGTH: 7
<212> TYPE: PRT
<213> ORGANISM: Oryctolagus cuniculus

<400> SEQUENCE: 245

```
Ala Ala Ser Thr Leu Ala Ser
 1               5
```

<210> SEQ ID NO 246
<211> LENGTH: 14
<212> TYPE: PRT
<213> ORGANISM: Oryctolagus cuniculus

<400> SEQUENCE: 246

```
Gln Ser Asn His Gly Ser Asn Ser Asp Ser Tyr Gly Asn Ala
 1               5                   10
```

<210> SEQ ID NO 247
<211> LENGTH: 5
<212> TYPE: PRT
<213> ORGANISM: Oryctolagus cuniculus

<400> SEQUENCE: 247

```
Asn Tyr Asn Met Gly
 1               5
```

<210> SEQ ID NO 248
<211> LENGTH: 16
<212> TYPE: PRT
<213> ORGANISM: Oryctolagus cuniculus

<400> SEQUENCE: 248

```
Tyr Ile Leu Gly Ser Gly Ile Thr Tyr Tyr Ala Thr Trp Ala Lys Gly
 1               5                   10                  15
```

<210> SEQ ID NO 249
<211> LENGTH: 11
<212> TYPE: PRT
<213> ORGANISM: Oryctolagus cuniculus

<400> SEQUENCE: 249

Ser Ile Tyr Tyr Arg Gly Tyr Gly Met Asp Pro
1               5                   10

<210> SEQ ID NO 250
<211> LENGTH: 375
<212> TYPE: DNA
<213> ORGANISM: Oryctolagus cuniculus

<400> SEQUENCE: 250
atggacacga gggcccccac tcagctgctg gggctcctgc tgctctggct cccaggtgcc     60
agatgtgctg acattgtgat gacgcagact ccagcctccg tgtccgaacc tgtgggaggc    120
acagtcacca tcaagtgtca ggccagtcag accatttaca gtagcttatc ctggtatcag    180
cagaaaccag gcagcgtcc caagctcctg atctatgctg catccactct ggcatctggg     240
gtcccatcgc ggttcaaagg cagtggatct gggacagatt tcactctcac cataagcgac    300
ctggagtgtg ccgatgctgc cacttactac tgtcaaagta atcatggtag taatagtgat    360
agttatggca atgct                                                     375

<210> SEQ ID NO 251
<211> LENGTH: 375
<212> TYPE: DNA
<213> ORGANISM: Oryctolagus cuniculus

<400> SEQUENCE: 251
atggagactg ggctgcgctg gcttctcctg gtcgctgtgc tcaaaggtgt ccagtgtcag     60
tcgctggagg agtccggggg tcgcctggtc aagcctgacg aaaccctgac aatcacctgc    120
acagtctctg gaatcgacct caataactac aacatgggct gggtccgcca ggctccaggg    180
aaggggctgg aatacatcgg atacattctt ggtagtggta tcacatacta cgcgacctgg    240
gcgaaaggcc gattcaccat ctcgaaaacc tcgtcgacca cggtggatct gaaaatgacc    300
agtctgacaa ccgaggacac ggccacgtat ttctgtgctg gtagtattta ttataggggg    360
tacggcatgg acccc                                                     375

<210> SEQ ID NO 252
<211> LENGTH: 33
<212> TYPE: DNA
<213> ORGANISM: Oryctolagus cuniculus

<400> SEQUENCE: 252
caggccagtc agaccattta cagtagctta tcc                                  33

<210> SEQ ID NO 253
<211> LENGTH: 21
<212> TYPE: DNA
<213> ORGANISM: Oryctolagus cuniculus

<400> SEQUENCE: 253
gctgcatcca ctctggcatc t                                               21

<210> SEQ ID NO 254
<211> LENGTH: 42
<212> TYPE: DNA
<213> ORGANISM: Oryctolagus cuniculus

<400> SEQUENCE: 254
caaagtaatc atggtagtaa tagtgatagt tatggcaatg ct                        42

<210> SEQ ID NO 255

<210> SEQ ID NO 255
<211> LENGTH: 15
<212> TYPE: DNA
<213> ORGANISM: Oryctolagus cuniculus

<400> SEQUENCE: 255
aactacaaca tgggc                                                       15

<210> SEQ ID NO 256
<211> LENGTH: 48
<212> TYPE: DNA
<213> ORGANISM: Oryctolagus cuniculus

<400> SEQUENCE: 256
tacattcttg gtagtggtat cacatactac gcgacctggg cgaaaggc                   48

<210> SEQ ID NO 257
<211> LENGTH: 33
<212> TYPE: DNA
<213> ORGANISM: Oryctolagus cuniculus

<400> SEQUENCE: 257
agtatttatt ataggggta cggcatggac ccc                                    33

<210> SEQ ID NO 258
<211> LENGTH: 125
<212> TYPE: PRT
<213> ORGANISM: Oryctolagus cuniculus

<400> SEQUENCE: 258

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ala
            20                  25                  30

Ser Val Ser Glu Pro Val Gly Gly Thr Val Thr Ile Lys Cys Gln Ala
        35                  40                  45

Ser Gln Ser Ile Tyr Ser Thr Leu Ala Trp Tyr Gln Gln Lys Pro Gly
    50                  55                  60

Gln Pro Pro Lys Leu Leu Ile Ser Leu Ala Ser Thr Leu Ala Ser Gly
65                  70                  75                  80

Val Pro Ser Arg Phe Lys Gly Ser Gly Ser Gly Thr Gln Phe Thr Leu
                85                  90                  95

Thr Ile Ser Asp Leu Glu Cys Ala Asp Ala Ala Thr Tyr Tyr Cys Gln
            100                 105                 110

Thr Asn His Gly Ser Asn Ser Asp Ser Phe Gly Tyr Ala
        115                 120                 125

<210> SEQ ID NO 259
<211> LENGTH: 124
<212> TYPE: PRT
<213> ORGANISM: Oryctolagus cuniculus

<400> SEQUENCE: 259

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Gly Ser Leu Thr Leu Thr Cys Thr Val Ser Gly Ile Asp Leu Ser
        35                  40                  45

Ser Tyr Ala Met Gly Trp Val Arg Gln Ala Pro Gly Lys Gly Leu Glu
    50                  55                  60

```
Tyr Ile Gly Tyr Val Leu Gly Ser Gly Ile Thr Tyr Tyr Ala Ser Trp
 65                  70                  75                  80

Ala Arg Gly Arg Phe Thr Ile Ser Lys Thr Ser Ser Thr Val Asp
                 85                  90                  95

Leu Lys Met Thr Ser Leu Thr Thr Glu Asp Thr Ala Thr Tyr Phe Cys
            100                 105                 110

Val Arg Asn Asp Asn Tyr Asn Ser Gly Thr Asp Ile
        115                 120

<210> SEQ ID NO 260
<211> LENGTH: 11
<212> TYPE: PRT
<213> ORGANISM: Oryctolagus cuniculus

<400> SEQUENCE: 260

Gln Ala Ser Gln Ser Ile Tyr Ser Thr Leu Ala
1               5                   10

<210> SEQ ID NO 261
<211> LENGTH: 7
<212> TYPE: PRT
<213> ORGANISM: Oryctolagus cuniculus

<400> SEQUENCE: 261

Leu Ala Ser Thr Leu Ala Ser
1               5

<210> SEQ ID NO 262
<211> LENGTH: 14
<212> TYPE: PRT
<213> ORGANISM: Oryctolagus cuniculus

<400> SEQUENCE: 262

Gln Thr Asn His Gly Ser Asn Ser Asp Ser Phe Gly Tyr Ala
1               5                   10

<210> SEQ ID NO 263
<211> LENGTH: 5
<212> TYPE: PRT
<213> ORGANISM: Oryctolagus cuniculus

<400> SEQUENCE: 263

Ser Tyr Ala Met Gly
1               5

<210> SEQ ID NO 264
<211> LENGTH: 16
<212> TYPE: PRT
<213> ORGANISM: Oryctolagus cuniculus

<400> SEQUENCE: 264

Tyr Val Leu Gly Ser Gly Ile Thr Tyr Tyr Ala Ser Trp Ala Arg Gly
1               5                   10                  15

<210> SEQ ID NO 265
<211> LENGTH: 10
<212> TYPE: PRT
<213> ORGANISM: Oryctolagus cuniculus

<400> SEQUENCE: 265

Asn Asp Asn Tyr Asn Ser Gly Thr Asp Ile
1               5                   10
```

<210> SEQ ID NO 266
<211> LENGTH: 375
<212> TYPE: DNA
<213> ORGANISM: Oryctolagus cuniculus

<400> SEQUENCE: 266

```
atggacacga gggcccccac tcagctgctg gggctcctgc tgctctggct cccaggtgcc      60
agatgtgctg acattgtgat gacccagact ccagcctccg tgtctgaacc tgtgggaggc     120
acagtcacca tcaagtgcca ggccagtcag agcatttaca gcaccttagc ctggtatcag     180
cagaaaccag gcagcctcc caaactcctg atctcgctgg catccactct ggcatctggg      240
gtcccatcgc ggttcaaagg cagtggatct gggacacagt tcactctcac catcagcgac     300
ctggagtgtg ccgatgctgc cacttattac tgtcaaacca atcatggtag taatagtgat     360
agttttggtt atgct                                                      375
```

<210> SEQ ID NO 267
<211> LENGTH: 372
<212> TYPE: DNA
<213> ORGANISM: Oryctolagus cuniculus

<400> SEQUENCE: 267

```
atggagactg ggctgcgctg gcttctcctg gtcgctgtgc tcaaaggtgt ccagtgtcag      60
tcgctggagg agtccggggg tcgcctggta acgcctggag atccctgac actcacctgc     120
acagtctctg gaatcgacct cagtagctat gcaatgggct gggtccgcca ggctccaggg     180
aaggggctgg aatacatcgg atacgttctt ggtagtggta tcacatacta cgcgagttgg     240
gcgagaggcc gattcaccat ctccaaaacc tcgtcgacca cggtggatct gaagatgacc     300
agtctgacaa ccgaggacac ggccacctat ttctgtgtca gaaatgataa ttataatagt     360
ggcacggaca tc                                                         372
```

<210> SEQ ID NO 268
<211> LENGTH: 33
<212> TYPE: DNA
<213> ORGANISM: Oryctolagus cuniculus

<400> SEQUENCE: 268

```
caggccagtc agagcattta cagcaccta gcc                                    33
```

<210> SEQ ID NO 269
<211> LENGTH: 21
<212> TYPE: DNA
<213> ORGANISM: Oryctolagus cuniculus

<400> SEQUENCE: 269

```
ctggcatcca ctctggcatc t                                                21
```

<210> SEQ ID NO 270
<211> LENGTH: 42
<212> TYPE: DNA
<213> ORGANISM: Oryctolagus cuniculus

<400> SEQUENCE: 270

```
caaaccaatc atggtagtaa tagtgatagt tttggttatg ct                         42
```

<210> SEQ ID NO 271
<211> LENGTH: 15
<212> TYPE: DNA
<213> ORGANISM: Oryctolagus cuniculus
```

<400> SEQUENCE: 271
agctatgcaa tgggc                                                                15

<210> SEQ ID NO 272
<211> LENGTH: 48
<212> TYPE: DNA
<213> ORGANISM: Oryctolagus cuniculus

<400> SEQUENCE: 272
tacgttcttg gtagtggtat cacatactac gcgagttggg cgagaggc                             48

<210> SEQ ID NO 273
<211> LENGTH: 30
<212> TYPE: DNA
<213> ORGANISM: Oryctolagus cuniculus

<400> SEQUENCE: 273
aatgataatt ataatagtgg cacggacatc                                                 30

<210> SEQ ID NO 274
<211> LENGTH: 125
<212> TYPE: PRT
<213> ORGANISM: Oryctolagus cuniculus

<400> SEQUENCE: 274

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ala
            20                  25                  30

Ser Val Ser Glu Pro Val Gly Gly Thr Val Thr Ile Lys Cys Gln Ala
        35                  40                  45

Ser Gln Asn Ile Tyr Ser Thr Leu Ala Trp Tyr Gln Gln Lys Pro Gly
    50                  55                  60

Gln Pro Pro Lys Leu Leu Ile Tyr Leu Ala Ser Thr Leu Glu Ser Gly
65                  70                  75                  80

Val Pro Ser Arg Phe Lys Gly Ser Gly Ser Gly Thr Glu Phe Thr Leu
                85                  90                  95

Thr Ile Ser Asp Leu Glu Cys Ala Asp Ala Ala Thr Tyr Tyr Cys Gln
            100                 105                 110

Thr Ser His Gly Ser Asn Ser Glu Ser Phe Gly Tyr Ala
        115                 120                 125

<210> SEQ ID NO 275
<211> LENGTH: 124
<212> TYPE: PRT
<213> ORGANISM: Oryctolagus cuniculus

<400> SEQUENCE: 275

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Ser Tyr Ala Met Gly Trp Val Arg Gln Ala Pro Gly Lys Gly Leu Glu
    50                  55                  60

Tyr Ile Gly Tyr Ile Leu Ser Ser Gly Ile Thr Tyr Tyr Ala Ser Trp
65                  70                  75                  80

```
Ala Arg Gly Arg Phe Thr Ile Ser Lys Thr Ser Ser Thr Thr Val Asp
                85                  90                  95

Leu Lys Met Thr Ser Leu Thr Glu Asp Thr Ala Thr Tyr Phe Cys
            100                 105                 110

Val Arg Asn Gly Asn Tyr Asn Val Gly Thr Asp Ile
        115                 120

<210> SEQ ID NO 276
<211> LENGTH: 11
<212> TYPE: PRT
<213> ORGANISM: Oryctolagus cuniculus

<400> SEQUENCE: 276

Gln Ala Ser Gln Asn Ile Tyr Ser Thr Leu Ala
1               5                   10

<210> SEQ ID NO 277
<211> LENGTH: 7
<212> TYPE: PRT
<213> ORGANISM: Oryctolagus cuniculus

<400> SEQUENCE: 277

Leu Ala Ser Thr Leu Glu Ser
1               5

<210> SEQ ID NO 278
<211> LENGTH: 14
<212> TYPE: PRT
<213> ORGANISM: Oryctolagus cuniculus

<400> SEQUENCE: 278

Gln Thr Ser His Gly Ser Asn Ser Glu Ser Phe Gly Tyr Ala
1               5                   10

<210> SEQ ID NO 279
<211> LENGTH: 5
<212> TYPE: PRT
<213> ORGANISM: Oryctolagus cuniculus

<400> SEQUENCE: 279

Ser Tyr Ala Met Gly
1               5

<210> SEQ ID NO 280
<211> LENGTH: 16
<212> TYPE: PRT
<213> ORGANISM: Oryctolagus cuniculus

<400> SEQUENCE: 280

Tyr Ile Leu Ser Ser Gly Ile Thr Tyr Tyr Ala Ser Trp Ala Arg Gly
1               5                   10                  15

<210> SEQ ID NO 281
<211> LENGTH: 10
<212> TYPE: PRT
<213> ORGANISM: Oryctolagus cuniculus

<400> SEQUENCE: 281

Asn Gly Asn Tyr Asn Val Gly Thr Asp Ile
1               5                   10

<210> SEQ ID NO 282
<211> LENGTH: 375
```

```
<212> TYPE: DNA
<213> ORGANISM: Oryctolagus cuniculus

<400> SEQUENCE: 282
atggacacga gggcccccac tcagctgctg gggctcctgc tgctctggct cccaggtgcc      60
agatgtgctg acattgtgat gacccagact ccagcctccg tgtctgaacc tgtgggaggc     120
acagtcacca tcaagtgcca ggccagtcag aacatttaca gcaccttagc ctggtatcag     180
cagaaaccag gcagcctcc caagctcctg atctatctgg catccactct ggaatctggg      240
gtcccatcgc ggttcaaagg cagtggatct gggacagagt tcactctcac catcagcgac     300
ctggagtgtg ccgatgctgc cacttattac tgtcaaacca gtcatggtag taatagtgaa     360
agttttggtt atgct                                                     375

<210> SEQ ID NO 283
<211> LENGTH: 372
<212> TYPE: DNA
<213> ORGANISM: Oryctolagus cuniculus

<400> SEQUENCE: 283
atggagactg ggctgcgctg gcttctcctg gtcgctgtgc tcaaaggtgt ccagtgtcag      60
tcggtggagg agtccggggg tcgcctggtc acgcctggga caccctgac actcacttgc      120 acggtctctg gaatcgacct cagtagctat gcaatgggct gggtccgcca ggctccaggg     180
aaggggctgg aatacatcgg atacattctt agtagtggta tcacatacta cgcgagttgg     240
gcgagaggcc gattcaccat ctccaaaacc tcgtcgacca cggtggatct gaaaatgacc     300
agtctgacaa ccgaggacac ggccacctat ttctgtgtca gaaatggtaa ttataatgtt     360
ggtacggaca tc                                                        372

<210> SEQ ID NO 284
<211> LENGTH: 33
<212> TYPE: DNA
<213> ORGANISM: Oryctolagus cuniculus

<400> SEQUENCE: 284
caggccagtc agaacattta cagcacctta gcc                                  33

<210> SEQ ID NO 285
<211> LENGTH: 21
<212> TYPE: DNA
<213> ORGANISM: Oryctolagus cuniculus

<400> SEQUENCE: 285
ctggcatcca ctctggaatc t                                               21

<210> SEQ ID NO 286
<211> LENGTH: 42
<212> TYPE: DNA
<213> ORGANISM: Oryctolagus cuniculus

<400> SEQUENCE: 286
caaaccagtc atggtagtaa tagtgaaagt tttggttatg ct                        42

<210> SEQ ID NO 287
<211> LENGTH: 15
<212> TYPE: DNA
<213> ORGANISM: Oryctolagus cuniculus

<400> SEQUENCE: 287
```

```
agctatgcaa tgggc                                                      15
```

<210> SEQ ID NO 288
<211> LENGTH: 48
<212> TYPE: DNA
<213> ORGANISM: Oryctolagus cuniculus

<400> SEQUENCE: 288

```
tacattctta gtagtggtat cacatactac gcgagttggg cgagaggc                  48
```

<210> SEQ ID NO 289
<211> LENGTH: 30
<212> TYPE: DNA
<213> ORGANISM: Oryctolagus cuniculus

<400> SEQUENCE: 289

```
aatggtaatt ataatgttgg tacggacatc                                      30
```

<210> SEQ ID NO 290
<211> LENGTH: 125
<212> TYPE: PRT
<213> ORGANISM: Oryctolagus cuniculus

<400> SEQUENCE: 290

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ser
                20                  25                  30

Ser Val Ser Glu Pro Val Arg Gly Thr Val Thr Ile Lys Cys Gln Ala
            35                  40                  45

Ser Gln Asn Ile Tyr Ser Tyr Leu Ser Trp Tyr Arg Gln Ser Pro Gly
        50                  55                  60

Gln Pro Pro Asn Leu Leu Ile Tyr Lys Ala Ser Thr Leu Ala Ser Gly
65                  70                  75                  80

Val Pro Ser Arg Phe Lys Gly Ser Gly Ser Gly Thr Asp Phe Thr Leu
                85                  90                  95

Thr Ile Ser Asp Leu Glu Cys Ala Asp Ala Ala Thr Tyr Tyr Cys Gln
            100                 105                 110

Ser Asn Tyr Gly Ser Asn Ser Asp Ser Phe Gly Asn Ala
        115                 120                 125

<210> SEQ ID NO 291
<211> LENGTH: 122
<212> TYPE: PRT
<213> ORGANISM: Oryctolagus cuniculus

<400> SEQUENCE: 291

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
                20                  25                  30

Gly Thr Pro Leu Thr Leu Thr Cys Ser Val Ser Gly Phe Ser Leu Asn
            35                  40                  45

Asn Tyr Ile Met Gly Trp Val Arg Gln Ala Pro Gly Lys Gly Leu Glu
        50                  55                  60

Phe Ile Gly Tyr Ile Ala Phe Gly Ile Gly Pro Tyr Tyr Ala Ser Trp
65                  70                  75                  80

Ala Lys Gly Arg Phe Thr Ser Ser Ser Thr Ser Thr Thr Val Asp
                85                  90                  95

Leu Lys Met Thr Ser Leu Thr Pro Glu Asp Thr Ala Thr Tyr Phe Cys
            100                 105                 110

Ala Arg Gly Asp Val Ser Gly Asn Asp Ile
        115                 120

<210> SEQ ID NO 292
<211> LENGTH: 11
<212> TYPE: PRT
<213> ORGANISM: Oryctolagus cuniculus

<400> SEQUENCE: 292

Gln Ala Ser Gln Asn Ile Tyr Ser Tyr Leu Ser
1               5                   10

<210> SEQ ID NO 293
<211> LENGTH: 7
<212> TYPE: PRT
<213> ORGANISM: Oryctolagus cuniculus

<400> SEQUENCE: 293

Lys Ala Ser Thr Leu Ala Ser
1               5

<210> SEQ ID NO 294
<211> LENGTH: 14
<212> TYPE: PRT
<213> ORGANISM: Oryctolagus cuniculus

<400> SEQUENCE: 294

Gln Ser Asn Tyr Gly Ser Asn Ser Asp Ser Phe Gly Asn Ala
1               5                   10

<210> SEQ ID NO 295
<211> LENGTH: 5
<212> TYPE: PRT
<213> ORGANISM: Oryctolagus cuniculus

<400> SEQUENCE: 295

Asn Tyr Ile Met Gly
1               5

<210> SEQ ID NO 296
<211> LENGTH: 16
<212> TYPE: PRT
<213> ORGANISM: Oryctolagus cuniculus

<400> SEQUENCE: 296

Tyr Ile Ala Phe Gly Ile Gly Pro Tyr Tyr Ala Ser Trp Ala Lys Gly
1               5                   10                  15

<210> SEQ ID NO 297
<211> LENGTH: 8
<212> TYPE: PRT
<213> ORGANISM: Oryctolagus cuniculus

<400> SEQUENCE: 297

Gly Asp Val Ser Gly Asn Asp Ile
1               5

<210> SEQ ID NO 298
<211> LENGTH: 375
<212> TYPE: DNA
<213> ORGANISM: Oryctolagus cuniculus

```
<400> SEQUENCE: 298
atggacacga gggcccccac tcagctgctg gggctcctgc tgctctggct cccaggtgcc      60
agatgtgctg acattgtgat gacccagact ccatcctccg tgtctgaacc tgtgcgaggc     120
acagtcacca tcaagtgcca ggccagtcag aacatttaca gctacttgtc ctggtatcga     180
cagagcccag ggcagcctcc caacctcctg atctacaagg catccactct ggcatctggg     240
gtcccatcgc ggttcaaagg cagtggatct gggacagatt tcactctcac catcagcgac     300
ctggagtgtg ccgatgctgc cacttactac tgtcaaagca attatggtag taatagtgat     360
agttttggga atgct                                                       375

<210> SEQ ID NO 299
<211> LENGTH: 366
<212> TYPE: DNA
<213> ORGANISM: Oryctolagus cuniculus

<400> SEQUENCE: 299
atggagactg ggctgcgctg gcttctcctg gtcgctgtgc tcaaaggtgt ccagtgtcag      60
tcggtggagg agtccggggg tcgcctggtc acgcctggga cacccctgac actcacctgc     120
tcagtctctg gattctccct caataactat ataatgggct gggtccgcca ggctccaggg     180
aaggggctgg aattcatcgg atacattgct tttggtattg gcccatacta cgcgagctgg     240
gcgaaaggcc gattcaccag ctccagcacc tcgtcgacca cggtggatct gaaaatgacc     300
agtctgacac ccgaggacac ggccacctat ttctgtgcca gaggtgatgt tagtggtaat     360
gacatt                                                                 366

<210> SEQ ID NO 300
<211> LENGTH: 33
<212> TYPE: DNA
<213> ORGANISM: Oryctolagus cuniculus

<400> SEQUENCE: 300
caggccagtc agaacattta cagctacttg tcc                                   33

<210> SEQ ID NO 301
<211> LENGTH: 21
<212> TYPE: DNA
<213> ORGANISM: Oryctolagus cuniculus

<400> SEQUENCE: 301
aaggcatcca ctctggcatc t                                                21

<210> SEQ ID NO 302
<211> LENGTH: 42
<212> TYPE: DNA
<213> ORGANISM: Oryctolagus cuniculus

<400> SEQUENCE: 302
caaagcaatt atggtagtaa tagtgatagt tttgggaatg ct                         42

<210> SEQ ID NO 303
<211> LENGTH: 15
<212> TYPE: DNA
<213> ORGANISM: Oryctolagus cuniculus

<400> SEQUENCE: 303
aactatataa tgggc                                                       15
```

-continued

<210> SEQ ID NO 304
<211> LENGTH: 48
<212> TYPE: DNA
<213> ORGANISM: Oryctolagus cuniculus

<400> SEQUENCE: 304
tacattgctt ttggtattgg cccatactac gcgagctggg cgaaaggc                48

<210> SEQ ID NO 305
<211> LENGTH: 24
<212> TYPE: DNA
<213> ORGANISM: Oryctolagus cuniculus

<400> SEQUENCE: 305
ggtgatgtta gtggtaatga catt                24

<210> SEQ ID NO 306
<211> LENGTH: 125
<212> TYPE: PRT
<213> ORGANISM: Oryctolagus cuniculus

<400> SEQUENCE: 306

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ala
            20                  25                  30

Ser Val Ser Glu Pro Val Gly Thr Val Thr Ile Lys Cys Gln Ala
        35                  40                  45

Ser Gln Asn Ile Tyr Thr Thr Leu Ala Trp Tyr Gln Gln Lys Pro Gly
    50                  55                  60

Gln Pro Pro Lys Leu Leu Ile Tyr Leu Ala Ser Thr Leu Ala Ser Gly
65                  70                  75                  80

Val Pro Ser Arg Phe Lys Gly Ser Gly Ser Glu Thr Gln Phe Thr Leu
                85                  90                  95

Thr Ile Ser Asp Leu Glu Cys Ala Asp Ala Ala Thr Tyr Tyr Cys Gln
            100                 105                 110

Thr Ser His Gly Ser Asn Ser Asp Ser Phe Gly Tyr Val
        115                 120                 125

<210> SEQ ID NO 307
<211> LENGTH: 124
<212> TYPE: PRT
<213> ORGANISM: Oryctolagus cuniculus

<400> SEQUENCE: 307

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Asn
        35                  40                  45

Ser Tyr Ala Met Gly Trp Val Arg Gln Ala Pro Gly Lys Gly Leu Glu
    50                  55                  60

Tyr Ile Gly Tyr Ile Leu Ser Ser Gly Ile Thr Tyr Tyr Ala Thr Trp
65                  70                  75                  80

Ala Lys Gly Arg Phe Thr Ile Ser Lys Thr Ser Ser Thr Thr Val Asp
                85                  90                  95

Leu Lys Met Thr Ser Leu Thr Thr Glu Asp Thr Ala Thr Tyr Phe Cys
            100                 105                 110

Val Arg Asn Gly Asn Tyr Asn Ser Gly Thr Asp Ile
            115                 120

<210> SEQ ID NO 308
<211> LENGTH: 11
<212> TYPE: PRT
<213> ORGANISM: Oryctolagus cuniculus

<400> SEQUENCE: 308

Gln Ala Ser Gln Asn Ile Tyr Thr Thr Leu Ala
1               5                   10

<210> SEQ ID NO 309
<211> LENGTH: 7
<212> TYPE: PRT
<213> ORGANISM: Oryctolagus cuniculus

<400> SEQUENCE: 309

Leu Ala Ser Thr Leu Ala Ser
1               5

<210> SEQ ID NO 310
<211> LENGTH: 14
<212> TYPE: PRT
<213> ORGANISM: Oryctolagus cuniculus

<400> SEQUENCE: 310

Gln Thr Ser His Gly Ser Asn Ser Asp Ser Phe Gly Tyr Val
1               5                   10

<210> SEQ ID NO 311
<211> LENGTH: 5
<212> TYPE: PRT
<213> ORGANISM: Oryctolagus cuniculus

<400> SEQUENCE: 311

Ser Tyr Ala Met Gly
1               5

<210> SEQ ID NO 312
<211> LENGTH: 16
<212> TYPE: PRT
<213> ORGANISM: Oryctolagus cuniculus

<400> SEQUENCE: 312

Tyr Ile Leu Ser Ser Gly Ile Thr Tyr Tyr Ala Thr Trp Ala Lys Gly
1               5                   10                  15

<210> SEQ ID NO 313
<211> LENGTH: 10
<212> TYPE: PRT
<213> ORGANISM: Oryctolagus cuniculus

<400> SEQUENCE: 313

Asn Gly Asn Tyr Asn Ser Gly Thr Asp Ile
1               5                   10

<210> SEQ ID NO 314
<211> LENGTH: 375
<212> TYPE: DNA
<213> ORGANISM: Oryctolagus cuniculus

<400> SEQUENCE: 314
atggacacga gggccccac tcagctgctg gggctcctgc tgctctggct cccaggtgcc     60

```
agatgtgctg acattgtgat gacccagact ccagcctccg tgtctgaacc tgtgggaggc    120
acagtcacca tcaaatgcca ggccagtcag aacatttaca ccaccttagc ctggtatcag    180
cagaaaccag ggcagcctcc caagctcctg atctatctgg catccactct ggcatctggg    240
gtcccatcgc ggttcaaagg cagtggatct gagacacagt tcactctcac catcagcgac    300
ctggagtgtg ccgatgctgc cacttattac tgtcaaacca gtcatggtag taatagtgat    360
agttttggtt atgtt                                                     375
```

<210> SEQ ID NO 315
<211> LENGTH: 372
<212> TYPE: DNA
<213> ORGANISM: Oryctolagus cuniculus

<400> SEQUENCE: 315

```
atggagactg ggctgcgctg gcttctcctg gtcgctgtgc tcaaaggtgt ccagtgtcag     60
tcagtggagg agtccggggg tcgcctggtc acgcctggga caccctgac actcacttgc    120 acagtctctg gaatcgacct caatagctat gcaatgggct gggtccgcca ggctccaggg    180
aaggggctgg aatacatcgg atacattctt agtagtggta tcacatacta cgcgacctgg    240
gcgaaaggcc gattcaccat ctccaaaacc tcgtcgacca cggtggatct gaaaatgacc    300
agtctgacaa ccgaggacac ggccacctat ttctgtgtca ggaatggtaa ttataatagt    360
ggtacggaca tc                                                        372
```

<210> SEQ ID NO 316
<211> LENGTH: 33
<212> TYPE: DNA
<213> ORGANISM: Oryctolagus cuniculus

<400> SEQUENCE: 316

```
caggccagtc agaacattta caccacctta gcc                                  33
```

<210> SEQ ID NO 317
<211> LENGTH: 21
<212> TYPE: DNA
<213> ORGANISM: Oryctolagus cuniculus

<400> SEQUENCE: 317

```
ctggcatcca ctctggcatc t                                               21
```

<210> SEQ ID NO 318
<211> LENGTH: 42
<212> TYPE: DNA
<213> ORGANISM: Oryctolagus cuniculus

<400> SEQUENCE: 318

```
caaaccagtc atggtagtaa tagtgatagt tttggttatg tt                        42
```

<210> SEQ ID NO 319
<211> LENGTH: 15
<212> TYPE: DNA
<213> ORGANISM: Oryctolagus cuniculus

<400> SEQUENCE: 319

```
agctatgcaa tgggc                                                      15
```

<210> SEQ ID NO 320
<211> LENGTH: 48
<212> TYPE: DNA

<213> ORGANISM: Oryctolagus cuniculus

<400> SEQUENCE: 320
tacattctta gtagtggtat cacatactac gcgacctggg cgaaaggc    48

<210> SEQ ID NO 321
<211> LENGTH: 30
<212> TYPE: DNA
<213> ORGANISM: Oryctolagus cuniculus

<400> SEQUENCE: 321
aatggtaatt ataatagtgg tacggacatc    30

<210> SEQ ID NO 322
<211> LENGTH: 125
<212> TYPE: PRT
<213> ORGANISM: Oryctolagus cuniculus

<400> SEQUENCE: 322

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ser
            20                  25                  30

Ser Val Ser Ala Ala Val Gly Gly Thr Val Thr Ile Lys Cys Gln Ala
        35                  40                  45

Ser Gln Ser Ile Asp Thr Tyr Leu Ala Trp Tyr Gln Gln Lys Pro Gly
    50                  55                  60

Gln Arg Pro Lys Leu Leu Ile Tyr Gly Ala Ser Asn Leu Ala Ser Gly
65                  70                  75                  80

Val Ser Ser Arg Phe Lys Gly Ser Gly Ser Gly Thr Glu Phe Ala Leu
                85                  90                  95

Thr Ile Ser Asp Leu Glu Cys Ala Asp Ala Ala Thr Tyr Tyr Cys Gln
            100                 105                 110

Ser Asn Tyr Gly Ser Asn Ser Asp Ser Phe Gly Asn Gly
        115                 120                 125

<210> SEQ ID NO 323
<211> LENGTH: 127
<212> TYPE: PRT
<213> ORGANISM: Oryctolagus cuniculus

<400> SEQUENCE: 323

Met Glu Thr Gly Leu Arg Trp Leu Leu Leu Val Ala Val Phe Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Thr Tyr Thr Met Gly Trp Val Arg Gln Ala Pro Gly Lys Gly Leu Glu
    50                  55                  60

Tyr Ile Gly Tyr Ile Ser Tyr Gly Gly Leu Ala Tyr Tyr Ala Thr Trp
65                  70                  75                  80

Val Asn Gly Arg Phe Thr Ile Ser Lys Thr Ser Thr Thr Val Asp Leu
                85                  90                  95

Lys Met Thr Ser Leu Thr Ala Ser Asp Thr Ala Thr Tyr Phe Cys Ala
            100                 105                 110

Arg Ala Ala Ser Gly Ala Trp Gly His Ala Tyr Gly Leu Asp Leu
        115                 120                 125

<210> SEQ ID NO 324
<211> LENGTH: 11
<212> TYPE: PRT
<213> ORGANISM: Oryctolagus cuniculus

<400> SEQUENCE: 324

Gln Ala Ser Gln Ser Ile Asp Thr Tyr Leu Ala
1               5                   10

<210> SEQ ID NO 325
<211> LENGTH: 7
<212> TYPE: PRT
<213> ORGANISM: Oryctolagus cuniculus

<400> SEQUENCE: 325

Gly Ala Ser Asn Leu Ala Ser
1               5

<210> SEQ ID NO 326
<211> LENGTH: 14
<212> TYPE: PRT
<213> ORGANISM: Oryctolagus cuniculus

<400> SEQUENCE: 326

Gln Ser Asn Tyr Gly Ser Asn Ser Asp Ser Phe Gly Asn Gly
1               5                   10

<210> SEQ ID NO 327
<211> LENGTH: 5
<212> TYPE: PRT
<213> ORGANISM: Oryctolagus cuniculus

<400> SEQUENCE: 327

Thr Tyr Thr Met Gly
1               5

<210> SEQ ID NO 328
<211> LENGTH: 16
<212> TYPE: PRT
<213> ORGANISM: Oryctolagus cuniculus

<400> SEQUENCE: 328

Tyr Ile Ser Tyr Gly Gly Leu Ala Tyr Tyr Ala Thr Trp Val Asn Gly
1               5                   10                  15

<210> SEQ ID NO 329
<211> LENGTH: 14
<212> TYPE: PRT
<213> ORGANISM: Oryctolagus cuniculus

<400> SEQUENCE: 329

Ala Ala Ser Gly Ala Trp Gly His Ala Tyr Gly Leu Asp Leu
1               5                   10

<210> SEQ ID NO 330
<211> LENGTH: 375
<212> TYPE: DNA
<213> ORGANISM: Oryctolagus cuniculus

<400> SEQUENCE: 330
atggacacga gggcccccac tcagctgctg gggctcctgc tgctctggct cccaggtgcc      60
agatgtgctg acattgtgat gacccagact ccatcctccg tgtctgcagc tgtgggaggc     120

```
acagtcacca tcaagtgcca ggccagtcag agcattgata cctacttagc ctggtatcag    180
cagaaaccag ggcagcgtcc caagctcctg atctatggtg catccaatct ggcatctggg    240
gtctcatcgc ggttcaaagg cagtggatct gggacagaat tcgctctcac catcagcgac    300
ctggagtgtg ccgatgctgc cacttactac tgtcaaagca attatggtag taatagtgat    360
agttttggta atggt                                                    375

<210> SEQ ID NO 331
<211> LENGTH: 381
<212> TYPE: DNA
<213> ORGANISM: Oryctolagus cuniculus

<400> SEQUENCE: 331
atggagactg ggctgcgctg gcttctcctg gtcgctgtgt tcaaaggtgt ccagtgtcag     60
tcggtggagg agtccggggg tcgcctggtc acgcctggga cacccctgac actcacctgc    120
acagtctctg gattctccct cagtacctat acaatgggct gggtccgcca ggctccaggg    180
aaggggctgg aatacatcgg gtacattagt tatggtggtc tcgcatacta cgcgacctgg    240
gtgaatggcc gattcaccat ctccaaaacc tcgaccacgg tggatctgaa aatgaccagt    300
ctgacagctt cagacacggc cacctatttc tgtgccagag cggctagtgg tgcctggggt    360
catgcctacg gcttggacct c                                             381

<210> SEQ ID NO 332
<211> LENGTH: 33
<212> TYPE: DNA
<213> ORGANISM: Oryctolagus cuniculus

<400> SEQUENCE: 332
caggccagtc agagcattga tacctactta gcc                                 33

<210> SEQ ID NO 333
<211> LENGTH: 21
<212> TYPE: DNA
<213> ORGANISM: Oryctolagus cuniculus

<400> SEQUENCE: 333
ggtgcatcca atctggcatc t                                              21

<210> SEQ ID NO 334
<211> LENGTH: 42
<212> TYPE: DNA
<213> ORGANISM: Oryctolagus cuniculus

<400> SEQUENCE: 334
caaagcaatt atggtagtaa tagtgatagt tttggtaatg gt                        42

<210> SEQ ID NO 335
<211> LENGTH: 15
<212> TYPE: DNA
<213> ORGANISM: Oryctolagus cuniculus

<400> SEQUENCE: 335
acctatacaa tgggc                                                     15

<210> SEQ ID NO 336
<211> LENGTH: 48
<212> TYPE: DNA
<213> ORGANISM: Oryctolagus cuniculus

<400> SEQUENCE: 336
```

```
tacattagtt atggtggtct cgcatactac gcgacctggg tgaatggc                    48
```

<210> SEQ ID NO 337
<211> LENGTH: 42
<212> TYPE: DNA
<213> ORGANISM: Oryctolagus cuniculus

<400> SEQUENCE: 337

```
gcggctagtg gtgcctgggg tcatgcctac ggcttggacc tc                         42
```

<210> SEQ ID NO 338
<211> LENGTH: 125
<212> TYPE: PRT
<213> ORGANISM: Oryctolagus cuniculus

<400> SEQUENCE: 338

```
Met Asp Thr Arg Ala Pro Thr Gln Leu Leu Gly Leu Leu Leu Leu Trp
 1               5                  10                  15

Leu Pro Gly Ala Arg Cys Ala Asp Ile Val Met Thr Gln Thr Pro Ala
            20                  25                  30

Ser Val Ser Gly Pro Val Gly Gly Thr Val Thr Ile Lys Cys Gln Ala
        35                  40                  45

Ser Gln Asn Ile Tyr Ser Ser Phe Ser Trp Tyr Gln Gln Ile Pro Gly
    50                  55                  60

Gln Arg Pro Lys Leu Leu Ile Tyr Tyr Ala Ser Thr Leu Ala Ser Gly
65                  70                  75                  80

Val Pro Ser Arg Phe Ser Gly Ser Gly Ser Gly Thr Asp Phe Thr Leu
                85                  90                  95

Thr Ile Ser Asp Leu Glu Cys Ala Asp Ala Ala Thr Tyr Tyr Cys Gln
            100                 105                 110

Ser Asn His Gly Ser Asn Gly Asp Ser Phe Gly Asn Ala
        115                 120                 125
```

<210> SEQ ID NO 339
<211> LENGTH: 121
<212> TYPE: PRT
<213> ORGANISM: Oryctolagus cuniculus

<400> SEQUENCE: 339

```
Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Ser Pro
            20                  25                  30

Gly Thr Pro Leu Thr Leu Thr Cys Thr Val Ser Gly Ile Asp Leu Ser
        35                  40                  45

Ser Tyr Gly Met Gly Trp Val Arg Gln Ala Pro Gly Lys Gly Leu Asp
    50                  55                  60

Tyr Ile Gly Tyr Met Leu Pro Ser Gly Ile Thr Tyr Tyr Ala Ala Trp
65                  70                  75                  80

Ala Lys Gly Arg Phe Thr Ile Ser Lys Thr Ser Ser Thr Thr Val Asp
                85                  90                  95

Leu Lys Ile Thr Ser Pro Thr Thr Glu Asp Thr Ala Thr Tyr Phe Cys
            100                 105                 110

Ala Arg Asn Tyr Tyr Gly Met Asp Pro
        115                 120
```

<210> SEQ ID NO 340

<211> LENGTH: 11
<212> TYPE: PRT
<213> ORGANISM: Oryctolagus cuniculus

<400> SEQUENCE: 340

Gln Ala Ser Gln Asn Ile Tyr Ser Ser Phe Ser
1               5                   10

<210> SEQ ID NO 341
<211> LENGTH: 7
<212> TYPE: PRT
<213> ORGANISM: Oryctolagus cuniculus

<400> SEQUENCE: 341

Tyr Ala Ser Thr Leu Ala Ser
1               5

<210> SEQ ID NO 342
<211> LENGTH: 14
<212> TYPE: PRT
<213> ORGANISM: Oryctolagus cuniculus

<400> SEQUENCE: 342

Gln Ser Asn His Gly Ser Asn Gly Asp Ser Phe Gly Asn Ala
1               5                   10

<210> SEQ ID NO 343
<211> LENGTH: 5
<212> TYPE: PRT
<213> ORGANISM: Oryctolagus cuniculus

<400> SEQUENCE: 343

Ser Tyr Gly Met Gly
1               5

<210> SEQ ID NO 344
<211> LENGTH: 16
<212> TYPE: PRT
<213> ORGANISM: Oryctolagus cuniculus

<400> SEQUENCE: 344

Tyr Met Leu Pro Ser Gly Ile Thr Tyr Tyr Ala Ala Trp Ala Lys Gly
1               5                   10                  15

<210> SEQ ID NO 345
<211> LENGTH: 7
<212> TYPE: PRT
<213> ORGANISM: Oryctolagus cuniculus

<400> SEQUENCE: 345

Asn Tyr Tyr Gly Met Asp Pro
1               5

<210> SEQ ID NO 346
<211> LENGTH: 375
<212> TYPE: DNA
<213> ORGANISM: Oryctolagus cuniculus

<400> SEQUENCE: 346
atggacacga gggcccccac tcagctgctg gggctcctgc tgctctggct cccaggtgcc      60
agatgtgctg acattgtgat gacccagact ccagcctccg tgtctggacc tgtgggaggc     120
acagtcacca tcagtgccca ggccagtcag aacatttaca gctcctttc ctggtatcaa     180 caaataccag ccagcgtcc aagctcctg atctattatg catccactct ggcctctggg     240
gtcccatcgc ggttcagcgg cagtggatct gggacagatt tcactctcac catcagcgac      300
ctggagtgtg ccgatgctgc cacttactac tgtcaaagca atcatggtag taatggtgat      360
agttttggta atgct                                                       375

<210> SEQ ID NO 347
<211> LENGTH: 363
<212> TYPE: DNA
<213> ORGANISM: Oryctolagus cuniculus

<400> SEQUENCE: 347
atggagactg ggctgcgctg gcttctcctg gtcgctgtgc tcaaaggtgt ccagtgtcag       60
tcggtggagg agtccggggg tcgcctggtg tcgcctggga cacccctgac actcacctgc      120
acagtctctg gaatcgacct cagtagctat ggaatgggct gggtccgcca ggctccaggg      180
aaggggctgg attacatcgg atacatgctt cctagtggta tcacatatta cgcggcctgg      240
gcgaaaggcc gattcaccat ctccaaaacc tcgtcgacca cggtggatct gaaaatcacc      300
agtccgacaa ccgaggacac ggccacctat ttctgtgcca gaattactac cggcatggac      360
ccc                                                                    363

<210> SEQ ID NO 348
<211> LENGTH: 33
<212> TYPE: DNA
<213> ORGANISM: Oryctolagus cuniculus

<400> SEQUENCE: 348
caggccagtc agaacattta cagctccttt tcc                                    33

<210> SEQ ID NO 349
<211> LENGTH: 21
<212> TYPE: DNA
<213> ORGANISM: Oryctolagus cuniculus

<400> SEQUENCE: 349
tatgcatcca ctctggcctc t                                                 21

<210> SEQ ID NO 350
<211> LENGTH: 42
<212> TYPE: DNA
<213> ORGANISM: Oryctolagus cuniculus

<400> SEQUENCE: 350
caaagcaatc atggtagtaa tggtgatagt tttggtaatg ct                          42

<210> SEQ ID NO 351
<211> LENGTH: 15
<212> TYPE: DNA
<213> ORGANISM: Oryctolagus cuniculus

<400> SEQUENCE: 351
agctatggaa tgggc                                                        15

<210> SEQ ID NO 352
<211> LENGTH: 48
<212> TYPE: DNA
<213> ORGANISM: Oryctolagus cuniculus

<400> SEQUENCE: 352
tacatgcttc ctagtggtat cacatattac gcggcctggg cgaaaggc                    48

<210> SEQ ID NO 353
<211> LENGTH: 21
<212> TYPE: DNA
<213> ORGANISM: Oryctolagus cuniculus

<400> SEQUENCE: 353
aattactacg gcatggaccc c                                                 21

<210> SEQ ID NO 354
<211> LENGTH: 125
<212> TYPE: PRT
<213> ORGANISM: Oryctolagus cuniculus

<400> SEQUENCE: 354

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ala
            20                  25                  30

Ser Val Ser Glu Pro Val Gly Gly Thr Val Thr Ile Lys Cys Gln Ala
        35                  40                  45

Ser Gln Ser Ile Tyr Arg Tyr Leu Ser Trp Tyr His His Lys Pro Gly
    50                  55                  60

Gln Pro Pro Lys Leu Leu Ile Tyr Gly Ala Ser Asn Leu Glu Ser Gly
65                  70                  75                  80

Val Pro Ser Arg Phe Lys Gly Ser Gly Ser Gly Thr Glu Tyr Thr Leu
                85                  90                  95

Thr Ile Ser Asp Leu Glu Cys Asp Asp Ala Ala Thr Tyr Tyr Cys Gln
            100                 105                 110

Ser Asn Tyr Gly Ala Asn Ser Asp Ser Tyr Gly Asp Ala
        115                 120                 125

<210> SEQ ID NO 355
<211> LENGTH: 129
<212> TYPE: PRT
<213> ORGANISM: Oryctolagus cuniculus

<400> SEQUENCE: 355

Met Glu Thr Gly Leu Arg Trp Leu Leu Leu Val Ala Val Leu Lys Gly
1               5                   10                  15

Val Gln Cys Gln Glu Gln Leu Glu Ser Gly Gly Asp Leu Val Lys
            20                  25                  30

Pro Gly Ala Ser Leu Thr Leu Thr Cys Lys Ala Ser Gly Phe Ser Phe
        35                  40                  45

Ser Ser Gly Tyr Tyr Met Gly Trp Val Arg Gln Ala Pro Gly Lys Gly
    50                  55                  60

Leu Gln Tyr Ile Gly Tyr Ile Asp Tyr Gly Ser Ala Tyr Tyr Ala
65                  70                  75                  80

Ser Trp Ala Lys Gly Arg Phe Thr Ile Ser Lys Thr Ser Ser Thr
                85                  90                  95

Val Thr Leu Gln Met Thr Ser Leu Thr Ala Ala Asp Thr Ala Thr Phe
            100                 105                 110

Phe Cys Thr Arg Arg Asp Tyr Thr Gly Gly Val Val Arg Gly Leu Asp
        115                 120                 125

Leu

<210> SEQ ID NO 356
<211> LENGTH: 11

<210> SEQ ID NO 356
<211> LENGTH: 11
<212> TYPE: PRT
<213> ORGANISM: Oryctolagus cuniculus

<400> SEQUENCE: 356

Gln Ala Ser Gln Ser Ile Tyr Arg Tyr Leu Ser
1               5                   10

<210> SEQ ID NO 357
<211> LENGTH: 7
<212> TYPE: PRT
<213> ORGANISM: Oryctolagus cuniculus

<400> SEQUENCE: 357

Gly Ala Ser Asn Leu Glu Ser
1               5

<210> SEQ ID NO 358
<211> LENGTH: 14
<212> TYPE: PRT
<213> ORGANISM: Oryctolagus cuniculus

<400> SEQUENCE: 358

Gln Ser Asn Tyr Gly Ala Asn Ser Asp Ser Tyr Gly Asp Ala
1               5                   10

<210> SEQ ID NO 359
<211> LENGTH: 6
<212> TYPE: PRT
<213> ORGANISM: Oryctolagus cuniculus

<400> SEQUENCE: 359

Ser Gly Tyr Tyr Met Gly
1               5

<210> SEQ ID NO 360
<211> LENGTH: 16
<212> TYPE: PRT
<213> ORGANISM: Oryctolagus cuniculus

<400> SEQUENCE: 360

Tyr Ile Asp Tyr Gly Gly Ser Ala Tyr Tyr Ala Ser Trp Ala Lys Gly
1               5                   10                  15

<210> SEQ ID NO 361
<211> LENGTH: 13
<212> TYPE: PRT
<213> ORGANISM: Oryctolagus cuniculus

<400> SEQUENCE: 361

Arg Asp Tyr Thr Gly Gly Val Val Arg Gly Leu Asp Leu
1               5                   10

<210> SEQ ID NO 362
<211> LENGTH: 375
<212> TYPE: DNA
<213> ORGANISM: Oryctolagus cuniculus

<400> SEQUENCE: 362
atggacacga gggcccccac tcagctgctg gggctcctgc tgctctggct cccaggtgcc      60
agatgtgctg acattgtgat gacccagact ccagcctccg tgtctgaacc tgtgggaggc     120
acagtcacca tcaagtgcca ggccagtcag agcatttaca ggtacttatc ctggtatcac     180
cacaaaccag ggcagcctcc caagctcctg atctatggtg catccaatct ggaatctggg     240

```
gtcccatcgc ggttcaaagg cagtggatct gggacagagt acactctcac catcagcgac      300
ctggagtgtg acgatgctgc cacttattac tgtcagagca attatggtgc taatagtgat      360
agttatgggg atgct                                                      375
```

<210> SEQ ID NO 363
<211> LENGTH: 387
<212> TYPE: DNA
<213> ORGANISM: Oryctolagus cuniculus

<400> SEQUENCE: 363

```
atggagactg ggctgcgctg gcttctcctg gtcgctgtgc tcaaaggtgt ccagtgtcag       60
gagcagctgg aggagtccgg gggagacctg gtcaagcctg ggcatccct gacactcacc      120 tgcaaagcct ctggattctc cttcagtagc ggctactaca tgggctgggt ccgccaggct      180
ccagggaaag ggctgcaata catcggttac attgattatg tggtagcgc atactacgcg      240 agctgggcga aaggccgatt caccatctcc aaaacctcgt cgaccacggt gactctgcaa      300
atgaccagtc tgacagccgc ggacacggcc acctttttct gtacgagacg tgactatact      360
ggtggtgttg tcagagggct ggatctc                                          387
```

<210> SEQ ID NO 364
<211> LENGTH: 33
<212> TYPE: DNA
<213> ORGANISM: Oryctolagus cuniculus

<400> SEQUENCE: 364

```
caggccagtc agagcattta caggtactta tcc                                    33
```

<210> SEQ ID NO 365
<211> LENGTH: 21
<212> TYPE: DNA
<213> ORGANISM: Oryctolagus cuniculus

<400> SEQUENCE: 365

```
ggtgcatcca atctggaatc t                                                 21
```

<210> SEQ ID NO 366
<211> LENGTH: 42
<212> TYPE: DNA
<213> ORGANISM: Oryctolagus cuniculus

<400> SEQUENCE: 366

```
cagagcaatt atggtgctaa tagtgatagt tatggggatg ct                          42
```

<210> SEQ ID NO 367
<211> LENGTH: 18
<212> TYPE: DNA
<213> ORGANISM: Oryctolagus cuniculus

<400> SEQUENCE: 367

```
agcggctact acatgggc                                                     18
```

<210> SEQ ID NO 368
<211> LENGTH: 48
<212> TYPE: DNA
<213> ORGANISM: Oryctolagus cuniculus

<400> SEQUENCE: 368

```
tacattgatt atggtggtag cgcatactac gcgagctggg cgaaaggc                    48
```

-continued

```
<210> SEQ ID NO 369
<211> LENGTH: 39
<212> TYPE: DNA
<213> ORGANISM: Oryctolagus cuniculus

<400> SEQUENCE: 369
cgtgactata ctggtggtgt tgtcagaggg ctggatctc                            39

<210> SEQ ID NO 370
<211> LENGTH: 125
<212> TYPE: PRT
<213> ORGANISM: Oryctolagus cuniculus

<400> SEQUENCE: 370
```

Met Asp Thr Arg Ala Pro Thr Gln Leu Leu Gly Leu Leu Leu Trp
1               5                   10                  15

Leu Pro Gly Ala Arg Cys Ala Asp Ile Val Met Thr Gln Thr Pro Ser
            20                  25                  30

Ser Val Ser Ala Ala Val Gly Gly Thr Val Thr Ile Asn Cys Gln Ala
        35                  40                  45

Ser Gln Asn Ile Tyr Ser Ser Leu Ala Trp Tyr Gln Gln Lys Pro Gly
    50                  55                  60

Gln Pro Pro Lys Leu Leu Ile Phe Gly Ala Ser Asn Leu Glu Ser Gly
65                  70                  75                  80

Val Pro Ser Arg Phe Lys Gly Ser Gly Ser Gly Thr Glu Phe Thr Leu
                85                  90                  95

Thr Ile Ser Asp Leu Glu Cys Ala Asp Ala Ala Thr Tyr Tyr Cys Gln
            100                 105                 110

Ser His His Gly Ser Asn Ser Asp Ser Tyr Gly Asn Ala
        115                 120                 125

```
<210> SEQ ID NO 371
<211> LENGTH: 123
<212> TYPE: PRT
<213> ORGANISM: Oryctolagus cuniculus

<400> SEQUENCE: 371
```

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Leu Asn
        35                  40                  45

Asn Tyr Tyr Met Thr Trp Val Arg Gln Ala Pro Gly Lys Gly Leu Glu
    50                  55                  60

Ser Ile Gly Tyr Phe Ala Ser Gly Gly Gly Thr Tyr Tyr Ala Asn Trp
65                  70                  75                  80

Ala Lys Gly Arg Phe Thr Ile Ser Lys Thr Ser Thr Thr Val Asp Leu
                85                  90                  95

Lys Ile Thr Ser Pro Thr Thr Asp Asp Thr Ala Thr Tyr Phe Cys Ala
            100                 105                 110

Arg Gly Gly Ala Tyr Leu Gly Thr Gly Ser Leu
        115                 120

```
<210> SEQ ID NO 372
<211> LENGTH: 11
<212> TYPE: PRT
<213> ORGANISM: Oryctolagus cuniculus
```

<400> SEQUENCE: 372

Gln Ala Ser Gln Asn Ile Tyr Ser Ser Leu Ala
1               5                   10

<210> SEQ ID NO 373
<211> LENGTH: 7
<212> TYPE: PRT
<213> ORGANISM: Oryctolagus cuniculus

<400> SEQUENCE: 373

Gly Ala Ser Asn Leu Glu Ser
1               5

<210> SEQ ID NO 374
<211> LENGTH: 14
<212> TYPE: PRT
<213> ORGANISM: Oryctolagus cuniculus

<400> SEQUENCE: 374

Gln Ser His His Gly Ser Asn Ser Asp Ser Tyr Gly Asn Ala
1               5                   10

<210> SEQ ID NO 375
<211> LENGTH: 5
<212> TYPE: PRT
<213> ORGANISM: Oryctolagus cuniculus

<400> SEQUENCE: 375

Asn Tyr Tyr Met Thr
1               5

<210> SEQ ID NO 376
<211> LENGTH: 16
<212> TYPE: PRT
<213> ORGANISM: Oryctolagus cuniculus

<400> SEQUENCE: 376

Tyr Phe Ala Ser Gly Gly Gly Thr Tyr Tyr Ala Asn Trp Ala Lys Gly
1               5                   10                  15

<210> SEQ ID NO 377
<211> LENGTH: 10
<212> TYPE: PRT
<213> ORGANISM: Oryctolagus cuniculus

<400> SEQUENCE: 377

Gly Gly Ala Tyr Leu Gly Thr Gly Ser Leu
1               5                   10

<210> SEQ ID NO 378
<211> LENGTH: 375
<212> TYPE: DNA
<213> ORGANISM: Oryctolagus cuniculus

<400> SEQUENCE: 378

```
atggacacga gggcccccac tcagctgctg ggctcctgc tgctctggct cccaggtgcc      60
agatgtgccg acattgtgat gacccagact ccatcctccg tgtctgcagc tgtgggaggc    120
acagtcacca tcaattgcca ggccagtcag aacatttaca gctctttagc ctggtatcag    180
cagaaaccag ggcagcctcc caagctcctg atctttggtg catccaatct ggaatctggg    240
gtcccatcgc ggttcaaagg cagtggatct gggacagagt tcactctcac catcagcgac    300
ctggagtgtg ccgatgctgc cgcttactac tgtcagagcc atcatggtag taatagtgat    360
```

```
agttatggta atgct                                              375

<210> SEQ ID NO 379
<211> LENGTH: 369
<212> TYPE: DNA
<213> ORGANISM: Oryctolagus cuniculus

<400> SEQUENCE: 379
atggagactg ggctgcgctg gcttctcctg gtcgctgtgc tcaaaggtgt ccagtgtcag    60
tcggtggagg agtccggggg tcgcctggtc acgcctggga caccctgac actcacctgc    120 acagcctctg gattctccct aataactac tacatgacct gggtccgcca ggctccaggg    180
aaggggctgg aatccatcgg atattttgct tctggtggtg gcacatacta cgcgaactgg    240
gcgaaaggcc gattcaccat ctccaaaacc tcgaccacgg tggatctgaa gatcaccagt    300
ccgacaaccg acgatacggc cacctatttc tgtgccaggg gtggtgctta tttgggtact    360
gggagtttg                                                      369

<210> SEQ ID NO 380
<211> LENGTH: 33
<212> TYPE: DNA
<213> ORGANISM: Oryctolagus cuniculus

<400> SEQUENCE: 380
caggccagtc agaacattta cagctcttta gcc                            33

<210> SEQ ID NO 381
<211> LENGTH: 21
<212> TYPE: DNA
<213> ORGANISM: Oryctolagus cuniculus

<400> SEQUENCE: 381
ggtgcatcca atctggaatc t                                         21

<210> SEQ ID NO 382
<211> LENGTH: 42
<212> TYPE: DNA
<213> ORGANISM: Oryctolagus cuniculus

<400> SEQUENCE: 382
cagagccatc atggtagtaa tagtgatagt tatggtaatg ct                   42

<210> SEQ ID NO 383
<211> LENGTH: 15
<212> TYPE: DNA
<213> ORGANISM: Oryctolagus cuniculus

<400> SEQUENCE: 383
aactactaca tgacc                                                15

<210> SEQ ID NO 384
<211> LENGTH: 48
<212> TYPE: DNA
<213> ORGANISM: Oryctolagus cuniculus

<400> SEQUENCE: 384
tattttgctt ctggtggtgg cacatactac gcgaactggg cgaaaggc             48

<210> SEQ ID NO 385
<211> LENGTH: 30
<212> TYPE: DNA
```

<213> ORGANISM: Oryctolagus cuniculus

<400> SEQUENCE: 385
ggtggtgctt atttgggtac tgggagtttg                                      30

<210> SEQ ID NO 386
<211> LENGTH: 125
<212> TYPE: PRT
<213> ORGANISM: Oryctolagus cuniculus

<400> SEQUENCE: 386

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ser
            20                  25                  30

Ser Val Ser Val Pro Val Gly Gly Thr Val Thr Ile Lys Cys Gln Ala
        35                  40                  45

Ser Gln Asn Ile Tyr Ser Ser Leu Ala Trp Tyr Gln Gln Lys Pro Gly
    50                  55                  60

Gln Pro Pro Lys Arg Leu Ile Tyr Tyr Ala Ala Thr Leu Ala Ser Gly
65                  70                  75                  80

Val Pro Ser Arg Phe Lys Gly Ser Gly Ser Gly Thr Asp Phe Thr Leu
                85                  90                  95

Thr Ile Ser Asp Leu Glu Cys Ala Asp Ala Ala Thr Tyr Tyr Cys Gln
            100                 105                 110

Ser Asn His Gly Ser Asn Ser Asp Ser Tyr Gly Asn Pro
        115                 120                 125

<210> SEQ ID NO 387
<211> LENGTH: 123
<212> TYPE: PRT
<213> ORGANISM: Oryctolagus cuniculus

<400> SEQUENCE: 387

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ala Gly Phe Ser Leu Ser
        35                  40                  45

Thr Tyr Gly Val Thr Trp Val Arg Gln Ala Pro Gly Lys Gly Leu Glu
    50                  55                  60

Ser Ile Gly Tyr Ile Thr Tyr Gly Asn Ile Lys Tyr Tyr Ala Thr Trp
65                  70                  75                  80

Ala Lys Gly Arg Phe Thr Ile Ser Lys Thr Ser Thr Thr Val Asp Leu
                85                  90                  95

Lys Met Thr Ser Pro Thr Thr Glu Asp Thr Ala Thr Tyr Phe Cys Thr
            100                 105                 110

Arg Tyr Gly Gly Ser Gly Ile Gly Glu Asp Leu
        115                 120

<210> SEQ ID NO 388
<211> LENGTH: 11
<212> TYPE: PRT
<213> ORGANISM: Oryctolagus cuniculus

<400> SEQUENCE: 388

Gln Ala Ser Gln Asn Ile Tyr Ser Ser Leu Ala

<210> SEQ ID NO 389
<211> LENGTH: 7
<212> TYPE: PRT
<213> ORGANISM: Oryctolagus cuniculus

<400> SEQUENCE: 389

Tyr Ala Ala Thr Leu Ala Ser
1               5

<210> SEQ ID NO 390
<211> LENGTH: 14
<212> TYPE: PRT
<213> ORGANISM: Oryctolagus cuniculus

<400> SEQUENCE: 390

Gln Ser Asn His Gly Ser Asn Ser Asp Ser Tyr Gly Asn Pro
1               5                   10

<210> SEQ ID NO 391
<211> LENGTH: 5
<212> TYPE: PRT
<213> ORGANISM: Oryctolagus cuniculus

<400> SEQUENCE: 391

Thr Tyr Gly Val Thr
1               5

<210> SEQ ID NO 392
<211> LENGTH: 16
<212> TYPE: PRT
<213> ORGANISM: Oryctolagus cuniculus

<400> SEQUENCE: 392

Tyr Ile Thr Tyr Gly Asn Ile Lys Tyr Tyr Ala Thr Trp Ala Lys Gly
1               5                   10                  15

<210> SEQ ID NO 393
<211> LENGTH: 10
<212> TYPE: PRT
<213> ORGANISM: Oryctolagus cuniculus

<400> SEQUENCE: 393

Tyr Gly Gly Ser Gly Ile Gly Glu Asp Leu
1               5                   10

<210> SEQ ID NO 394
<211> LENGTH: 375
<212> TYPE: DNA
<213> ORGANISM: Oryctolagus cuniculus

<400> SEQUENCE: 394

```
atggacacga gggccccccac tcagctgctg gggctcctgc tgctctggct cccaggtgcc      60
agatgtgctg acattgtgat gacccagact ccatcctccg tgtctgtacc tgtgggaggc     120
acagtcacca tcaagtgcca ggccagtcag aacatttaca gctctttagc ctggtatcag     180
cagaaaccag acagcctcc caagcgcctg atctattatg ccgccactct ggcatctggg     240
gtcccatcgc ggttcaaagg cagtggatct ggacagatt tcactctcac catcagcgac     300
ctggagtgtg ccgatgctgc cacttactat tgtcaaagca atcatggtag taatagtgat     360
agttatggta atcct                                                      375
```

<210> SEQ ID NO 395
<211> LENGTH: 369
<212> TYPE: DNA
<213> ORGANISM: Oryctolagus cuniculus

<400> SEQUENCE: 395

```
atggagactg ggctgcgctg gcttctcctg gtcgctgtgc tcaagggtgt ccagtgtcag    60
tcggtggagg agtccggggg tcgcctggtc acgcctggga caccccctgac actcacctgc   120
acagtcgctg gattctccct cagtacctat ggagtgacct gggtccgcca ggctccaggg   180
aaggggctgg aatccatcgg atacattact tatggtaata ttaaatacta cgcgacctgg   240
gcgaaaggcc gattcaccat ctccaaaacc tcgaccacgg tggatctgaa aatgaccagt   300
ccgacaaccg aggacacggc cacctatttc tgtaccagat atggtggtag tgggattggt   360
gaggacttg                                                            369
```

<210> SEQ ID NO 396
<211> LENGTH: 33
<212> TYPE: DNA
<213> ORGANISM: Oryctolagus cuniculus

<400> SEQUENCE: 396

```
caggccagtc agaacattta cagctcttta gcc                                 33
```

<210> SEQ ID NO 397
<211> LENGTH: 21
<212> TYPE: DNA
<213> ORGANISM: Oryctolagus cuniculus

<400> SEQUENCE: 397

```
tatgccgcca ctctggcatc t                                              21
```

<210> SEQ ID NO 398
<211> LENGTH: 42
<212> TYPE: DNA
<213> ORGANISM: Oryctolagus cuniculus

<400> SEQUENCE: 398

```
caaagcaatc atggtagtaa tagtgatagt tatggtaatc ct                       42
```

<210> SEQ ID NO 399
<211> LENGTH: 15
<212> TYPE: DNA
<213> ORGANISM: Oryctolagus cuniculus

<400> SEQUENCE: 399

```
acctatggag tgacc                                                     15
```

<210> SEQ ID NO 400
<211> LENGTH: 48
<212> TYPE: DNA
<213> ORGANISM: Oryctolagus cuniculus

<400> SEQUENCE: 400

```
tacattactt atggtaatat taaatactac gcgacctggg cgaaaggc                 48
```

<210> SEQ ID NO 401
<211> LENGTH: 30
<212> TYPE: DNA
<213> ORGANISM: Oryctolagus cuniculus

<400> SEQUENCE: 401
```
tatggtggta gtgggattgg tgaggacttg                                        30

<210> SEQ ID NO 402
<211> LENGTH: 124
<212> TYPE: PRT
<213> ORGANISM: Oryctolagus cuniculus

<400> SEQUENCE: 402

Met Asp Thr Arg Ala Pro Thr Gln Leu Leu Gly Leu Leu Leu Leu Trp
1               5                   10                  15

Leu Pro Gly Ala Arg Cys Ala Asp Val Val Met Thr Gln Thr Pro Ser
            20                  25                  30

Ser Val Ser Glu Pro Val Gly Gly Thr Val Thr Ile Lys Cys Gln Ala
        35                  40                  45

Ser Glu Thr Ile Gly Asn Tyr Leu Ser Trp Tyr Gln Gln Lys Pro Gly
    50                  55                  60

Gln Pro Pro Lys Arg Leu Ile Tyr Tyr Ala Ser Thr Leu Ser Ser Gly
65                  70                  75                  80

Val Pro Ser Arg Phe Lys Gly Ser Gly Ser Gly Thr Asp Phe Thr Leu
                85                  90                  95

Thr Ile Ser Asp Leu Glu Cys Ala Asp Ala Ala Thr Tyr Tyr Cys Gln
            100                 105                 110

Lys Asn Tyr Gly Ser Gly Ala Ser Ser Leu Gly Ala
        115                 120

<210> SEQ ID NO 403
<211> LENGTH: 125
<212> TYPE: PRT
<213> ORGANISM: Oryctolagus cuniculus

<400> SEQUENCE: 403

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Tyr Met Ala Trp Val Arg Gln Ala Pro Gly Lys Gly Leu Glu
    50                  55                  60

Trp Ile Gly Tyr Ile Gly Phe Gly Gly Ser Thr Tyr Tyr Ala Thr Trp
65                  70                  75                  80

Ala Lys Gly Arg Val Thr Ile Ser Arg Thr Ser Thr Thr Val Asp Leu
                85                  90                  95

Gln Ile Thr Ser Pro Thr Thr Glu Asp Thr Ala Thr Tyr Phe Cys Ala
            100                 105                 110

Arg Gly Val Tyr Gly Asp Phe Arg Thr Gly Ala Asp Leu
        115                 120                 125

<210> SEQ ID NO 404
<211> LENGTH: 11
<212> TYPE: PRT
<213> ORGANISM: Oryctolagus cuniculus

<400> SEQUENCE: 404

Gln Ala Ser Glu Thr Ile Gly Asn Tyr Leu Ser
1               5                   10

<210> SEQ ID NO 405
<211> LENGTH: 7
<212> TYPE: PRT
<213> ORGANISM: Oryctolagus cuniculus

<400> SEQUENCE: 405

Tyr Ala Ser Thr Leu Ser Ser
1               5

<210> SEQ ID NO 406
<211> LENGTH: 13
<212> TYPE: PRT
<213> ORGANISM: Oryctolagus cuniculus

<400> SEQUENCE: 406

Gln Lys Asn Tyr Gly Ser Gly Ala Ser Ser Leu Gly Ala
1               5                   10

<210> SEQ ID NO 407
<211> LENGTH: 5
<212> TYPE: PRT
<213> ORGANISM: Oryctolagus cuniculus

<400> SEQUENCE: 407

Ser Tyr Tyr Met Ala
1               5

<210> SEQ ID NO 408
<211> LENGTH: 16
<212> TYPE: PRT
<213> ORGANISM: Oryctolagus cuniculus

<400> SEQUENCE: 408

Tyr Ile Gly Phe Gly Gly Ser Thr Tyr Tyr Ala Thr Trp Ala Lys Gly
1               5                   10                  15

<210> SEQ ID NO 409
<211> LENGTH: 12
<212> TYPE: PRT
<213> ORGANISM: Oryctolagus cuniculus

<400> SEQUENCE: 409

Gly Val Tyr Gly Asp Phe Arg Thr Gly Ala Asp Leu
1               5                   10

<210> SEQ ID NO 410
<211> LENGTH: 372
<212> TYPE: DNA
<213> ORGANISM: Oryctolagus cuniculus

<400> SEQUENCE: 410

```
atggacacga gggcccccac tcagctgctg gggctcctgc tgctctggct cccaggtgcc    60
agatgtgccg acgtcgtgat gacccagact ccatcctccg tgtctgaacc tgtgggaggc   120
acagtcacca tcaagtgcca ggccagtgaa accattggta actacttatc ctggtatcag   180
cagaaaccag gcagcctcc caagcgcctg atctattatg catccactct gtcatctggg   240
gtcccatcgc ggttcaaagg cagtggatct gggacagatt tcactctcac catcagcgac   300
ctggagtgtg ccgatgctgc cacttactac tgccaaaaga attatggtag tggtgctagt   360
agtttgggtg ct                                                       372
```

<210> SEQ ID NO 411
<211> LENGTH: 375

```
<212> TYPE: DNA
<213> ORGANISM: Oryctolagus cuniculus

<400> SEQUENCE: 411
atggagactg ggctgcgctg gcttctcctg gtcgctgtgc tcaaaggtgt ccagtgtcag      60
tcggtggagg agtccggggg tcgcctggtc acgcctggga cacccctgac actcacctgc    120
acagtctctg gattctccct cagtagctac tacatggcct gggtccgcca ggctccaggg    180
aaggggctgg agtggatcgg atatattggt tttggtggta gcacatacta cgcgacctgg    240
gcgaaaggcc gggtcaccat ctccaggacc tcgaccacgg tggatctgca aatcaccagt    300
ccgacaaccg aggacacggc cacctatttc tgtgccagag gagtttatgg tgattttcgt    360
actggtgccg acttg                                                     375

<210> SEQ ID NO 412
<211> LENGTH: 33
<212> TYPE: DNA
<213> ORGANISM: Oryctolagus cuniculus

<400> SEQUENCE: 412
caggccagtg aaaccattgg taactactta tcc                                   33

<210> SEQ ID NO 413
<211> LENGTH: 21
<212> TYPE: DNA
<213> ORGANISM: Oryctolagus cuniculus

<400> SEQUENCE: 413
tatgcatcca ctctgtcatc t                                                21

<210> SEQ ID NO 414
<211> LENGTH: 39
<212> TYPE: DNA
<213> ORGANISM: Oryctolagus cuniculus

<400> SEQUENCE: 414
caaaagaatt atggtagtgg tgctagtagt ttgggtgct                             39

<210> SEQ ID NO 415
<211> LENGTH: 15
<212> TYPE: DNA
<213> ORGANISM: Oryctolagus cuniculus

<400> SEQUENCE: 415
agctactaca tggcc                                                       15

<210> SEQ ID NO 416
<211> LENGTH: 48
<212> TYPE: DNA
<213> ORGANISM: Oryctolagus cuniculus

<400> SEQUENCE: 416
tatattggtt ttggtggtag cacatactac gcgacctggg cgaaaggc                   48

<210> SEQ ID NO 417
<211> LENGTH: 36
<212> TYPE: DNA
<213> ORGANISM: Oryctolagus cuniculus

<400> SEQUENCE: 417
ggagtttatg gtgattttcg tactggtgcc gacttg                                36
```

<210> SEQ ID NO 418
<211> LENGTH: 105
<212> TYPE: PRT
<213> ORGANISM: Artificial
<220> FEATURE:
<223> OTHER INFORMATION: Kappa constant domain

<400> SEQUENCE: 418

```
Val Ala Ala Pro Ser Val Phe Ile Phe Pro Ser Asp Glu Gln Leu
1               5                   10                  15

Lys Ser Gly Thr Ala Ser Val Val Cys Leu Leu Asn Asn Phe Tyr Pro
                20                  25                  30

Arg Glu Ala Lys Val Gln Trp Lys Val Asp Asn Ala Leu Gln Ser Gly
            35                  40                  45

Asn Ser Gln Glu Ser Val Thr Glu Gln Asp Ser Lys Asp Ser Thr Tyr
        50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105
```

<210> SEQ ID NO 419
<211> LENGTH: 315
<212> TYPE: DNA
<213> ORGANISM: Artificial
<220> FEATURE:
<223> OTHER INFORMATION: Kappa constant domain

<400> SEQUENCE: 419

```
gtggctgcac catctgtctt catcttcccg ccatctgatg agcagttgaa atctggaact    60
gcctctgttg tgtgcctgct gaataacttc tatcccagag aggccaaagt acagtggaag   120
gtggataacg ccctccaatc gggtaactcc caggagagtg tcacagagca ggacagcaag   180
gacagcacct acagcctcag cagcaccctg acgctgagca agcagactac gagaaacac   240 aaagtctacg cctgcgaagt cacccatcag ggcctgagct cgcccgtcac aaagagcttc   300
aacaggggag agtgt                                                    315
```

<210> SEQ ID NO 420
<211> LENGTH: 330
<212> TYPE: PRT
<213> ORGANISM: Artificial
<220> FEATURE:
<223> OTHER INFORMATION: Gamma-1 constant domain

<400> SEQUENCE: 420

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

85                  90                  95
Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 421
<211> LENGTH: 990
<212> TYPE: DNA
<213> ORGANISM: Artificial
<220> FEATURE:
<223> OTHER INFORMATION: Gamma-1 constant domain

<400> SEQUENCE: 421
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctggggga     360 ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacgcc     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660

```
aaagccaaag ggcagcccg agaaccacag gtgtacaccc tgcccccatc ccgggaggag       720
atgaccaaga accaggtcag cctgacctgc ctggtcaaag gcttctatcc cagcgacatc       780
gccgtggagt gggagagcaa tgggcagccg gagaacaact acaagaccac gcctcccgtg       840
ctggactccg acggctcctt cttcctctac agcaagctca ccgtggacaa gagcaggtgg       900 cagcaggga acgtcttctc atgctccgtg atgcatgagg ctctgcacaa ccactacacg        960
cagaagagcc tctccctgtc tccgggtaaa                                        990
```